US008518916B2

(12) United States Patent
Leonardi et al.

(10) Patent No.: US 8,518,916 B2
(45) Date of Patent: Aug. 27, 2013

(54) HETEROCYCLIC DERIVATIVES AS M-GLU5 ANTAGONISTS

(75) Inventors: Amedeo Leonardi, Milan (IT); Gianni Motta, Barlassina (IT); Carlo Riva, Varese (IT); Elena Poggesi, Milan (IT); Davide Graziani, Milan (IT); Matteo Longhi, Castellanza (IT)

(73) Assignee: Recordati Ireland Limited, Cork (IE)

( * ) Notice: Subject to any disclaimer, the term of this patent is extended or adjusted under 35 U.S.C. 154(b) by 765 days.

(21) Appl. No.: 12/185,639

(22) Filed: Aug. 4, 2008

(65) Prior Publication Data
US 2009/0042841 A1 Feb. 12, 2009

Related U.S. Application Data

(60) Provisional application No. 60/953,677, filed on Aug. 2, 2007, provisional application No. 61/045,175, filed on Apr. 15, 2008.

(51) Int. Cl.
A61K 31/60 (2006.01)
A61K 31/4545 (2006.01)
A61K 31/506 (2006.01)
A61K 31/5377 (2006.01)
A61P 13/00 (2006.01)
C07D 401/06 (2006.01)
C07D 401/14 (2006.01)
C07D 413/14 (2006.01)

(52) U.S. Cl.
USPC ........ 514/161; 514/235.5; 514/274; 514/318; 544/130; 544/316; 546/194

(58) Field of Classification Search
None
See application file for complete search history.

(56) References Cited

U.S. PATENT DOCUMENTS

| 2,867,620 | A | 1/1959 | Biel et al. |
| 5,990,114 | A | 11/1999 | Leonardi et al. |
| 6,265,434 | B1 | 7/2001 | Caldwell et al. |
| 6,306,861 | B1 | 10/2001 | Leonardi et al. |
| 6,365,591 | B1 | 4/2002 | Leonardi et al. |
| 6,369,222 | B1 | 4/2002 | Binggeli et al. |
| 6,387,909 | B1 | 5/2002 | Leonardi et al. |
| 6,403,594 | B1 | 6/2002 | Leonardi et al. |
| 2004/0077671 | A1 | 4/2004 | Chu-Moyer et al. |
| 2004/0186292 | A1 | 9/2004 | Wang et al. |
| 2005/0065156 | A1 | 3/2005 | Li et al. |
| 2006/0264415 | A1 | 11/2006 | Leit de Moradei et al. |

FOREIGN PATENT DOCUMENTS

| EP | 0537993 | 4/1993 |
| JP | 59095249 | 6/1984 |
| WO | WO-00/63166 | 10/2000 |
| WO | WO-01/02386 | 1/2001 |
| WO | WO-01/27070 | 4/2001 |
| WO | WO-01/32632 | 5/2001 |
| WO | WO-02/00196 | 1/2002 |
| WO | WO-03/093236 | 11/2003 |
| WO | WO-2004/020435 | 3/2004 |
| WO | WO-2004/041777 | 5/2004 |
| WO | WO-2004/067002 | 8/2004 |
| WO | WO-2004/069158 | 8/2004 |
| WO | WO-2005/090347 | 9/2005 |
| WO | WO-2005/97760 | 10/2005 |
| WO | WO-2006/089700 | 8/2006 |
| WO | WO-2007/006530 | 1/2007 |
| WO | WO-2007/070173 | 6/2007 |
| WO | WO-2007/118137 | 10/2007 |
| WO | WO-2008/011007 | 1/2008 |

OTHER PUBLICATIONS

Sharma et al., Synthesis and SAR of a mGluR5 Allosteric Partial Antagonist Lead: Unexpected Modulation of Pharmacology with Slight Structural to a 5-(phenyl ethynyl)pyrimidine Scaffold, 18 Bioorg. & Med. Chem. Letts., 4098-4101 (2008).*
Anderson et al.: "Pharmacology of the Lower Urinary Tract: Basis for Current and Furture Treaments of Uringary Incontinence" Pharmacol Rev. 56: 581-631 (2004).
Spooren et al. "Novel allosteric antagonists shed light on mglu5 receptors and CNS Disorders" Trends in Pharmacological Sciences vol. 22 No. 7 Jul. 2001.
Brunton et al: "Goodman & Gilman's the Pharmacological Basis of Therapeutics", 11th Edition, McGraw-Hill (2006) pp. 11-22.
Abrams et al.: "The Standardisation of Terminaology of Lower Urinary Tract Function: Report from the Standardisation Sub-committee of the International Continence Society" Neurourology and Urodynamics 21:167-178 (2002).
Hidenori et al.: "Cobalt-catalyzed Sequential Cyclization/Cross-coupling Reactions of 6-halo1-hexen Dervatives with Grignard Reagents and their Application to the Syntesis of 1,3-diols" Tetrahedron, Elsevier Sicence Publishers, vol. 63 (2007) 8609-8618.
Anand et al.: "A Simple, Milde Catalytic, Enatioselective Addition of Terminal Acetylenes to Aldehydes" Jouranal of the American Chemical Society vol. 123, No. 39 (2001) pp. 9687-9688.
Biel et al.: "Hypotensive Agents. I. Acetylenic Diamines" Journal of the American Chemical Society, vol. 80, 1958 pp. 4609-4614.
Dener et al.: "Dibasic Inhibitors of Human Mast Cell Tryptase. Part 3: Identification of a Series of Potent and Selective Inhibitosrs Containing the Benzamidine Functionality." Bioorganic & Medicinal Chemistry Letters. vol. 11. No. 13, 2001. pp. 1629-1633.
Boehmer et al.: "Synthesis of Oligo-enynes Using [FE(alkene)(CO)n] Scaffolds. Z/E-Selective Wittig- and Horner-type Olefination Reactions of β- Carbonyl Groups in $\eta^4$ -Diene and γ-Carbonyl Groups in $\eta^2$ —Alkene Complexes of Iron" Journal of Chemical Research (1998) 372-373.
John Wiley & Sons: Organic Syntheses vol. 81 (2005) pp. 157-171.
N. J. Lawrence: "The Wittig Reaction and Related Methods" in Preparation of Alkenes, A Practical Approach. J.M. J. Williams, Ed., Oxford University Press, Oxford (1996) pp. 19-58.

(Continued)

Primary Examiner — Janet Andres
Assistant Examiner — Timothy R Rozof
(74) Attorney, Agent, or Firm — Merchant & Gould P.C.

(57) ABSTRACT

This invention relates to novel heterocyclic compounds having selective affinity for the mGlu5 subtype of metabotropic receptors, pharmaceutical compositions thereof and uses for such compounds and compositions in the treatment of lower urinary tract disorders, such as neuromuscular dysfunction of the lower urinary tract, and in the treatment of migraine and gastroesophagael reflux disease (GERD).

40 Claims, 3 Drawing Sheets

(56) References Cited

OTHER PUBLICATIONS

E.J. McGuire: "Neuromuscular Dysfunction of the Lower Urinary Tract" Cambell's Urology 5th Edition (1986). W.B. Saunders Company pp. 616-638.

Gibtner et al.: "End-Cap Stabilized Oligoynes: Model Compounds for the Linear sp Carbon Allotrope Carbyne" Chem. Eur. J. (2002) pp. 408-432.

Corely et al: "Direct Synthesis of 4-Arylpiperidines via Palladium/ Coppr (I)-Cocatalyzed Negishi Coupling of a 4-Piperidylzinc Iodide with Aromatic Halides and Triflates" J. Org. Chem (2004) 69, pp. 5120-5123.

Egbertson et al.: "Non-Peptide GPIIb/IIIa Inhibitors. 20. Centrally Constrained Thienothiophene α- Sulfonamides are Potent, Long Acting in Vivo Inhibitors of Platelet Aggregation" J. Med Chem. 1999, 42 pp. 2409-2421.

Klein et. al.: "Design of a New Class of Orally Active Fibrinogen Receptor Antagonists" J. Med. Chem 1998, 41, pp. 2492-2502.

De Luca et al.: "An Easy and Convenient Synthesis of Weinreb Amides and Hydroxamates" J. Org. Chem. 2001, 66, 2534-2537.

Sorensen et al.: Copper-free PalladiumCatalyzed Sonogashira-type Coupling of Arly Halides and 1-aryl-2-(trimethylilyl) Acetylenes . E. Tetrahedron 61 (2005) 2697-2703.

Greene et al.: "Protection for the Alkyne-Ch" Protective Groups in Organic Synthesis, Third Edition. 1999. pp. 654-659.

Shen et al.: "Synthesis of Terminal Trimethylsilyl Enynes via a Silylated Arsonium Ylide" Journal of Organometallic Chemistry 346, (1988) 181-184.

Nicolaou et al.: "Total Synthesis of 5 (S), 15(S)-Dihydroxy-6,13-trans -8,11-ciseicosatetraenoic Acid (5,15-DiHETE): Two Novel Metabolites of Arachidonic Acid" J. American Chem. Soc. 1984. 106, 5734.

Hann et al.: "On the Double Bond Isotere of the Peptide Bond: Preparation of an Enkephalin Analogue" J. Chem Soc. Perkin Trans 1, 1982 pp. 307-314.

Gibson et al.: "Diethyl (3-Trimethylsilyl-2-propynyl) phosphonate, a New Reagent for the Prepartion of Terminal Conjugated Enynes" Synthesis (1991) pp. 414-416.

Wenk et al.: "A Nitric Oxide-Donating Flurbiprofen Derivative Reduces Neruoinflammation without Interacting with Galantamine in the Rat" European Journal Pharmacology 453 (2002) pp. 319-324.

Hermans et al.: "Structural, Signalling and Regulatory Properites of the Group I Mateabotropi Glutamate Receptors: Prototypic Family C G-Protein-Coupled Receptors" Biochem J. (2001) 359, 465-484.

* cited by examiner

HETEROCYCLIC DERIVATIVES AS M-GLU5 ANTAGONISTS

CROSS-REFERENCE TO RELATED APPLICATIONS

This application claims the benefit under 35 U.S.C. §120 of prior provisional applications 60/953,677 filed on Aug. 2, 2007 and 61/045,175 filed on Apr. 15, 2008. The disclosure of each of these prior applications is incorporated by reference in its entirety.

FIELD OF THE INVENTION

This invention relates to novel heterocyclic compounds having selective affinity for the mGlu5 subtype of metabotropic receptors, pharmaceutical compositions thereof and uses for such compounds and compositions.

BACKGROUND OF THE INVENTION

Lower urinary tract disorders encompass an assortment of syndromes that affect normal micturition. Lower urinary tract disorders may develop through combination of pathological and/or age-related changes of the urogenital system, or other etiology, e.g., neurological disorders. Individuals suffering from lower urinary tract disorders suffer from impaired quality of life, including embarrassment, poor self-perception, and a general reduction in emotional well-being, social function, and general health. Lower urinary tract disorders, moreover, may be associated with other physical ailments, including cellulitis, pressure ulcers, urinary tract infections, falls with fractures, sleep deprivation, social withdrawal, depression, and sexual dysfunction. Older individuals suffering from lower urinary tract disorders may require more care from health care providers, both family and profession, which may be a factor in decisions to place them in institutions.

According to the U.S. National Institutes of Health (NIH), up to 35 million Americans are estimated to suffer lower urinary tract disorders. Lower urinary tract disorders are more common among women than men (2:1) until age 80, after which men and women are equally affected. The prevalence of lower urinary tract disorders increases with age. By the age 65, lower urinary tract disorders affect 15% to 30% of all individuals and approximately 50% of individuals in long-term care.

Agents with various modes of action have been used to treat lower urinary tract disorders. These include agents that act directly on the lower urinary tract, e.g., antimuscarinics and alpha-1 antagonists, and agents that act through the central nervous system, e.g., serotonin and/or noradrenaline reuptake inhibitors. According to the NIH, however, while some progress has been made in the diagnosis, management, and treatment of lower urinary tract disorders, these disorders frequently remain intractable. Thus, there is a continued need for improved agents, formulations and therapies to treat lower urinary tract disorders.

Glutamic acid, an excitatory amino acid, is present at synapses throughout the central nervous system and is known to act on at least two types of receptors: ionotropic and metabotropic glutamate receptors.

The principle function of ionotropic glutamate receptors is that their activation forms ligand-gated ion channels and, thereby, directly mediates electrical signaling of nerve cells, producing rapid and relatively large conductance changes in the post-synaptic membranes. Metabotropic glutamate receptors (mGluRs) regulate electrical signaling indirectly, by influencing intracellular metabolic processes via G-proteins. Changes in the post-synaptic cell that are mediated through mGluRs are consequently relatively slow over time and are not linked to rapid and large changes in neuronal membrane conductance.

Three subtypes of ionotropic glutamate receptors have been described, i.e., the NMDA, AMPA and kainate subtypes.

Eight subtypes of metabotropic glutamate receptors have been cloned. The subtypes are classified into three groups on the basis of sequence similarities, and pharmacological and biochemical properties (Spooren et al., *Trends Pharmacol. Sci.* 22: 331-337, 2001): Group I mGlu receptors (mGlu1 and mGlu5), Group II mGlu receptors (mGlu2 and mGlu3) and Group III mGlu receptors (mGlu4, mGlu6, mGlu7 and mGlu8).

Group I receptor mGlu5 (either human or rat) is known to comprise at least two subtypes, "a" and "b". Subtype "b" is longer than subtype "a", because of an alternative splicing of a 32-amino-acid stretch in the C-terminal (intracellular) domain, 50 residues downstream of the beginning of the domain.

So the human mGlu5b is 1212 amino acids long, while the "a" form lacks the amino acids from 877 to 908 (n. 828 being the first of the intracellular domain). The rat mGlu5b is 1203 amino acids long, while the "a" form lacks the amino acids from 876 to 907 (n. 827 being the first of the intracellular domain). (Hermans and Challis, *Biochem. J.* 359: 465-484, 2001).

The mGlu receptors, belonging to family 3 of GPCRs, are characterized by two distinct topological domains: a large extracellular N-terminal domain containing a "Venus flytrap" module responsible for agonist binding and the 7-TM domain plus intracellular C-terminal domain that is involved in receptor activation and G-protein coupling.

The 7-TMD of mGlu I receptors has been shown to form a binding pocket for positive and negative allosteric modulators; the negative ones have been identified thanks to high throughput screening technologies and act as non-competitive antagonists, having no effect on agonist binding. The most interesting property of these molecules, in addition to their high potency, is their remarkable subtype selectivity.

The 7-TM binding region is located in a pocket-lined by TM-III, TM-V, TM-VI and TM-VII; this site corresponds to the retinal binding pocket in rhodopsin.

Allosteric modulators of mGlu5 represent an exciting advance in demonstrating the potentiality for developing novel research tools and therapeutic agents that regulate activity of specific mGluR subtypes.

The compounds of the instant invention are reported herein as mGlu5 antagonists but actually are negative allosteric modulators acting at the 7-TM binding region.

WO 00/63166 discloses tricyclic carbamic acid derivatives useful for the treatment of different diseases, including urinary incontinence. The derivatives are disclosed to be agonists or antagonists of Group I mGlu receptors with specificity for the mGlu1 receptor.

WO 01/32632 discloses pyrimidine derivatives useful for the treatment of different diseases, including urinary incontinence. The derivatives are disclosed as selective antagonists of the mGlu 1 receptor with at least 10-fold selectivity for the mGlu1 receptor over the mGlu 5 receptor.

WO 01/27070 discloses new bisarylacetamides useful for the treatment of urinary incontinence, among other conditions. The molecules are disclosed to be agonists or antagonists selective for the mGlu 1 receptor.

U.S. Pat. No. 6,369,222 discloses heterocycloazepinyl pyrimidine derivatives useful for the treatment of urinary incontinence, among other conditions. The derivatives are disclosed to be antagonists of the mGlu 1 receptor.

The aforementioned applications and patent, therefore, disclose mGlu1 receptor antagonists as useful for treating urinary incontinence. None of the references, however, provide experimental support for treatment of urinary incontinence, either in human patients or in an animal model of lower urinary tract disease.

There is a need in the art to develop novel compounds and compositions for the treatment of lower urinary tract disorders and for the alleviation of the symptoms associated with such disorders. The present inventors have addressed this need through the development of novel heterocyclic compounds that are selective mGlu5 antagonists. The compounds of the present invention provide potent inhibition of the micturition reflex through a novel mechanism of action.

SUMMARY OF THE INVENTION

The invention is based on the finding that selective mGlu5 antagonists are useful in the treatment of lower urinary tract disorders, such as neuromuscular dysfunction of the lower urinary tract, and in the treatment of migraine and gastroesophagael reflux disease (GERD) in mammals.

In certain aspects, the invention provides therapy with selective mGlu5 antagonists to treat a disorder of the lower urinary tract in a mammal.

In certain aspects, the invention provides therapy with a mGlu5 antagonists to treat at least one symptom of a disorder of the lower urinary tract in a mammal.

Thus, in certain embodiments, the invention provides a method of treating a symptom of urinary incontinence in a subject suffering from a lower urinary tract disorder, comprising administering to said subject a therapeutically effective amount of one or more of the compounds of the invention, alone or in combination with other therapeutic agents, to treat urge incontinence, stress incontinence, mixed incontinence or overflow incontinence.

In certain embodiments, the compounds of the present invention are used for the treatment of a lower urinary tract disorder selected from the group consisting of overactive bladder (OAB), interstitial cystitis, prostatitis, prostadynia and benign prostatic hyperplasia (BPH). In preferred embodiments, the invention provides treatment of urinary incontinence caused by or associated with such disorders.

In certain aspects, the compounds of the present invention are used for the treatment of migraine.

In certain embodiments, compounds of the present invention are used for the treatment of gastroesophagael reflux disease (GERD) in mammals.

In a preferred embodiment, the novel compounds of the present invention are selective mGlu5 antagonists represented by Formula A

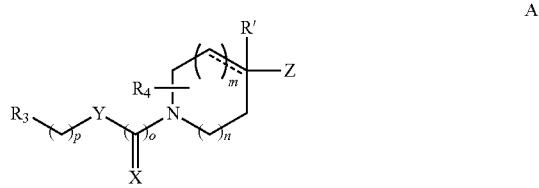

wherein:
R' is absent or is selected from the group consisting of hydrogen and hydroxyl;

Z is chosen from the group consisting of

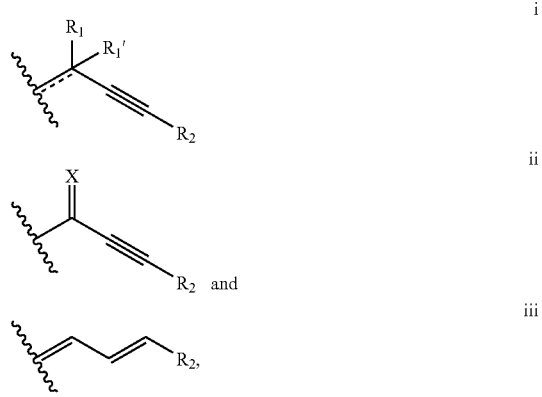

wherein
X' is chosen from the group consisting of O and $CH_2$;
$R_1$ is chosen from the group consisting of hydrogen, $C_1$-$C_6$ alkyl, $C_3$-$C_{14}$ cycloalkyl, hydroxyl, cyano, halogen, —C(O)O $C_1$-$C_6$ alkyl, —C(O)$C_1$-$C_6$ alkyl, —OC(O)O $C_1$-$C_6$ alkyl, —OC(O)$C_1$-$C_6$ alkyl, $C_1$-$C_6$ alkylthio, $C_1$-$C_6$ alkoxy, phenyl, di $C_1$-$C_6$ alkyl amino, and optionally substituted $C_2$-$C_9$ heterocyclic group containing 1 to 3 heteroatoms chosen from the group consisting of N, $NR_5$, S, $SO_2$ and O wherein $R_5$ is chosen from the group consisting of H, —C(O)$C_1$-$C_6$ alkyl, benzyl, phenyl and $C_1$-$C_6$ alkyl;
$R_1'$ is absent or is hydroxy; and
$R_2$ is chosen from the group consisting of an optionally substituted mono or bicyclic $C_1$-$C_9$ heteroaromatic group containing from 1 to 3 heteroatoms chosen from the group consisting of N, $NR_6$, S, $SO_2$ and O wherein $R_6$ is chosen from the group consisting of H, benzyl, —C(O)$C_1$-$C_6$ alkyl, phenyl and $C_1$-$C_6$ alkyl; optionally substituted mono or bicyclic $C_2$-$C_9$ heterocyclic group containing 1-3 heteroatoms chosen from the group consisting of N, $NR_7$, S, $SO_2$ and O, wherein $R_7$ is chosen from the group consisting of H, —C(O)$C_1$-$C_6$ alkyl, benzyl, phenyl and $C_1$-$C_6$ alkyl; optionally substituted mono, bi, or tricyclic $C_6$-$C_{14}$ aromatic; optionally substituted $C_1$-$C_6$ alkyl; optionally substituted $C_3$-$C_6$ cycloalkyl; or $R_2$ is —C(O)$R_2$ wherein $R_2$ is as defined above;
$R_3$ is chosen from the group consisting of hydrogen, optionally substituted $C_1$-$C_6$ alkyl optionally interrupted by 1-3 heteroatoms selected from the group consisting of —$NR_8$—, —S—, —O—, and —$SO_2$—, wherein $R_8$ is chosen from the group consisting of H, —C(O)$C_1$-$C_6$ alkyl, benzyl, phenyl and $C_1$-$C_6$ alkyl; optionally substituted mono, bi, or tricyclic $C_1$-$C_{14}$ heteroaromatic group containing 1 to 3 heteroatoms chosen from the group consisting of N, $NR_9$, S, $SO_2$, and O wherein $R_9$ is chosen from the group consisting of H, —C(O)$C_1$-$C_6$ alkyl, benzyl, phenyl and $C_1$-$C_6$ alkyl; optionally substituted mono, bi, or tricyclic $C_2$-$C_{14}$ heterocyclic group containing 1 to 3 heteroatoms chosen from the group consisting of N, $NR_{10}$, S, $SO_2$ and O wherein $R_{10}$ is chosen from the group consisting of H, —C(O)$C_1$-$C_6$ alkyl, benzyl, phenyl and $C_1$-$C_6$ alkyl; optionally substituted mono, bi or tricyclic $C_6$-$C_{14}$ aromatic; and optionally substituted $C_3$-$C_6$ cycloalkyl;
$R_4$ is chosen independently for each position capable of substitution from the group consisting of hydrogen and $C_1$-$C_6$ alkyl;
X is chosen from the group consisting of O and S;

Y is absent or chosen from the group consisting of —SO$_2$—, —NH—, —N(C$_1$-C$_6$ alkyl)- and —O—;
m is 0, 1 or 2
n is 0, 1 or 2
o is 0 or 1
p is 0, 1, 2, 3, 4 or 5;
---- is an optional double bond with the proviso that there cannot be two or more optional double bonds present;

represents the point of attachment to the nitrogen containing ring and; enantiomers, diastereomers and N-oxides thereof; and pharmaceutically acceptable salts thereof; with the proviso that two heteroatoms may not be covalently bound to one another unless present in a heteroaromatic ring, a sulfonamide linkage or as an N-oxide;

In preferred embodiments, the novel selective mGlu5 antagonist has a structure represented by formula I

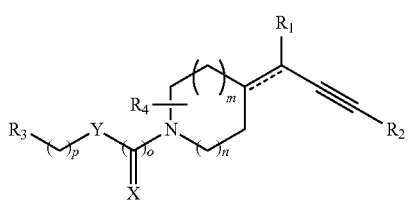

wherein:

R$_1$ is chosen from the group consisting of hydrogen, C$_1$-C$_6$ alkyl, C$_3$-C$_{14}$ cycloalkyl, hydroxyl, cyano, halogen, —C(O)O C$_1$-C$_6$ alkyl, —C(O)C$_1$-C$_6$ alkyl, —OC(O)O C$_1$-C$_6$ alkyl, —OC(O)C$_1$-C$_6$ alkyl, C$_1$-C$_6$ alkylthio, C$_1$-C$_6$ alkoxy, phenyl, di C$_1$-C$_6$ alkyl amino, and optionally substituted C$_2$-C$_9$ heterocyclic group containing 1 to 3 heteroatoms chosen from the group consisting of N, NR$_5$, S, SO$_2$ and O wherein R$_5$ is chosen from the group consisting of H, —C(O)C$_1$-C$_6$ alkyl, benzyl, phenyl and C$_1$-C$_6$ alkyl;

R$_2$ is chosen from the group consisting of an optionally substituted mono or bicyclic C$_1$-C$_9$ heteroaromatic group containing from 1 to 3 heteroatoms chosen from the group consisting of N, NR$_6$, S, SO$_2$ and O wherein R$_6$ is chosen from the group consisting of H, benzyl, —C(O)C$_1$-C$_6$ alkyl, phenyl and C$_1$-C$_6$ alkyl; optionally substituted mono or bicyclic C$_2$-C$_9$ heterocyclic group containing 1-3 heteroatoms chosen from the group consisting of N, NR$_7$, S, SO$_2$ and O wherein R$_7$ is chosen from the group consisting of H, —C(O)C$_1$-C$_6$ alkyl, benzyl, phenyl and C$_1$-C$_6$ alkyl; optionally substituted mono, bi, or tricyclic C$_6$-C$_{14}$ aromatic; optionally substituted C$_1$-C$_6$ alkyl; optionally substituted C$_3$-C$_6$ cycloalkyl; or R$_2$ is —C(O)R$_2$ wherein R$_2$ is as defined above;

R$_3$ is chosen from the group consisting of hydrogen, optionally substituted C$_1$-C$_6$ alkyl optionally interrupted by 1-3 heteroatoms selected from the group consisting of —NR$_8$—, —S—, —O—, and —SO$_2$—, wherein R$_8$ is chosen from the group consisting of H, —C(O)C$_1$-C$_6$ alkyl, benzyl, phenyl and C$_1$-C$_6$ alkyl; optionally substituted mono, bi, or tricyclic C$_1$-C$_{14}$ heteroaromatic group containing 1 to 3 heteroatoms chosen from the group consisting of N, NR$_9$, S, SO$_2$, and O wherein R$_9$ is chosen from the group consisting of H, —C(O)C$_1$-C$_6$ alkyl, benzyl, phenyl and C$_1$-C$_6$ alkyl; optionally substituted mono, bi, or tricyclic C$_2$-C$_{14}$ heterocyclic group containing 1 to 3 heteroatoms chosen from the group consisting of N, NR$_{10}$, S, SO$_2$ and O wherein R$_{10}$ is chosen from the group consisting of H, —C(O)C$_1$-C$_6$ alkyl, benzyl, phenyl and C$_1$-C$_6$ alkyl; optionally substituted mono, bi or tricyclic C$_6$-C$_{14}$ aromatic; and optionally substituted C$_3$-C$_6$ cycloalkyl;

R$_4$ is chosen independently for each position capable of substitution from the group consisting of hydrogen and C$_1$-C$_6$ alkyl;

X is chosen from the group consisting of O and S;

Y is absent or chosen from the group consisting of —SO$_2$—, —NH—, —N(C$_1$-C$_6$ alkyl)- and —O—;
m is 0, 1 or 2
n is 0, 1 or 2
o is 0 or 1
p is 0, 1, 2, 3, 4 or 5
---- is an optional double bond and;
enantiomers, diastereomers and N-oxides thereof; and pharmaceutically acceptable salts thereof; with the proviso that two heteroatoms may not be covalently bound to one another unless present in a heteroaromatic ring or as a sulfonamide linkage In a further preferred embodiments, the novel selective mGlu5 antagonist has a structure represented by formula II or III

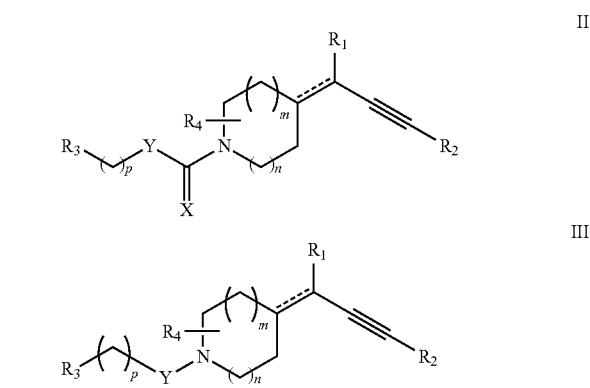

where the variables are as in Formula I and enantiomers, diastereomers and N-oxides thereof;
and pharmaceutically acceptable salts thereof; with the proviso that two heteroatoms may not be covalently bound to one another unless present in a heteroaromatic ring or as a sulfonamide linkage.

DETAILED DESCRIPTION OF THE INVENTION

Figure 1:
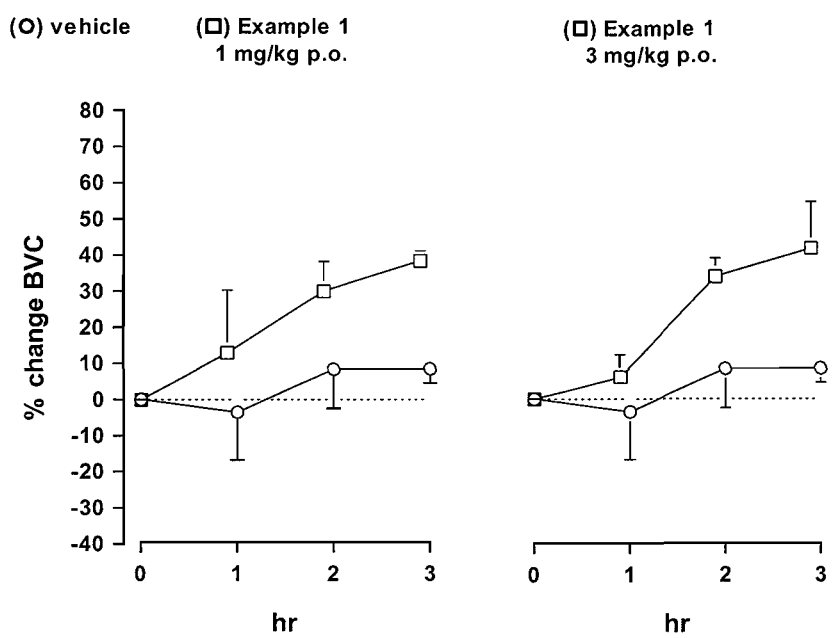
FIG. 1: time course of the effect on rat bladder volume capacity of Example 1, administered at 1 and 3 mg/kg, orally, vs vehicle treated controls.

We have tested the activity of selective mGlu1 and selective mGlu5 antagonists in a rat model that is useful to detect activity on the lower urinary tract. Surprisingly, good activity was found for antagonists selective for the mGlu5 receptor, whereas two commercially available antagonists selective for mGlu1 receptor failed to exhibit an effect. An antagonist selective for Group II mGluR receptors also failed to exhibit an effect in the rat model. Given these results, selective mGlu5 antagonists can be an effective means to treat lower urinary tract disorders.

Accordingly, the present inventors have unexpectedly found that administration of negative allosteric modulators of the glutamate mGlu5 receptor, hereinafter "mGlu5 antagonists," provide a potent inhibition of the micturition reflex. These modulators are thus useful for treatment of lower urinary tract disorders and symptoms thereof as described in, e.g., International Patent Application WO 04/067002 (Recordati), which is incorporated by reference herein, in its entirety.

Without wishing to be bound to any particular mechanism or theory, the novel compounds of the invention act in the CNS by negatively modulating the excitatory signaling to the bladder giving as a final result an increase of the bladder volume capacity.

Novel Compounds of the Invention

The present invention is related to the novel compounds of formulas A, I, II and III as disclosed above. The invention includes the enantiomers, diastereomers, N-oxides (e.g., piperidine N-oxides), crystalline forms, hydrates, solvates or pharmaceutically acceptable salts of these compounds, as well as active metabolites of these compounds having the a similar type of activity. The novel compounds of the invention are selective mGlu5 antagonists useful in the treatment of lower urinary tract disorders and for the alleviation of the symptoms associated therewith.

Except where stated otherwise, the following definitions apply throughout the present specification and claims. These definitions apply regardless of the whether a term is used by itself or in combination with other terms. Hence the definition of "alkyl" applies to "alkyl" as well as to the "alkyl" portions of "alkoxy", "alkylamino" etc. Furthermore, all ranges described for chemical group, for example, the ranges "from 1 to 20 carbon atoms" and "$C_1$-$C_6$ alkyl" include all combinations and subcombinations of ranges and specific numbers of carbon atoms therein.

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain, which may be straight or branched. Branched means that one or more lower alkyl groups such as methyl, ethyl or propyl are attached to a linear alkyl chain. "Lower alkyl" means an alkyl group having about 1 to about 6 carbon atoms in the chain which may be straight or branched. The term "optionally substituted alkyl" means that the alkyl group may be substituted by one or more substituents preferably 1-6 substituents, which may be the same or different, each substituent being independently selected from the groups as defined below. Non-limiting examples of suitable alkyl groups include methyl, ethyl, n-propyl, isopropyl, sec-butyl, n-butyl, and t-butyl.

"Alkenyl" means an aliphatic hydrocarbon group comprising at least one carbon-carbon double bond and which may be straight or branched and comprising about 2 to about 15 carbon atoms in the chain. Preferred alkenyl groups have about 2 to about 12 carbon atoms in the chain. More preferably about 2 to about 6 carbon atoms in the chain. Branched means that one or more lower alkyl groups such as methyl, ethyl or propyl, are attached to a linear alkenyl chain. "Lower alkenyl" means an alkenyl group having 2 to about 6 carbon atoms in the chain, which may be straight or branched. The term "optionally substituted alkenyl" means that the alkenyl group may be substituted by one or more substituents, preferably 1-6 substituents, which may be the same or different, each substituents being independently selected from the groups as defined below. Non-limiting examples of suitable alkenyl groups include ethenyl, propenyl, isopropenyl, n-butenyl, 1-hexenyl and 3-methylbut-2-enyl.

"Alkynyl" means an aliphatic hydrocarbon group comprising at least one carbon-carbon triple bond and which may be straight or branched and comprising 2 to about 15 carbon atoms in the chain. Preferred alkynyl groups have 2 to about 12 carbon atoms in the chain. More preferably 2 to about 6 carbon atoms in the chain. Branched means that one or more lower alkyl groups such as methyl, ethyl or propyl, are attached to a linear alkynyl chain. "Lower alkynyl" means an alkynyl group having 2 to about 6 carbon atoms in the chain, which may be straight or branched. The term "optionally substituted alkynyl" means that the alkynyl group may be substituted by one or more substituents, preferably 1-6 substituents, which may be the same or different, each substituents being independently selected from the groups as defined below. Non-limiting examples of suitable alkynyl groups include ethynyl, propynyl and 2-butynyl.

"Mono, bi, or tricyclic aryl" means an aromatic monocyclic, bi, or tricyclic ring system comprising 6 to 14 carbon atoms. Bi- and tricyclic aryl groups are fused at 2 or 4 points and/or joined at one or two points via a bond and/or a heteroatom linker (O, S, NH, or N($C_1$-$C_6$ alkyl)) (e.g., biphenyl, 1-phenylnapthyl). The aryl group can be optionally substituted on the ring with one or more substituents, preferably 1 to 6 substituents, which may be the same or different each substituents being independently selected from the groups as defined below. Non-limiting examples of suitable aryl groups include phenyl and naphthyl. The "mono, bi, or tricyclic aryl" group can also be substituted by linking two adjacent carbons on its aromatic ring via a combination of 1 to 4 carbon atoms and 1 to 3 oxygen atoms such as, for example, methylenedioxy, ethylenedioxy, and the like. Also included within the scope of the term "aryl" as it is used herein is a group in which the aryl ring is fused at two points directly or joined at one point via a bond or a heteroatom linker (O, S, NH, or N($C_1$-$C_6$ alkyl)) to one or two non aromatic carbacyclic or heterocyclic, or heteroaromatic rings. Non limiting examples include indenyl, 1-phenyl-1H-imidazole, 5-phenylisoxazole, 4-phenyl-1,2,3 thiadiazole, 2-phenylpyrimidine, quinoline, 3,4-dihydro-2H-benzo[b][1,4]oxazine, benzo[d]thiazol-2(3H)-one, 1-phenylpyrrolidin-2-one, 1-phenylazetidin-2-one and the like.

"Mono, bi, or tricyclic heteroaromatic" means an aromatic mono-, bi, or tricyclic ring system having 1 to 14 ring carbon atoms, containing 1-5 ring atoms chosen from N, NH, N—(CO)—$C_{1-6}$ alkyl, N$C_{1-6}$-alkyl, O, S, $SO_2$ alone or in combination. Bi- and tricyclic aryl groups are fused at 2 or 4 points or joined at one or two points via a bond and/or a heteroatom linker (O, S, NH, or N($C_1$-$C_6$ alkyl). The "mono, bi, or tricyclic heteroaromatic" can be optionally substituted on the ring by replacing an available hydrogen on the ring by one or more substituents which may be the same or different, each being independently selected from the groups defined below. A nitrogen atom of the mono or bicyclic heteroaromatic can be optionally oxidized to the corresponding N-oxide. Non-limiting examples of suitable heteroaromatics include furanyl, imidazolyl, isoxazolyl, oxadiazolyl, oxazolyl, pyrrolyl, pyridyl, pyrimidyl, pyridazinyl, thiazolyl, triazolyl, tetrazolyl, thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, or benzoisoxazolyl. Also included within the scope of the term "heteroaromatic", as it is used herein, is a group in which a heteroatomic ring is fused at two points or joined at one point via a bond or a heteroatom linker (O, S, NH, or N($C_1$-$C_6$ alkyl), to one nonaromatic, aromatic or heterocyclic rings where the radical or point of attachment is on the heteroaromatic ring. Non-limiting examples include tetrahydroquinolinyl, tetrahydroisoquinolinyl, 3-phenylpyridine, 3-cyclohexylpyridine, 3-(pyridin-3-yl)morpholine, 3-phenylisoxazole, 2-(piperidin-1-yl)pyrimidine and the like.

"Mono, bi, or tricyclic heterocyclic" means a non-aromatic saturated mono, bi, or tricyclic ring system having 2 to 14 ring carbon atoms, containing 1-5 ring atoms chosen from NH, N—(CO)—$C_{1-6}$ alkyl, N$C_{1-6}$-alkyl, O, $SO_2$ and S, alone or in combination. Bi- and tricyclic heterocyclic groups are fused at 2 or 4 points or joined at one point via a bond or a heteroatom linker (O, S, NH, or N($C_1$-$C_6$ alkyl)) The "mono, bi, or tricyclic heterocyclic" can be optionally substituted on the ring by replacing an available hydrogen on the ring by one or more substituents which may be the same or different, each being independently selected from the groups defined below. There are no adjacent oxygen and or sulfur atoms present in the ring system. The nitrogen or sulfur atom of the heterocyclic can be optionally oxidized to the corresponding N-oxide, S-oxide or S-dioxide. Non-limiting examples of suitable heterocyclic rings include aziridinyl, piperidinyl, pyrrolidinyl, piperazinyl, tetrahydropyranyl, tetrahydrofuranyl, tetrahydrothiophenyl, morpholinyl, thiomorpholinyl and the like. Also included with in the scope of the term "heterocyclic" as it is used herein is a group in which the heterocyclic ring is fused at two points or joined at one point via a bond or a heteroatom linker (O, S, NH, or N($C_1$-$C_6$ alkyl), to one aromatic, or cycloalkyl ring, non limiting examples include isoindoline-1,3-dione 1-methyl-2-phenyl-1H-pyrazole-3 (2H)-one, indoline and the like.

"Mono or bicyclic cycloalkyl" means a non-aromatic mono or bicyclic ring system comprising 3 to 14 carbon atoms, preferably 3-6 carbon atoms. The cycloalkyl group may optionally contain one or two double bonds within the ring (e.g., cyclohexenyl, cyclohexadiene). The cycloalkyl can be optionally substituted on the ring by replacing an available hydrogen on the ring by one or more substituents which may be the same or different, each being independently selected from the groups as defined below. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Alkoxyl" means an alkyl-O— group in which the alkyl group is as previously described. Non-limiting examples of suitable alkoxy groups include methoxy, ethoxy, n-propoxy and isopoxy. The alkyl group is linked to an adjacent moiety through the ether oxygen.

"Halogen" or "Hal" means fluorine, chlorine, bromine or iodine. Preferred are fluorine, chlorine or bromine, and more preferred are fluorine and chlorine.

"Haloalkyl" means an alkyl as defined above wherein one or more hydrogen atoms on the alkyl is replaced by a halo group defined above.

"Oxo" means a =O moiety.

The term "alkanoyl" refers to radicals having a carbonyl radical as defined below, attached to an alkyl radical. Preferred alkanoyl radicals are "lower alkanoyl" radicals having 1-6 carbon atoms. The alkanoyl radicals may be substituted or unsubstituted, such as formyl, acetyl, propionyl (propanoyl), butanoyl (butyryl), isobutanoyl (isobutyryl), valeryl (pentanoyl), isovaleryl, pivaloyl, hexanoyl or the like.

The term "carbonyl", whether used alone or with other terms, such as "alkylcarbonyl", denotes —(C=O)—. The term "alkylcarbonyl" refers to radicals having a carbonyl radical substituted with an alkyl radical. More preferred alkylcarbonyl radicals are "lower alkylcarbonyl" radicals having one to six carbon atoms. Examples of such radicals include methylcarbonyl and ethylcarbonyl. The terms "alkanoyl" and "alkylcarbonyl" are synonymous.

The term "alkanoyloxy" refers to an "alkanoyl" radical as defined above linked to an oxygen radical, to generate an ester group.

The term "aminocarbonyl" when used by itself or with other terms such as "aminocarbonylalkyl", "N-alkylaminocarbonyl", "N,N-dialkylaminocarbonyl", "N-alkyl-N-arylaminocarbonyl", "N-alkyl-N-hydroxyaminocarbonyl" and "N-alkyl-N-hydroxyaminocarbonylalkyl", denotes an amide group of the formula —C(=O)$NH_2$. The terms "N-alkylaminocarbonyl" and "N,N-dialkylaminocarbonyl" denote aminocarbonyl radicals in which the amino groups have been substituted with one alkyl radical and two alkyl radicals, respectively. Preferred are "lower alkylaminocarbonyl" having lower alkyl radicals as described above attached to an aminocarbonyl radical The term "alkylthio" refers to radicals containing a linear or branched alkyl radical, of one to ten carbon atoms, attached to a divalent sulfur atom. An example of "alkylthio" is methylthio, ($CH_3$—S—).

The term "amino" refers to the radical —$NH_2$.

The terms "N-alkylamino" and "N,N-dialkylamino" denote amino groups which have been substituted with one alkyl radical and with two alkyl radicals, respectively. More preferred alkylamino radicals are "lower alkylamino" radicals having one or two alkyl radicals of one to six carbon atoms, attached to the nitrogen atom. Examples of "alkylamino" include N-methylamino, N-ethylamino, N,N-dimethylamino, N,N-diethylamino or the like.

The term "acyl", whether used alone, or within a term such as "acylamino", denotes a radical provided by the residue after removal of hydroxyl from an organic acid. The term "acylamino" refers an amino radical substituted with an acyl group. An examples of an "acylamino" radical is acetylamino or acetamido ($CH_3$C(=O)—NH—) where the amine may be further substituted with alkyl, aryl or aralkyl.

The term "aryloxy" refers to the radical —O-aryl. Examples of such radicals include phenoxy.

The term "cyano" refers to the radical —C≡N.

The term "nitro" refers to the radical —$NO_2$.

The term "heterocycloalkyl" refers to the radical-Alkyl-Heterocycle.

The term "hydroxy" refers to the radical —OH.

The term "optionally substituted" means optional substitution on a specified moiety with one or more, preferably 1-8 groups, radicals or moieties which have a molecular mass of less than 300 (preferably less than 200; and more preferably, less than 150); independently selected for each position capable of substitution on the specified moiety.

A combination of substituents or variables is permissible only if such a combination results in a stable or chemically feasible compound. A stable compound or chemically feasible compound is one in which the chemical structure is not substantially altered when kept a temperature of about 50° C. or less, in the absence of moisture or other chemically reactive conditions, for at least 7 days.

Preferred optional substitutents for the compounds according to formulas A, I, II, or III are where said optional substituent is chosen from the group consisting of $C_1$-$C_6$ alkyl, $C_2$-$C_6$ alkenyl, $C_2$-$C_6$ alkynyl and $C_3$-$C_9$ mono or bicycloalkyl which can be optionally interrupted by 1-3 heteroatoms chosen from the group consisting of NR*, S, $SO_2$, and O wherein R* is chosen from the group consisting of H, —C(O)$C_1$-$C_6$ alkyl, benzyl, phenyl and $C_1$-$C_6$ alkyl; and can be further substituted with 1-8 substituents chosen from the group consisting of oxo, halogen, cyano, nitro, hydroxy, phenyl and —$NH_2$ with the proviso that oxo groups are not adjacent to one another.

Further preferred optional substitutents for the compounds according to formulas A, I, II, or III are where said optional substituent is chosen from the group consisting of oxo, nitro, halogen, cyano, hydroxy, —$SO_2$($C_1$-$C_6$ alkyl), —O($C_1$-$C_6$ alkyl), —NRR wherein R** is independently chosen for each occurrence from the group consisting of H, —C(O)$C_1$-$C_6$ alkyl, benzyl, phenyl and $C_1$-$C_6$ alkyl.

Further preferred optional substitutents for the compounds according to formulas A, I, II, or III is chosen from the group consisting of —O—($C_1$-$C_8$ heteroaromatic), —O—($C_2$-$C_9$ heterocyclic), —C(O)—($C_1$-$C_8$ heteroaromatic), —C(O)—($C_2$-$C_9$ heterocyclic)-$(CH_2)_q$—($C_1$-$C_8$ heteroaromatic), —$(CH_2)_q$—($C_2$-$C_9$ heterocyclic), —NR*-($C_1$-$C_8$ heteroaromatic)-NR*-($C_2$-$C_8$ heterocyclic); —O-(phenyl), —C(O)-(phenyl), —C(O)NR*—($C_1$-$C_8$ heteroaromatic), —C(O)NR*—($C_2$-$C_9$ heterocyclic), —C(O)NR*-(phenyl), —$(CH_2)_q$-(phenyl), —NR*-(phenyl), —NR*C(O)-(phenyl), —NR*C(O)—($C_1$-$C_8$ heteroaromatic), —NR*C(O)—($C_2$-$C_8$ heterocyclic); —OC(O)-(phenyl), —OC(O)—($C_1$-$C_8$ heteroaromatic), and —OC(O)—($C_2$-$C_8$ heterocyclic) wherein said heteroaromatic and heterocyclic rings contain from 1 to 3 heteroatoms chosen from the group consisting of —N—, —N($C_1$-$C_6$ alkyl), O, S, and $SO_2$; and said phenyl, heterocyclic and heteroaromatic rings can be further substituted with 1 to 3 groups selected from halogen, hydroxy, cyano, nitro, and $C_1$-$C_6$ alkyl; R* is chosen independently for each occurrence from the group consisting of H and $C_1$-$C_6$ alkyl; and q is 0-6.

Preferred compounds according to formula A are where Z is formulas II or iii, $R_2$ is optionally substituted phenyl, $R_3$ is optionally substituted mono, bi, or tricyclic $C_1$-$C_{14}$ heteroaromatic group containing 1 to 3 heteroatoms chosen from the group consisting of N, $NR_9$, S, $SO_2$, and O wherein $R_9$ is chosen from the group consisting of H, —C(O)$C_1$-$C_6$ alkyl, benzyl, phenyl and $C_1$-$C_6$ alkyl; m, n are 1; X' is O, or $CH_2$ Y is absent and p and o is 0.

Preferred compounds according to formula A are where $R_3$ is

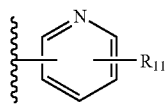

wherein $R_{11}$ is independently chosen for each position capable of substitution from the group consisting of H, halogen, $CF_3$, trifluoromethoxy, —C(O)—($C_{1-6}$ alkyl), —NH ($C_{1-6}$ alkyl), —N(di $C_{1-6}$ alkyl), nitro, cyano, hydroxy, $C_{1-6}$ alkyl, and $C_{1-6}$ alkoxy.

Further preferred compounds according to formulas I, II, or III are where $R_1$ is hydrogen.

Further preferred compounds according to formulas I, II, or III are where $R_4$ is hydrogen.

Further preferred compounds according to formulas I, II, or III are where m is 1 and n is 0 or 1.

Further preferred compounds according to formulas I, or II, are where X is O and Y is NH or —N($C_1$-$C_6$ alkyl)-.

Further preferred compounds according to formulas I, or II, are where X is S and Y is NH or —N($C_1$-$C_6$ alkyl).

Further preferred compounds according to formulas I, or II, are where X is O and Y is O.

Further preferred compounds according to formulas I, or II, are where X is O and Y is absent.

Further preferred compounds according to formulas I or III are where o is 0 and Y is $SO_2$.

Further preferred compounds according to formulas I, II, or III are where $R_2$ is chosen from the group consisting of

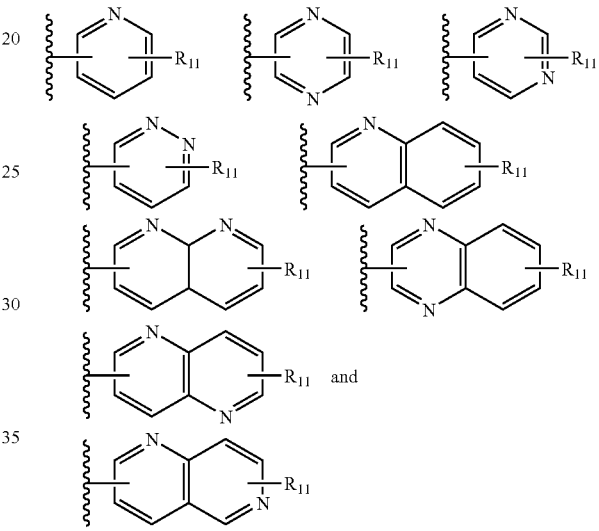

wherein $R_{11}$ is independently chosen for each position capable of substitution from the group consisting of H, halogen, $CF_3$, trifluoromethoxy, —C(O)—($C_{1-6}$ alkyl), —NH ($C_{1-6}$ alkyl), —N(di-$C_{1-6}$ alkyl), nitro, cyano, hydroxy, $C_{1-6}$ alkyl, and $C_{1-6}$ alkoxy.

Further preferred compounds according to formulas I, II, or III are where $R_2$ is

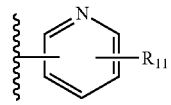

wherein
$R_{11}$ is as defined above.

Further preferred compounds according to formulas I, II, or III are where $R_2$ is

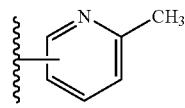

Further preferred compounds according to formulas I, II, or III are where $R_2$ is

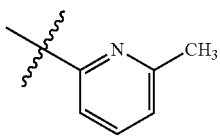 [SMILES: *c1cccc(C)n1]

Further preferred compounds according to formulas I, II, or III are where $R_2$ is

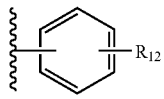

wherein $R_{12}$ is independently chosen for each position capable of substitution from the group consisting of H, halogen, $CF_3$, trifluoromethoxy, —C(O)—($C_{1-6}$ alkyl), —NH ($C_{1-6}$ alkyl), —N(di $C_{1-6}$ alkyl), nitro, cyano, hydroxy, $C_{1-6}$ alkyl, and $C_{1-6}$ alkoxy Further preferred compounds according to formulas I, II, or III are where $R_2$ is

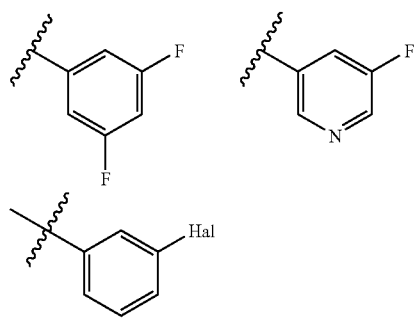

Further preferred compounds according to formulas I, II, or III are where $R_3$ is chosen from the group consisting of

wherein $R_{13}$ is independently selected for each position capable of substitution from the group consisting of H, halogen, $CF_3$, trifluoromethoxy, —C(O)—($C_{1-6}$ alkyl), —NH ($C_{1-6}$ alkyl), —N(di $C_{1-6}$ alkyl), nitro, cyano, hydroxy, $C_{1-6}$ alkyl, and $C_{1-6}$ alkoxy.

Further preferred compounds according to formulas I, II, or III are where $R_3$ is chosen from

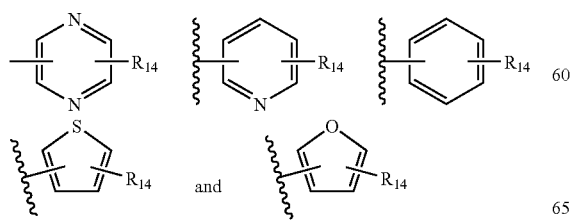

wherein $R_{14}$ is independently selected for each position capable of substitution from the group consisting of H, halogen, $CF_3$, trifluoromethoxy, —C(O)—($C_{1-6}$ alkyl), —NH ($C_{1-6}$ alkyl), —N(di $C_{1-6}$ alkyl), nitro, cyano, hydroxy, $C_{1-6}$ alkyl, and $C_{1-6}$ alkoxy.

Further preferred compounds according to formulas I, II, and III are where $R_3$ is selected from the group consisting of:

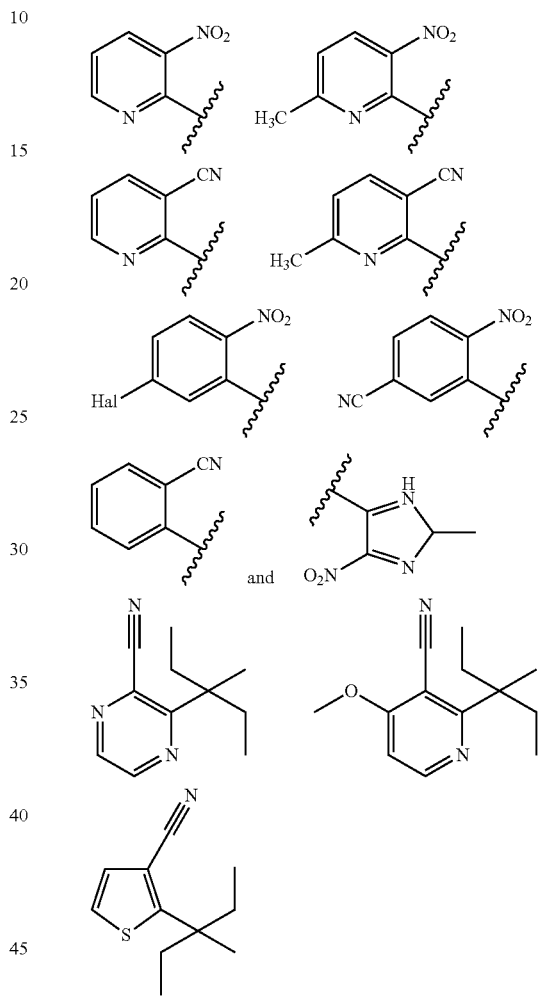

Further preferred are compounds of formulas IV and V

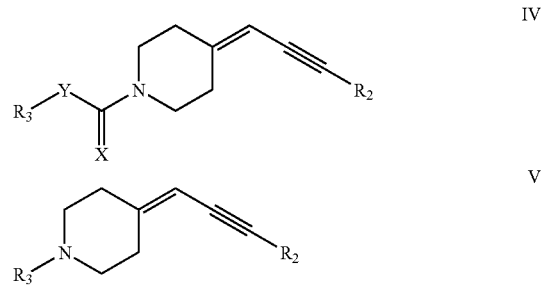

wherein R2, R3, X, and Y are as defined for Formula A above, and enantiomers, diastereomers and N-oxides thereof, and pharmaceutically acceptable salts thereof.

Further preferred are compounds selected from the group consisting of

2-{4-[3-(6-Methylpyridin-2-yl)prop-2-ynylidene]piperidin-1-yl}-3-nitropyridine
tert-Butyl 4-[3-(6-methylpyridin-2-yl)prop-2-ynylidene]piperidine-1-carboxylate
2-Methyl-6-(3-piperidin-4-ylideneprop-1-ynyl)pyridine
2-Methyl-6-{3-[1-(2-nitrophenyl)piperidin-4-ylidene]prop-1-ynyl}pyridine
6-Methyl-2-{4-[3-(6-methylpyridin-2-yl)prop-2-ynylidene]piperidin-1-yl}-3-nitropyridine
6-Methoxy-2-{4-[3-(6-methylpyridin-2-yl)prop-2-ynylidene]piperidin-1-yl}-3-nitropyridine
2-Methyl-6-{3-[1-(5-methyl-2-nitrophenyl)piperidin-4-ylidene]prop-1-ynyl}pyridine
2-{3-[1-(5-Methoxy-2-nitrophenyl)piperidin-4-ylidene]prop-1-ynyl}-6-methylpyridine
3-Nitro-2-[4-(3-pyridin-2-ylprop-2-ynylidene)piperidin-1-yl]pyridine
3-Nitro-2-[4-(3-phenylprop-2-ynylidene)piperidin-1-yl]pyridine
3-Nitro-2-[4-(3-pyridin-3-ylprop-2-ynylidene)piperidin-1-yl]pyridine
4-[3-(6-Methylpyridin-2-yl)prop-2-ynylidene]-N-phenylpiperidine-1-carboxamide
4-({4-[3-(6-Methylpyridin-2-yl)prop-2-ynylidene]piperidin-1-yl}carbonyl)morpholine
2-[3-(1-Benzoylpiperidin-4-ylidene)prop-1-ynyl]-6-methylpyridine
N-Butyl-4-[3-(6-methylpyridin-2-yl)prop-2-ynylidene]piperidine-1-carbothioamide
N-Ethyl-4-[3-(6-methylpyridin-2-yl)prop-2-ynylidene]piperidine-1-carbothioamide
N-(tert-Butyl)-4-[3-(6-methylpyridin-2-yl)prop-2-ynylidene]piperidine-1-carboxamide
4-[3-(6-Methylpyridin-2-yl)prop-2-ynylidene]-N-(3-nitrophenyl)piperidine-1-carboxamide
2-Methyl-6-{3-[1-(3-nitrobenzoyl)piperidin-4-ylidene]prop-1-ynyl}pyridine
Ethyl 4-[3-(6-methylpyridin-2-yl)prop-2-ynylidene]piperidine-1-carboxylate
N-Cyclohexyl-4-[3-(6-methylpyridin-2-yl)prop-2-ynylidene]piperidine-1-carbothioamide
4-[3-(6-Methylpyridin-2-yl)prop-2-ynylidene]-N-phenylpiperidine-1-carbothioamide
4-[3-(6-Methylpyridin-2-yl)prop-2-ynylidene]-N-(1-phenylethyl)piperidine-1-carboxamide
2-[3-(1-Butyrylpiperidin-4-ylidene)prop-1-ynyl]-6-methylpyridine
N-Butyl-4-[3-(6-methylpyridin-2-yl)prop-2-ynylidene]piperidine-1-carboxamide
N-Ethyl-4-[3-(6-methylpyridin-2-yl)prop-2-ynylidene]piperidine-1-carboxamide
2-[3-(1-Benzylpiperidin-4-ylidene)prop-1-ynyl]-6-methylpyridine
2-[3-(1-Butylpiperidin-4-ylidene)prop-1-ynyl]-6-methylpyridine tert-Butyl 4-[3-(6-methylpyridin-2-yl)-1-phenylprop-2-ynylidene]piperidine-1-carboxylate
tert-Butyl 4-[3-(6-methylpyridin-2-yl)prop-2-ynyl]piperidine-1-carboxylate
2-{4-[3-(6-Methylpyridin-2-yl)prop-2-ynyl]piperidin-1-yl}-3-nitropyridine
3-Nitro-2-[4-(3-pyridin-4-ylprop-2-ynylidene)piperidin-1-yl]pyridine
3-{3-[1-(3-Nitropyridin-2-yl)piperidin-4-ylidene]prop-1-ynyl}quinoline
4-{5-[3-[1-(3-Nitropyridin-2-yl)piperidin-4-ylidene]prop-1-ynyl]pyridin-2-yl}morpholine
2-{4-[3-(6-Fluoropyridin-3-yl)prop-2-ynylidene]piperidin-1-yl}-3-nitropyridine
1-(6-{3-[1-(3-Nitropyridin-2-yl)piperidin-4-ylidene]prop-1-ynyl}pyridin-2-yl)ethanone
2-{4-[3-(6-Isopropoxypyridin-3-yl)prop-2-ynylidene]piperidin-1-yl}-3-nitropyridine
2-{4-[3-(3-Methoxypyridin-2-yl)prop-2-ynylidene]piperidin-1-yl}-3-nitropyridine
tert-Butyl 4-[1-hydroxy-3-(6-methylpyridin-2-yl)prop-2-ynyl]piperidine-1-carboxylate
tert-Butyl 4-[1-(dimethylamino)-3-(6-methylpyridin-2-yl)prop-2-ynyl]piperidine-1-carboxylate
tert-Butyl 4-[3-(6-methylpyridyn-2-yl)-1-piperidin-1-yl-prop-2-ynyl)piperidine-1-carboxylate
2-Methyl-6-[3-(1-phenylpiperidin-4-ylidene)prop-1-ynyl]pyridine
2-{4-[3-(6-Methylpyridin-2-yl)prop-2-ynylidene]piperidin-1-yl}benzonitrile
2-{3-[1-(4-Methoxy-2-nitrophenyl)piperidin-4-ylidene]prop-1-ynyl}-6-methylpyridine
tert-Butyl 4-[3-(5-cyanopyridin-3-yl)prop-2-ynylidene]piperidine-1-carboxylate
tert-Butyl 4-[3-(6-cyanopyridin-3-yl)prop-2-ynylidene]piperidine-1-carboxylate
5-{3-[1-(3-Nitropyridin-2-yl)piperidin-4-ylidene]prop-1-ynyl}nicotinonitrile
5-{3-[1-(3-Nitropyridin-2-yl)piperidin-4-ylidene]prop-1-ynyl}pyridine-2-carbonitrile
tert-Butyl 4-[3-(2-methyl-1,3-thiazol-4-yl)prop-2-ynylidene]piperidine-1-carboxylate
4-[3-(2-Methyl-1,3-thiazol-4-yl)prop-2-ynylidene]piperidine
2-{4-[3-(2-Methyl-1,3-thiazol-4-yl)prop-2-ynylidene]piperidin-1-yl}-3-nitropyridine
2,6-Difluoro-4-{4-[3-(6-methylpyridin-2-yl)prop-2-ynylidene]piperidin-1-yl}benzonitrile
4-Methoxy-3-{4-[3-(6-methylpyridin-2-yl)prop-2-ynylidene]piperidin-1-yl}benzonitrile
4-Bromo-2-fluoro-6-{4-[3-(6-methylpyridin-2-yl)prop-2-ynylidene]piperidin-1-yl}benzonitrile
2-{3-[1-(4-Fluoro-2-nitrophenyl)piperidin-4-ylidene]prop-1-ynyl}-6-methylpyridine
4-{4-[3-(6-Methylpyridin-2-yl)prop-2-ynylidene]piperidin-1-yl}-3-nitrobenzonitrile
2-(2,5-Dimethyl-1H-pyrrol-1-yl)-5-[4-[3-(6-methylpyridin-2-yl)prop-2-yn-1-ylidene]piperidin-1-yl]pyrimidine
6-{4-[3-(6-Methylpyridin-2-yl)prop-2-yn-1-ylidene]piperidin-1-yl}quinoxaline
2-Methyl-6-[3-(1-pyridin-2-ylpiperidin-4-ylidene)prop-1-yn-1-yl]pyridine
6-{4-[3-(6-Methylpyridin-2-yl)prop-2-yn-1-ylidene]piperidin-1-yl}pyridine-2-carbonitrile
(4-{4-[3-(6-Methylpyridin-2-yl)prop-2-ynylidene]piperidin-1-yl}-3-nitrophenyl)methanol
2-{4-[3-(6-Methylpyridin-2-yl)prop-2-yn-1-ylidene]piperidin-1-yl}-3-(trifluoromethyl)pyridine
2-Methyl-6-(3-{1-[6-(trifluoromethyl)pyridin-2-yl]piperidin-4-ylidene}prop-1-yn-1-yl)pyridine
2-{4-[3-(6-Methylpyridin-2-yl)prop-2-yn-1-ylidene]piperidin-1-yl}-5-(trifluoromethyl)pyridine
2-{4-[3-(6-Methylpyridin-2-yl)prop-2-ynylidene]piperidin-1-yl}nicotinonitrile
tert-Butyl 4-(1-Fluoro-3-phenylprop-2-ynylidene)piperidine-1-carboxylate 2-[4-(1-Fluoro-3-phenylprop-2-yn-1-ylidene)piperidin-1-yl]-3-nitropyridine
2-Methoxyethyl 4-[3-(6-methylpyridin-2-yl)prop-2-ynylidene]piperidine-1-carboxylate
2-Cyanoethyl 4-[3-(6-methylpyridin-2-yl)prop-2-ynylidene]piperidine-1-carboxylate
Benzyl 4-[3-(6-methylpyridin-2-yl)prop-2-ynylidene]piperidine-1-carboxylate
2-Fluoro-4-nitrophenyl 4-[3-(6-methylpyridin-2-yl)prop-2-ynylidene]piperidine-1-carboxylate
Thiophen-2-ylmethyl 4-[3-(6-methylpyridin-2-yl)prop-2-ynylidene]piperidine-1-carboxylate
Pyridin-2-yl 4-[3-(6-methylpyridin-2-yl)prop-2-ynylidene]piperidine-1-carboxylate
1-Methylpiperidin-4-yl 4-[3-(6-methylpyridin-2-yl)prop-2-ynylidene]piperidine-1-carboxylate
2-(1H-Indol-3-yl)ethyl 4-[3-(6-methylpyridin-2-yl)prop-2-ynylidene]piperidine-1-carboxylate
2,2,2-Trifluoro-1-trifluoromethylethyl 4-[3-(6-methylpyridin-2-yl)prop-2-ynylidene]piperidine-1-carboxylate
2,3,4-Trifluorophenyl 4-[3-(6-methylpyridin-2-yl)prop-2-ynylidene]piperidine-1-carboxylate
Cyclohexyl 4-[3-(6-methylpyridin-2-yl)prop-2-ynylidene]piperidine-1-carboxylate
Cyclobutylmethyl 4-[3-(6-methylpyridin-2-yl)-prop-2-ynylidene]piperidine-1-carboxylate
5-Bromopyridin-2-yl 4-[3-(6-methylpyridin-2-yl)prop-2-ynylidene]piperidine-1-carboxylate
3-Benzyloxypropyl 4-[3-(6-methylpyridin-2-yl)prop-2-ynylidene]piperidine-1-carboxylate
4,6-Dimethylpyrimidin-2-yl 4-[3-(6-methylpyridin-2-yl)prop-2-ynylidene]piperidine-1-carboxylate
N-Methyl-4-[3-(6-methylpyridin-2-yl)prop-2-ynylidene]-N-phenylpiperidine-1-carboxamide
N-Diethyl-4-[3-(6-methylpyridin-2-yl)prop-2-ynylidene]piperidine-1-carboxamide
N-Dimethyl-4-[3-(6-methylpyridin-2-yl)prop-2-ynylidene]piperidine-1-carboxamide
N-Methyl-4-[3-(6-methylpyridin-2-yl)prop-2-ynylidene]-N-(3-nitrophenyl)piperidine-1-carboxamide
N-Butyl-N-methyl-4-{3-(6-methylpyridin-2-yl)prop-2-ynylidene]piperidine-1-carboxamide
N-tert-Butyl-N-methyl-4-[3-(6-methylpyridin-2-yl)prop-2-ynylidene]piperidine-1-carboxamide
N-Ethyl-N-methyl-4-[3-(6-methylpyridin-2-yl)prop-2-ynylidene]piperidine-1-carboxamide
N-(1-Phenylethyl)-N-methyl-4-[3-(6-methylpyridin-2-yl)prop-2-ynylidene]piperidine-1-carboxamide
N-Ethyl-N-(1-methylethyl)-4-[3-(6-methylpyridin-2-yl)prop-2-ynylidene]piperidine-1-carboxamide
2-Methyl-6-{3-[1-(toluene-4-sulfonyl)piperidin-4-ylidene]prop-1-ynyl}pyridine
2-Methyl-6-{3-[1-(2-nitrobenzenesulfonyl)piperidin-4-ylidene]prop-1-ynyl}pyridine
2-[3-(1-Benzenesulfonylpiperidin-4-ylidene)prop-1-ynyl]-6-methylpyridine
1-(4-Methyl-3-{4-[3-(6-methylpyridin-2-yl)prop-2-ynylidene]piperidine-1-sulfonyl}phenyl)pyrrolidin-2-one
2-{3-[1-(4-Methoxybenzenesulfonyl)piperidin-4-ylidene]prop-1-ynyl}-6-methylpyridine
2-{3-[1-(4-Bromo-2,5-difluorobenzenesulfonyl)piperidin-4-ylidene]prop-1-ynyl}-6-methylpyridine
2-Methyl-6-[3-(1-phenylmethanesulfonylpiperidin-4-ylidene)prop-1-ynyl]pyridine
2-[3-(1-Ethanesulfonylpiperidin-4-ylidene)prop-1-ynyl]-6-methylpyridine 3-Chloro-4-{4-[3-(6-methylpyridin-2-yl)prop-2-ynylidene]piperidine-1-sulfonyl}benzonitrile
2-{3-[1-(3-Fluorophenylmethanesulfonyl)piperidin-4-ylidene]prop-1-ynyl}-6-methylpyridine
2-[3-(1-Cyclohexylmethanesulfonylpiperidin-4-ylidene)prop-1-ynyl]-6-methylpyridine
2-Methyl-6-{3-[1-(4-methyl-3-nitrobenzenesulfonyl)piperidin-4-ylidene]prop-1-ynyl}pyridine
2-Methyl-6-{3-[1-(2,2,2-trifluoroethanesulfonyl)piperidin-4-ylidene]prop-1-ynyl}pyridine
2-{3-[1-(4-Isopropylbenzenesulfonyl)piperidin-4-ylidene]prop-1-ynyl}-6-methyl-pyridine
4-{4-[3-(6-Methylpyridin-2-yl)prop-2-ynylidene]piperidine-1-sulfonyl}benzonitrile
2-{3-[1-(5-Chloro-2-methoxy-4-methylbenzenesulfonyl)piperidin-4-ylidene]prop-1-ynyl}-6-methylpyridine
(1S,4R)-7,7-Dimethyl-1-{4-[3-(6-methylpyridin-2-yl)prop-2-ynylidene]piperidine-1-sulfonylmethyl}bicyclo[2.2.1]heptan-2-one
2-(3-{1-[3-(4-Methoxyphenoxy)propane-1-sulfonyl]piperidin-4-ylidene}prop-1-ynyl)-6-methylpyridine
2-{3-[1-(3-Bromobenzenesulfonyl)piperidin-4-ylidene]prop-1-ynyl}-6-methylpyridine
2-{3-[1-(4-Bromo-2-fluorobenzenesulfonyl)piperidin-4-ylidene]prop-1-ynyl}-6-methylpyridine
6-Chloro-5-{4-[3-(6-methylpyridin-2-yl)prop-2-ynylidene]piperidine-1-sulfonyl}imidazo[2,1-b]thiazole
2-{3-[1-(1,2-Dimethyl-1H-imidazole-4-sulfonyl)piperidin-4-ylidene]prop-1-ynyl}-6-methylpyridine
2-Methyl-6-{3-[1-(4-[1,2,3]thiadiazol-4-ylbenzenesulfonyl)piperidin-4-ylidene]prop-1-ynyl}pyridine
2-{3-[1-(5-tert-Butyl-2-methoxybenzenesulfonyl)piperidin-4-ylidene]prop-1-ynyl}-6-methylpyridine
2-Methyl-6-{3-[1-(2-nitrobenzoyl)piperidin-4-ylidene]prop-1-ynyl}pyridine
2-({4-[3-(6-Methylpyridin-2-yl)prop-2-ynylidene]piperidin-1-yl}carbonyl)pyrazine
2-{3-[1-(3-Bromobenzoyl)piperidin-4-ylidene]prop-1-ynyl}-6-methylpyridine
4-Oxo-4-[4-[3-(6-methylpyridin-2-yl)prop-2-ynylidene)piperidin-1-yl]-1-phenylbutan-1-one
2-{3-[1-(3,4,5-Trimethoxybenzoyl)piperidin-4-ylidene]prop-1-ynyl}-6-methylpyridine
2-Methyl-6-{3-[1-(4-nitrobenzoyl)piperidin-4-ylidene]prop-1-ynyl}pyridine
2-Methyl-6-{3-[1-(3-methyl-2-nitrobenzoyl)piperidin-4-ylidene]prop-1-ynyl}pyridine
2-[3-(1-Heptanoylpiperidin-4-ylidene)prop-1-ynyl]-6-methylpyridine
2-Methyl-6-{3-[1-(thien-2-ylcarbonyl)piperidin-4-ylidene]prop-1-ynyl}pyridine
2-Methyl-6-{3-[1-(4,4,4-trifluorobutanoyl)piperidin-4-ylidene]prop-1-ynyl}pyridine
2-{3-[4-[3-(6-Methylpyridin-2-yl)prop-2-ynylidene]piperidin-1-yl]carbonyl]phenoxy}pyrimidine
2-(3-{1-[(5-Bromopyridin-3-yl)acetyl]piperidin-4-ylidene}prop-1-ynyl)-6-methylpyridine
5-({4-[3-(6-Methylpyridin-2-yl)prop-2-ynylidene]piperidin-1-yl}carbonyl)quinoline
3-(4-Chlorophenyl)-5-{4-[3-(6-methylpyridin-2-yl)prop-2-ynylidene]piperidin-1-yl}-5-oxopentanamide
2-(3-{4-[3-(6-Methylpyridin-2-yl)prop-2-ynylidene]piperidin-1-yl}-3-oxopropyl)isoindole-1,3-dione
2-{3-[1-(3-Chloro-4,5-dimethoxybenzoyl)piperidin-4-ylidene]prop-1-ynyl}-6-methylpyridine
2-Methoxy-3-({4-[3-(6-methylpyridin-2-yl)prop-2-ynylidene]piperidin-1-yl}carbonyl)pyridine 2-(3-{1-[(5-Methyl-1-(4-fluorophenyl)-1H-1,2,4-triazol-3-yl)carbonyl]piperidin-4-ylidene}prop-1-ynyl)-6-methylpyridine
2-(3-{1-[(3-Bromophenoxy)acetyl]piperidin-4-ylidene}prop-1-ynyl)-6-methylpyridine
2-Methyl-6-(3-{1-[3-(5-methyl-1,2,4-oxadiazol-3-yl)benzoyl]piperidin-4-ylidene}prop-1-ynyl)pyridine
2-(2-{4-[3-(6-Methylpyridin-2-yl)prop-2-ynylidene]piperidin-1-yl}-2-oxoethyl)isoindole-1,3-dione
5-Fluoro-2-(2-{4-[3-(6-methylpyridin-2-yl)prop-2-ynylidene]piperidin-1-yl}-2-oxoethyl)-1H-indole
2-Chloro-6-methoxy-4-({4-[3-(6-methylpyridin-2-yl)prop-2-ynylidene]piperidin-1-yl}carbonyl)pyridine
1-Methyl-5-({4-[3-(6-methylpyridin-2-yl)prop-2-ynylidene]piperidin-1-yl}carbonyl)-1H-1,2,3-benzotriazole
2-Methyl-6-(3-{1-[(2-nitrophenoxy)acetyl]piperidin-4-ylidene}prop-1-ynyl)pyridine
2-{3-[1-(2,5-Dimethyl-3-furoyl)piperidin-4-ylidene]prop-1-ynyl}-6-methylpyridine
2-(3-{1-[(5-Chlorothien-2-yl)carbonyl]piperidin-4-ylidene}prop-1-ynyl)-6-methylpyridine
2-{3-[1-(3-Iodobenzoyl)piperidin-4-ylidene]prop-1-ynyl}-6-methylpyridine
2-(3-{1-[(3,5-Difluorophenyl)acetyl]piperidin-4-ylidene}prop-1-ynyl)-6-methylpyridine
2,6-Dimethoxy-3-({4-[3-(6-methylpyridin-2-yl)prop-2-ynylidene]piperidin-1-yl}carbonyl)pyridine
2-Chloro-6-methyl-4-({4-[3-(6-methylpyridin-2-yl)prop-2-ynylidene]piperidin-1-yl}carbonyl)pyridine
5-Methoxy-3-({4-[3-(6-methylpyridin-2-yl)prop-2-ynylidene]piperidin-1-yl}carbonyl)-1H-indole
2-{3-[1-(3,3-Dimethylbutanoyl)piperidin-4-ylidene]prop-1-ynyl}-6-methylpyridine
2-{3-[1-(Methoxyacetyl)piperidin-4-ylidene]prop-1-ynyl}-6-methylpyridine
2-{3-[1-(4-Methoxybenzoyl)piperidin-4-ylidene]prop-1-ynyl}-6-methylpyridine
2-{3-[1-(3-Methoxybenzoyl)piperidin-4-ylidene]prop-1-ynyl}-6-methylpyridine
2-{3-[1-(2-Methoxybenzoyl)piperidin-4-ylidene]prop-1-ynyl}-6-methylpyridine
2-Ethoxy-3-({4-[3-(6-methylpyridin-2-yl)prop-2-ynylidene]piperidin-1-yl}carbonyl)pyridine
2-Methyl-6-{3-[1-(1-(4-pyridyl)piperidin-4-ylcarbonyl)piperidin-4-ylidene]prop-1-ynyl}pyridine
6-({4-[3-(6-Methylpyridin-2-yl)prop-2-ynylidene]piperidin-1-yl}carbonyl)-2H-1,4-benzoxazin-3(4H)-one
2-{3-[1-[3-(3-Fluorophenoxy)propanoyl]piperidin-4-ylidene]prop-1-ynyl}-6-methylpyridine
2-(1-Piperidinyl)-5-({4-[3-(6-methylpyridin-2-yl)prop-2-ynylidene]piperidin-1-yl}carbonyl)pyrimidine
1-(3-Fluoro-4-methylphenyl)-4-({4-[3-(6-methylpyridin-2-yl)prop-2-ynylidene]piperidin-1-yl}carbonyl)pyrrolidin-2-one
3-Methyl-4-{[4-(6-methyl-3-pyridin-2-ylprop-2-ynylidene)piperidin-1-yl]carbonyl}phenylacetamide
2-{3-[1-(3-Chlorobenzoyl)piperidin-4-ylidene]prop-1-ynyl}-6-methylpyridine
2-[3-[1-(1,1'-biphenyl-3-ylcarbonyl)piperidin-4-ylidene]prop-1-ynyl]-6-methylpyridine
2-{3-[1-(2-Furoyl)piperidin-4-ylidene]prop-1-ynyl}-6-methylpyridine
2-Methyl-6-{3-[1-(phenylacetyl)piperidin-4-ylidene]prop-1-ynyl}pyridine
2-Methyl-6-{3-[1-(4-phenylbutanoyl)piperidin-4-ylidene]prop-1-ynyl}pyridine 2-{3-[1-(3-Fluorobenzoyl)piperidin-4-ylidene]prop-1-ynyl}-6-methylpyridine
2-{3-[1-(3-Methylbenzoyl)piperidin-4-ylidene]prop-1-ynyl}-6-methylpyridine
3-({4-[3-(6-Methylpyridin-2-yl)prop-2-ynylidene]piperidin-1-yl}carbonyl)benzonitrile
2-Methyl-6-{3-[1-(3-trifluoromethoxybenzoyl)piperidin-4-ylidene]prop-1-ynyl}pyridine
2-Methyl-6-{3-[1-(3-trifluoromethylbenzoyl)piperidin-4-ylidene]prop-1-ynyl}pyridine
2-{3-[1-(5-Bromo-2-furoyl)piperidin-4-ylidene]prop-1-ynyl}-6-methylpyridine
2-Methyl-6-{3-[1-(5-nitro-2-furoyl)piperidin-4-ylidene]prop-1-ynyl}pyridine
2-Methyl-6-{3-[1-(5-phenyl-2-furoyl)piperidin-4-ylidene]prop-1-ynyl}pyridine
2-(3-{1-[(3-Chlorothien-2-yl)carbonyl]piperidin-4-ylidene}prop-1-ynyl)-6-methylpyridine
2-Methyl-6-(3-{1-[(4-methylthien-2-yl)carbonyl]piperidin-4-ylidene}prop-1-ynyl)pyridine
2-Methyl-6-(3-{1-[(5-methylthien-2-yl)carbonyl]piperidin-4-ylidene}prop-1-ynyl)pyridine
2-(3-{1-[(2,5-Dichlorothien-3-yl)carbonyl]piperidin-4-ylidene}prop-1-ynyl)-6-methylpyridine
2-{3-[1-(3-Furoyl)piperidin-4-ylidene]prop-1-ynyl}-6-methylpyridine
2-Methyl-6-(3-{1-[(5-phenylisoxazol-3-yl)carbonyl]piperidin-4-ylidene}prop-1-ynyl)pyridine
2-Methyl-6-(3-{1-[(5-thien-2-yl-1H-pyrazol-3-yl)carbonyl]piperidin-4-ylidene}prop-1-ynyl)pyridine
2-[3-(1-{[5-(2-Furyl)-1H-pyrazol-3-yl]carbonyl}piperidin-4-ylidene)prop-1-ynyl]-6-methylpyridine
2-Methyl-6-(3-{1-[(5-nitrothien-2-yl)carbonyl]piperidin-4-ylidene}prop-1-ynyl)pyridine
2-{3-[1-[3-(Benzyloxy)benzoyl]piperidin-4-ylidene]prop-1-ynyl}pyridine
2-Methyl-6-{3-[1-(3-methyl-2-furoyl)piperidin-4-ylidene]prop-1-ynyl}pyridine
2-(3-{1-[(3-Ethoxythien-2-yl)carbonyl]piperidin-4-ylidene}prop-1-ynyl)-6-methylpyridine
1-[5-({4-[3-(6-methylpyridin-2-yl)prop-2-ynylidene]piperidin-1-yl}carbonyl)thien-2-yl]ethanone
2-Methyl-6-(3-{1-[(5-phenylthien-2-yl)carbonyl]piperidin-4-ylidene}prop-1-ynyl)pyridine
2-[3-[1-(2-Methyl-1,3-thiazol-4-yl)benzoylpiperidin-4-ylidene]prop-1-ynyl]-6-methylpyridine
2-(3-{1-[(5-Chloro-4-methoxythien-3-yl)carbonyl]piperidin-4-ylidene}prop-1-ynyl)-6-methylpyridine
2-Methyl-6-[3-(1-{[5-(methylthio)thien-2-yl]carbonyl}piperidin-4-ylidene)prop-1-ynyl]pyridine
2-(3-{1-[(3-Chloro-4-methylthien-2-yl)carbonyl]piperidin-4-ylidene}prop-1-ynyl)-6-methylpyridine
2-Methyl-6-(3-{1-[3-(1,3-thiazol-2-yl)benzoyl]piperidin-4-ylidene}prop-1-ynyl)pyridine
2-(3-{[4-[3-(6-Methylpyridin-2-yl)prop-2-ynylidene]piperidin-1-yl]carbonyl}phenyl)pyrimidine
5-[1-(3-Nitropyridin-2-yl)piperidin-4-ylidene]pent-3-yn-2-one
1-(4-Fluorophenyl)-4-[1-(3-nitropyridin-2-yl)piperidin-4-ylidene]but-2-yn-1-one
2,2-Dimethyl-6-[1-(3-nitropyridin-2-yl)piperidin-4-ylidene]hex-4-yn-3-one
4-[1-(3-Nitropyridin-2-yl)piperidin-4-ylidene]-1-thiophen-2-ylbut-2-yn-1-one
1-Cyclohexyl-4-[1-(3-nitropyridin-2-yl)piperidin-4-ylidene]but-2-yn-1-one 2-Methyl-6-[1-(3-nitropyridin-2-yl)piperidin-4-ylidene] hex-1-en-4-yn-3-one
2-{4-[3-(3,5-Difluoro-4-methoxyphenyl)prop-2-ynylidene] piperidin-1-yl}-3-nitropyridine
2-Fluoro-4-{3-[1-(3-nitropyridin-2-yl)piperidin-4-ylidene] prop-1-yn-1-yl}benzonitrile
2-{4-[3-(5-Fluoro-2-methoxyphenyl)prop-2-ynylidene]piperidin-1-yl}-3-nitropyridine
2-{4-[3-(3,5-Difluorophenyl)prop-2-yn-1-ylidene]piperidin-1-yl}-3-nitropyridine
4-{3-[1-(3-Nitropyridin-2-yl)piperidin-4-ylidene]prop-1-yn-1-yl}benzonitrile
3,3-Dimethyl-1-{4-[1-(3-nitropyridin-2-yl)piperidin-4-ylidene]prop-1-ynylphenyl}azetidin-2-one
3-Nitro-2-{4-[3-(3-pyrrolidin-1 ylmethylphenyl)prop-2-yn-1-ylidene]piperidin-1-yl}pyridine
2-{4-[3-(2,3-Dimethoxyphenyl)prop-2-yn-1-ylidene]piperidin-1-yl}-3-nitropyridine
3-Nitro-2-(4-{3-[3-(trifluoromethyl)phenyl]prop-2-yn-1-ylidene}piperidin-1-yl)pyridine
2-{4-[3-(3-Bromophenyl)prop-2-yn-1-ylidene]piperidin-1-yl}-3-nitropyridine
2-{4-[3-(3-Methylphenyl)prop-2-yn-1-ylidene]piperidin-1-yl}-3-nitropyridine
2-{4-[3-(3-Methoxyphenyl)prop-2-yn-1-ylidene]piperidin-1-yl}-3-nitropyridine
6-{3-[1-(3-Nitropyridin-2-yl)piperidin-4-ylidene]prop-1-yn-1-yl}quinoxaline
(3-{3-[1-(3-Nitropyridin-2-yl)piperidin-4-ylidene]prop-1-yn-1-yl}phenyl)acetonitrile
3-Nitro-2-{4-[3-(3-Nitrophenyl)prop-2-yn-1-ylidene]piperidin-1-yl}pyridine
3-{3-[1-(3-Nitropyridin-2-yl)piperidin-4-ylidene]prop-1-yn-1-yl}benzonitrile
2-{4-[3-(3-Chlorophenyl)prop-2-yn-1-ylidene]piperidin-1-yl}-3-nitropyridine
tert-Butyl 4-(3-phenylprop-2-yn-1-yl)piperidine-1-carboxylate
tert-Butyl 4-hept-2-ynylidenepiperidine-1-carboxylate
3-Nitro-2-(4-{3-[6-(trifluoromethyl)pyridin-3-yl]prop-2-ynylidene}piperidin-1-yl)pyridine
2-Fluoro-6-methyl-3-{3-[1-(3-nitropyridin-2-yl)piperidin-4-ylidene]prop-1-yn-1-yl}pyridine
3-Bromo-2-chloro-4-{3-[1-(3-nitropyridin-2-yl)piperidin-4-ylidene]prop-1-yn-1-yl}pyridine
3-Bromo-2-fluoro-4-{3-[1-(3-nitropyridin-2-yl)piperidin-4-ylidene]prop-1-yn-1-yl}pyridine
3-Fluoro-4-methyl-2-{3-[1-(3-nitropyridin-2-yl)piperidin-4-ylidene]prop-1-yn-1'-yl}pyridine
2-{4-[3-(5-Fluoropyridin-3-yl)prop-2-yn-1-ylidene]piperidin-1-yl}-3-nitropyridine
2-{4-[3-(6-Fluoropyridin-2-yl)prop-2-yn-1-ylidene]piperidin-1-yl}-3-nitropyridine
2-{4-[3-(6-Isopropoxypyridin-3-yl)prop-2-ynylidene]piperidin-1-yl}-3-nitropyridine
2-Ethoxy-3-{3-[1-(3-nitropyridin-2-yl)piperidin-4-ylidene] prop-1-yn-1-yl}pyridine
2-{4-[3-(6-Methylpyridin-2-yl)prop-2-yn-1-ylidene]piperidin-1-yl}-5-nitropyridine
2-{4-[3-(3,5-Difluorophenyl)prop-2-yn-1-ylidene]piperidin-1-yl}-6-methoxy-3-nitropyridine
5-Bromo-2-{4-[3-(6-methylpyridin-2-yl)prop-2-yn-1-ylidene]piperidin-1-yl}pyrimidine
3-Methyl-2-{4-[3-(6-methylpyridin-2-yl)prop-2-yn-1-ylidene]piperidin-1-yl}-5-nitropyridine
5-Methyl-6-{4-[3-(6-methylpyridin-2-yl)prop-2-yn-1-ylidene]piperidin-1-yl}pyridine-3-carbonitrile
5-{4-[3-(6-Methylpyridin-2-yl)prop-2-yn-1-ylidene]piperidin-1-yl}pyridine-2-carbonitrile
2-Methyl-6-{3-[1-(4-methylpyridin-3-yl)piperidin-4-ylidene]prop-1-yn-1-yl}pyridine
4-{4-[3-(6-Methylpyridin-2-yl)prop-2-yn-1-ylidene]piperidin-1-yl}isoquinoline
5-Methyl-2-{4-[3-(6-methylpyridin-2-yl)prop-2-ynylidene] piperidin-1-yl}cyclopent-2-en-1-one
tert-Butyl 4-{1-[(methoxycarbonyl)oxy]-3-(6-methylpyridin-2-yl)prop-2-yn-1-yl}piperidine-1-carboxylate
3-(6-Methylpyridin-2-yl)-1-[1-(3-nitropyridin-2-yl)piperidin-4-yl]prop-2-yn-1-ol
2-Methyl-6-{3-[1-(3-nitrothien-2-yl)piperidin-4-ylidene] prop-1-ynyl}pyridine
2-Methyl-6-{3-[1-(5-nitrofuran-2-yl)piperidin-4-ylidene] prop-1-yn-1-yl}pyridine
5-{4-[3-(6-Methylpyridin-2-yl)prop-2-ynylidene]piperidin-1-yl}-N-phenyl-2-furamide
2-Methyl-6-{3-[1-(2-methyl-4-nitro-1H-imidazol-5-yl)piperidin-4-ylidene]prop-1-yn-1-yl}pyridine
2-{4-[1-Methoxy-3-(6-methylpyridin-2-yl)prop-2-yn-1-yl] piperidin-1-yl}-3-nitropyridine
Methyl 3-(6-methylpyridin-2-yl)-1-[1-(2-nitropyridin-2-yl) piperidin-4-yl]prop-2-yn-1-yl carbonate
3-Nitro-2-[4-(3-phenylprop-2-yn-1-yl)piperidin-1-yl]pyridine
6-Methyl-3-nitro-2-[4-(3-phenylprop-2-yn-1-yl)piperidin-1-yl]pyridine
6-Methyl-2-{4-[3-(6-methylpyridin-2-yl)prop-2-yn-1-yl]piperidin-1-yl}-3-nitropyridine
tert-Butyl 4-[3-(3,5-difluorophenyl)prop-2-yn-1-yl]piperidine-1-carboxylate
2-{4-[3-(3,5-Difluorophenyl)prop-2-yn-1-yl]piperidin-1-yl}-6-methyl-3-nitropyridine
2-{4-[3-(3,5-Difluorophenyl)prop-2-yn-1-yl]piperidin-1-yl}benzonitrile
tert-Butyl 4-[1-fluoro-3-(6-methylpyridin-2-yl)prop-2-yn-1-yl]piperidine-1-carboxylate
2-{4-[1-Fluoro-3-(6-methylpyridin-2-yl)prop-2-ynyl]piperidin-1-yl}-6-methyl-3-nitropyridine
tert-Butyl (3E)-3-[3-(6-methylpyridin-2-yl)prop-2-ynylidene]pyrrolidine-1-carboxylate
2-[4-(1-Methyl-3-phenylprop-2-ynylidene)piperidin-1-yl]-3-nitropyridine
2-[4-(1-Methylene-3-phenylprop-2-ynyl)piperidin-1-yl]-3-nitropyridine
3-Nitro-2-{4-[(2E)-3-phenylprop-2-enylidene]piperidin-1-yl}pyridine
1-(3-Nitropyridin-2-yl)-4-(3-phenylprop-2-ynyl)piperidin-4-ol
2-{4-[3-(6-Methylpyridin-2-yl)prop-2-ynylidene]piperidin-1-yl}-3-nitroimidazo[1,2-a]pyridine
1-[1-(3-Nitropyridin-2-yl)piperidin-4-yl]-3-phenylprop-2-yn-1-one
3-Nitro-2-(4-{3-[3-(trifluoromethoxy)phenyl]prop-2-ynylidene}piperidin-1-yl)pyridine
1-3'-(Nitro-3,6-dihydro-2H-1,2'-bipyridin-4-yl)-3-phenylprop-2-yn-1-one
1-{3-[1-(3-Nitropyridin-2-yl)piperidin-4-ylidene]prop-1-ynyl}pyrrolidin-2-one
2-Methyl-6-(3-{1-[5-(trifluoromethyl)pyridin-3-yl]piperidin-4-ylidene}-prop-1-ynyl)pyridine
2-{4-[3-(6-Methylpyridin-2-yl)prop-2-ynylidene]piperidin-1-yl}-5-phenylnicotinonitrile
2-Methyl-6-(3-{1-[2-propoxypyridin-3-yl]piperidin-4-ylidene}prop-1-ynyl)pyridine 7-{4-[3-(6-Methylpyridin-2-yl)prop-2-ynylidene]piperidin-1-yl}pyrido[2,3-b]pyrazine
2-{4-[3-(6-Methylpyridin-2-yl)prop-2-ynylidene]piperidin-1-yl}thiophene-3-carbonitrile
2-Ethoxy-5-{4-[3-(6-methylpyridin-2-yl)prop-2-ynylidene]piperidin-1-yl}pyridine
2-{4-[3-(2,6-Difluorophenyl)prop-2-ynylidene]piperidin-1-yl}-3-nitropyridine
2-{4-[3-(4-Fluoropyridin-2-yl)prop-2-ynylidene]piperidin-1-yl}-6-methyl-3-nitropyridine
2-{4-[3-(3,5-Difluorophenyl)prop-2-ynylidene]piperidin-1-yl}-6-methyl-3-nitropyridine
2-{4-[3-(3-Fluorophenyl)prop-2-ynylidene]piperidin-1-yl}-6-methyl-3-nitropyridine
6-Methyl-3-nitro-2-[4-(3-pyridin-2-ylprop-2-ynylidene)piperidin-1-yl]pyridine
2-{4-[3-(6-Fluoropyridin-2-yl)prop-2-ynylidene]piperidin-1-yl}-6-methyl-3-nitropyridine
2-{4-[3-(2-Fluoropyridin-5-yl)prop-2-ynylidene]piperidin-1-yl}-6-methyl-3-nitropyridine
2-{4-[3-(2-Fluoropyridin-4-yl)prop-2-ynylidene]piperidin-1-yl}-6-methyl-3-nitropyridine
2-{4-[3-(3-Fluoropyridin-5-yl)prop-2-ynylidene]piperidin-1-yl}-6-methyl-3-nitropyridine
5-{3-[1-(6-Methyl-3-nitropyridin-2-yl)piperidin-4-ylidene]prop-1-ynyl}nicotinonitrile
2-{4-[3-(2,5-Difluorophenyl)prop-2-ynylidene]piperidin-1-yl}-6-methyl-3-nitropyridine
2-{4-[3-(3,5-Difluorophenyl)prop-2-ynylidene]piperidin-1-yl}-6-methylnicotinonitrile
2-{4-[3-(3-Fluorophenyl)prop-2-ynylidene]piperidin-1-yl}-6-methylnicotinonitrile
6-Methyl-2-[4-[3-(4-pyridyl)prop-2-ynylidene]piperidin-1-yl]nicotinonitrile
6-Methyl-2-[4-[3-(2-fluoro-6-pyridyl)prop-2-ynylidene]piperidin-1-yl]nicotinonitrile
6-Methyl-2-[4-[3-(5-cyano-3-pyridyl)prop-2-ynylidene]piperidin-1-yl]nicotinonitrile
6-Methyl-2-[4-[3-(2-fluoro-4-pyridyl)prop-2-ynylidene]piperidin-1-yl]nicotinonitrile
6-Methyl-2-[4-[3-(2-pyridyl)prop-2-ynylidene]piperidin-1-yl]nicotinonitrile
6-Methyl-2-[4-[3-(2,5-difluorophenyl-pyridyl)prop-2-ynylidene]piperidin-1-yl]nicotinonitrile
6-ethyl-2-[4-[3-(5-cyano-2-pyridyl)prop-2-ynylidene]piperidin-1-yl]nicotinonitrile
6-Methyl-2-[4-(1-methyl-3-(5-fluoro-2-pyridyl)prop-2-ynylidene)piperidin-1-yl]nicotinonitrile
6-Methyl-2-[4-(1-methyl-3-(5-fluoro-3-pyridyl)prop-2-ynylidene)piperidin-1-yl]nicotinonitrile
2-{4-[3-(3-Fluorophenyl)prop-2-ynylidene]piperidin-1-yl}-4-ethoxynicotinonitrile
2-{4-[3-(3,5-difluorophenyl)prop-2-ynylidene]piperidin-1-yl}-4-methoxynicotinonitrile
2-{4-[3-(2,5-difluorophenyl)prop-2-ynylidene]piperidin-1-yl}-4-methoxynicotinonitrile
4-Methoxy-2-[4-(3-pyridin-2-ylprop-2-ynylidene)piperidin-1-yl]nicotinonitrile
2-{4-[3-(6-fluoro-2-pyridyl)prop-2-ynylidene]piperidin-1-yl}-4-methoxynicotinonitrile
2-{4-[3-(6-fluoro-3-pyridyl)prop-2-ynylidene]piperidin-1-yl}-4-methoxynicotinonitrile
2-{4-[3-(2-fluoro-4-pyridyl)prop-2-ynylidene]piperidin-1-yl}-4-methoxynicotinonitrile
2-{4-[3-(5-fluoro-3-pyridyl)prop-2-ynylidene]piperidin-1-yl}-4-methoxynicotinonitrile
2-{4-[3-(5-cyanopyridin-3-yl)prop-2-ynylidene]piperidin-1-yl}-4-ethoxynicotinonitrile
2-{4-[3-(5-cyanopyridin-2-yl)prop-2-ynylidene]piperidin-1-yl}-4-ethoxynicotinonitrile
6-Methyl-2-[4-(1-methyl-3-phenylprop-2-ynylidene)piperidin-1-yl]nicotinonitrile
6-Methyl-2-[4-[3-(6-bromo-2-pyridyl)prop-2-ynylidene]piperidin-1-yl]nicotinonitrile
2-{4-[3-(3-Ethoxyphenyl)prop-2-ynylidene]piperidin-1-yl}-6-methyl-3-nitropyridine
1-(3-{3-[1-(6-methyl-3-nitropyridin-2-yl)piperidin-4-ylidene]prop-1-ynyl}phenyl)ethanone
3-{3-[1-(6-Methyl-3-nitropyridin-2-yl)piperidin-4-ylidene]prop-1-ynyl}phenylacetamide
(1-{3-[1-(6-Methyl-3-nitropyridin-2-yl)piperidin-4-ylidene]prop-1-ynyl}phenyl)acetone
6-methyl-2-{(3Z)-3-[3-(6-methylpyridin-2-yl)prop-2-ynylidene]piperidin-1-yl}-3-nitropyridine
6-methyl-2-{(3E)-3-[3-(6-methylpyridin-2-yl)prop-2-ynylidene]piperidin-1-yl}-3-nitropyridine
2-[1-(6-Methyl-3-nitropyridin-2-yl)piperidin-4-yl]-4-(6-methylpyridin-2-yl)but-3-yn-2-ol
6-Methyl-2-[4-(1-methyl-3-phenylprop-2-ynylidene)piperidin-1-yl]-3-nitropyridine
1-(1-Methyl-4-nitro-1H-imidazol-5-yl)-4-(1-methyl-3-phenylprop-2-ynylidene)piperidine
4-[3-(3,5-Difluorophenyl)prop-2-ynylidene]-1-(1-methyl-4-nitro-1H-imidazol-5-yl)piperidine
2-Methyl-6-{3-[1-(1-methyl-4-nitro-1H-imidazol-5-yl)piperidin-4-ylidene]prop-1-ynyl}pyridine;
2-Methyl-6-{3-[1-(4-nitro-1H-imidazol-5-yl)piperidin-4-ylidene]prop-1-ynyl}pyridine;
2-{4-[3-(2,5-Difluorophenyl)prop-2-ynylidene]piperidin-1-yl}thiophene-3-carbonitrile;
6-Methyl-[4-{3-[3-(3-methyl-1,2,4-oxadiazol-5-yl)phenyl]prop-2-ynylidene}piperidin-1-yl]-3-nitropyridine; and
3-{4-[3-(6-Methylpyridin-2-yl)prop-2-ynylidene]piperidin-1-yl}pyrazine-2-carbonitrile;
or a pharmaceutically acceptable salt thereof.

Another embodiment of the present invention are pharmaceutical compositions comprising a pharmaceutically acceptable excipient or diluent and a therapeutically effective amount of a compound of the invention or a pharmaceutically acceptable salt thereof.

Another embodiment of the present invention is method of diseases or disorders of the lower urinary tract, including neuromuscular dysfunctions of the lower urinary tract comprising administering to a mammal in need of such treatment an effective amount of a compound according to Formulas A, I, II, and III or a pharmaceutically acceptable salt thereof. Compounds also useful for treating neuromuscular dysfunctions of the lower urinary tract are those compounds according to formulas A, I, II, or III wherein $R_2$ is an optionally substituted 8,9 dihydro-7H-purin-6-amine or an optionally substituted 9H-purin-6-amine.

Further preferred are where the aforementioned neuromuscular dysfunction is selected from the group consisting of urinary urgency, overactive bladder, increased urinary frequency, decreased urinary compliance (decreased bladder storage capacity), cystitis, interstitial cystitis, incontinence, urine leakage, enuresis, dysuria, urinary hesitancy and difficulty in emptying the bladder.

Another embodiment of the present invention is method of treating neuromuscular dysfunctions of the lower urinary tract comprising administering to a mammal in need of such treatment an effective amount of a compound according to Formulas A, I, II, and III, or a pharmaceutically acceptable salt thereof, administered in combination with an antimuscarinic drug. Preferably the antimuscarinic drug is selected from the group consisting of oxybuynin, tolterodine, darifenacin, solifenacin, trospium, imidafenacin, fesoterodine and temiverine. Compounds also useful for treating neuromuscular dysfunctions of the lower urinary tract are those compounds according to formulas A, I, II, or III wherein $R_2$ is optionally substituted 8,9 dihydro-7H-purin-6-amines or optionally substituted 9H-purin-6-amines.

Another embodiment of the present invention is method of treating neuromuscular dysfunctions of the lower urinary tract comprising administering to a mammal in need of such treatment an effective amount of a compound according to Formulas A, I, II, and III, or a pharmaceutically acceptable salt thereof, administered with α1-adrenergic antagonists. Preferably the adrenergic antagonists is selected from the group consisting of prazosin, doxazosin, terazosin, alfuzosin, silodosin and tamsulosin. Compounds also useful for treating neuromuscular dysfunctions of the lower urinary tract are those compounds according to formulas A, I, II, or III wherein $R_2$ is optionally substituted 8,9 dihydro-7H-purin-6-amines or optionally substituted 9H-purin-6-amines.

Another embodiment of the present invention is method of treating neuromuscular dysfunctions of the lower urinary tract comprising administering to a mammal in need of such treatment an effective amount of a compound according to Formulas A, I, II, and III, or a pharmaceutically acceptable salt thereof, administered in combination with a serotonin and/or noradrenaline reuptake inhibitor. Preferably the serotonin and/or noradrenaline reuptake inhibitor is selected form the group consisting of duloxetine, milnacipran, amoxapine, venlafaxine, des-venlafaxine, sibutramine, tesofensine and des-methylsibutramine. Compounds also useful for treating neuromuscular dysfunctions of the lower urinary tract are those compounds according to formulas A, I, II, or III wherein $R_2$ is optionally substituted 8,9 dihydro-7H-purin-6-amines or optionally substituted 9H-purin-6-amines.

Another embodiment of the present invention is method of treating neuromuscular dysfunctions of the lower urinary tract comprising administering to a mammal in need of such treatment an effective amount of a compound according to Formulas A, I, II, and III, or a pharmaceutically acceptable salt thereof, administered in combination with a selective or non-selective COX inhibitor. Preferably the selective or non-selective COX inhibitor is selected from the group consisting of ibuprofen, naproxen, benoxaprofen, flurbiprofen, fenoprfen, ketoprofen, indoprofen, pirprofen, carprofen, tioxaprofe, suprofen, tiaprofenic acid, fluprofen, indomethacin, sulindac, tolmetin, zomepirac, diclofenac, fenclofenac, ibufenac, acetyl salicylic acid, piroxicam, tenoxicam, nabumetone, ketorolac, azapropazone, mefenamic acid, tolfenamic acid, diflunisal, acemetacin, fentiazac, clidanac, meclofenamic acid, flufenamic acid, niflumic acid, flufenisal, sudoxicam, etodolac, salicylic acid, benorylate, isoxicam, 2-fluoro-α-methyl[1,1'-biphenyl]-4-acetic acid 4-(nitrooxy) butyl ester, meloxicam, parecoxib and nimesulide. Compounds also useful for treating neuromuscular dysfunctions of the lower urinary tract are those compounds according to formulas A, I, II, or III wherein $R_2$ is optionally substituted 8,9 dihydro-7H-purin-6-amines or optionally substituted 9H-purin-6-amines.

Another embodiment of the present invention is a method of treating migraine comprising administering to a mammal in need of such treatment an effective amount of a compound according to Formulas A, I, II, and III, or a pharmaceutically acceptable salt thereof. Compounds also useful for treating migraine are those compounds according to formulas A, I, II, or III wherein $R_2$ is optionally substituted 8,9 dihydro-7H-purin-6 amines or optionally substituted 9H-purin-6 amines.

Another embodiment of the present invention is a method of treating GERD comprising administering to a mammal in need of such treatment an effective amount of a compound according to Formulas A, I, II, and III, or a pharmaceutically acceptable salt thereof. Compounds also useful for treating GERD are those compounds according to formulas A, I, II, or III wherein $R_2$ is optionally substituted 8,9 dihydro-7H-purin-6 amines or optionally substituted 9H-purin-6 amines.

The present invention also includes the enantiomers, diastereomers, N-oxides, crystalline forms, hydrates, solvates and pharmaceutically acceptable salts of the compounds of general formulas A, I, II and III that are selective antagonists of mGlu5 receptors.

The present invention also includes metabolites of the compounds of formulas A, I, II, or III that are selective mGlu5 antagonists, hereinafter referred to as active metabolites.

The present invention also contemplates pro-drugs which are metabolised in the body to generate the compounds of formulas I that are selective mGlu5 antagonists.

In another embodiment, the present invention provides pharmaceutical compositions comprising compounds of formulas A, I, II, or III that are selective mGlu5 antagonist and enantiomers, diastereomers, N-oxides, crystalline forms, hydrates, solvates or pharmaceutically acceptable salts thereof, in admixture with pharmaceutically acceptable diluents or carriers such as those disclosed.

Those of skill in the art recognize that the aforementioned compounds may contain one or more chiral centers, and thus can exist as racemic mixtures. For many applications, it is preferred to carry out stereoselective syntheses and/or to subject the reaction product to appropriate purification steps so as to produce substantially optically pure materials. Suitable stereoselective synthetic procedures for producing optically pure materials are well known in the art, as are procedures for purifying racemic mixtures into optically pure fractions. Those of skill in the art will further recognize that invention compounds may exist in polymorphic forms wherein a compound is capable of crystallizing in different forms. Suitable methods for identifying and separating polymorphisms are known in the art.

In yet another embodiment, this invention provides a method for identifying a compound useful for treating neuromuscular dysfunction of the lower urinary tract comprising:

(a) individually measuring the binding affinity of a test compound for the mGlu5 receptor, mGlu1 receptor and Group II mGlu receptors;

(b) identifying those test compounds that:

(1) bind to a mGlu5 receptor with an affinity of at least $10^{-6}$ M, and (2) bind to a mGlu5 receptor with an affinity at least 10-fold stronger than the affinity for the mGlu1 receptor and Group II mGlu receptors.

(c) individually measuring the ability of each of the compounds identified in step (b) to act as an antagonist or inverse agonist at the mGlu5 receptor.

Preferably, the activity of compounds identified in steps (a), (b), and (c) above is confirmed by evaluating the activity of the compound in treatment of lower urinary tract disease in humans or an animal model system. More preferably the compounds identified exhibit activity in increasing bladder volume capacity in conscious rats.

In certain embodiments a selective mGlu5 antagonist is used to treat the aforementioned disorders by administering the antagonist in combination with known antimuscarinic drugs or serotonin and/or noradrenaline reuptake inhibitors. Analogously, a selective mGlu5 antagonist may be administered in combination with α1-adrenergic antagonists, for the therapy of lower urinary tract symptoms, whether or not these are associated with BPH. Additionally, a selective mGlu5 antagonist is used to treat the aforementioned disorders by administering the antagonist in combination with known drugs from the treatment of migraine or GERD.

To the same purpose, selective mGlu5 antagonists may be administered in combination with inhibitors of the enzyme cyclooxygenase (COX) which may be selective or non selective for the COX-2 isozyme.

The term "salts" can include acid addition salts or addition salts of free bases. Preferably, the salts are pharmaceutically acceptable. Examples of acids which may be employed to form pharmaceutically acceptable acid addition salts include, but are not limited to, salts derived from nontoxic inorganic acids such as nitric, phosphoric, sulfuric, or hydrobromic, hydroiodic, hydrofluoric, phosphorous, as well as salts derived from nontoxic organic acids such as aliphatic mono- and dicarboxylic acids, phenyl-substituted alkanoic acids, hydroxyl alkanoic acids, alkanedioic acids, aromatic acids, aliphatic and aromatic sulfonic acids, and acetic, maleic, succinic, or citric acids. Non-limiting examples of such salts include napadisylate, besylate, sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, et al. "Pharmaceutical Salts," *J. Pharm. Sci.* 1977; 66:1).

The phrase "pharmaceutically acceptable", as used in connection with compositions of the invention, refers to molecular entities and other ingredients of such compositions that are physiologically tolerable and do not typically produce untoward reactions when administered to a mammal (e.g., human). Preferably, as used herein, the term "pharmaceutically acceptable" means approved by a regulatory agency of the federal or a state government or listed in the U.S. Pharmacopoeia or other generally recognized pharmacopeias for use in mammals, and more particularly in humans.

Compounds of formulas A, I, II, or III having basic groups may form acid addition salts, and compounds of the formulas A, I, II or III having acidic groups may form salts with bases. Compounds of formulas A, I, II, or III having basic groups and in addition having at least one acidic group, may also form internal salts.

Typically, a pharmaceutically acceptable salt of a compound of formulas A, I, II, or III may be readily prepared by using a desired acid or base as appropriate. The salt may precipitate from solution and be collected by filtration or may be recovered by evaporation of the solvent. For example, an aqueous solution of an acid such as hydrochloric acid may be added to an aqueous suspension of a compound of formulas A, I, II, or III and the resulting mixture evaporated to dryness (lyophilized) to obtain the acid addition salt as a solid. Alternatively, a compound of formulas A, I, II, or III may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

The acid addition salts of the compounds of formulas A, I, II, or III may be prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine.

The base addition salts of said acidic compounds are prepared by contacting the free acid form with a sufficient amount of the desired base to produce the salt in the conventional manner. The free acid form may be regenerated by contacting the salt form with an acid and isolating the free acid.

Compounds of the invention may have both a basic and an acidic center and therefore be in the form of zwitterions.

Also included are both total and partial salts, that is to say salts with 1, 2 or 3, preferably 2, equivalents of base per mole of acid of formulas A, I, II, or III or salts with 1, 2 or 3 equivalents, preferably 1 equivalent, of acid per mole of base of formulas A, I, II, or III.

For the purposes of isolation or purification it is also possible to use pharmaceutically unacceptable salts. Only the pharmaceutically acceptable, non-toxic salts are used therapeutically and they are therefore preferred. Compounds described in WO 2008/011007 are excluded from the compound claims.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The salts of the compound of formulas A, I, II, or III may form solvates (e.g., hydrates) and the invention also includes all such solvates. The meaning of the word "solvates" is well known to those skilled in the art as a compound formed by interaction of a solvent and a solute (i.e., solvation). Techniques for the preparation of solvates are well established in the art (see, for example, Brittain. *Polymorphism in Pharmaceutical solids*. Marcel Decker, New York, 1999.).

Compounds of formulas A, I, II, or III can exist in racemic mixtures or in any other combination. Racemic mixtures can be subjected to methods for enantiomeric enrichment, to yield compositions enriched in a particular enantiomer, or resolved to a composition comprising a single enantiomer. Enantiomeric enrichment can be expressed as percent ee (enantiomeric excess) as defined below. Enantioenriched compounds can also be prepared through synthetic methods that utilize a chiral auxiliary or a chiral catalyst.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. As used herein, the term "optical isomer" is equivalent to the term "enantiomer". Compounds that are stereoisomers of one another, but are not enantiomers of one another, are called diastereomers. The terms "racemate" or "racemic mixture" refer to a mixture of equal parts of enantiomers. The term "chiral center" refers to a carbon atom to which four different groups are attached. The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E1 - E2}{E1 + E2} * 100$$

wherein E1 is the amount of the first enantiomer and E2 is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. According to one embodiment of the invention, an ee of greater than 90% is preferred, an ee of greater than 95% is most preferred and an ee of greater than 99% is most especially preferred. Enantiomeric enrichment is readily determined by one of ordinary skill in the art using standard techniques and procedures, such as high performance liquid chromatography with a chiral column. Choice of the appropriate chiral column, eluent and conditions necessary to effect separation of the enantiomeric pair is within the knowledge of one of ordinary skill in the art. In addition, the enantiomers of compounds of formula I can be resolved by one of ordinary skill in the art using standard techniques well known in the art, such as those described by J. Jacques, et al., "Enantiomers, Racemates, and Resolutions", John Wiley and Sons, Inc., 1981. Examples of resolutions include recrystallization techniques or chiral chromatography.

Diastereisomers differ in both physical properties and chemical reactivity. A mixture of diastereomers can be separated into enantiomeric pairs based on solubility, fractional crystallization or chromatographic properties, e.g., thin layer chromatography, column chromatography or HPLC.

Purification of complex mixtures of diastereomers into enantiomers typically requires two steps. In a first step, the mixture of diastereomers is resolved into enantiomeric pairs, as described above. In a second step, enantiomeric pairs are further purified into compositions enriched for one or the other enantiomer or, more preferably resolved into compositions comprising pure enantiomers. Resolution of enantiomers typically requires reaction or molecular interaction with a chiral agent, e.g., solvent or column matrix. Resolution may be achieved, for example, by converting the mixture of enantiomers, e.g., a racemic mixture, into a mixture of diastereomers by reaction with a pure enantiomer of a second agent, i.e., a resolving agent. The two resulting diasteromeric products can then be separated. The separated diastereomers are then reconverted to the pure enantiomers by reversing the initial chemical transformation.

Resolution of enantiomers can also be accomplished by differences in their non-covalent binding to a chiral substance, e.g., by chromatography on homochiral adsorbants. The noncovalent binding between enantiomers and the chromatographic adsorbant establishes diastereomeric complexes, leading to differential partitioning in the mobile and bound states in the chromatographic system. The two enantiomers therefore move through the chromatographic system, e.g., column, at different rates, allowing for their separation.

Chiral resolving columns are well known in the art and are commercially available (e.g., from MetaChem Technologies Inc., a division of ANSYS Technologies, Inc., Lake Forest, Calif.). Enantiomers can be analyzed and purified using, for example, chiral stationary phases (CSPs) for HPLC. Chiral HPLC columns typically contain one form of an enantiomeric compound immobilized to the surface of a silica packing material.

D-phenylglycine and L-leucine are examples of Type I CSPs and use combinations of π-π interactions, hydrogen bonds, dipole-dipole interactions, and steric interactions to achieve chiral recognition. To be resolved on a Type I column, analyte enantiomers must contain functionality complementary to that of the CSP so that the analyte undergoes essential interactions with the CSP. The sample should preferably contain one of the following functional groups: π-acid or π-base, hydrogen bond donor and/or acceptor, or an amide dipole. Derivatization is sometimes used to add the interactive sites to those compounds lacking them. The most common derivatives involve the formation of amides from amines and carboxylic acids.

The MetaChiral ODM™ is an example of a type II CSP. The primary mechanisms for the formation of solute-CSP complexes is through attractive interactions, but inclusion complexes also play an important role. Hydrogen bonding, π-π interactions, and dipole stacking are important for chiral resolution on the MetaChiral™ ODM. Derivatization maybe necessary when the solute molecule does not contain the groups required for solute-column interactions. Derivatization, usually to benzylamides, may be required for some strongly polar molecules like amines and carboxylic acids, which would otherwise interact strongly with the stationary phase through non-specific-stereo interactions.

Compounds of formula I can be separated into diastereomeric pairs by, for example, separation by column chromatography or TLC on silica gel. These diastereomeric pairs are referred to herein as diastereomer with upper TLC Rf; and diastereomer with lower TLC Rf. The diastereomers can further be enriched for a particular enantiomer or resolved into a single enantiomer using methods well known in the art, such as those described herein.

The relative configuration of the diastereomeric pairs can be deduced by the application of theoretical models or rules (e.g., Cram's rule, the Felkin-Ahn model) or using more reliable three-dimensional models generated by computational chemistry programs. In many instances, these methods are able to predict which diastereomer is the energetically favored product of a chemical transformation. As an alternative, the relative configuration of the diastereomeric pairs can be indirectly determined by discovering the absolute configurations of a single enantiomer in one (or both) of the diastereomeric pair(s).

The absolute configuration of the stereocenters can be determined by very well known method to those skilled in the art (e.g., X-Ray diffraction, circular dichroism). Determination of the absolute configuration can be useful also to confirm the predictability of theoretical models and can be helpful to extend the use of these models to similar molecules prepared by reactions with analogous mechanisms (e.g., ketone reductions and reductive amination of ketones by hydrides).

The present invention also encompasses stereoisomers of the syn-anti type, and mixtures thereof encountered when is a double bond and $R_2$ is an alkyl group and/or m is not 1. The group of highest Cahn-Ingold-Prelog priority attached to one of the terminal doubly bonded atoms of the oxime, is compared with hydroxyl group of the oxime. The stereoisomer is designated as Z (zusammen=together) or Syn if the oxime hydroxyl lies on the same side of a reference plane passing through the C=N double bond as the group of highest priority; the other stereoisomer is designated as E (entgegen=opposite) or Anti.

It will be appreciated by those skilled in the art that it may be desirable to use protected derivatives of intermediates used in the preparation of the compounds of formulas I, II, or III. Protection and deprotection of functional groups may be performed by methods known in the art (see, for example, Green and Wuts *Protective Groups in Organic Synthesis*. John Wiley and Sons, New York, 1999.). Hydroxyl or amino groups may be protected with any hydroxyl or amino protecting group. The amino protecting groups may be removed by conventional techniques. For example, acyl groups, such as alkanoyl, alkoxycarbonyl and aroyl groups, may be removed by solvolysis, e.g., by hydrolysis under acidic or basic conditions. Arylmethoxycarbonyl groups (e.g., benzyloxycarbonyl) may be cleaved by hydrogenolysis in the presence of a catalyst such as palladium-on-charcoal.

The present invention also encompasses pro-drugs of the compounds of formulas A, I, II, or III, i.e., compounds which release an active parent drug according to formulas A, I, II, or III in vivo when administered to a mammalian subject. A pro-drug is a pharmacologically active or more typically an inactive compound that is converted into a pharmacologically active agent by a metabolic transformation. Pro-drugs of a compound of formulas A, I, II, or III are prepared by modifying functional groups present in the compound of formulas A, I, II, or III in such a way that the modifications may be cleaved in vivo to release the parent compound. In vivo, a pro-drug readily undergoes chemical changes under physiological conditions (e.g., are acted on by naturally occurring enzyme(s)) resulting in liberation of the pharmacologically active agent. Pro-drugs include compounds of formulas A, I, II, or III wherein a hydroxy, amino, or carboxy group of a formulas I, II, or III compound is bonded to any group that may be cleaved in vivo to regenerate the free hydroxyl, amino or carboxy group, respectively. Examples of pro-drugs include, but are not limited to esters (e.g., acetate, formate, and benzoate derivatives) of compounds of formulas A, I, II, or III or any other derivative which upon being brought to the physiological pH or through enzyme action is converted to the active parent drug. Conventional procedures for the selection and preparation of suitable pro-drug derivatives are described in the art (see, for example, Bundgaard. Design of Pro-drugs. Elsevier, 1985).

Pro-drugs may be administered in the same manner as the active ingredient to which they convert or they may be delivered in a reservoir form, e.g., a transdermal patch or other reservoir which is adapted to permit (by provision of an enzyme or other appropriate reagent) conversion of a pro-drug to the active ingredient slowly over time, and delivery of the active ingredient to the patient.

Unless specifically indicated, the term "active ingredient" is to be understood as referring to a compound of formulas A, I, II, or III as defined herein.

The present invention also encompasses metabolites. "Metabolite" of a compound disclosed herein is a derivative of a compound which is formed when the compound is metabolised. The term "active metabolite" refers to a biologically active derivative of a compound which is formed when the compound is metabolised. The term "metabolised" refers to the sum of the processes by which a particular substance is changed in the living body. In brief, all compounds present in the body are manipulated by enzymes within the body in order to derive energy and/or to remove them from the body. Specific enzymes produce specific structural alterations to the compound. For example, cytochrome P450 catalyses a variety of oxidative and reductive reactions while uridine diphosphate glucuronyltransferases catalyse the transfer of an activated glucuronic-acid molecule to aromatic alcohols, aliphatic alcohols, carboxylic acids, amines and free sulfhydryl groups. Further information on metabolism may be obtained from *The Pharmacological Basis of Therapeutics*, 9th Edition, McGraw-Hill (1996), pages 11-17.

Metabolites of the compounds disclosed herein can be identified either by administration of compounds to a host and analysis of tissue samples from the host, or by incubation of compounds with hepatic cells in vitro and analysis of the resulting compounds. Both methods are well known in the art.

Lower-Urinary Tract Disorders

The nomenclature of lower urinary tract symptoms and pathologies used herein is set forth in Abrams et al., *Neurol. and Urodyn.* 21:167-178 (2002) and Andersson et al., *Pharmacol. Rev.* 56:581-631 (2004).

Voiding dysfunctions can be roughly classified as disturbances of storage or emptying. Storage symptoms are experienced during the storage phase of the bladder, and include increased daytime frequency, nocturia (the waking at night one or more times to void), urgency (a sudden, compelling desire to pass urine that is difficult to defer), and urinary incontinence (the any involuntary leakage of urine). Urinary incontinence may be further characterized according to symptoms. Stress urinary incontinence is the involuntary leakage on effort or exertion, or on sneezing or coughing. Urge urinary incontinence is the involuntary leakage of urine accompanied by or immediately preceded by urgency. Mixed urinary incontinence is the involuntary leakage of urine associated with urgency and also with exertion, effort, sneezing or coughing. Overflow incontinence is the involuntary leakage of urine occurring after the bladder capacity has been exceeded, e.g., from a failure to empty. Enuresis also refers to any involuntary loss of urine. Nocturnal enuresis is the loss of urine occurring during sleep.

Voiding symptoms include slow stream, splitting or spraying of the urine stream, intermittent stream (intermittency, i.e., the stopping and restarting of urine flow during micturition, hesitancy (difficulty in initiating micturition resulting in a delay in the onset of voiding after the individual is ready to pass urine), straining and terminal dribble (a prolonged final part of micturition, when the flow has slowed to a trickle/dribble).

Lower urinary tract disorders may further be categorized by a constellation of symptoms (i.e., a syndrome) or by etiology. Individuals suffering from overactive bladder (OAB) syndrome, e.g., typically suffer from symptoms of urgency, urge incontinence, increased daytime frequency or nocturia. OAB occurs as a result of detrusor muscle overactivity referred to as detrusor muscle instability. Detrusor muscle instability can arise from non-neurological abnormalities, such as bladder stones, muscle disease, urinary tract infection or drug side effects or can be idiopathic.

Neurogenic overactive bladder (or neurogenic bladder) is a type of overactive bladder which occurs as a result of detrusor muscle overactivity referred to as detrusor hyperreflexia, secondary to known neurological disorders. Patients with neurological disorders, such as stroke, Parkinson's disease, diabetes, multiple sclerosis, peripheral neuropathy, or spinal cord lesions often suffer from neurogenic overactive bladder.

Cystitis (including interstitial cystitis) is a lower urinary tract disorder of unknown etiology that predominantly affects young and middle-aged females, although men and children can also be affected. Symptoms of interstitial cystitis can include voiding symptoms, increased daytime frequency, urgency, nocturia or suprapubic or pelvic pain related to and relieved by voiding. Many interstitial cystitis patients also experience headaches as well as gastrointestinal and skin problems. In some cases, interstitial cystitis can also be associated with ulcers or scars of the bladder.

Prostatitis and prostadynia are other lower urinary tract disorders that have been suggested to affect approximately 2-9% of the adult male population. Prostatitis is an inflammation of the prostate, and includes bacterial prostatitis (acute and chronic) and non-bacterial prostatitis. Acute and chronic bacterial prostatitis are characterized by inflammation of the prostate and bacterial infection of the prostate gland, usually associated with symptoms of pain, increased daytime frequency and/or urgency. Chronic bacterial prostatitis is distinguished from acute bacterial prostatitis based on the recurrent nature of the disorder. Chronic non-bacterial prostatitis is characterized by inflammation of the prostate which is of unknown etiology accompanied by the presence of an excessive amount of inflammatory cells in prostatic secretions not currently associated with bacterial infection of the prostate gland, and usually associated with symptoms of pain, increased daytime frequency and/or urgency. Prostadynia is a disorder which mimics the symptoms of prostatitis absent inflammation of the prostate, bacterial infection of the prostate and elevated levels inflammatory cells in prostatic secretions. Prostadynia can be associated with symptoms of pain, increased daytime frequency and/or urgency.

Benign prostatic hyperplasia (BPH) is a non-malignant enlargement of the prostate that is very common in men over 40 years of age. BPH is thought to be due to excessive cellular growth of both glandular and stromal elements of the prostate. Symptoms of BPH can include increased frequency, urgency, urge incontinence, nocturia, and voiding symptoms, including slow stream, splitting or spraying of the urine stream, intermittency, hesitancy, straining and terminal dribble.

In certain aspects the present invention provides the use of an effective amount of a selective mGlu5 antagonist, for treating lower urinary tract disorders, including those described above, in a patient in need of such treatment. For example, treatment of lower urinary tract disorders includes treatment of storage symptoms or voiding symptoms. Treatment of lower urinary tract disorders also includes treatment of increased daytime frequency, nocturia, urgency, urinary incontinence, including urge incontinence, stress incontinence, mixed incontinence and overflow incontinence, enuresis, including nocturnal enuresis, slow stream, splitting or spraying of the urine stream, intermittency, hesitancy, straining and terminal dribble.

Treatment of lower urinary tract disorders also includes treatment of OAB syndrome, including treatment of one or more symptoms of urgency, urge incontinence, daytime frequency or nocturia.

Treatment of lower urinary tract disorders further encompasses treatment of any of the aforementioned conditions, symptoms and/or syndromes when caused by or associated with cystitis, including interstitial cystitis, prostatitis, BPH, neurological disorders, decreased urinary compliance (i.e., decreased bladder storage capacity).

In certain preferred aspects of the invention, a mGlu5 antagonist is used to treat the involuntary passage of urine, i.e., urinary incontinence, e.g., urge incontinence, stress incontinence, mixed incontinence or overflow incontinence. In further preferred aspects of the invention, a mGlu5 antagonists is used to treat the involuntary passage of urine, i.e., urinary incontinence, e.g., urge incontinence, stress incontinence, mixed incontinence or overflow incontinence, that is caused by and/or associated with OAB or BPH.

Pharmaceutical Compositions Comprising a Compound of Formulas A, I, II, or III

While it is possible that, for use in the methods of the invention, a compound of formulas A, I, II, or III may be administered as the bulk substance, it is preferable to present the active ingredient in a pharmaceutical formulation, e.g., wherein the agent is in admixture with a pharmaceutically acceptable carrier selected with regard to the intended route of administration and standard pharmaceutical practice.

Accordingly, in one aspect, the present invention provides a pharmaceutical composition comprising at least one compound of formulas A, I, II, or III, or a pharmaceutically acceptable derivative (e.g., a salt or solvate) thereof, and, optionally, a pharmaceutically acceptable carrier. In particular, the invention provides a pharmaceutical composition comprising a therapeutically effective amount of at least one compound of formulas I, II, or III, or a pharmaceutically acceptable derivative thereof, and, optionally, a pharmaceutically acceptable carrier.

For the methods of the invention, a compound of formulas A, I, II, or III may be used in combination with other therapies and/or active agents. Accordingly, the present invention provides, in a further aspect, a pharmaceutical composition comprising at least one compound of formulas A, I, II, or III or a pharmaceutically acceptable derivative thereof, a second active agent, and, optionally a pharmaceutically acceptable carrier.

When combined in the same formulation it will be appreciated that the two compounds must be stable and compatible with each other and the other components of the formulation. When formulated separately they may be provided in any convenient formulation, conveniently in such manner as are known for such compounds in the art.

The phrase "pharmaceutically acceptable" refers to molecular entities and compositions that are generally regarded as safe. In particular, pharmaceutically acceptable carriers used in the pharmaceutical compositions of this invention are physiologically tolerable and do not typically produce an allergic or similar untoward reaction (for example, gastric upset, dizziness and the like) when administered to a patient. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans.

The term "carrier" refers to a diluent, excipient, and/or vehicle with which an active compound is administered. The pharmaceutical compositions of the invention may contain combinations of more than one carrier. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

The compounds of the invention may be formulated for administration in any convenient way for use in human or veterinary medicine and the invention therefore includes within its scope pharmaceutical compositions comprising a compound of the invention adapted for use in human or veterinary medicine. Such compositions may be presented for use in a conventional manner with the aid of one or more suitable carriers. Acceptable carriers for therapeutic use are well-known in the pharmaceutical art, and are described, for example, in Remington's Pharmaceutical Sciences, Mack Publishing Co. (A. R. Gennaro edit. 1985). The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s), coating agent(s), and/or solubilizing agent(s).

Preservatives, stabilizers, dyes and even flavoring agents may be provided in the pharmaceutical composition. Examples of preservatives include sodium benzoate, ascorbic acid and esters of p-hydroxybenzoic acid. Antioxidants and suspending agents may be also used.

The compounds of the invention may be milled using known milling procedures such as wet milling to obtain a particle size appropriate for tablet formation and for other formulation types. Finely divided (nanoparticulate) preparations of the compounds of the invention may be prepared by processes known in the art, for example see International Patent Application No. WO 02/00196 (SmithKline Beecham).

Routes of Administration and Unit Dosage Forms

The routes for administration (delivery) include, but are not limited to, one or more of: oral (e.g., as a tablet, capsule, or as an ingestible solution), topical, mucosal (e.g. as a nasal spray or aerosol for inhalation), nasal, parenteral (e.g., by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual.

Therefore, the compositions of the invention include those in a form especially formulated for, e.g., parenteral, oral, buccal, rectal, topical, implant, ophthalmic, nasal or genitourinary use. In preferred embodiments, the pharmaceutical compositions of the invention are formulated in a form that is suitable for oral delivery.

There may be different composition/formulation requirements depending on the different delivery systems. It is to be understood that not all of the compounds need to be administered by the same route. Likewise, if the composition comprises more than one active component, then those components may be administered by different routes. By way of example, the pharmaceutical composition of the present invention may be formulated to be delivered using a minipump or by a mucosal route, for example, as a nasal spray or aerosol for inhalation or ingestible solution, or parenterally in which the composition is formulated by an injectable form, for delivery, by, for example, an intravenous, intramuscular or subcutaneous route. Alternatively, the formulation may be designed to be delivered by multiple routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile. For example, the a compound of formulas A, I, II, or III may be coated with an enteric coating layer. The enteric coating layer material may be dispersed or dissolved in either water or in a suitable organic solvent. As enteric coating layer polymers, one or more, separately or in combination, of the following can be used; e.g., solutions or dispersions of methacrylic acid copolymers, cellulose acetate phthalate, cellulose acetate butyrate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating layer polymer(s). For environmental reasons, an aqueous coating process may be preferred. In such aqueous processes methacrylic acid copolymers are most preferred.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavoring or coloring agents, or they can be injected parenterally, for example intravenously, intramuscularly or subcutaneously. For buccal or sublingual administration the compositions may be administered in the form of tablets or lozenges, which can be formulated in a conventional manner.

Where the composition of the invention is to be administered parenterally, such administration includes one or more of: intravenously, intraarterially, intraperitoneally, intrathecally, intraventricularly, intraurethrally, intrasternally, intracranially, intramuscularly or subcutaneously administering the agent; and/or by using infusion techniques.

Pharmaceutical compositions of the present invention can be administered parenterally, e.g., by infusion or injection. Pharmaceutical compositions suitable for injection or infusion may be in the form of a sterile aqueous solution, a dispersion or a sterile powder that contains the active ingredient, adjusted, if necessary, for preparation of such a sterile solution or dispersion suitable for infusion or injection. This preparation may optionally be encapsulated into liposomes. In all cases, the final preparation must be sterile, liquid, and stable under production and storage conditions. To improve storage stability, such preparations may also contain a preservative to prevent the growth of microorganisms. Prevention of the action of micro-organisms can be achieved by the addition of various antibacterial and antifungal agents, e.g., paraben, chlorobutanol, or acsorbic acid. In many cases isotonic substances are recommended, e.g., sugars, buffers and sodium chloride to assure osmotic pressure similar to those of body fluids, particularly blood. Prolonged absorption of such injectable mixtures can be achieved by introduction of absorption-delaying agents, such as aluminium monostearate or gelatin.

Dispersions can be prepared in a liquid carrier or intermediate, such as glycerin, liquid polyethylene glycols, triacetin oils, and mixtures thereof. The liquid carrier or intermediate can be a solvent or liquid dispersive medium that contains, for example, water, ethanol, a polyol (e.g., glycerol, propylene glycol or the like), vegetable oils, non-toxic glycerine esters and suitable mixtures thereof. Suitable flowability may be maintained, by generation of liposomes, administration of a suitable particle size in the case of dispersions, or by the addition of surfactants.

For parenteral administration, the compound is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Sterile injectable solutions can be prepared by mixing a compound of formulas I, II, or III with an appropriate solvent and one or more of the aforementioned carriers, followed by sterile filtering. In the case of sterile powders suitable for use in the preparation of sterile injectable solutions, preferable preparation methods include drying in vacuum and lyophilization, which provide powdery mixtures of the aldosterone receptor antagonists and desired excipients for subsequent preparation of sterile solutions.

The compounds according to the invention may be formulated for use in human or veterinary medicine by injection (e.g., by intravenous bolus injection or infusion or via intramuscular, subcutaneous or intrathecal routes) and may be presented in unit dose form, in ampoules, or other unit-dose containers, or in multi-dose containers, if necessary with an added preservative. The compositions for injection may be in the form of suspensions, solutions, or emulsions, in oily or aqueous vehicles, and may contain formulatory agents such as suspending, stabilizing, solubilizing and/or dispersing agents. Alternatively the active ingredient may be in sterile powder form for reconstitution with a suitable vehicle, e.g., sterile, pyrogen-free water, before use.

The compounds of the invention can be administered (e.g., orally or topically) in the form of tablets, capsules, ovules, elixirs, solutions or suspensions, which may contain flavoring or coloring agents, for immediate-, delayed-, modified-, sustained-, pulsed- or controlled-release applications.

The compounds of the invention may also be presented for human or veterinary use in a form suitable for oral or buccal administration, for example in the form of solutions, gels, syrups, mouth washes or suspensions, or a dry powder for constitution with water or other suitable vehicle before use, optionally with flavoring and coloring agents. Solid compositions such as tablets, capsules, lozenges, pastilles, pills, boluses, powder, pastes, granules, bullets or premix preparations may also be used. Solid and liquid compositions for oral use may be prepared according to methods well-known in the art. Such compositions may also contain one or more pharmaceutically acceptable carriers and excipients which may be in solid or liquid form.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia.

Additionally, lubricating agents such as magnesium stearate, stearic acid, glyceryl behenate and talc may be included.

The compositions may be administered orally, in the form of rapid or controlled release tablets, microparticles, mini tablets, capsules, sachets, and oral solutions or suspensions, or powders for the preparation thereof. In addition to the new solid-state forms of pantoprazole of the present invention as the active substance, oral preparations may optionally include various standard pharmaceutical carriers and excipients, such as binders, fillers, buffers, lubricants, glidants, dyes, disintegrants, odorants, sweeteners, surfactants, mold release agents, antiadhesive agents and coatings. Some excipients may have multiple roles in the compositions, e.g., act as both binders and disintegrants.

Examples of pharmaceutically acceptable disintegrants for oral compositions useful in the present invention include, but are not limited to, starch, pre-gelatinized starch, sodium starch glycolate, sodium carboxymethylcellulose, croscarmellose sodium, microcrystalline cellulose, alginates, resins, surfactants, effervescent compositions, aqueous aluminum silicates and cross-linked polyvinylpyrrolidone.

Examples of pharmaceutically acceptable binders for oral compositions useful herein include, but are not limited to, acacia; cellulose derivatives, such as methylcellulose, carboxymethylcellulose, hydroxypropylmethylcellulose, hydroxypropylcellulose or hydroxyethylcellulose; gelatin, glucose, dextrose, xylitol, polymethacrylates, polyvinylpyrrolidone, sorbitol, starch, pre-gelatinized starch, tragacanth, xanthane resin, alginates, magnesium-aluminum silicate, polyethylene glycol or bentonite.

Examples of pharmaceutically acceptable fillers for oral compositions include, but are not limited to, lactose, anhydrolactose, lactose monohydrate, sucrose, dextrose, mannitol, sorbitol, starch, cellulose (particularly microcrystalline cellulose), dihydro- or anhydro-calcium phosphate, calcium carbonate and calcium sulfate.

Examples of pharmaceutically acceptable lubricants useful in the compositions of the invention include, but are not limited to, magnesium stearate, talc, polyethylene glycol, polymers of ethylene oxide, sodium lauryl sulfate, magnesium lauryl sulfate, sodium oleate, sodium stearyl fumarate, and colloidal silicon dioxide.

Examples of suitable pharmaceutically acceptable odorants for the oral compositions include, but are not limited to, synthetic aromas and natural aromatic oils such as extracts of oils, flowers, fruits (e.g., banana, apple, sour cherry, peach) and combinations thereof, and similar aromas. Their use depends on many factors, the most important being the organoleptic acceptability for the population that will be taking the pharmaceutical compositions.

Examples of suitable pharmaceutically acceptable dyes for the oral compositions include, but are not limited to, synthetic and natural dyes such as titanium dioxide, beta-carotene and extracts of grapefruit peel.

Examples of useful pharmaceutically acceptable coatings for the oral compositions, typically used to facilitate swallowing, modify the release properties, improve the appearance, and/or mask the taste of the compositions include, but are not limited to, hydroxypropylmethylcellulose, hydroxypropylcellulose and acrylate-methacrylate copolymers.

Suitable examples of pharmaceutically acceptable sweeteners for the oral compositions include, but are not limited to, aspartame, saccharin, saccharin sodium, sodium cyclamate, xylitol, mannitol, sorbitol, lactose and sucrose.

Suitable examples of pharmaceutically acceptable buffers include, but are not limited to, citric acid, sodium citrate, sodium bicarbonate, dibasic sodium phosphate, magnesium oxide, calcium carbonate and magnesium hydroxide.

Suitable examples of pharmaceutically acceptable surfactants include, but are not limited to, sodium lauryl sulfate and polysorbates.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

The compounds of the invention may also, for example, be formulated as suppositories e.g., containing conventional suppository bases for use in human or veterinary medicine or as pessaries e.g., containing conventional pessary bases.

The compounds according to the invention may be formulated for topical administration, for use in human and veterinary medicine, in the form of ointments, creams, gels, hydrogels, lotions, solutions, shampoos, powders (including spray or dusting powders), pessaries, tampons, sprays, dips, aerosols, drops (e.g., eye ear or nose drops) or pour-ons.

For application topically to the skin, the agent of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax, sorbitan monostearate, a polyethylene glycol, liquid paraffin, polysorbate 60, cetyl esters wax, cetearyl alcohol, 2-octyldodecanol, benzyl alcohol, and water. Such compositions may also contain other pharmaceutically acceptable excipients, such as polymers, oils, liquid carriers, surfactants, buffers, preservatives, stabilizers, antioxidants, moisturizers, emollients, colorants, and odorants.

Examples of pharmaceutically acceptable polymers suitable for such topical compositions include, but are not limited to, acrylic polymers; cellulose derivatives, such as carboxymethylcellulose sodium, methylcellulose or hydroxypropylcellulose; natural polymers, such as alginates, tragacanth, pectin, xanthan and cytosan.

Examples of suitable pharmaceutically acceptable oils which are so useful include but are not limited to, mineral oils, silicone oils, fatty acids, alcohols, and glycols.

Examples of suitable pharmaceutically acceptable liquid carriers include, but are not limited to, water, alcohols or glycols such as ethanol, isopropanol, propylene glycol, hexylene glycol, glycerol and polyethylene glycol, or mixtures thereof in which the pseudopolymorph is dissolved or dispersed, optionally with the addition of non-toxic anionic, cationic or non-ionic surfactants, and inorganic or organic buffers.

Suitable examples of pharmaceutically acceptable preservatives include, but are not limited to, various antibacterial and antifungal agents such as solvents, for example ethanol, propylene glycol, benzyl alcohol, chlorobutanol, quaternary ammonium salts, and parabens (such as methyl paraben, ethyl paraben, propyl paraben, etc.).

Suitable examples of pharmaceutically acceptable stabilizers and antioxidants include, but are not limited to, ethylenediaminetetracetic acid (EDTA), thiourea, tocopherol and butyl hydroxyanisole.

Suitable examples of pharmaceutically acceptable moisturizers include, but are not limited to, glycerine, sorbitol, urea and polyethylene glycol.

Suitable examples of pharmaceutically acceptable emollients include, but are not limited to, mineral oils, isopropyl myristate, and isopropyl palmitate.

The compounds may also be dermally or transdermally administered, for example, by use of a skin patch.

For ophthalmic use, the compounds can be formulated as micronized suspensions in isotonic, pH adjusted, sterile saline, or, preferably, as solutions in isotonic, pH adjusted, sterile saline, optionally in combination with a preservative such as a benzylalkonium chloride.

As indicated, the compound of the present invention can be administered intranasally or by inhalation and is conveniently delivered in the form of a dry powder inhaler or an aerosol spray presentation from a pressurized container, pump, spray or nebulizer with the use of a suitable propellant, e.g., dichlorodifluoromethane, trichlorofluoromethane, dichlorotetrafluoroethane, a hydrofluoroalkane such as 1,1,1,2-tetrafluoroethane (HFA 134AT) or 1,1,1,2,3,3,3-heptafluoropropane (HFA 227EA), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e.g., using a mixture of ethanol and the propellant as the solvent, which may additionally contain a lubricant, e.g., sorbitan trioleate.

Capsules and cartridges (made, for example, from gelatin) for use in an inhaler or insufflator may be formulated to contain a powder mix of the compound and a suitable powder base such as lactose or starch.

For topical administration by inhalation the compounds according to the invention may be delivered for use in human or veterinary medicine via a nebulizer.

The pharmaceutical compositions of the invention may contain from 0.01 to 99% weight per volume of the active material. For topical administration, for example, the composition will generally contain from 0.01-10%, more preferably 0.01-1% of the active material.

The active agents can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The pharmaceutical composition or unit dosage forms comprising an effective amount of the present invention may be administered to an animal, preferably a human, in need of treatment of neuromuscular dysfunction of the lower urinary tract described by E. J. McGuire in "Campbell's UROLOGY", 5$^{th}$ Ed., 616-638, 1986, W.B. Saunders Company.

As used herein, the term "effective amount" refers to an amount that results in measurable amelioration of at least one symptom or parameter of a specific disorder. In a preferred embodiment, the compound treats disorders of the urinary tract, such as urinary urgency, overactive bladder, increased urinary frequency, reduced urinary compliance (reduced bladder storage capacity), cystitis (including interstitial cystitis), incontinence, urine leakage, enuresis, dysuria, urinary hesitancy and difficulty in emptying the bladder. In another preferred embodiment the compound treats migraine. In other preferred embodiment the compound is used to treat GERD.

The pharmaceutical composition or unit dosage form of the present invention may be administered according to a dosage and administration regimen defined by routine testing in the light of the guidelines given above in order to obtain optimal activity while minimizing toxicity or side effects for a particular patient. However, such fine tuning of the therapeutic regimen is routine in the light of the guidelines given herein.

The dosage of the active agents of the present invention may vary according to a variety of factors such as underlying disease conditions, the individual's condition, weight, sex and age, and the mode of administration. An effective amount for treating a disorder can easily be determined by empirical methods known to those of ordinary skill in the art, for example by establishing a matrix of dosages and frequencies of administration and comparing a group of experimental units or subjects at each point in the matrix. The exact amount to be administered to a patient will vary depending on the state and severity of the disorder and the physical condition of the patient. A measurable amelioration of any symptom or parameter can be determined by a person skilled in the art or reported by the patient to the physician. It will be understood that any clinically or statistically significant attenuation or amelioration of any symptom or parameter of urinary tract disorders is within the scope of the invention. Clinically significant attenuation or amelioration means perceptible to the patient and/or to the physician.

For example, a single patient may suffer from several symptoms of dysuria simultaneously, such as, for example, urgency and excessive frequency of urination or both, and these may be reduced using the methods of the present invention. In the case of incontinence, any reduction in the frequency or volume of unwanted passage of urine is considered a beneficial effect of the present method of treatment.

The amount of the agent to be administered can range between about 0.01 and about 25 mg/kg/day, preferably between about 0.1 and about 10 mg/kg/day and most preferably between 0.2 and about 5 mg/kg/day. It will be understood that the pharmaceutical formulations of the present invention need not necessarily contain the entire amount of the agent that is effective in treating the disorder, as such effective amounts can be reached by administration of a plurality of doses of such pharmaceutical formulations.

In a preferred embodiment of the present invention, the compounds of Formulas A, I, II, or III are formulated in capsules or tablets, preferably containing 10 to 200 mg of the compounds of the invention, and are preferably administered to a patient at a total daily dose of 10 to 300 mg, preferably 20 to 150 mg and most preferably about 50 mg, for relief of urinary incontinence and other dysfunctions.

A pharmaceutical composition for parenteral administration contains from about 0.01% to about 100% by weight of the active agents of the present invention, based upon 100% weight of total pharmaceutical composition.

Generally, transdermal dosage forms contain from about 0.01% to about 100% by weight of the active agents versus 100% total weight of the dosage form.

For treatment of lower urinary tract disorders, a mGlu5 antagonist may be administered in combination with at least one compound of an additional class of therapeutic agents. Such additional class could be that of antimuscarinic drugs such as, without limitation, oxybutynin, tolterodine, darifenacin, solifenacin, trospium, fesoterodine and temiverine.

Combination therapy with at least one mGlu5 antagonist may further include treatment with an alpha1-adrenergic antagonist. Preferred alpha1-adrenergic antagonists suitable for administration in combination with mGlu5 antagonists are, for example, and without limitation, prazosin, doxazosin, terazosin, alfuzosin, silodosin, and tamsulosin. Additional alpha1-adrenergic antagonists suitable for administration in combination with mGlu5 antagonists are described in U.S. Pat. Nos. 5,990,114; 6,306,861; 6,365,591; 6,387,909; and 6,403,594, incorporated herein by reference in their entireties.

Combination therapy with at least one mGlu5 antagonist may further include treatment with a serotonin and/or noradrenaline reuptake inhibitor. Examples of serotonin and/or noradrenaline reuptake inhibitors include, without limitation, duloxetine, milnacipran, amoxapine, venlafaxine, des-venlafaxine, sibutramine, tesofensine and des-methylsibutramine.

In certain embodiments, a serotonin and/or noradrenaline reuptake inhibitor suitable for administration in combination with mGlu5 antagonists is a selective serotonin reuptake inhibitor (i.e., an SSRI). In certain embodiments, a serotonin and/or noradrenaline reuptake inhibitors suitable for administration in combination with mGlu5 antagonists is a selective noradrenaline reuptake inhibitor (i.e., a NARI).

Combination therapy with at least one mGlu5 antagonist may further include treatment with a selective or non selective COX inhibitor. Examples of COX inhibitors include, without limitations, ibuprofen, naproxen, benoxaprofen, flurbiprofen, fenoprofen, fenbufen, ketoprofen, indoprofen, pirprofen, carprofen, tioxaprofen, suprofen, tiaprofenic acid, fluprofen, indomethacin, sulindac, tolmetin, zomepirac, diclofenac, fenclofenac, ibufenac, acetyl salicylic acid, piroxicam, tenoxicam, nabumetone, ketorolac, azapropazone, mefenamic acid, tolfenamic acid, diflunisal, acemetacin, fentiazac, clidanac, meclofenamic acid, flufenamic acid, niflumic acid, flufenisal, sudoxicam, etodolac, salicylic acid, benorylate, isoxicam, 2-fluoro-α-methyl[1,1'-biphenyl]-4-acetic acid 4-(nitrooxy)butyl ester (see Wenk et al. Europ. J. Pharmacol. 453, 319-324 (2002)), meloxicam, parecoxib, nimesulide.

The pharmaceutical composition or unit dosage form may be administered in a single daily dose, or the total daily dosage may be administered in divided doses. In addition, co-administration or sequential administration of another compound for the treatment of the disorder may be desirable. To this purpose, the combined active principles are formulated into a simple dosage unit.

For combination treatment where the compounds are in separate dosage formulations, the compounds can be administered concurrently, or each can be administered at staggered intervals. For example, the compound of the invention may be administered in the morning and the antimuscarinic compound may be administered in the evening, or vice versa. Additional compounds may be administered at specific intervals too. The order of administration will depend upon a variety of factors including age, weight, sex and medical condition of the patient; the severity and aetiology of the disorders to be treated, the route of administration, the renal and hepatic function of the patient, the treatment history of the patient, and the responsiveness of the patient. Determination of the order of administration may be fine-tuned and such fine-tuning is routine in the light of the guidelines given herein.

Synthesis of the Compounds of the Invention

It will be appreciated by those skilled in the art that it may be desirable to use protected derivatives of intermediates used in the preparation of the compounds of formulas A, I, II, or III. Protection and deprotection of functional groups may be performed by methods known in the art. Hydroxyl or amino groups may be protected with any hydroxyl or amino protecting group (for example, as described in Green and Wuts, Protective Groups in Organic Synthesis. John Wiley and Sons, New York, 1999). The protecting groups may be removed by conventional techniques. For example, acyl groups (such as alkanoyl, alkoxycarbonyl and aryloyl groups) may be removed by solvolysis (e.g., by hydrolysis under acidic or basic conditions). Arylmethoxycarbonyl groups (e.g., benzyloxycarbonyl) may be cleaved by hydrogenolysis in the presence of a catalyst such as palladium-on-carbon.

The synthesis of the target compounds is completed by removing any protecting groups which may be present in the penultimate intermediates using standard techniques, which are well-known to those skilled in the art. The deprotected final products are then purified, as necessary, using standard techniques such as silica gel chromatography, HPLC on silica gel and the like, or by recrystallization.

The compounds of the invention where R1 is H are generally prepared according to the following schemes:

vent, preferably THF or DME at a temperature between −78° C. and 0° C. This ylide is then reacted with the piperidones 3 in the same reaction vessel at −60 to 0° C. affording compounds 4 (Gibson, A. W.; Humphrey, G. R.; Kennedy, D. J.; Wright, S. H. B.; Synthesis 1991 (5), 414 or Boehmer, J.; Schobert, R.; J Chem Res, Synop, 1998, (7), 372-373).

The acetylenic compounds 4 could be alternatively obtained by reacting the piperidones 3 with the ylide obtained from (3-trimethylsilyl-2-propynyl)triphenylphosphonium bromide and e.g. BuLi in THF (Hann, M. M.; Sammes, P. G.; Kennewell, P. D.; Taylor, J. B.; J Chem Soc, Perkin Trans 1, 1982, 307 or Nicolaou, K. C.; Webber, S. E.; J Am Chem Soc 1984, 106, 5734) and reacting it in a similar way as above. Another suitable procedure consists in using (3-trimethylsilyl-2-propynyl)triphenylarsonium bromide (Shen, Yanchang; Liao, Quimu; J. Organomet. Chem.; 346; 1988; 181-184) and

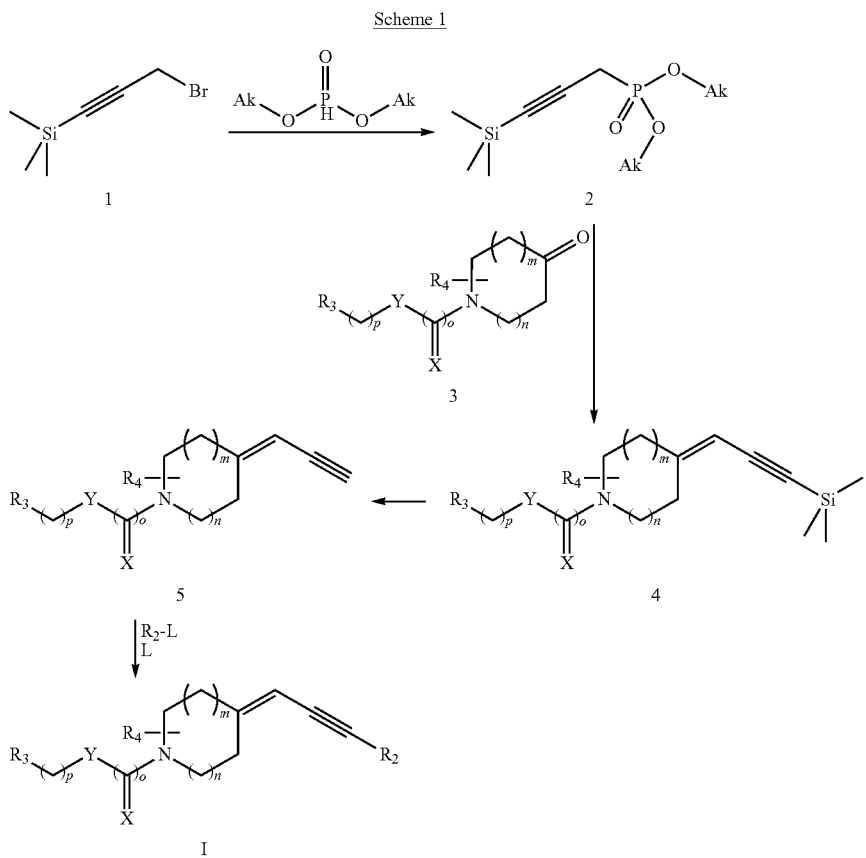

Scheme 1

$R_{1-4}$, Y, X, m, n, o, and p are the same as given in the general formula I.

In some embodiments, commercially available starting material (1) is added at a temperature of −10° C. to 25° C. to a solution of the pre-formed phosphanion generated in situ from an appropriate dialkyl phosphite (e.g. diethyl phosphite) treated with a base, preferably sodium or lithium bis-trimethylsilylamide, in an aprotic solvent, preferably THF or DME at a temperature between −50° C. and 0° C. This procedure affords compound 2 (see also Gibson, A. W.; Humphrey, G. R.; Kennedy, D. J.; Wright, S. H. B.; Synthesis 1991 (5), 414).

Compound 2 is then converted to the corresponding stabilized ylide by reaction with a base, preferably sodium or lithium bis-trimethylsilylamide (LiHMDS), in an aprotic sol-generating the arsenic ylide with BuLi or other suitable base and reacting it with piperidones 3.

The silyl protecting group of 4 is then removed by treatment with, for example, tetrabutylammonium fluoride in THF at a temperature in the range from room temperature to reflux or by hydrolysis with base ($K_2CO_3$ or KOH in MeOH) or other suitable method chosen from those reported in Greene-Wuts (Greene's Protective Groups in Organic Synthesis, 3rd Edition, Peter G. M. Wuts, Theodora W. Greene 1999, Wiley Interscience page 654-659) and well known by people skilled in the art. The so-obtained acetylenic compounds 5 are then transformed into compounds of Formula I by reacting them with $R_2$-L (where L=leaving group) following, for example, the Sonogashira procedure (Science of Synthesis, H. Heaney and S. Christie, October 2003, Vol. 3, Page 402 and following), that uses cuprous iodide and a palladium complex chosen from (Ph₃P)₂PdCl₂, (Ph₃P)₂Pd(OAc)₂, (Ph₃P)₄Pd (which can also be generated in situ e.g. from triphenylphosphine and Pd(OAc)₂) and all the other palladium complexes cited in the literature and used for this kind of reaction, in the presence of a base such as TEA, DEA, DIPEA, TMA, butylamine, piperidine. Solvents are chosen among THF, DME, DMF, DMA, EtOAc, DMSO, toluene and others suitable for the purpose of the reaction; or the same base in excess can be used as the reaction solvent. If one carries out the reaction in DMF or DME, the isolation of compounds 5 can be avoided by adding the tetrabutylammonium fluoride or tetrabutylammonium chloride directly to the reaction medium containing 4, before the coupling (Sorensen, U.S., Pombo-Villar, E. Tetrahedron 2005, 61, 2697-2703). The R₂ substituents are introduced using aryl or heteroaryl halogenides (preferred in decreasing order iodide, bromide, chloride), aryl or heteroaryl triflates, alkyl halogenides or acyl chlorides, aroyl chlorides, heteroaroyl chlorides. Triflates are synthesized using very well known method to people who have skills in the art, e.g. from phenols or hydroxyaryls (heteroaryls) using trifluoromethanesulphonic anhydride in a chlorinated solvent or using N-phenyltriflimide in toluene or a chlorinated solvent in the presence or not of a base (e.g. TEA). Both processes can be accelerated with the aid of microwaves performing the reaction in a microwave oven. Other suitable leaving groups L for R₂-L are nonaflates, tosylates and potassium trifluoborates.

Piperidones 3 are commercially available or can be easily prepared from piperidones, with the keto group free or protected as ketal, following easy procedures of acylation, (thio)carbamoylation, reductive amination, alkylation, arylation at the basic nitrogen very well known to those skilled in the art and well documented in the literature.

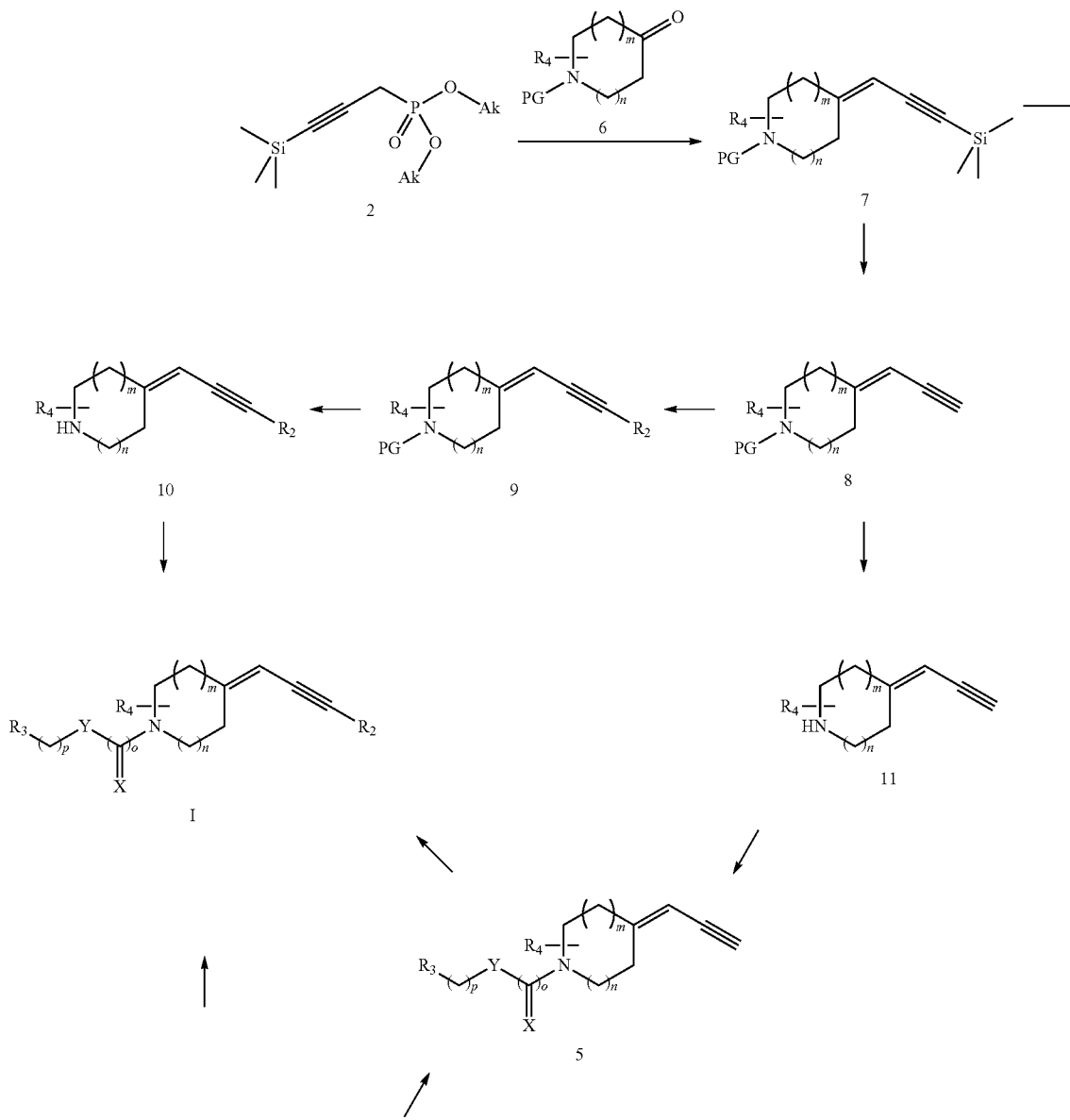

Scheme 2

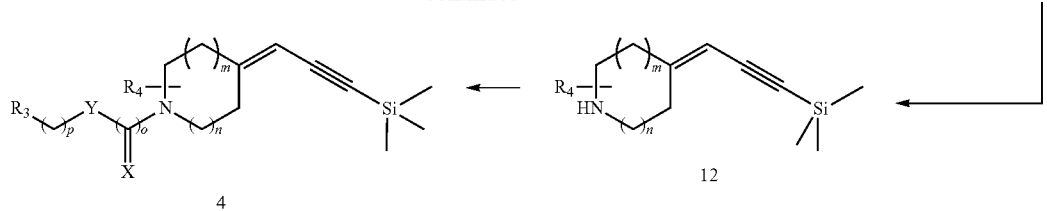

Scheme 2 represents a feasible and possible alternative to Scheme 1 for the obtention of compound I with $R_1$=H.

This synthetic path makes use of N-protected piperidones (commercially available or easily prepared by standard procedures), where PG is a properly chosen protective group like tert-butoxycarbonyl (Boc), fluorenylmethoxycarbonyl (Fmoc), benzyl (Bn), benzyloxycarbonyl (Z), trityl (Tr), arylsulphonyl or other. The protected piperidones 6 are reacted by the same methods described for compounds 3 to afford compounds 7. Compounds 7 are designed to provide orthogonal protection (i.e., the TMS can be deprotected while leaving the PG in tact and vice versa). So, compounds 7 can be sequentially converted, as described above for Scheme 1, to compounds 8 and 9 and deprotected to 10, following standard deprotection procedures chosen from those reported in Greene-Wuts (Greene's Protective Groups in Organic Synthesis, 3rd Edition, Peter G. M. Wuts, Theodora W. Greene 1999, Wiley Interscience page 654-659). 10 are synthons useful for synthesizing compounds of Formula I with a previously determined and fixed $R_2$ substituent by simple reaction procedures such as the Sonagashira reaction described above.

Alternatively, compounds 8 can be further N-deprotected by known procedures to afford compounds 11, which, in turn, are sequentially N-derivatized and subjected to the acetylenic CH derivatization as described above for compounds 5 in scheme 1.

Alternatively, selective deprotection of the N-PG groups of 7 leads to compounds 12, which can be reacted as described above to provide compounds 4, further derivatizable following scheme 1 to afford the compounds of Formula I The compounds I of the invention where R1 is as described in the general formula I (H also included) can be generally prepared according to the following scheme 3:

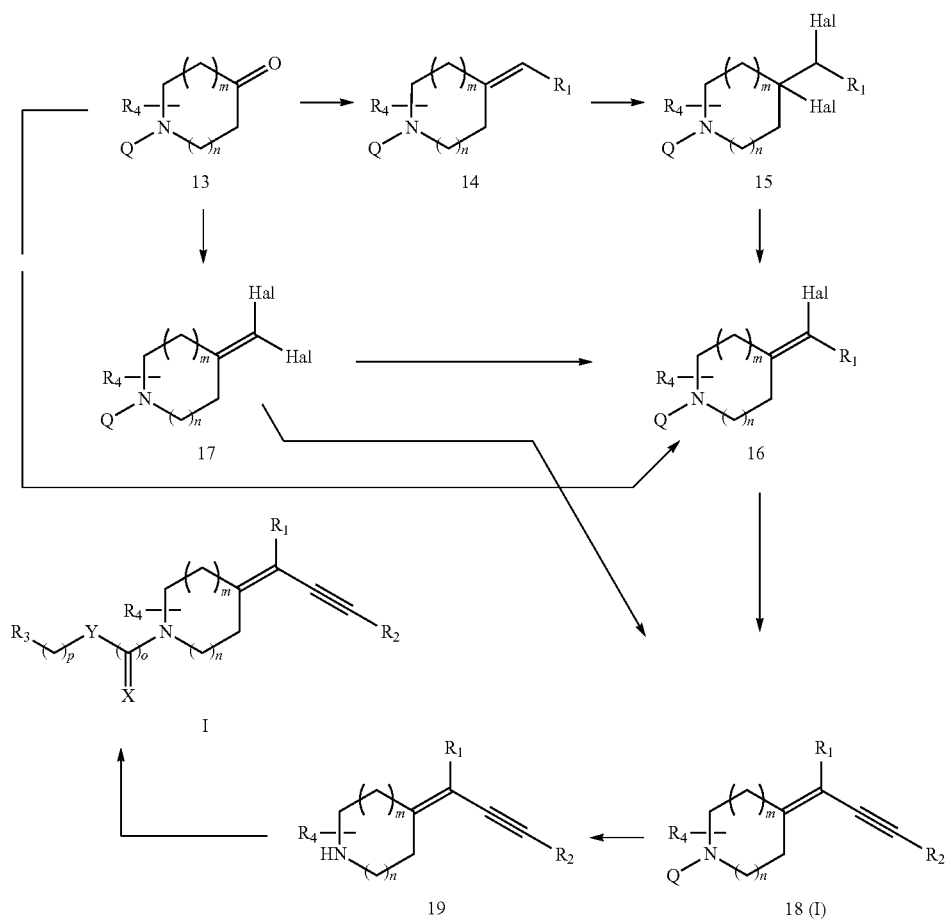

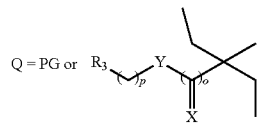

Protective group (PG) is as defined above and $R_{1-4}$, Y, X, m, n, o, and p are the same as given in the general formula I.

Compounds 14 can be obtained from piperidones 13 using standard olefination conditions such as Wittig, Horner-Hemmons, Petersen or arsenic based methodologies. Some general reviews of these methodologies and directions are contained in the following references: 'The Wittig reaction and related methods', N. J. Lawrence in Preparation of Alkenes, J. M. J. Williams, Ed., Oxford University Press, Oxford (1996); pp 19-58; Phosphorus Ylides, 0.1. Kolodiazhnyi, Wiley, N.Y. (1999); A. W. Johnson, Ylides and Imines of Phosphorus, Wiley, N.Y. (1993); Ager, D. J. *Org. React.* 1990, 38, 1-223.

When the reaction is conducted using a triphenylphosphonium salt, butyl lithium or LDA (lithium diisopropylamide) or LHMDS (lithium hexamethyldisilylamide) can be used to generate the phosphorus ylide in THF or other aprotic solvent (e.g. DME) and the ylide is reacted with the proper piperidone to provide the desired product. The phosphinate, phosphine oxide or phosphonate based reagents can be used with similar bases or with sodium or potassium methoxide or ethoxide in alcoholic solvents or with sodium hydride in aprotic solvents.

Compounds 14 are then easily converted to compounds 16, usually without isolation of the intermediate dihaloderivatives 15, carrying out first a dihalogenation of the olefinic bond using $Br_2$, NCS, NBS or other reagents in a suitable solvent e.g. AcOH or a chlorinated solvent, followed by dehydrohalogenation of compounds 15 by using a suitable base ($K_2CO_3$, DBU, DMAP or alike).

If one reacts compounds 13 using the same olefination reactions as above but using $CHBr_3$ or $CBr_4$ or $CHFBr_2$ or $CFBr_3$ and triphenylphosphine (or other triarylphosphine bounded or not to a polymeric resin) in the presence or not of a catalyst like $ZnBr_2$ or diethylzinc, compounds 17 are easily obtained. Use of $CBr_4$ leads to the 1,1-dibromovinyl derivative 17, which can be reacted on turn with an organometallic species e.g. methylmagnesium bromide to give the derivative 16 (R1=Alkyl, Phenyl) or reacted with a strong organic base (e.g. BuLi or NaHMDS or alike) to generate the carbanion, which is in turn reacted with an electrophile (e.g. $CH_3I$) to afford 16 (R1=Alkyl, Phenyl).

The use of an halomethylphosphorous reagent (e.g. chloromethyltriphenyl phosphonium chloride or diphenylchloromethylphenylphosphonate) leads, using the same methodologies described above for the Horner reaction, directly to compounds 16 starting from Compounds 13.

An alternative methodology useful for executing the conversion of 13 to 17 concerns the use of $CH_2Br_2$ or $CH_2I_2$ or $CH_2Cl_2$ or $CHI_3$ in the presence of $TiCl_4$ and magnesium or in the presence of a titanium complex or with $CrCl_2$.

Compounds 16 (or Compounds 17 where (Hal, Hal is fluoro and iodo, or fluoro and bromo) are then reacted in a Sonogashira fashion (see above) to give Compounds 18 (I) with R1=F.

Compounds 18, where Q is equal to PG (Protecting Group), must be submitted to a further deprotection step leading to Compounds 19, as described above in Scheme 2. Compounds 19 can be properly converted into Compounds I with the standard procedures described above.

Scheme 4

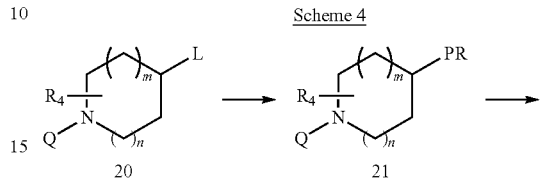

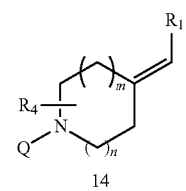

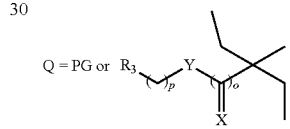

Scheme 4, where L is a proper leaving group (halogen, mesylate, tosylate or other), PR is a phosphorous containing residue (e.g., dialkoxyphosphoryl, diphenoxyphosphoryl, triphenylphosphinyl, triphenylarsinyl or the like), Protective group (PG) is as defined above and $R_{1-4}$, Y, X, m, n, o, and p are the same as given in the general formula I, describes an alternative procedure for preparing compounds 14 with R1=alkyl or phenyl. This method involves reacting compounds 20 (which are commercially available, like 4-bromo-1-Bocpiperidine, or easily prepared by standard procedures very well known to those who have skills in the art, e.g. by reacting the corresponding 4-piperidinol derivatives (commercially available or easily synthesized from piperidones) with methanesulphonyl chloride or para-toluenesulphonyl chloride in a suitable solvent like THF or dichloromethane or toluene in the presence of a base like TEA or DMAP (4-dimethylaminopyridine) (WO 200597760) or by halogenating the same piperidinol derivatives via Mitsonobu procedure using $CBr_4$ or $CCl_4$, $Ph_3P$, THF or other solvent or by derivatizing 4-bromopiperidine hydrobromide commercially available), following the Arbuzov procedure or other suitable method and generating phosphonium salts or phosphonates or other phosphorous intermediates, which on turn can be coupled with an aldehyde or ketone by a Wittig-Horner procedure to afford compounds 14 (R1=Alkyl, Phenyl).

Scheme 5

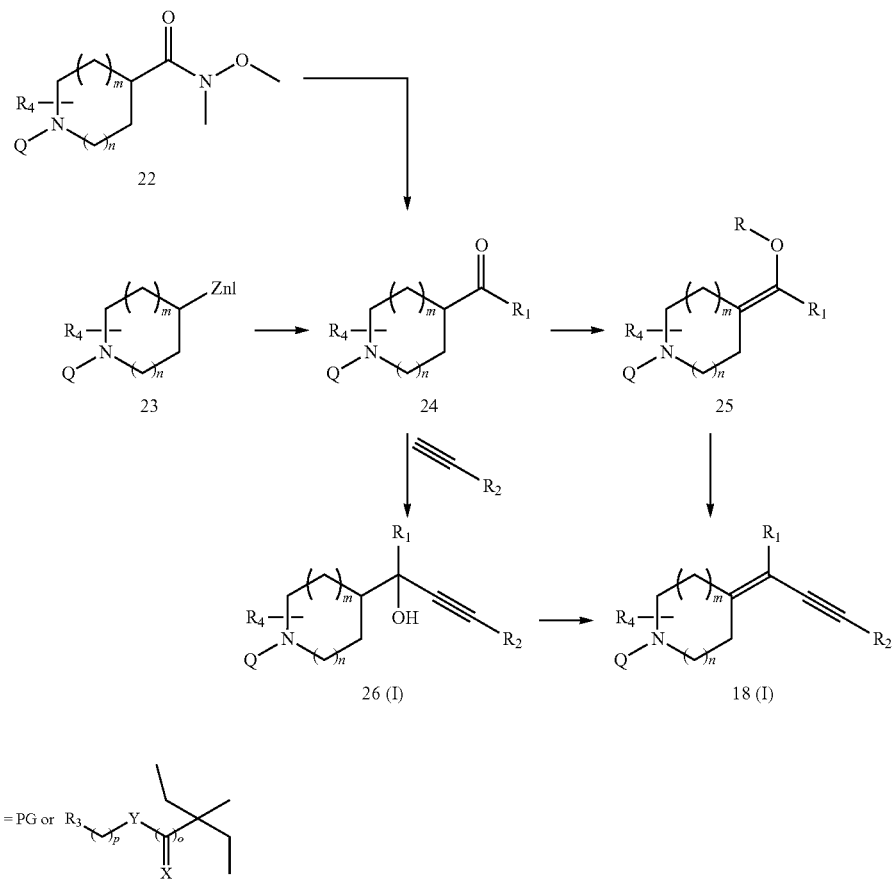

Scheme 5, where Protective group (PG) is as defined above and $R_{1-4}$, Y, X, m, n, o, and p are the same as given in the general formula I, shows another synthetic opportunity to obtain compounds 18 (I). Weinreb amides 22 (L. De Luca, G. Giacomelli, M. Taddei, *J. Org. Chem.*, 2001, 66, 2535-2537) can be reacted according to the well known methods, with Grignard reagents or lithium reagents to afford ketones 24. In the case where R1=H compounds 24 are commercially available or are very easily synthesized from commercially available starting materials e.g. by reacting a commercially available N-protected-4-piperidinecarboxylic acid with N-methoxy-N-methylamine hydrochloride through a condensing agent (e.g. BOP-Cl) and transforming it into the corresponding Weinreb amide 22, which is readily reduced to afford compounds 24 with $LiAlH_4$ in THF or diethyl ether (*J. Med. Chem.* 1998, 41, 2492-2502) or by oxidizing the corresponding 4-piperidinylmethanol derivatives (on turn prepared by borane reduction from the acid) e.g. by pyridinium chlorochromate in dichloromethane (*J. Med. Chem.* 1999, 42, 2409-2421. The facile conversion to enol triflates or enol sulphonates 25 (R=$CF_3SO_2$, p-MePhSO_2$) by pre-forming the enol derivative from 24 with a strong base like LDA or LiHMDS and sulphonylating it with $Tf_2O$ or N-phenyltriflimide or other activated triflimide or para-toluenesulphonyl chloride in a proper solvent like THF or other aprotic solvent at −78° C. to r.t. in the presence or not of a base like TEA guarantees a good starting material for conversion to compounds 18 (I) by the Sonogashira coupling described above.

Alternatively compounds 23 (Corley, E. G. et al., J Org Chem, 69, (15), 2004, 5120-5123) can be reacted in a Palladium-catalyzed coupling with acyl chlorides to afford compounds 24.

Compounds 24 can be also condensed with acetylenic compounds $R_2C\equiv CH$ using Lewis acid methodologies or Aldol type reactions by the use of bases to afford compounds 26 (I), which can be in turn dehydrated to give Compounds 18 (I).

Compounds 18 and 26, where Q is equal to PG (Protecting Group), must be submitted to a further deprotection step leading to N-deprotected compounds, as described above in Scheme 2. The so-obtained compounds can be properly N-derivatized to Compounds I with the standard procedures described above.

Scheme 6

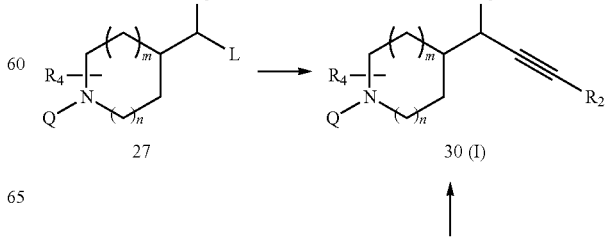

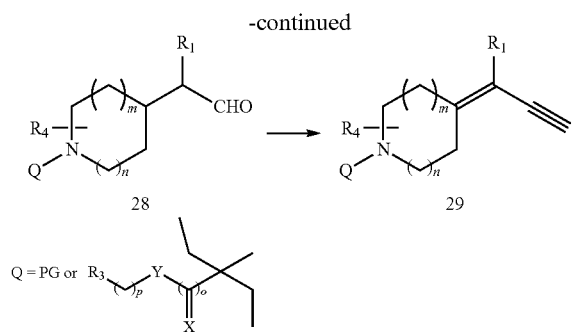

Scheme 6, in which Protective Group (PG) is as defined above and $R_{14}$, Y, X, m, n, o, and p are the same as given in the general formula I, describes the synthetic pathways useful for the preparation of Compounds 30, where the $R_1$C-piperidine bond (/)

is a single bond. Compounds 27, where L is a leaving group, are commercially available or easily prepared by standard procedures very well known to those skilled in the art e.g. by halogenating the corresponding 4-hydroxymethylpiperidino derivatives with $CBr_4$ or $CCl_4$, triphenylphosphine in dichloromethane or by more conventional method of halogenation or converting the same hydroxymethyl derivatives into the tosylate or mesylate by the use of methanesulphonyl chloride or para-toluenesulphonyl chloride in the presence of a base. They can be reacted with acetylenic compounds in aprotic solvents after deprotonation of the acetylenic CH by the use of a strong base (e.g. butyl lithium). An alternative procedure consists in converting aldehydes 28, which are commercially available or easily prepared by standard procedures very well known to those skilled in the art e.g. using the same procedure described above for preparing Compound 24 with R1=H but starting from corresponding piperidine-4-acetic acid derivatives or piperidine-4-(2-hydroxyethyl) derivatives, into acetylenes 29 (T. Gibtner et al., *Chem. Eur. J.*, 2002, 68, 408-432). This transformation can be done by using e.g. the Corey-Fuchs procedure or other similar procedures, cited in the literature.

A convenient procedure, especially when $R_2$ is alkyl, consists in reacting the aldehyde 28 with lithiated dichloromethane (e.g., by LDA), that leads to the dichloromethyl alcohol, which is then tosylated in situ and eliminated by BuLi generating the alkynyl lithium species, quenched by an electrophile (*Organic Syntheses*, Vol. 81, p. 157 (2005)).

Compounds 30 or 29, where Q is equal to PG (Protecting Group), must be submitted to a further deprotection step leading to N-deprotected compounds, as described above in Scheme 2. The so-obtained compounds can be properly N-derivatized to Compounds I with the standard procedures described above.

The syntheses of other compounds of the invention included in the Examples, which are not currently described in this general description of the synthesis of the compounds of the invention are well documented inside the experimental part of this invention.

The free bases of formula I, their diastereomers or enantiomers can be converted to the corresponding pharmaceutically acceptable salts under standard conditions well known in the art. For example, the free base is dissolved in a suitable organic solvent, such as methanol, treated with, for example one equivalent of maleic or oxalic acid, one or two equivalents of hydrochloric acid or methanesulphonic acid, and then concentrated under vacuum to provide the corresponding pharmaceutically acceptable salt. The residue can then be purified by recrystallization from a suitable organic solvent or organic solvent mixture, such as methanol/diethyl ether.

The N-oxides of compounds of formula I can be synthesized by simple oxidation procedures well known to those skilled in the art which comprises the use of oxidizing reagents like magnesium monoperoxyphtalate in EtOAc, hydrogen peroxide in acetic acid, meta-chloroperbenzoic acid or other peracids.

The following examples represent synthesis of the compounds of Formula I as described generally above. These examples are illustrative only and are not intended to limit the scope of the invention. The reagents and starting materials are readily available to one of ordinary skill in the art.

As used herein, the following terms have the meanings indicated: "aq." refers to aqueous; "eq." refers to equivalents; "g" refers to grams; "mg" refers to milligrams; "L" refers to liters; "mL" refers to milliliters; "µL" refers to microliters; "mol" refers to moles; "mmol" refers to millimoles; "psi" refers to pounds per square inch; "min" refers to minutes; "h" refers to hours; "° C." refers to degrees Celsius; "TLC" refers to thin layer chromatography; "HPLC" refers to high performance liquid chromatography; "Rf" refers to retention factor; "Rt" refers to retention time; "δ" refers to part per million down-field from tetramethylsilane; "HRMS" refers to high resolution mass spectrometry; "r.t." refers to room temperature.

All patents, patent applications and literature references cited in the description are hereby incorporated herein by reference in their entirety. In the case of inconsistencies, the present disclosure, including definitions, will prevail.

The present invention is not limited in scope by the specific embodiments described herein. Indeed, various modifications of the invention in addition to those described herein will become apparent to those skilled in the art from the foregoing description. Such modifications are intended to fall within the scope of the appended claims. It is further to be understood that all values given in the examples herein are approximate, and are provided for purposes of illustration.

EXAMPLE 1

2-{4-[3-(6-Methylpyridin-2-yl)prop-2-ynylidene] piperidin-1-yl}-3-nitropyridine

Diethyl (3-trimethylsilylprop-2-ynyl)phosphonate (Compound 1a)

Into a solution of LiHMDS (1M in THF, 63.8 mL, 63.8 mmol) in anhydrous THF (162 mL) was added dropwise under stirring at −10° C. in nitrogen atmosphere diethyl phosphite (7.4 mL, 63.8 mmol). The obtained solution was stirred at the same temperature for 20 min. Afterwards, 3-bromo-1-trimethylsilyl-1-propyne (10 mL, 63.8 mmol) was dropped into and the reaction mixture was stirred at −10° C. for 2 h., then quenched with water and extracted with EtOAc. The combined organic layers were washed with brine, dried on $Na_2SO_4$ and evaporated to dryness in vacuo to afford 14.86 g of the title product.

$^1$H-NMR (CDCl$_3$, δ): conform to Feringa, Ben L. et al., Org. Biomol. Chem., Volume 3 (14), 2005, 2524-2533

MS: [M+NH4]$^+$=266.15

2-[4-(1-Trimethysilylbut-2-ynylidenepiperidin-1-yl)-3-nitropyridine (Compound 1b)

Into a solution of Compound 1a (0.68 g, 2.74 mmol) in anhydrous THF (15 mL) stirred at −60° C. under $N_2$ stream, was dropped a solution of LiHMDS (1M in THF, 2.74 mL, 2.74 mmol) and the mixture was stirred at −60° C. for 15 min. To the resulting solution was added dropwise a solution of 1-(3-nitropyridin-2-yl)piperidin-4-one (0.55 g, 2.49 mmol) in anhydrous THF (12 mL). The reaction mixture was stirred at −60° for 15 min., then it was allowed to warm up to r.t. over 2 h. Afterwards, it was quenched with water and extracted with EtOAc. The combined organic layers were washed with brine, dried on $Na_2SO_4$ and evaporated to dryness in vacuo to afford 0.79 g of the title product. The crude was enough pure to be used in the following step without any further purification

MS: $[M+H]^+$=316.16

3-Nitro-2-(4-prop-2-ynylidenepiperidin-1-yl)pyridine (Compound 1c)

A solution of Compound 1b (0.57 g, 1.81 mmol), tetra-n-butylammonium fluoride hydrate (0.57 g, 2.03 mmol) in 38 mL of THF was stirred at r.t. for 2 h. The reaction mixture was poured into water and extracted with EtOAc. The combined organic layers were washed with brine, dried on $Na_2SO_4$ and evaporated to dryness in vacuo to afford a residue, which was purified by flash chromatography (EtOAc—Petroleum Ether 1:9) giving the title product (0.21 g).

MS: $[M+H]^+$=244.13

2-{4-[3-(6-Methylpyridin-2-yl)prop-2-ynylidene]piperidin-1-yl}-3-nitropyridine A mixture of Compound 1c (0.21 g, 0.86 mmol), 2-bromo-6-methylpyridine (0.11 mL, 0.95 mmol), tetrakis(triphenylphosphine)palladium(0) (70 mg, 0.06 mmol), CuI (16 mg, 0.09 mmol) in anhydrous and degassed triethylamine (10 mL) was heated at 80° C. under a nitrogen atmosphere for 2 h in sealed vessel. The reaction mixture was cooled, poured into water and extracted with EtOAc. The combined organic layers were washed with brine, dried on $Na_2SO_4$ and evaporated to dryness in vacuo to afford a residue, which was purified by flash chromatography (EtOAc—Petroleum Ether 3.5:6.5) affording the title product (0.20 g).

$^1$H-NMR (CDCl$_3$, δ): 2.48-2.55 (m, 2H), 2.61 (s, 3H), 2.80-2.85 (m, 2H), 3.50-3.58 (m, 4H), 5.66 (s, 1H), 6.75-6.80 (m, 1H), 7.09 (d, 1H, J=7.46 Hz), 7.24-7.29 (m, 1H), 7.55 (t, 1H, J=7.46 Hz), 8.14-8.19 (m, 1H), 8.35-8.38 (m, 1H)

MS: $[M+H]^+$=335.12

EXAMPLE 2 tert-Butyl 4-[3-(6-methylpyridin-2-yl)prop-2-ynylidene]piperidin-1-carboxylate tert-Butyl 4-(3-trimethylsilylprop-2-ynylidene)piperidin-1-carboxyate (Compound 2a)

The title compound was obtained following the procedure described for Compound 1b but using 1-tert-butoxycarbonylpiperidin-4-one instead of 1-(3-nitropyridin-2-yl)piperidin-4-one. After the usual work-up procedure, evaporation of the combined EtOAc extracts afforded a crude which was enough pure to be used in the next step without further purification.

$^1$H-NMR (CDCl$_3$, δ): 0.21 (s, 9H), 1.50 (s, 9H), 2.21-2.27 (m, 2H), 2.48-2.53 (m, 2H), 3.40-3.51 (m, 4H), 5.40 (s, 1H)

MS: $[M+H]^+$=294.29 tert-Butyl 4-prop-2-ynylidenepiperidine-1-carboxyate (Compound 2b)

The title compound was obtained following the procedure described for Compound 1c but using Compound 2a instead of Compound 1c. After the usual work-up procedure, evaporation of the combined EtOAc extracts afforded a crude which was enough pure to be used in the next step without further purification.

$^1$H-NMR (CDCl$_3$, δ): 1.50 (s, 9H), 2.20-2.27 (m, 2H), 2.48-2.53 (m, 2H), 3.02 (s, 1H), 3.40-3.51 (m, 4H), 5.48 (s, 1H)

MS: $[M+H]^+$=222.23 tert-Butyl 4-[3-(6-methylpyridin-2-yl)prop-2-ynylidene]piperidine-1-carboxylate The title compound was obtained following the procedure described for the Compound of Example 1, but starting from Compound 2b instead of Compound 1c. After the usual work-up procedure, evaporation of the combined EtOAc extracts afforded a crude which was purified by flash chromatography (EtOAc—Petroleum Ether 3.5:6.5) affording the title product.

$^1$H-NMR (CDCl3, δ): 1.50 (s, 9H), 2.29-2.35 (m, 2H), 2.58 (s, 3H), 2.59-2.65 (m, 2H), 3.45-3.55 (m, 4H), 5.60 (s, 1H), 7.09 (d, 1H, J=7.51 Hz), 7.26 (d, 1H, 7.51 Hz), 7.55 (t, 1H, J=7.51 Hz)

MS: $[M+H]^+$=313.27

EXAMPLE 3

2-Methyl-6-(3-piperidin-4-ylideneprop-1-ynyl)pyridine

To a solution of the Compound of Example 2 (17 g, 54.4 mmol) in CHCl$_3$ (840 mL) was added trifluoroacetic acid (60 mL, 779 mmol) and the reaction mixture was then stirred at 70° C. for 15 min. until the complete conversion of the reagent was observed by LC-MS. After cooling to r.t., water was added followed by aq. NaOH (2N) to make alkaline the pH. Separation of the organic layer and extraction of the aqueous layer with CH$_2$Cl$_2$, washing with brine and drying over Na$_2$SO$_4$ afforded the title compound (11.6 g).

$^1$H-NMR (CDCl3, δ): 2.29-2.35 (m, 2H), 2.58 (s, 3H), 2.59-2.65 (m, 2H), 2.91-2.99 (m, 4H), 5.52 (s, 1H), 7.07 (d, 1H, J=7.54 Hz), 7.24 (d, 2H, 7.54 Hz), 7.53 (t, 1H, J=7.54 Hz)

MS: $[M+H]^+$=213.25

EXAMPLE 4

2-Methyl-6-{3-[1-(2-nitrophenyl)piperidin-4-ylidene]prop-1-ynyl}pyridine

A well homogenised mixture of the Compound of Example 3 (20 mg, 0.09 mmol) and 1-bromo-2-nitrobenzene (22.8 mg, 0.11 mmol) was stirred at 90° C. for 0.5 h, then at 110° C. for 1 h. The reaction crude was purified by flash chromatography (EtOAc—Petroleum Ether gradient from 3:7 to 4:6) affording the title product (8.3 mg).

$^1$H-NMR (CDCl3, δ): 2.50-2.55 (m, 2H), 2.61 (s, 3H), 2.82-2.87 (m, 2H), 3.11-3.16 (m, 2H), 3.16-3.21 (m, 2H), 5.62 (s, 1H), 7.03-7.16 (m, 2H), 7.19 (d, 1H, J=7.51 Hz), 7.26-7.30 (m, 1H), 7.48 (t, 1H, J=7.51 Hz), 7.52-7.64 (m, 1H), 7.81 (d, 1H)

MS: [M+H]$^+$=334.30

EXAMPLE 5

6-Methyl-2-[4-[3-(6-methylpyridin-2-yl)prop-2-ynylidene]piperidin-1-yl]-3-nitropyridine A well homogenised mixture of the Compound of Example 3 (23 mg, 0.11 mmol) and 6-chloro-5-nitro-2-picoline (26.2 mg, 0.15 mmol) was stirred at 120° C. for 0.5 h. The reaction crude was purified by flash chromatography (EtOAc—Petroleum Ether gradient from 3:7 to 4:6) affording the title product (21 mg).

$^1$H-NMR (CDCl3, δ): 2.48 (s, 3H), 2.49-2.53 (m, 2H), 2.67 (s, 3H), 2.81-2.86 (m, 2H), 3.49-3.55 (m, 2H), 3.56-3.60 (m, 2H), 5.66 (s, 1H), 6.61 (d, 1H, J=8.2 Hz), 7.13-7.18 (m, 1H), 7.29-7.35 (m, 1H), 7.60-7.70 (m, 1H), 8.09 (d, 1H, J=8.2 Hz)

MS: [M+H]$^+$=349.41

EXAMPLE 6

6-Methoxy-2-{4-[3-(6-methylpyridin-2-yl)prop-2-ynylidene]piperidin-1-yl}-3-nitropyridine A well homogenised mixture of the Compound of Example 3 (23 mg, 0.11 mmol) and 2-chloro-3-nitro-5-methoxypyridine (24.4 mg, 0.13 mmol) was stirred at 120° C. for 0.5 h. The reaction crude was purified by flash chromatography (EtOAc—Petroleum Ether gradient from 2:8 to 3:7) affording the title product (24 mg).

$^1$H-NMR (CDCl3, δ): 2.50-2.55 (m, 2H), 2.66 (s, 3H), 2.85-2.90 (m, 2H), 3.50-3.55 (m, 2H), 3.60-3.65 (m, 2H), 3.97 (s, 3H), 5.68 (s, 1H), 6.17 (d, 1H, J=8.76 Hz), 7.13-7.18 (m, 1H), 7.29-7.35 (m, 1H), 7.60-7.70 (m, 1H), 8.25 (d, 1H, J=8.76 Hz)

MS: [M+H]$^+$=365.36

EXAMPLE 7

2-Methyl-6-{3-[1-(5-methyl-2-nitrophenyl)piperidin-4-ylidene]prop-1-ynyl}pyridine A well homogenised mixture of the Compound of Example 3 (19 mg, 0.89 mmol) and 3-fluoro-4-nitrotoluene (20.2 mg, 0.13 mmol) was stirred at 120° C. for 0.5 h. The reaction crude was purified by flash chromatography (EtOAc—Petroleum Ether gradient from 2:8 to 3:7) affording the title product (18 mg).

$^1$H-NMR (CDCl3, δ): 2.40 (s, 3H), 2.52-2.57 (m, 2H), 2.68 (s, 3H), 2.85-2.92 (m, 2H), 3.10-3.15 (m, 2H), 3.17-3.22 (m, 2H), 5.64 (s, 1H), 6.85 (d, 1H, J=8.19 Hz), 6.93 (s, 1H), 7.13-7.20 (m, 1H), 7.30-7.37 (m, 1H), 7.60-7.72 (m, 1H), 7.78 (d, 1H, J=8.19 Hz)

MS: [M+H]$^+$=348.36

EXAMPLE 8

2-{3-[1-(5-Methoxy-2-nitrophenyl)piperidin-4-ylidene]prop-1-ynyl}-6-methylpyridine A well homogenised mixture of the Compound of Example 3 (20 mg, 0.93 mmol) and 2-fluoro-4-methoxynitrobenzene (21.3 mg, 0.12 mmol) was stirred at 120° C. for 0.5 h. The reaction crude was purified by flash chromatography (EtOAc—Petroleum Ether 1:1) affording the title product (21 mg).

$^1$H-NMR (CDCl3, δ): 2.55-2.62 (m, 2H), 2.80 (s, 3H), 2.93-3.02 (m, 2H), 3.10-3.18 (m, 2H), 3.22-3.28 (m, 2H), 3.88 (s, 3H), 5.66 (s, 1H), 6.51-6.59 (m, 2H), 7.19-7.31 (m, 1H), 7.36-7.46 (m, 1H), 7.73-7.87 (m, 1H), 8.05 (d, 1H)

MS: [M+H]$^+$=364.31

EXAMPLE 9

3-Nitro-2-[4-(3-pyridin-2-ylprop-2-ynylidene)piperidin-1-yl]pyridine

The title compound was obtained as described for the Compound of Example 1, reacting Compound 1c with 2-iodopyridine instead of 2-bromo-6-methylpyridine. The crude was purified by flash chromatography (EtOAc—Petroleum Ether 1:1) affording the title compound.

$^1$H-NMR (CDCl3, δ): 2.50-2.55 (m, 2H), 2.80-2.85 (m, 2H), 3.50-3.60 (m, 4H), 5.68 (s, 1H), 6.78 (dd, 1H, J=4.6 and 7.8 Hz), 7.27-7.32 (m, 1H), 7.48 (d, 1H, J=7.84 Hz), 7.81 (t, 1H, J=4.2 Hz), 8.16 (dd, 1H, J=7.8 Hz and 1.7 Hz), 8.36 (dd, 1H, J=1.7 Hz and 4.2 Hz), 8.60-8.65 (m, 1H)

MS: [M+H]$^+$=321.10

EXAMPLE 10

3-Nitro-2-[4-(3-phenylprop-2-ynylidene)piperidin-1-yl]pyridine

The title compound was obtained as described for the Compound of Example 1, reacting Compound 1c with iodobenzene instead of 2-bromo-6-methylpyridine. Purification by flash chromatography with Petroleum Ether-EtOAc 65:35 afforded the title product.

$^1$H-NMR (CDCl3, δ): 2.50-2.55 (m, 2H), 2.76-2.81 (m, 2H), 3.52-3.60 (m, 4H), 5.65 (s, 1H), 6.80 (dd, 1H, J=4.6 and 7.8 Hz), 7.30-7.36 (m, 3H), 7.43-7.47 (m, 2H), 8.19 (d, 1H, J=7.8 Hz), 8.38 (d, 1H, J=4.2 Hz)

MS: [M+H]$^+$=320.24

EXAMPLE 11

3-Nitro-2-[4-(3-pyridin-3-ylprop-2-ynylidene)piperidin-1-yl]pyridine

The title compound was obtained as described for the Compound of Example 1, reacting Compound 1c with 3-iodopyridine instead of 2-bromo-6-methylpyridine. Purification by flash chromatography with Petroleum Ether-EtOAc 6:4 afforded the compound of Example 11.

$^1$H-NMR (CDCl3, δ): 2.52-2.57 (m, 2H), 2.74-2.79 (m, 2H), 3.50-3.60 (m, 4H), 5.67 (s, 1H), 6.82 (dd, 1H, J=4.4 and 7.8 Hz), 7.66-7.74 (m, 1H), 8.13-8.21 (m, 2H), 8.38 (dd, 1H), 8.58-8.63 (m, 1H), 8.72-8.77 (m, 1H).

MS: [M+H]$^+$=321.30

EXAMPLE 12

4-[3-(6-Methylpyridin-2-yl)prop-2-ynylidene]-N-phenylpiperidine-1-carboxamide To a solution of the Compound of Example 3 (0.11 g, 0.52 mmol) in $CH_2Cl_2$ (10 mL) was added phenylisocyanate (0.06 mL, 0.54 mmol) and the reaction mixture was stirred overnight at r.t.

Evaporation and purification of the crude by automated flash liquid chromatography (Horizon™-Biotage) eluting with a gradient Petroleum Ether-EtOAc from 87:13 to 0:100 gave the title product (154 mg).

$^1$H-NMR (CDCl3, δ): 2.41-2.46 (m, 2H), 2.64 (m, 3H), 2.74-2.79 (m, 2H), 3.57-3.62 (m, 4H), 5.65 (s, 1H), 6.58 (s, 1H), 7.05 (t, 1H, J=7.52 Hz), 7.14 (d, 1H, J=7.88 Hz), 7.28-7.34 (m, 3H), 7.38-7.42 (m, 2H), 7.63 (t, 1H, J=7.88 Hz)

MS: $[M+H]^+$=332.4

EXAMPLE 13-26

Table I

These compounds were synthesized following the procedure described in Example 12 substituting reagent B (see table I below) for phenylisocyanate. Purification was carried out by automated flash liquid chromatography (Horizon™-Biotage) eluting with a gradient Petroleum Ether-EtOAc from 100:0 to 20:80. The compounds of Example 17 and 18 were further purified by preparative RP LC-MS chromatography, using MS-C18 XTerra column 30×50 mm eluting with ammonium bicarbonate 20 mM pH 8 buffer-acetonitrile gradient.

| Ex. | Structure | Reagent B |
|---|---|---|
| 13 | 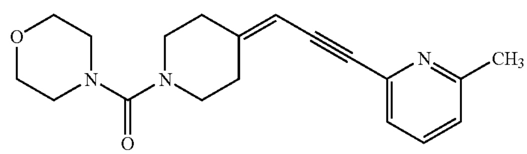 [SMILES: Cc1cccc(C#CC=C2CCN(C(=O)N3CCOCC3)CC2)n1] | |
| 14 | 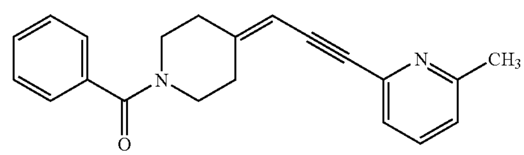 [SMILES: Cc1cccc(C#CC=C2CCN(C(=O)c3ccccc3)CC2)n1] | |
| 15 | 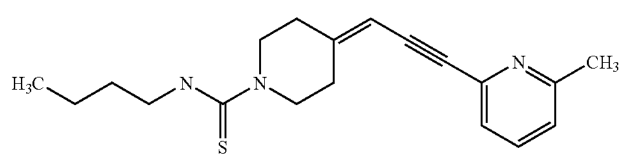 [SMILES: CCCCNC(=S)N1CCC(=CC#Cc2cccc(C)n2)CC1] | |
| 16 | 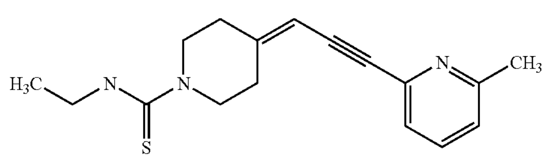 | |
| 17 | 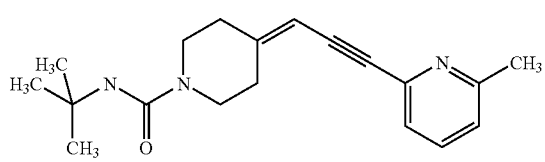 [SMILES: Cc1cccc(C#CC=C2CCN(C(=O)NC(C)(C)C)CC2)n1] | |
| 18 | 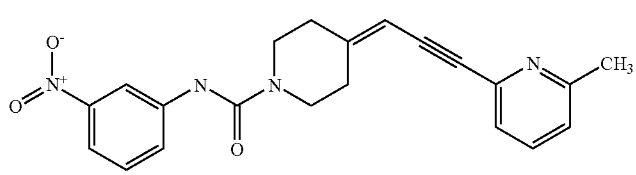 [SMILES: Cc1cccc(C#CC=C2CCN(C(=O)Nc3cccc([N+](=O)[O-])c3)CC2)n1] | |

-continued
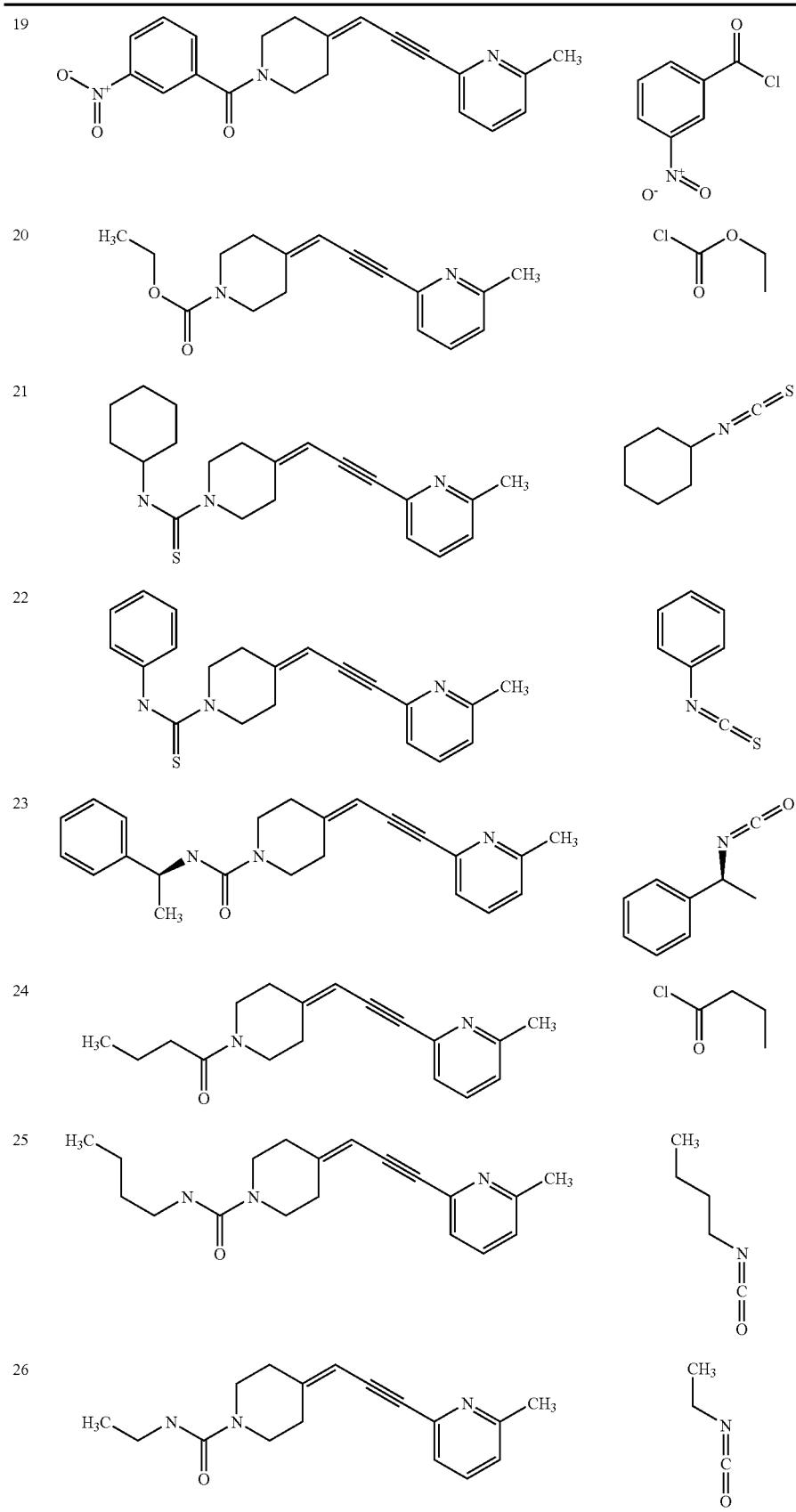

| Ex. | LC-MS [M + H]+ | 1H-NMR |
|---|---|---|
| 13 | 326.4 | 2.34-2.40 (m, 2H), 2.60 (s, 3H), 2.65-2.72 (m, 2H), 3.27-3.40 (m, 8H), 3.68-3.75 (m, 4H), 5.62 (s, 1H), 7.11 (d, 1H, J = 7.6 Hz), 7.28 (d, 1H, J = 7.6 Hz), 7.59 (t, 1H) |
| 14 | 317.3 | 2.25-2.54 (m, 2H), 2.63 (s, 3H), 2.65-2.82 (m, 2H), 3.38-3.86 (m, 4H), 5.66 (s, 1H), 7.11-7.17 (m, 1H), 7.25-7.33 (m, 1H), 7.40-7.47 (m, 5H), 7.57-7.66 (m, 1H) |
| 15 | 328.29 | 0.96 (t, 3H), 1.40 (sextet, 2H), 1.63 (quintet, 2H), 2.44-2.49 (m, 2H), 2.58 (s, 3H), 2.71-2.77 (m, 2H), 3.66-3.72 (m, 2H), 3.85-3.90 (m, 2H), 3.92-3.97 (m, 2H), 5.63 (s, 1H), 5.74 (br, 1H), 7.10 (d, 1H, J = 7.6 Hz), 7.26 (d, 1H, J = 7.6 Hz)), 7.57 (t, 1H, 7.6 Hz) |
| 16 | 300.31 | 1.26 (t, 3H), 2.44-2.49 (m, 2H), 2.61 (s, 3H), 2.74-2.79 (m, 2H), 3.70-3.78 (m, 2H), 3.86-3.90 (m, 2H), 3.94-3.98 (m, 2H), 5.63 (s, 1H), 5.70 (br, 1H), 7.12 (d, 1H, J = 7.6 Hz), 7.26 (d, 1H, J = 7.6 Hz)), 7.60 (t, 1H, 7.6 Hz) |
| 17 | 312.27 | 1.38 (s, 9H), 2.34-2.38 (m, 2H), 2.63 (s, 3H), 2.66-2.72 (m, 2H), 3.39-3.45 (m, 4H), 4.38 (br, 1H), 5.61 (s, 1H), 7.10-7.17 (m, 1H), 7.27-7.33 (m, 1H), 7.56-7.67 (m, 1H) |
| 18 | 377.3 | 2.41-2.49 (m, 2H), 2.58 (s, 3H), 2.70-2.77 (m, 2H), 3.59-3.63 (m, 4H), 5.66 (s, 1H), 6.93 (s, 1H), 7.09-7.14 (m, 1H), 7.25-7.33 (m, 1H), 7.46 (t, 1H), 7.58 (t, 1H), (d, 1H), 7.89 (d, 1H), 8.26 (s, 1H). |
| 19 | 362.3 | 2.27-2.89 (m, 4H), 2.58 (s, 3H), 3.40-3.58 (m, 2H), 3.76-3.97 (m, 2H), 5.68 (s, 1H), 7.09-7.14 (m, 1H), 7.18-7.31 (m, 1H), 7.56 (t, 1H), 7.65 (t, 1H), 7.80 (d, 1H), 8.30-8.36 (m, 2H). |
| 20 | 285.27 | 1.29 (t, 3H), 2.29-2.37 (m, 2H), 2.59 (s, 3H), 2.60-2.66 (m, 2H), 3.50-3.59 (m, 4H), 4.18 (q, 2H) 5.61 (s, 1H), 7.10 (d, 1H, J = 7.6 Hz), 7.26 (d, 1H, J = 7.6 Hz), 7.57 (t, 1H, 7.6 Hz) |
| 21 | 354.3 | 1.12-1.26 (m, 3H), 1.37-1.52 (m, 2H), 1.59-1.77 (m, 3H), 2.10-2.19 (m, 2H), 2.45-2.52 (m, 2H), 2.62 (s, 3H), 2.75-2.81 (m, 2H), 3.83-3.88 (m, 2H), 3.91-3.96 (m, 2H), 4.32-4.43 (m, 1H), 5.42, (brd, 1H), 5.65 (s, 1H), 7.13 (d, 1H, J = 7.6 Hz), 7.26 (d, 1H, J = 7.6 Hz), 7.61 (t, 1H, 7.6 Hz) |
| 22 | 348.3 | 2.45-2.52 (m, 2H), 2.56 (s, 3H), 2.75-2.81 (m, 2H), 3.83-3.88 (m, 2H), 3.91-3.96 (m, 2H), 5.65 (s, 1H), 7.09 (d, 1H, J = 7.6 Hz), 7.15-7.21 (m, 3H), 7.26 (d, 1H, J = 7.6 Hz), 7.31-7.42 (m, 3H), 7.54 (t, 1H, 7.6 Hz) |
| 23 | 360.3 | 1.52 (d, 3H), 2.32-2.38 (m, 2H), 2.58 (s, 3H), 2.62-2.69 (m, 2H), 3.42-3.49 (m, 4H), 4.76 (d, 1H), 5.05 (quintet, 1H), 5.60 (s, 1H), 7.09 (d, 1H), 7.23-7.29 (m, 2H), 7.33-7.38 (m, 4H), 7.56 (t, 1H) |
| 24 | 283.2 | 1.00 (t, 3H), 1.70 (sextet, 2H), 2.31-2.39 (m, 4H), 2.57 (s, 3H), 2.59-2.68 (m, 2H), 3.48-3.56 (m, 2H), 3.64-3.71 (m, 2H), 5.62 (s, 1H), 7.08 (d, 1H, J = 7.6 Hz), 7.22-7.29 (m, 1H), 7.54 (t, 1H, 7.6 Hz) |
| 25 | 312.3 | 0.95 (t, 3H), 1.35 (sextet, 2H), 1.53 (quintet, 2H), 2.35-2.39 (m, 2H), 2.69 (s, 3H), 2.60-2.80 (m, 2H), 3.26 (t, 2H), 3.42-3.52 (m, 4H), 4.52 (br, 1H), 5.61 (s, 1H), 7.17 (d, 1H), 7.34 (d, 1H), 7.65-7.71 (br, 1H) |
| 26 | 284.4 | 1.18 (t, 3H), 2.33-2.40 (m, 2H), 2.64 (s, 3H), 2.65-2.73 (m, 2H), 3.32 (q, 2H), 3.42-3.52 (m, 4H), 4.48 (br, 1H), 5.61 (s, 1H), 7.13 (d, 1H), 7.29 (d, 1H), 7.55-7.70 (m, 1H) |

EXAMPLE 27

2-[3-(1-Benzylpiperidin-4-ylidene)prop-1-ynyl]-6-methylpyridine

A mixture of the compound of Example 3 (0.22 g, 1.04 mmol), benzaldehyde (0.13 mL, 1.25 mmol), sodium triacetoxyborohydride (0.33 g, 1.56 mmol) and 15 mL of $CH_2Cl_2$ was stirred overnight at r.t. Afterwards, it was diluted with water, the organic layer was separated, washed with brine (2×15 mL), dried ($Na_2SO_4$) and evaporated to dryness in vacuo the give a crude, which was purified by automated flash liquid chromatography (Horizon™-Biotage) eluting with a gradient Petroleum Ether-EtOAc from 85:15 to 0:100 affording the title compound, which was further purified by preparative RP LC-MS chromatography, using MS-C18 XTerra column 30×50 mm eluting with ammonium bicarbonate 20 mM pH 8 buffer-acetonitrile gradient (0.12 g).

$^1$H-NMR (CDCl3, δ): 2.34-2.80 (m, 1H), 3.57-3.74 (m, 2H), 5.54 (s, 1H), 7.07 (d, 1H, J=7.65 Hz), 7.23 (d, 1H, J=7.65 Hz), 7.29-7.43 (m, 5H), 7.52 (t, 1H, J=7.65 Hz).

MS: $[M+H]^+$=303.3

EXAMPLE 28

2-[3-(1-Butylpiperidin-4-ylidene)prop-1-ynyl]-6-methylpyridine

The title compound was prepared following the procedure described for the compound of Example 27, but substituting butyraldehyde for benzaldehyde. After the usual work-up procedure, the crude was purified by automated flash liquid chromatography (Horizon™-Biotage) eluting with a gradient Petroleum Ether-(EtOAc+1.4 N methanolic ammonia 1:0.1) from 90:10 to 30:70 affording the title compound.

$^1$H-NMR (CDCl3, δ): 0.96 (t, 3H), 1.35 (sextet, 2H), 1.62 (br, 2H), 2.4-2.9 (m, 13H), 5.56 (s, 1H), 7.07 (d, 1H, J=7.65 Hz), 7.25 (d, 1H, J=7.65 Hz), 7.54 (t, 1H, J=7.65 Hz).

MS: [M+H]$^+$=269.3

EXAMPLE 29 tert-Butyl 4-[3-(6-methylpyridin-2-yl)-1-phenylprop-2-ynylidene]piperidine-1-carboxylate Into a solution of tert-butyl 4-(1-phenyl-3-trimethylsilyl-prop-2nylidene)piperidine-1-carboxylate (0.08 g, 0.216 mmol) prepared as described in US2004/0063744 in degassed DMF (2 mL) was dropped a solution of TBAF (0.056 g, 0.21 mmol) in DMF (1 mL). After 15 min. stirring at r.t., TEA (0.06 mL, 0.43 mmol), CuI (0.002 g, 0.01 mmol), tetrakis(triphenylphosphine)palladium(0) (0.012 g, 0.01 mmol) and 2-bromo-6-methylpyridine (0.026 mL, 0.23 mmol) were added. The reaction mixture was heated at 80° C. over 2 h., then it was cooled, poured into water and extracted with EtOAc. The combined organic layers were washed with brine, dried on Na$_2$SO$_4$ and evaporated to dryness in vacuo to afford a residue, which was purified by flash chromatography (EtOAc—Petroleum Ether 2:8) affording the title product (0.03 g).

$^1$H-NMR (CDCl3, δ): 1.50 (s, 9H), 2.36-2.43 (m, 2H), 2.56 (s, 3H), 2.81-2.89 (m, 2H), 3.37-3.46 (m, 2H), 3.58-3.63 (m, 2H), 7.07 (d, 1H, J=7.65 Hz), 7.23 (d, 1H, J=7.65 Hz), 7.29-7.43 (m, 5H), 7.52 (t, 1H, J=7.65 Hz).

MS: [M+H]$^+$=389.45

EXAMPLE 30 tert-Butyl 4-[3-(6-methylpyridin-2-yl)prop-2-ynyl]piperidine-1-carboxylate tert-Butyl 4-prop-2-ynylpiperidine-1-carboxylate (Compound 30a)

Method A: The title compound was synthesized following the methodology described in U.S. Pat. No. 6,265,434 (Caldwell et al., Jul. 24, 2001).

Method B: The title compound was synthesized following the methodology described for Compound 1c but using tert-butyl 4-(3-trimethylsilylprop-2-ynyl)piperidine-1-carboxylate (Tatsunori S. et Al. Heterocycles 54(2), 747-755, 2001) instead of Compound 1b. Traditional work-up procedure followed by flash column chromatography (EtOAc—Petroleum Ether 0.5:9.5) gave the title product as a colourless oil.

Method C: Into a solution of trimethylsilyldiazomethane (1.65 mL, 3.3 mmol) in THF (5 mL) cooled at −78° C. was dropped BuLi (2.5 N in n-hexane, 1.14 mL, 2.86 mmol). The reaction mixture was kept at the same temperature for 30 min., then 1-Boc-4-oxoethylpiperidine (0.5 g, 2.2 mmol) dissolved in THF (25 mL) was dropped and stirring was continued at the same temperature for 1 h. After having allowed the reaction to reach spontaneously r.t., it was quenched with a saturated aq. solution of ammonium chloride and extracted with EtOAc. The combined organic layers were washed with brine, dried on Na$_2$SO$_4$ and evaporated to dryness in vacuo to afford a residue, which was purified by flash chromatography (EtOAc—Petroleum Ether 1.5:8.5) affording the title product (0.19 g).

$^1$H-NMR (CDCl3, δ): 1.17-1.33 (m, 2H), 1.47 (s, 9H), 1.60-1.71 (m, 1H), 1.73-1.82 (m, 2H), 2.12-2.14 (dd, 1H), 2.18-2.21 (dd, 2H), 2.69-2.74 (m, 2H), 4.12-4.20 (m 2H)

MS: [M+H]$^+$=224.4 tert-Butyl 4-[3-(6-methylpyridin-2-yl)prop-2-ynyl]piperidine-1-carboxylate

The title compound was obtained as described for the Compound of Example 1, but using Compound 30a instead of Compound 1c in the last step. Purification by flash chromatography with Petroleum Ether-EtOAc 7:3 afforded the final product.

$^1$H-NMR (CDCl3, δ): 1.45-1.88 (m, 11H), 1.94-2.04 (m, 3H), 2.44-2.50 (m, 2H), 2.63 (s, 3H), 3.07 (m, 2H), 3.88 (m, 2H), 7.14-7.19 (m, 1H), 7.25-7.32 (m, 1H), 7.61-7.67 (m, 1H),

MS: [M+H]$^+$=315.6

EXAMPLE 31

2-{4-[3-(6-Methylpyridin-2-yl)prop-2-ynyl]piperidin-1-yl}-3-nitropyridine

2-Methyl-6-(3-piperidin-4-ylprop-2-ynyl)pyridine (Compound 31a)

The title compound was prepared following the synthesis method described for the Compound of Example 3 but using as a starting material the Compound of Example 30 instead of the compound of Example 2. The crude was used without further purification in the next step.

MS: [M+H]$^+$=215.4

2-{4-[3-(6-Methylpyridin-2-yl)prop-2-ynyl]piperidin-1-yl}-3-nitropyridine

A well homogenised mixture of Compound 31a (24 mg, 0.11 mmol) and 2-chloro-3-nitropyridine (19.5 mg, 0.12 mmol) was stirred at 120° C. for 40 min. The reaction crude was purified by flash chromatography (EtOAc—Petroleum Ether 3:7) affording the title product (20 mg).

$^1$H-NMR (CDCl3, δ): 2.45-2.58 (m, 2H), 1.96-2.04 (m, 3H), 2.48-2.54 (m, 2H), 2.68 (s, 3H), 3.07 (t, 2H, J=13.3 Hz), 3.88 (d, 2H, J=13.3 Hz), 6.70-6.75 (m, 1H), 7.13-7.20 (m, 1H), 7.28-7.33 (m, 1H), 7.60-7.70 (m, 1H), 8.10-8.16 (m, 1H), 8.31-8.35 (m, 1H).

MS: [M+H]$^+$ 337.39.

EXAMPLE 32

3-Nitro-2-[4-(4-pyridin-3-ylprop-2-ynylidene)piperidin-1-yl]pyridine

The title compound was obtained as described for the Compound of Example 1, but reacting Compound 1c with 4-iodopyridine instead of 2-bromo-6-methylpyridine. Purification by flash chromatography with Petroleum Ether-EtOAc 6.5:3.5 afforded the compound of Example 32.

$^1$H-NMR (CDCl3, δ): 2.52-2.57 (m, 2H), 2.75-2.80 (m, 2H), 3.50-3.60 (m, 4H), 5.68 (s, 1H), 6.79-6.84 (m, 1H), 7.44-7.48 (m, 2H), 8.18 (d, 1H), 8.36-8.39 (m, 1H), 8.48-8.82 (m, 2H).

MS: [M+H]$^+$=321.29

EXAMPLE 33

3-{3-[1-(3-Nitropyridin-2-yl)piperidin-4-ylidene]prop-1-ynyl}quinoline

A well homogenised mixture of the Compound 1c (50 mg, 0.21 mmol), 3-bromoquinoline (0.039 ml, 0.21 mmol), bis-(triphenylphosphine)palladium dichloride (5 mg, 0.007 mmol) and tetra-butylammonium fluoride (215 mg, 0.82 mmol) was stirred at 80° C. for 1 h in a sealed vessel. The reaction mixture was cooled, poured into water and extracted with EtOAc. The combined organic layers were washed with brine, dried on $Na_2SO_4$ and evaporated to dryness in vacuo to afford a residue, which was purified by flash chromatography (EtOAc—Petroleum Ether gradient from 2:8 to 4:6) affording the title product (0.51 g).

$^1$H-NMR (CDCl3, δ): 2.52-2.58 (m, 2H), 2.79-2.80 (m, 2H), 3.52-3.62 (m, 4H), 5.71 (s, 1H), 6.78-6.84 (m, 1H), 7.68-7.74 (m, 1H), 7.82-7.92 (m, 2H), 8.16-8.21 (m, 1H), 8.36-8.49 (m, 3H), 8.98 (s, 1H).
MS: $[M+H]^+$=371.38

EXAMPLE 34

4-{5-[3-[1-(3-Nitropyridin-2-yl)piperidin-4-ylidene]prop-1-ynyl]pyridin-2-yl}morpholine The title compound was obtained as described for the Compound of Example 33, but reacting Compound 1c with 5-iodo-2-(4-morpholinyl)pyridine instead of 3-bromoquinoline. Purification by flash chromatography with Petroleum Ether-EtOAc 6:4 afforded the compound of Example 34.

$^1$H-NMR (CDCl3, δ): 2.48-2.52 (m, 2H), 2.71-2.76 (m, 2H), 3.50-3.58 (m, 4H), 3.66-3.78 (m, 4H), 3.81-3.92 (m, 4H), 5.62 (s, 1H), 6.68-6.70 (m, 1H), 6.77-6.81 (m, 1H), 7.60-7.66 (m, 1H), 8.14-8.18 (m, 1H), 8.32 (s, 1H), 8.31-8.38 (m, 1H).
MS: $[M+H]^+$=406.28

EXAMPLE 35

2-{4-[3-(6-Fluoropyridin-3-yl)prop-2-ynylidene]piperidin-1-yl}-3-nitropyridine

The title compound was obtained as described for the Compound of Example 33, but using 5-bromo-2-fluoropyridine instead of 3-bromoquinoline in the coupling with Compound 1c. Purification by flash chromatography with Petroleum Ether-EtOAc 6:4 afforded the compound of Example 35.

$^1$H-NMR (CDCl3, δ): 2.50-2.54 (m, 2H), 2.74-2.78 (m, 2H), 3.52-3.59 (m, 4H), 5.64 (s, 1H), 6.80-6.84 (m, 1H), 6.90-6.95 (m, 1H), 7.80-7.85 (m, 1H), 8.19 (d, 1H), 8.31 (s, 1H), 8.39-8.41 (m, 1H).
MS: $[M+H]^+$=339.14

EXAMPLE 36

1-(6-{3-[1-(3-Nitropyridin-2-yl)piperidin-4-ylidene]prop-1-ynyl}pyridin-2-yl)ethanone The title compound was obtained as described for the Compound of Example 33, but using 2-acetyl-6-bromopyridine instead of 3-bromoquinoline in the coupling with Compound 1c. Purification by flash chromatography with Petroleum Ether-EtOAc 6:4 afforded the compound of Example 36.

$^1$H-NMR (CDCl3, δ): 2.53-2.58 (m, 2H), 2.77 (s, 3H), 2.81-2.86 (m, 2H), 3.55-3.61 (m, 4H), 5.70 (s, 1H), 6.80-6.84 (m, 1H), 7.58-7.62 (m, 1H), 7.78-7.84 (m, 1H), 7.95-7.99 (m, 1H), 8.18-8.22 (m, 1H), 8.38-8.41 (m, 1H).
MS: $[M+H]^+$=363.28

EXAMPLE 37

2-{4-[3-(6-Isopropoxyridin-3-yl)prop-2-ynylidene]piperidin-1-yl}-3-nitropyridine The title compound was obtained as described for the Compound of Example 33, but using 5-iodo-2-isopropoxypyridine instead of 3-bromoquinoline in the coupling with Compound 1c. Purification by flash chromatography with Petroleum Ether-EtOAc 3.5:6.5 afforded the compound of Example 37.

$^1$H-NMR (CDCl3, δ): 1.40 (s, 6H), 2.48-2.52 (m, 2H), 2.72-2.77 (m, 2H), 3.51-3.58 (m, 4H), 5.32-5.42 (m, 1H), 5.63 (s, 1H), 6.73 (d, 1H), 6.78-6.82 (m, 1H), 7.65-7.70 (m, 1H), 8.16-8.19 (m, 1H), 8.29 (m, 1H), 8.37-8.41 (m, 1H).
MS: $[M+H]^+$=379.30

EXAMPLE 38

3-Methoxy-2-{3-[1'-(3-nitropyridin-2-yl)piperidin-4-ylidene]prop-1-ynyl}pyridine The title compound was obtained as described for the Compound of Example 33, but using 2-iodo-3-methoxypyridine instead of 3-bromoquinoline. Purification by flash chromatography with Petroleum Ether-EtOAc 1:1 afforded the compound of Example 38.

$^1$H-NMR (CDCl3, δ): 2.50-2.56 (m, 2H), 2.86-2.92 (m, 2H), 3.52-3.60 (m, 4H), 3.98 (s, 3H), 5.75 (m, 1H), 6.76-6.81 (m, 1H), 7.35-7.38 (m, 2H), 8.16-8.19 (m, 1H), 8.23-8.31 (m, 1H), 8.35-8.41 (m, 1H).
MS: $[M+H]^+$=351.24

EXAMPLE 39 tert-Butyl 4-[1-hydroxy-3-(6-methylpyridin-2-yl)prop-2-ynyl]piperidine-1-carboxylate A mixture of zinc trifluoromethanesulfonate (0.07 g, 0.19 mmol) and triethylamine (0.065 mL, 0.47 mmol) in anhydrous toluene (5 mL) was stirred at room temperature under nitrogen atmosphere. After 1 h, 2-ethynyl-6-methyl-pyridine (0.13 g, 1.13 mmol) prepared as described in WO200544267 was added and after 15 min was dropped a solution of 1-Boc-4-piperidinecarboxaldehyde (0.2 g, 0.938 mmol) in toluene (1 mL): the resulting mixture was heated at 100° C. for 6 h. Afterwards, it was cooled to r.t., diluted with water and extracted with EtOAc. The combined organic layers were washed with brine, dried on $Na_2SO_4$ and evaporated to dryness in vacuo to give a crude, which was purified twice by automated flash liquid chromatography (Horizon™-Biotage) eluting with $CHCl_3$-MeOH 98-2 affording the title product (0.13 g) as a brown oil.

$^1$H-NMR (CDCl3, δ): 1.27-1.5 (m, 12H), 1.85-2.01 (m, 3H), 2.63 (s, 3H), 2.65-2.82 (m, 2H) 4.15-4.31 (m, 2H), 4.44-4.49 (m, 1H), 7.15-7.18 (m, 1H), 7.27-7.30 (m, 1H), 7.61-7.65 (m, 1H).
MS: $[M+H]^+$=331.6

EXAMPLE 40 tert-Butyl 4-[1-dimethylamino-3-(6-methylpyridin-2-yl)prop-2-ynyl]piperidine-1-carboxylate A mixture of 2-ethynyl-6-methyl-pyridine (0.08 g, 0.7 mmol), 1-Boc-4-piperidinecarboxaldehyde (0.1 g, 0.47 mmol), CuI (0.001 g, 0.11 mmol) and 33% w/w aqueous dimethylamine (0.077 mL, 0.56 mmol) in water (3 mL) was sonicated for 2 h in a laboratory ultrasonic bath. Afterwards, it was extracted with EtOAc and the combined organic layers were washed with brine, dried on Na₂SO₄ and evaporated to dryness in vacuo to give a crude, which was purified by automated flash liquid chromatography (Horizon™-Biotage) eluting with EtOAc—Petroleum Ether 1:1 affording the title product (0.11 g).

¹H-NMR (CDCl3, δ): 1.25-1.48 (m, 2H), 1.51 (s, 9H), 1.65-1.73 (m, 1H), 2.05-2.11 (m, 2H), 2.23-2.40 (br, 6H), 2.66 (s, 3H), 2.69-2.77 (m, 2H), 3.21-3.39 (m, 1H), 4.09-4.21 (m, 2H), 7.09-7.11 (m, 1H), 7.27-7.30 (m, 1H), 7.53-7.56 (m, 1H).

MS: [M+H]⁺=358.6

EXAMPLE 41 tert-Butyl 4-[3-(6-Methylpyridin-2-yl)-1-piperidin-1-ylprop-2-ynyl]piperidine-1-carboxylate The title compound was prepared following the procedure described for the compound of Example 40, but substituting piperidine for dimethylamine. After the usual work-up procedure, the crude was purified by automated flash liquid chromatography (Horizon™-Biotage) eluting with Petroleum Ether-EtOAc 70:30 affording the title compound.

¹H-NMR (CDCl3, δ): 1.05-2.11 (m, 20H), 2.35-2.86 (m, 9H), 3.15-3.35 (br, 1H), 4.05-4.21 (m, 2H), 7.08-7.14 (m, 1H), 7.25-7.30 (m, 1H), 7.52-7.57 (m, 1H).

MS: [M+H]⁺=398.7

EXAMPLE 42

2-Methyl-6-[3-(1-phenylpiperidin-4-ylidene)prop-1-ynyl]pyridine

A mixture of the compound of Example 3 (0.22 g, 1.04 mmol), bromobenzene (0.17 g, 1.04 mmol), cesium carbonate (0.68 g, 2.1 mmol), BINAP (0.031 g, 0.05 mmol), palladium(II)acetate (0.01 mg, 0.05 mmol), in anhydrous and degassed toluene (10 mL) was heated at 110° C. under a nitrogen atmosphere for 12 h in a sealed vessel. The reaction mixture was cooled, poured into water and extracted with EtOAc. The combined organic layers were washed with brine, dried on Na₂SO₄ and evaporated to dryness in vacuo to afford a residue, which was purified by flash chromatography (EtOAc—Petroleum Ether 2:8) affording the title product (0.30 g).

¹H-NMR (CDCl3, δ): 2.40-2.65 (m, 5H), 2.86 (brd, 2H), 3.38 (brd, 4H), 5.63 (s, 1H), 6.8-7.20 (m, 6H), 7.32 (d, 1H, J=7.65 Hz), 7.58 (t, 1H, J=7.65 Hz).

MS: [M+H]⁺=289.3

EXAMPLE 43

2-{4-[3-(6-Methylpyridin-2-yl)prop-2-ynylidene]piperidin-1-yl}benzonitrile

The title compound was prepared following the procedure described for the compound of Example 42, but substituting 2-bromobenzonitrile for bromobenzene. Purification by flash chromatography (EtOAc—Petroleum Ether 3:7) affording the title product.

¹H-NMR (CDCl3, δ): 2.55-2.65 (m, 5H), 2.91 (brd, 2H), 3.25-3.35 (m, 4H), 5.65 (s, 1H), 6.80-7.08 (m, 2H), 7.14 (d, 1H, J=7.65 Hz), 7.31 (d, 1H, J=7.65 Hz), 7.48 (t, 1H, J=7.65 Hz), 7.55-7.65 (m, 2H).

MS: [M+H]⁺=314.3

EXAMPLE 44

2-[3-[1-(4-Methoxy-2-nitrophenyl)piperidin-4-ylidene]prop-1-ynyl]-6-methylpyridine The title compound was prepared following the procedure described for the compound of Example 42, but substituting 4-bromo-3-nitroanisole for bromobenzene. Purification by flash chromatography (EtOAc—Petroleum Ether 3:7) affording the title product.

¹H-NMR (CDCl3, δ): 2.45-2.55 (m, 2H), 2.61 (s, 3H), 2.75-2.85 (m, 2H), 3.00-3.15 (m, 4H), 3.84 (s, 3H), 5.60 (s, 1H), 7.05-7.20 (m, 3H), 7.24-7.35 (m, 2H) 7.59 (t, 1H, J=7.65 Hz).

MS: [M+H]⁺=364.3

EXAMPLE 45 tert-Butyl 4-[3-(5-cyanopyridin-3-yl)prop-2-ynylidene]piperidine-1-carboxylate A mixture of Compound 2b (0.5 g, 2.26 mmol), 5-bromonicotinonitrile (0.511 g, 2.26 mmol), bis(triphenylphosphine)palladium(II)dichloride (80 mg, 0.05 mmol), CuI (43.1 mg, 0.1 mmol) in anhydrous and degassed triethylamine (12.6 mL) was heated at 80° C. under a nitrogen atmosphere for 2 h in a sealed vessel. The reaction mixture was cooled, filtered on Celite, poured into water and extracted with EtOAc. The combined organic layers were washed with brine, dried on Na₂SO₄ and evaporated to dryness in vacuo to afford a residue, which was purified by flash chromatography (EtOAc—Petroleum Ether gradient from 4:96 to 30:70) affording the title product (0.731 g).

MS: [M+H]⁺=324.2

EXAMPLE 46 tert-Butyl 4-[3-(6-cyanopyridin-3-yl)prop-2-ynylidene]piperidine-1-carboxylate The title compound was prepared following the procedure described for the compound of Example 45, but substituting 5-bromo-2-pyridincarbonitrile for 5-bromoisonicotinonitrile. Purification by flash chromatography (EtOAc—Petroleum Ether gradient from 5:95 to 40:60) afforded the title product.

MS: [M+H]⁺=324.2

EXAMPLE 47-48

5-{3-[1-(3-Nitropyridin-2-yl)piperidin-4-ylidene]prop-1-ynyl}nicotinonitrile

5-{3-[1-(3-Nitropyridin-2-yl)piperidin-4-ylidene]prop-1-ynyl}pyridine-2-carbonitrile

5-(3-piperidin-4-ylideneprop-1-ynyl)nicotinonitrile (Compound 47a)

5-(3-piperidin-4-ylideneprop-1-ynyl)pyridine-2-carbonitrile (Compound 48a)

The title compounds were prepared following the procedure described for the compound of Example 3 but starting respectively from the compounds of Example 45 and 46 instead of the compound of Example 2. The crudes were used in the next step without further purification.

MS: [M+H]⁺=224.3
MS: [M+H]⁺=224.3

5-{3-[1-(3-Nitropyridin-2-yl)piperidin-4-ylidene]prop-1-ynyl}nicotinonitrile (Compound 47)

5-{3-[1-(3-Nitropyridin-2-yl)piperidin-4-ylidene]prop-1-ynyl}pyridine-2-carbonitrile (Compound 48)

Using 2-bromo3-nitropyridyne instead of 1-bromo-2-nitrobenzene and carrying out the reaction as described in Example 4, but stirring overnight at r.t. in N,N-dimethylacetamide in the presence of a molar equivalent of TEA the title products were easily synthesized.
MS: [M+H]$^+$=346.2
MS: [M+H]$^+$=346.2

EXAMPLE 49 tert-Butyl 4-[3-(2-methyl-1,3-thiazol-4-yl)prop-2-ynylidene]piperidine-1-carboxylate tert-Butyl 4-(bromomethylene)piperidine-1-carboxylate (Compound 49a)

Lithium bis-trimethylsylylamide (1 M in THF, 7.38 mL, 7.38 mmol) was dropped into a suspension of bromomethyltriphenylphsphonium bromide (3.22 g, 7.38 mmol) at −15° C. under nitrogen atmosphere. After 15 min. under stirring at the same temperature, N-Boc piperidone (1.4 g, 7.03 mmol) dissolved in THF (10 ml) was added. Stirring was maintained and after 2 h at r.t., the reaction mixture was quenched with water and with EtOAc. The combined extracts were washed, dried over Na$_2$SO$_4$ and evaporated to dryness. The crude residue was purified by flash chromatography (EtOAc—Petroleum Ether 98:2) affording the title product (1.27 g).
MS: [M+H]$^+$=276.2 tert-Butyl 4-[3-(2-methyl-1,3-thiazol-4-yl)prop-2-ynylidene]piperidine-1-carboxylate A solution of tetrabutylammonium fluoride hydrate (818 mg, 2.93 mmol) in DMF (8 mL) was dropped into a solution of 2-methyl-4-trimethylsilanylethynylthiazole (Yasuyoshi et al., J. Med. Chem., 49, 3, 2006, 1080-1100, 0.52 g, 2.66 mmol) in DMF (7 mL). After 2 h under stirring, was added bis(triphenylphosphine)palladium(II)dichloride (93 mg, 0.13 mmol), CuI (51 mg, 0.27 mmol) and anhydrous and degassed triethylamine (1 mL) was heated at 80° C. under a nitrogen atmosphere for 2 h in sealed vessel. The reaction mixture was cooled, poured into water and extracted with EtOAc. The combined organic layers were washed with brine, dried on Na$_2$SO$_4$ and evaporated to dryness in vacuo to afford a residue, which was purified by flash chromatography (EtOAc—Petroleum Ether gradient from 4:96 to 30:70) affording the title product (0.847 g).
MS: [M+H]$^+$=319.2

EXAMPLE 50

4-[3-(2-Methyl-1,3-thiazol-4-yl)prop-2-ynylidene]piperidine

The title product was synthesized according to Example 3 but starting from the Compound of Example 49 instead of the compound of Example 2.
MS: [M+H]$^+$=219.2

EXAMPLE 51

2-{4-[3-(2-Methyl-1,3-thiazol-4-yl)prop-2-ynylidene]piperidin-1-yl}-3-nitropyridine The title product was synthesized according to Examples 47 or 48 but starting from the Compound of Example 50, instead of compounds 47a or 48a. After the usual work-up procedure, the crude was purified by flash chromatography (EtOAc—Petroleum Ether gradient from 8:92 to 40:60) affording the title product.
MS: [M+H]$^+$=341.1

EXAMPLE 52-58

Table II

These compounds were synthesized following the procedure described in Example 42 substituting Reagent B (Table II) for bromobenzene. Purification was carried out by automated flash liquid chromatography (Horizon™-Biotage) eluting with Petroleum Ether-EtOAc gradient from 95:5 to 30:70.

| Example | Reagent B | Structure |
|---|---|---|
| 52 | | 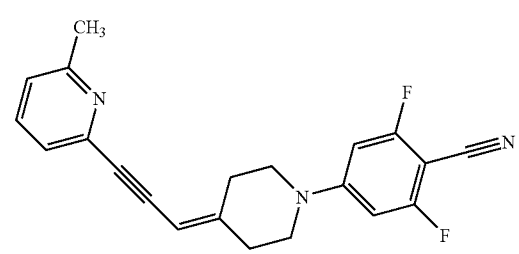 [SMILES: Cc1cccc(C#CC=C2CCN(c3cc(F)c(C#N)c(F)c3)CC2)n1] |

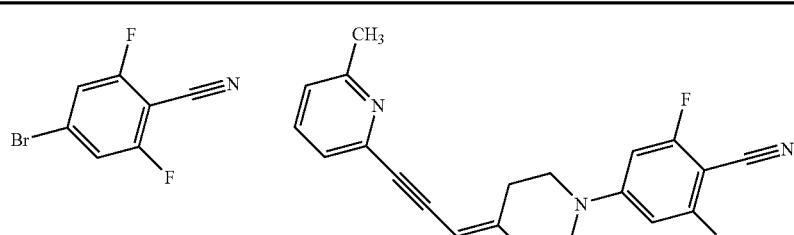

| | | | |
|---|---|---|---|
| 53 | 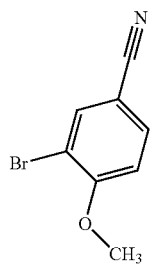 | 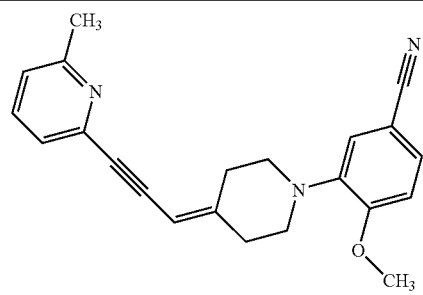 | |
| 54 | 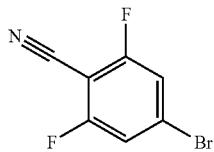 | 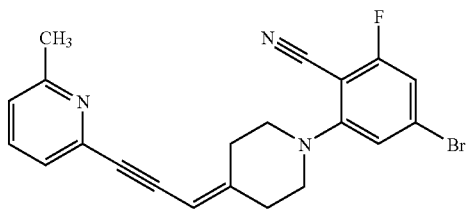 [SMILES: Cc1cccc(C#CC=C2CCN(c3cc(Br)cc(F)c3C#N)CC2)n1] | |
| 55 | 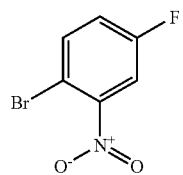 [SMILES: O=[N+]([O-])c1cc(F)ccc1Br] | 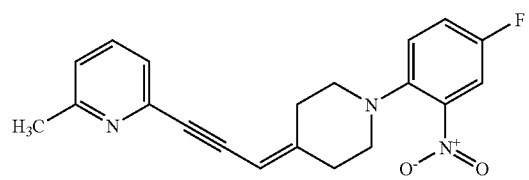 [SMILES: Cc1cccc(C#CC=C2CCN(c3ccc(F)cc3[N+](=O)[O-])CC2)n1] | |
| 56 | 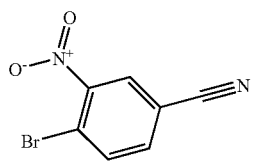 [SMILES: N#Cc1ccc(Br)c([N+](=O)[O-])c1] | 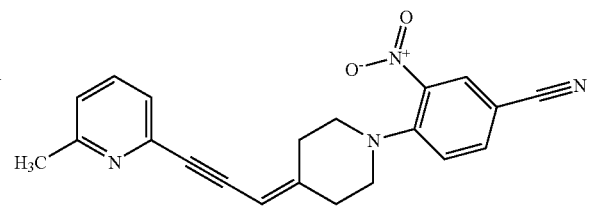 | |
| 57 | 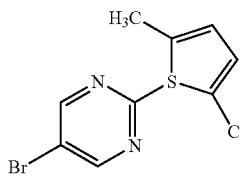 | 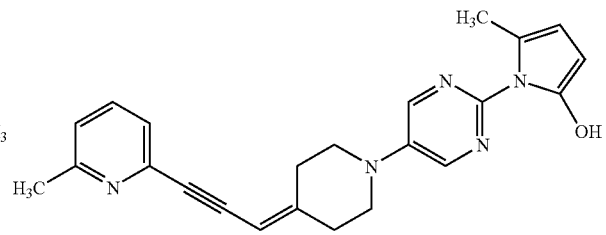 | |
| 58 | 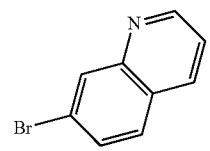 [SMILES: Brc1ccc2cccnc2c1] | 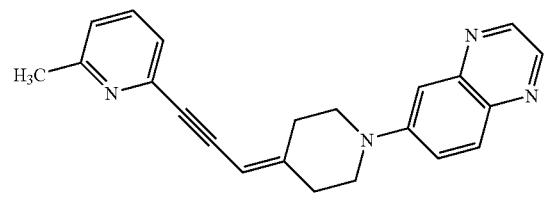 [SMILES: Cc1cccc(C#CC=C2CCN(c3ccc4nccnc4c3)CC2)n1] | |

| Example | Chem. Name | LC-MS M/Z |
|---|---|---|
| 52 | 2,6-Difluoro-4-{4-[3-(6-methylpyridin-2-yl)prop-2-ynylidene]piperidin-1-yl}benzonitrile | 350.21 |
| 53 | 4-Methoxy-3-{4-[3-(6-methylpyridin-2-yl)prop-2-ynylidene]piperidin-1-yl}benzonitrile | 344.25 |
| 54 | 4-Bromo-2-fluoro-6-{4-[3-(6-methylpyridin-2-yl)prop-2-ynylidene]piperidin-1-yl}benzonitrile | 410.01 |
| 55 | 2-{3-[1-(4-Fluoro-2-nitrophenyl)piperidin-4-ylidene]prop-1-ynyl}-6-methylpyridine | 352.25 |
| 56 | 4-{4-[3-(6-Methylpyridin-2-yl)prop-2-ynylidene]piperidin-1-yl}-3-nitrobenzonitrile | 359.16 |

| | | -continued | |
|---|---|---|---|
| 57 | | 2-(2,5-Dimethyl-1H-pyrrol-1-yl)-5-[4-[3-(6-methylpyridin-2yl)prop-2-yn-1-ylidene]piperidin-1-yl]pyrimidine | 384.2 |
| 58 | | 6-{4-[3-(6-Methylpyridin-2-yl)prop-2-yn-1-ylidene]piperidin-1-yl}quinoxaline | 341.3 |

EXAMPLE 59

2-Methyl-6-[3-(1-pyridin-2-ylpiperidin-4-ylidene)prop-1-yn-1-yl]pyridine

A solution of the Compound of Example 3 (100 mg, 0.47 mmol), 2-fluoropyridine (45.5 µL, 0.52 mmol), TEA (102 µL) in N-methylpyrrolidone was heated in a microwave oven at 160° C. for 20 min. Afterwards, the reaction mixture was cooled, poured into water and extracted with EtOAc. The combined organic layers were washed with brine, dried on $Na_2SO_4$ and evaporated to dryness in vacuo to afford a residue, which was purified by flash chromatography (EtOAc—Petroleum Ether gradient from 7:93 to 40:60) affording the title product (0.02 g).

MS: $[M+H]^+=290.34$

EXAMPLE 60-65

Table III

These compounds were synthesized following the procedure described in Example 59 substituting Reagent B for 2-fluoropyridine. Purification was carried out by automated flash liquid chromatography (Horizon™-Biotage) eluting with Petroleum Ether-EtOAc gradient from 95:5 to 30:70.

| Example | Reagent B | Structure |
|---|---|---|
| 60 | | 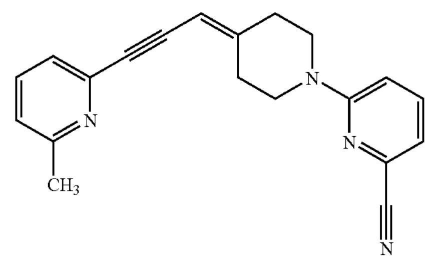 [SMILES: Cc1cccc(C#CC=C2CCN(c3cccc(C#N)n3)CC2)n1] |
| 61 | | 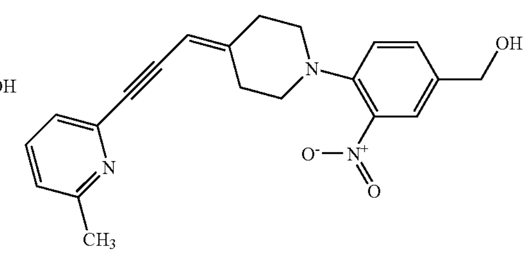 |
| 62 | | 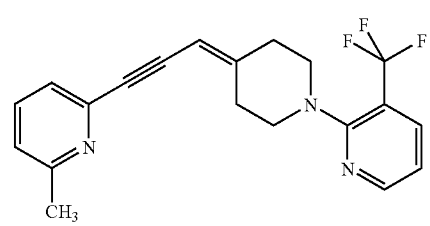 [SMILES: Cc1cccc(C#CC=C2CCN(c3ncccc3C(F)(F)F)CC2)n1] |
| 63 | | 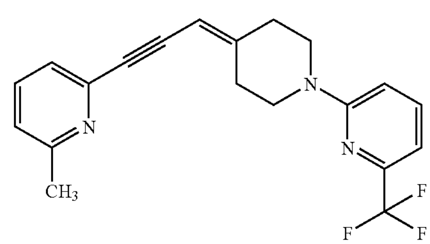 [SMILES: Cc1cccc(C#CC=C2CCN(c3cccc(C(F)(F)F)n3)CC2)n1] |

| | | |
|---|---|---|
| 64 |  | 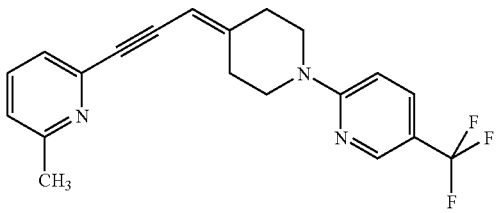 [SMILES: Cc1cccc(C#CC=C2CCN(c3ccc(C(F)(F)F)cn3)CC2)n1] |
| 65 | 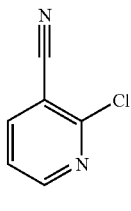 | 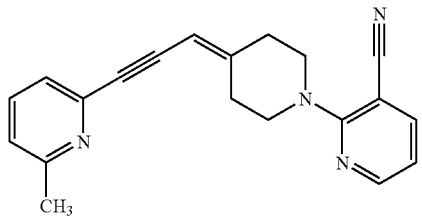 [SMILES: Cc1cccc(C#CC=C2CCN(c3ncccc3C#N)CC2)n1] |

| Example | Chem. Name | LC-MS M/Z |
|---|---|---|
| 60 | 6-{4-[3-(6-Methylpyridin-2-yl)prop-2-yn-1-ylidene]piperidin-1-yl}pyridine-2-carbonitrile | 315.4 |
| 61 | (4-{4-[3-(6-Methylpyridin-2-yl)prop-2-ynylidene]piperidin-1-yl}-3-nitrophenyl)methanol | 364.3 |
| 62 | 2-{4-[3-(6-Methylpyridin-2-yl)prop-2-yn-1-ylidene]piperidin-1-yl}-3-trifluoromethyl)pyridine | 358.2 |
| 63 | 2-Methyl-6-(3-{1-[6-(trifluoromethyl)pyridin-2-yl]piperidin-4-ylidene}prop-1-yn-1-yl)pyridine | 358.2 |
| 64 | 2-{4-[3-(6-Methylpyridin-2-yl)prop-2-yn-1-ylidene]piperidin-1-yl}-5-(trifluoromethyl)pyridine | 358.2 |
| 65 | 2-{4-[3-(6-Methylpyridin-2-yl)prop-2-ynylidene]piperidin-1-yl}nicotinonitrile | 315.2 |

EXAMPLE 66 tert-Butyl 4-(1-Fluoro-3-phenylprop-2-ynylidene)piperidine-1-carboxylate tert-Butyl 4-[bromo(fluoro)methylene]piperidine-1-carboxylate (Compound 66a)

To a solution of tert-butyl 4-oxopiperidine-1-carboxylate (500 mg, 2.52 mmol), triphenylphosphine (808 mg, 3.02 mmol) and tribromofluoromethane (818 mg, 3.02 mmol) in 50 mL of anhydrous THF was added dropwise a solution of diethylzinc (1 M in hexane, 3.02 mL, 3.02 mmol) stirring at r.t. After 2.5 h, the reaction mixture was quenched with MeOH (10 mL), stirred for 30 min., evaporated to dryness in vacuo. Purification was carried out by automated flash liquid chromatography (Horizon™-Biotage) eluting with Petroleum Ether-EtOAc gradient from 95:5:0 to 90:10 to afford the title compound (326 mg).

MS: [M+H]$^+$=295.16 tert-Butyl 4-(1-Fluoro-3-phenylprop-2-ynylidene)piperidine-1-carboxylate

The title product was prepared following the procedure reported for the Compound of Example 45 but using phenylacetylene instead of instead of Compound 2b and Compound 66a instead of 5-bromonicotinonitrile. The residue coming from the usual work-up procedure was purified by flash chromatography (EtOAc—Petroleum Ether gradient from 5:95 to 10:90).

MS: [M+H]$^+$=316.22

EXAMPLE 67

2-[4-(1-Fluoro-3-phenylprop-2-yn-1-ylidene)piperidin-1-yl]-3-nitropyridine 4-(1-fluoro-3-phenylprop-2-ynylidene)piperidine (Compound 67a)

The title product was synthesized following the procedure reported for Example 3 but starting from the Compound of Example 66 instead of the compound of Example 2.

MS: [M+H]$^+$=216.22

2-[4-(1-Fluoro-3-phenylprop-2-yn-1-ylidene)piperidin-1-yl]-3-nitropyridine

The title compound was prepared following the procedure described for the Compounds of Example 47 and 48 replacing compounds 47a and 48a with compound 67a. The crude was purified by flash chromatography (EtOAc—Petroleum Ether 1:9).

MS: [M+H]$^+$=338.22

EXAMPLE 68

2-Methoxyethyl 4-[3-(6-methylpyridin-2-yl)prop-2-ynylidene]piperidine-1-carboxylate To a solution of 2-methoxyethanol (26.9 µl, 0.34 mmol) and ditrichloromethyl carbonate (37.2 mg, 0.125 mmol) in $CH_2Cl_2$ (1.5 mL) stirred at r.t., was added dropwise a solution of DEA (139 µL, 0.814 mmol) in 1.5 mL of $CH_2Cl_2$ over 30'. After 40 min., was added a solution of the Compound of Example 3 (72 mg, 0.339 mmol) and 70 µL of DEA in 0.8 mL of $CH_2Cl_2$. After 24 h, the reaction mixture was evaporated to dryness in vacuo and the residue was purified by automated flash liquid chromatography (Horizon™-Biotage) eluting with Petroleum Ether-EtOAc gradient from 7:3 to 3:7 to afford the title compound (57 mg).

MS: $[M+H]^+$=315.17

EXAMPLE 69-82

Table IV

These compounds were synthesized following the procedure described in Example 68 substituting reagent B (see table IV below; commercially available) for 2-methoxyethanol. Purification was carried out by automated flash liquid chromatography (Horizon™-Biotage) eluting with Petroleum Ether-EtOAc gradient from 100:0 to 20:80 or $CH_2Cl_2$-EtOAc from 100:0 to 20:80. The compound of Example 82 was further purified by preparative RP LC-MS chromatography, using MS-C18 XTerra column 30×50 mm eluting with ammonium bicarbonate 20 mM pH 8 buffer-acetonitrile gradient.

| Example | Reagent B | Structure |
|---|---|---|
| 69 | HO-CH₂-CH₂-C≡N | (6-methylpyridin-2-yl)-C≡C-piperidinylidene-N-C(O)-O-CH₂CH₂-C≡N |
| 70 | H₃C-C₆H₄ (benzyl alcohol) | (6-methylpyridin-2-yl)-C≡C-piperidinylidene-N-C(O)-O-CH₂-C₆H₅ |
| 71 | HO-C₆H₃(F)(NO₂) (2-fluoro-4-nitrophenol) | (6-methylpyridin-2-yl)-C≡C-piperidinylidene-N-C(O)-O-C₆H₃(F)(NO₂) |
| 72 | HO-CH₂-(2-thienyl) | (6-methylpyridin-2-yl)-C≡C-piperidinylidene-N-C(O)-O-CH₂-(2-furyl) |
| 73 | HO-(2-pyridyl) | (6-methylpyridin-2-yl)-C≡C-piperidinylidene-N-C(O)-O-(2-pyridyl) |
| 74 | HO-(4-piperidinyl)-N-OH | (6-methylpyridin-2-yl)-C≡C-piperidinylidene-N-C(O)-O-(4-piperidinyl)-N-CH₃ |

US 8,518,916 B2
| | | |
|---|---|---|
| 75 | 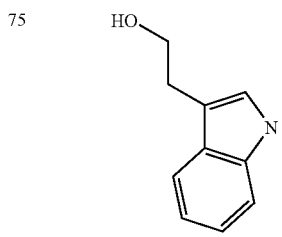 | 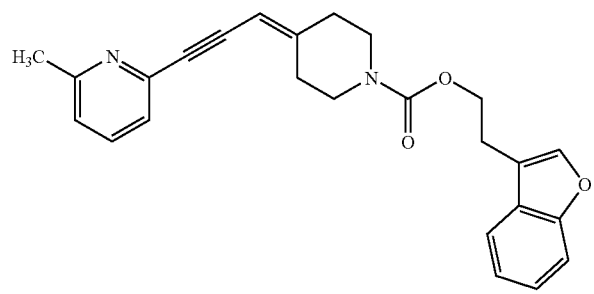 [SMILES: Cc1cccc(C#CC=C2CCN(C(=O)OCCc3coc4ccccc34)CC2)n1] |
| 76 | 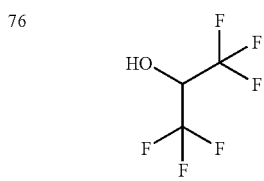 | 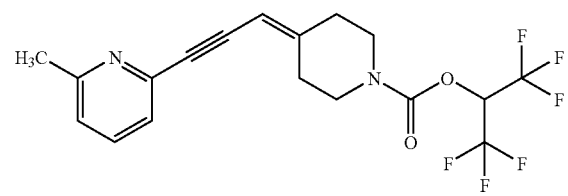 [SMILES: Cc1cccc(C#CC=C2CCN(C(=O)OC(C(F)(F)F)C(F)(F)F)CC2)n1] |
| 77 | 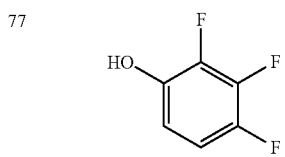 | 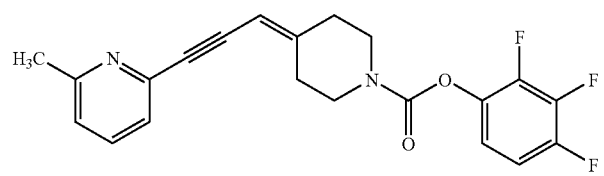 [SMILES: Cc1cccc(C#CC=C2CCN(C(=O)Oc3ccc(F)c(F)c3F)CC2)n1] |
| 78 | 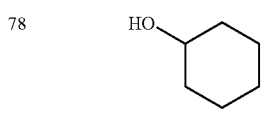 | 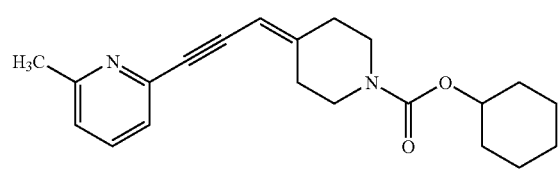 [SMILES: Cc1cccc(C#CC=C2CCN(C(=O)OC3CCCCC3)CC2)n1] |
| 79 | 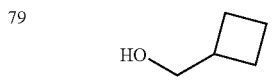 | 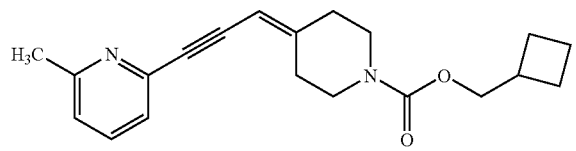 [SMILES: Cc1cccc(C#CC=C2CCN(C(=O)OCC3CCC3)CC2)n1] |
| 80 | 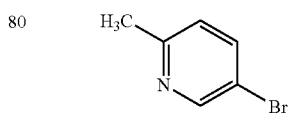 | 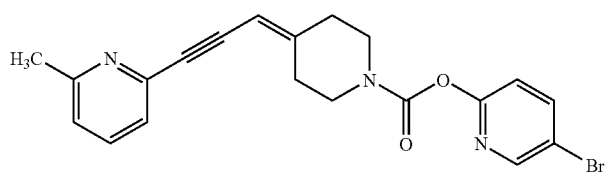 [SMILES: Cc1cccc(C#CC=C2CCN(C(=O)Oc3ccc(Br)cn3)CC2)n1] |
| 81 | 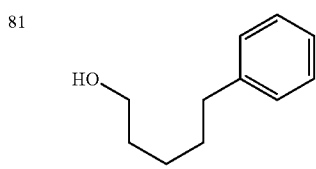 | 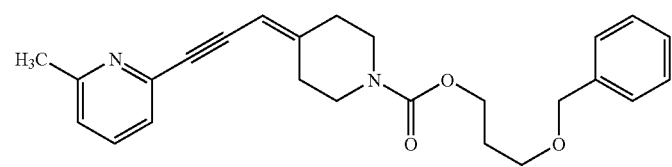 [SMILES: Cc1cccc(C#CC=C2CCN(C(=O)OCCCOCc3ccccc3)CC2)n1] |
| 82 | 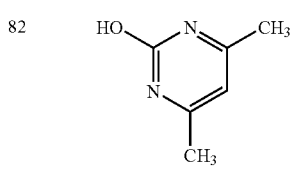 | 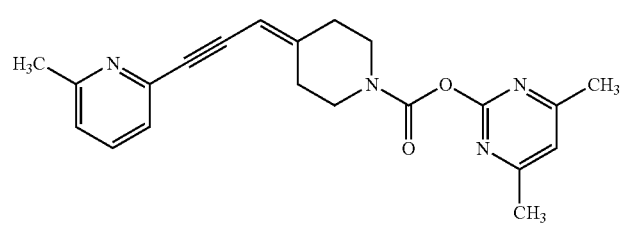 |

| Example | Chem. Name | LC-MS M/Z |
|---|---|---|
| 69 | 2-Cyanoethyl 4-[3-(6-methylpyridin-2-yl)prop-2-ynylidene]piperidine-1-carboxylate | 310.20 |
| 70 | Benzyl 4-[3-(6-methylpyridin-2-yl)prop-2-ynylidene]piperidine-1-carboxylate | 346.09 |
| 71 | 2-Fluoro-4-nitrophenyl 4-[3-(6-methylpyridin-2-yl)prop-2-ynylidene]piperidine-1-carboxylate | 396.09 |
| 72 | Thiophen-2-ylmethyl 4-[3-(6-methylpyridin-2-yl)prop-2-ynylidene]piperidine-1-carboxylate | 353.20 |
| 73 | Pyridin-2-yl 4-[3-(6-methylpyridin-2-yl)prop-2-ynylidene]-piperidine-1-carboxylate | 334.12 |
| 74 | 1-Methylpiperidin-4-yl 4-[3-(6-methylpyridin-2-yl)prop-2-ynylidene]piperidine-1-carboxylate | 354.19 |
| 75 | 2-(1H-indol-3-yl)ethyl 4-[3-(6-methylpyridin-2-yl)prop-2-ynylidene]piperidine-1-carboxylate | 400.15 |
| 76 | 2,2,2-Trifluoro-1-trifluoromethylethyl 4-[3-(6-methylpyridin-2-yl)prop-2-ynylidene]piperidine 1-carboxylate | 407.08 |
| 77 | 2,3,4-Trifluorophenyl 4-[3-(6-methylpyridin-2-yl)prop-2-ynylidene]piperidine-1-carboxylate | 387.07 |
| 78 | Cyclohexyl 4-[3-(6-methylpyridin-2-yl)prop-2-ynylidene]piperidine-1-carboxylate | 339.23 |
| 79 | Cyclobutylmethyl 4-[3-(6-methylpyridin-2-yl)-prop-2-ynylidene]piperidine-1-carboxylate | 325.17 |
| 80 | 5-Bromopyridin-2-yl 4-[3-(6-methylpyridin-2-yl)prop-2-ynylidene]piperidine-1-carboxylate | 414.00 |
| 81 | 3-Benzyloxypropyl 4-[3-(6-methylpyridin-2-yl)prop-2-ynylidene]piperidin-1-carboxylate | 405.19 |
| 82 | 4,6-Dimethylpyrimidin-2-yl 4-[3-(6-methylpyridin-2-yl)prop-2-ynylidene]piperidine 1-carboxylate | 363.15 |

EXAMPLE 83

N-Methyl-4-[3-(6-methylpyridin-2-yl)prop-2-ynylidene]-N-phenylpiperidine-1-carboxamide To a solution of ditrichloromethyl carbonate (43.6 mg, 0.147 mmol) in CH$_2$Cl$_2$ (1 mL) stirred at r.t., was added dropwise a solution of N-methylaniline (48.2 µL, 0.445 mmol) and DEA (168 µL, 0.98 mmol) in 1.5 mL of CH$_2$Cl$_2$ over 30'. After 40 min., was added a solution of the Compound of Example 3 (94.4 mg, 0.445 mmol) and 168 µL of DEA in 2 mL di CH$_2$Cl$_2$. After 24 h, the reaction mixture was evaporated to dryness in vacuo, taken up with water and extracted with EtOAc. The residue from extraction was purified by automated flash liquid chromatography (Horizon™-Biotage) eluting with Petroleum Ether-EtOAc gradient from 4:6 to 2:8 to afford the title compound (123 mg).

MS: [M+H]$^+$=346.22

EXAMPLE 84-91

Table V

These compounds were synthesized following the procedure described in Example 83 substituting reagent B (see table V below; commercially available) for N-methylaniline. Purification was carried out by automated flash liquid chromatography (Horizon™-Biotage) eluting with Petroleum Ether-EtOAc gradient from 100:0 to 20:80 or CH$_2$Cl$_2$-EtOAc from 100:0 to 20:80.

| Example | Reagent B | Structure | Chem. Name | LC-MS M/Z |
|---|---|---|---|---|
| 84 | HN(CH$_2$CH$_3$)$_2$ | 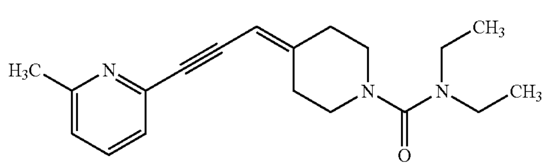 [SMILES: CCN(CC)C(=O)N1CCC(=CC#Cc2cccc(C)n2)CC1] | N-Diethyl-4-[3-(6-methylpyridin-2-yl)prop-2-ynylidene]piperidine-1-carboxamide | 312.23 |
| 85 | HN(CH$_3$)$_2$ | 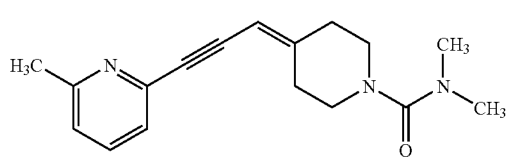 | N-Dimethyl-4-[3-(6-methylpyridin-2-yl)prop-2-ynylidene]piperidine-1-carboxamide | 284.25 |

| Example | Reagent B | Structure | Chem. Name | LC-MS M/Z |
|---|---|---|---|---|
| 86 | 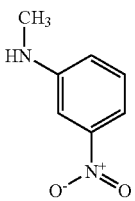 | 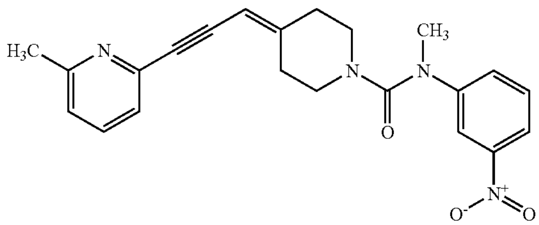 [SMILES: Cc1cccc(C#CC=C2CCN(C(=O)N(C)c3cccc([N+](=O)[O-])c3)CC2)n1] | N-Methyl-4-[3-(6-methylpyridin-2-yl)prop-2-ynylidene]-N-(3-nitrophenyl)piperidine-1-carboxamide | 391.2 |
| 87 | | 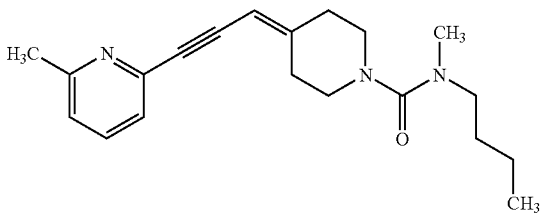 [SMILES: CCCCN(C)C(=O)N1CCC(=CC#Cc2cccc(C)n2)CC1] | N-Butyl-N-methyl-4-[3-(6-methylpyridin-2-yl)prop-2-ynylidene]piperidine-1-carboxamide | 326.22 |
| 88 | 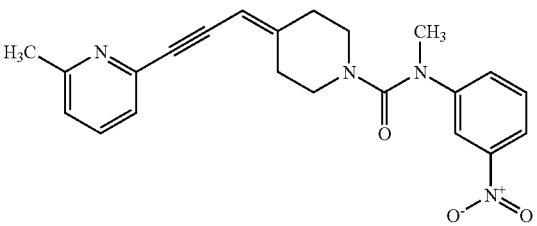 | 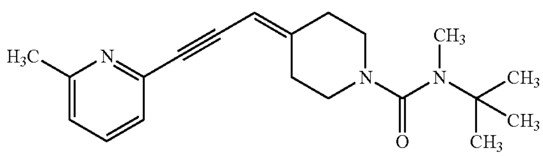 [SMILES: Cc1cccc(C#CC=C2CCN(C(=O)N(C)C(C)(C)C)CC2)n1] | N-tert-Butyl-N-methyl-4-[3-(6-methylpyridin-2-yl)prop-2-ynylidene]piperidine-1-carboxamide | 326.22 |
| 89 | 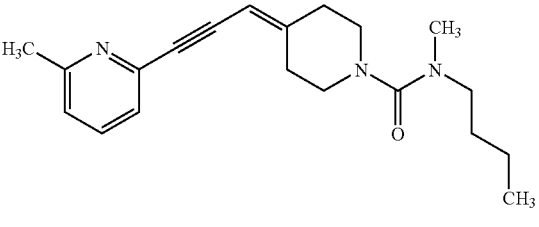 | 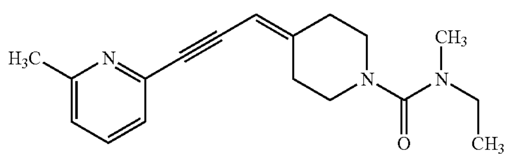 [SMILES: CCN(C)C(=O)N1CCC(=CC#Cc2cccc(C)n2)CC1] | N-Ethyl-N-methyl-4-[3-(6-methylpyridin-2-yl)prop-2-ynylidene]piperidine-1-carboxamide | 298.17 |
| 90 | 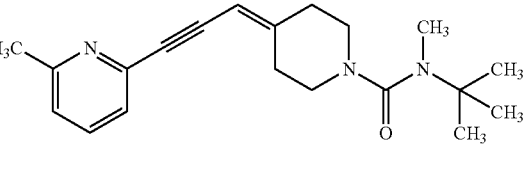 | 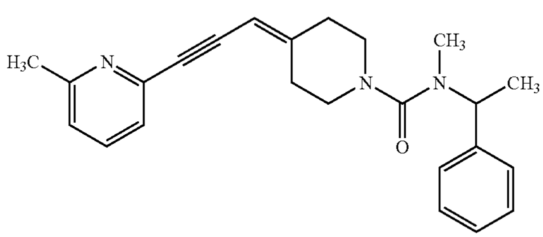 [SMILES: Cc1cccc(C#CC=C2CCN(C(=O)N(C)C(C)c3ccccc3)CC2)n1] | N-(1-Phenylethyl)-N-methyl-4-[3-(6-methylpyridin-2-yl)prop-2-ynylidene]piperidine-1-carboxamide | 374.2 |
| 91 | 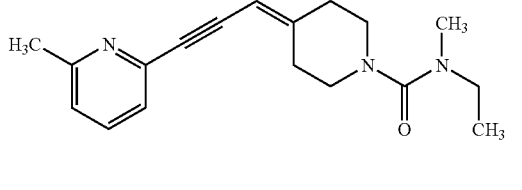 | 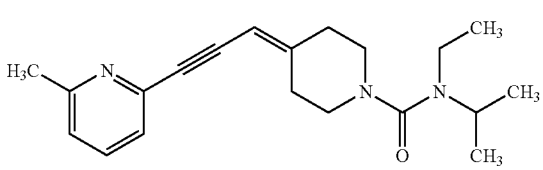 [SMILES: CCN(C(=O)N1CCC(=CC#Cc2cccc(C)n2)CC1)C(C)C] | N-Ethyl-N-(1-methylethyl)-4-[3-(6-methylpyridin-2-yl)prop-2-ynylidene]piperidine-1-carboxamide | 326.29 |

EXAMPLE 92

2-Methyl-6-{3-[1-(toluene-4-sulfonyl)piperidin-4-ylidene]prop-1-ynyl}pyridine

A solution of the Compound of Example 3 (60 mg, 0.283 mmol), p-toluenesulfonyl chloride (80.9 mg, 0.425 mmol), TEA (0.425 mmol) in 5 mL of CHCl₃ was stirred at r.t. for 1 h. The chloroform solution was washed with NaOH 0.1 N, water, dried over Na₂SO₄ and evaporated to dryness in vacuo. Purification by flash chromatography (EtOAc—Petroleum Ether 1:1), afforded 67 mg of the title product.
MS: [M+H]⁺=367.13

EXAMPLE 93-115

Table VI

These compounds were synthesized following the procedure described in Example 92 substituting reagent B (see table VI below; commercially available) for p-toluenesulphonyl chloride. Purification was carried out by flash chromatography eluting with Petroleum Ether-EtOAc.

| Example | Reagent B | Structure |
|---|---|---|
| 93 | 2-nitrobenzenesulfonyl chloride | 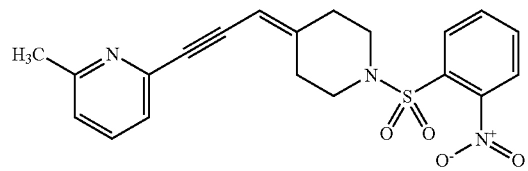 [SMILES: Cc1cccc(C#CC=C2CCN(S(=O)(=O)c3ccccc3[N+](=O)[O-])CC2)n1] |
| 94 | benzenesulfonyl chloride | 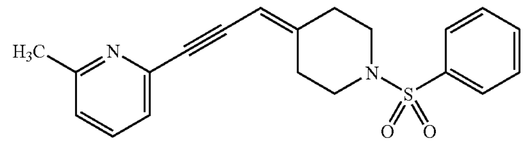 [SMILES: Cc1cccc(C#CC=C2CCN(S(=O)(=O)c3ccccc3)CC2)n1] |
| 95 | 2-methyl-5-(2-oxopyrrolidin-1-yl)benzenesulfonyl chloride | 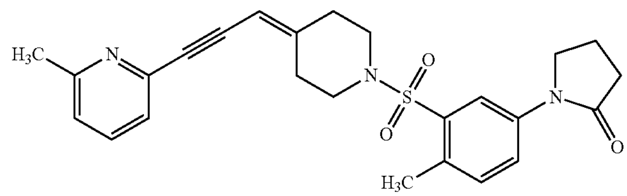 [SMILES: Cc1cccc(C#CC=C2CCN(S(=O)(=O)c3cc(N4CCCC4=O)ccc3C)CC2)n1] |
| 96 | 4-methoxybenzenesulfonyl chloride | 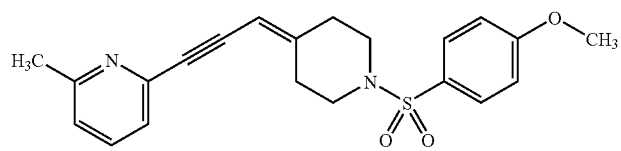 |
| 97 | 4-bromo-2,5-difluorobenzenesulfonyl chloride | 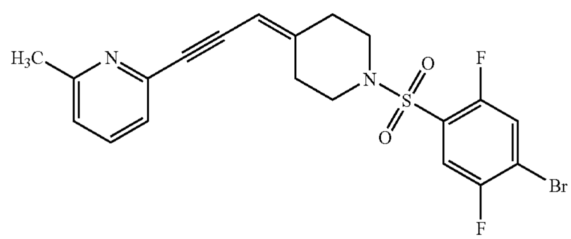 [SMILES: Cc1cccc(C#CC=C2CCN(S(=O)(=O)c3cc(F)c(Br)cc3F)CC2)n1] |
| 98 | phenylmethanesulfonyl chloride | 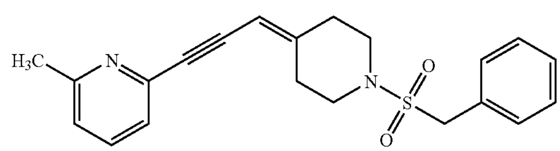 [SMILES: Cc1cccc(C#CC=C2CCN(S(=O)(=O)Cc3ccccc3)CC2)n1] |
| 99 | ethanesulfonyl chloride | 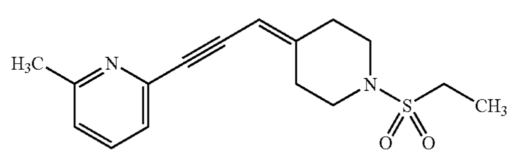 [SMILES: CCS(=O)(=O)N1CCC(=CC#Cc2cccc(C)n2)CC1] |
| 100 | 2-chloro-4-cyanobenzenesulfonyl chloride | 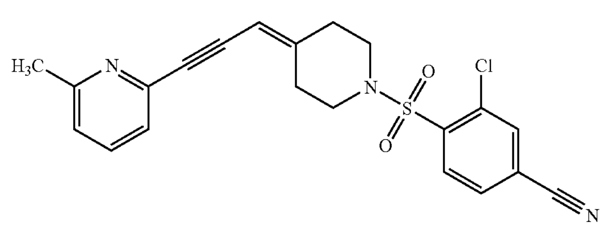 |

| 101 | 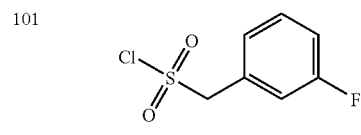 | 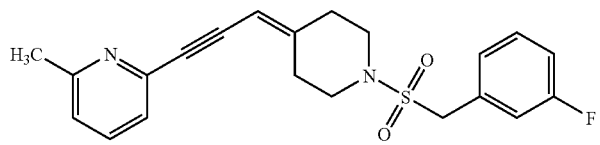 [SMILES: Cc1cccc(C#CC=C2CCN(S(=O)(=O)Cc3cccc(F)c3)CC2)n1] |
| 102 | 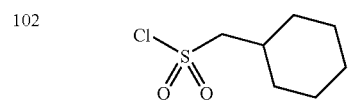 | 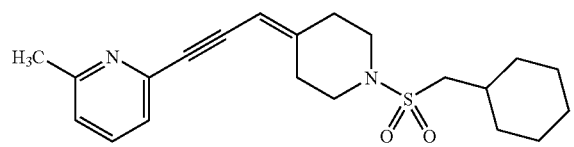 [SMILES: Cc1cccc(C#CC=C2CCN(S(=O)(=O)CC3CCCCC3)CC2)n1] |
| 103 | 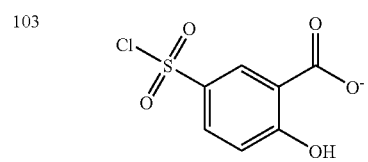 | 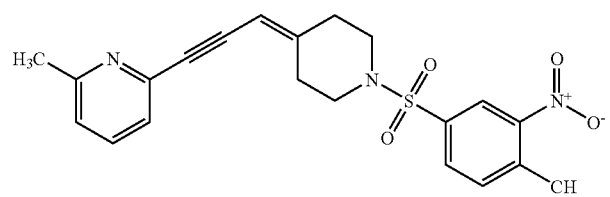 [SMILES: Cc1cccc(C#CC=C2CCN(S(=O)(=O)c3ccc(C)c([N+](=O)[O-])c3)CC2)n1] |
| 104 | 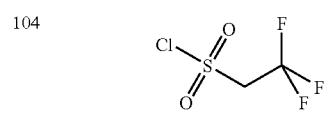 | 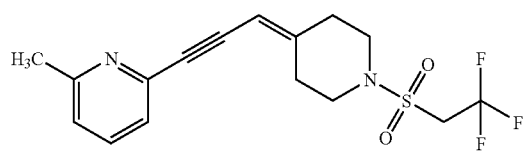 [SMILES: Cc1cccc(C#CC=C2CCN(S(=O)(=O)CC(F)(F)F)CC2)n1] |
| 105 | 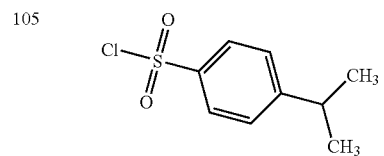 | 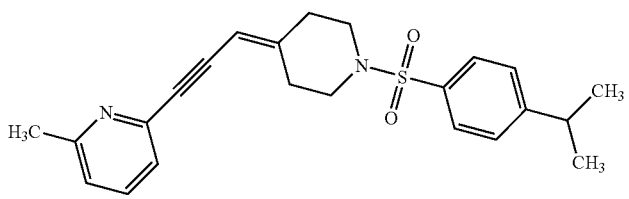 [SMILES: Cc1cccc(C#CC=C2CCN(S(=O)(=O)c3ccc(C(C)C)cc3)CC2)n1] |
| 106 | 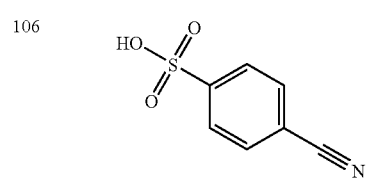 | 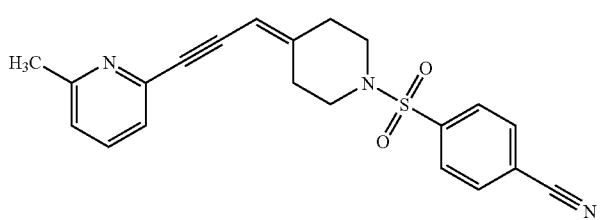 [SMILES: Cc1cccc(C#CC=C2CCN(S(=O)(=O)c3ccc(C#N)cc3)CC2)n1] |
| 107 | 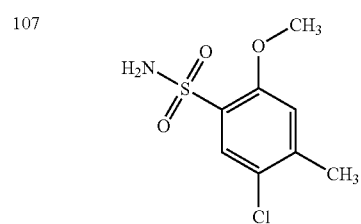 | 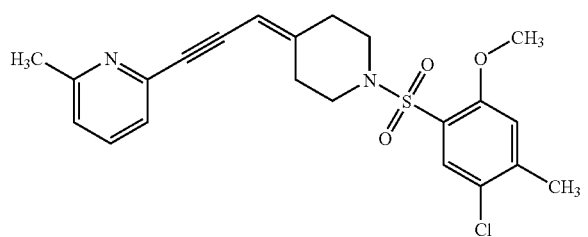 |
| 108 | 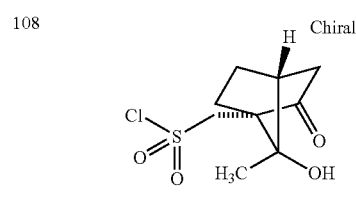 | 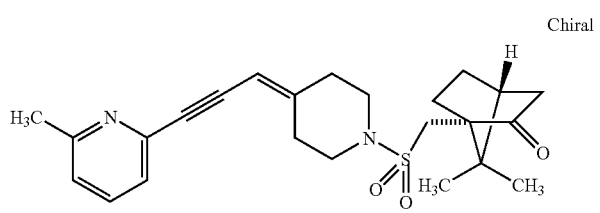 |

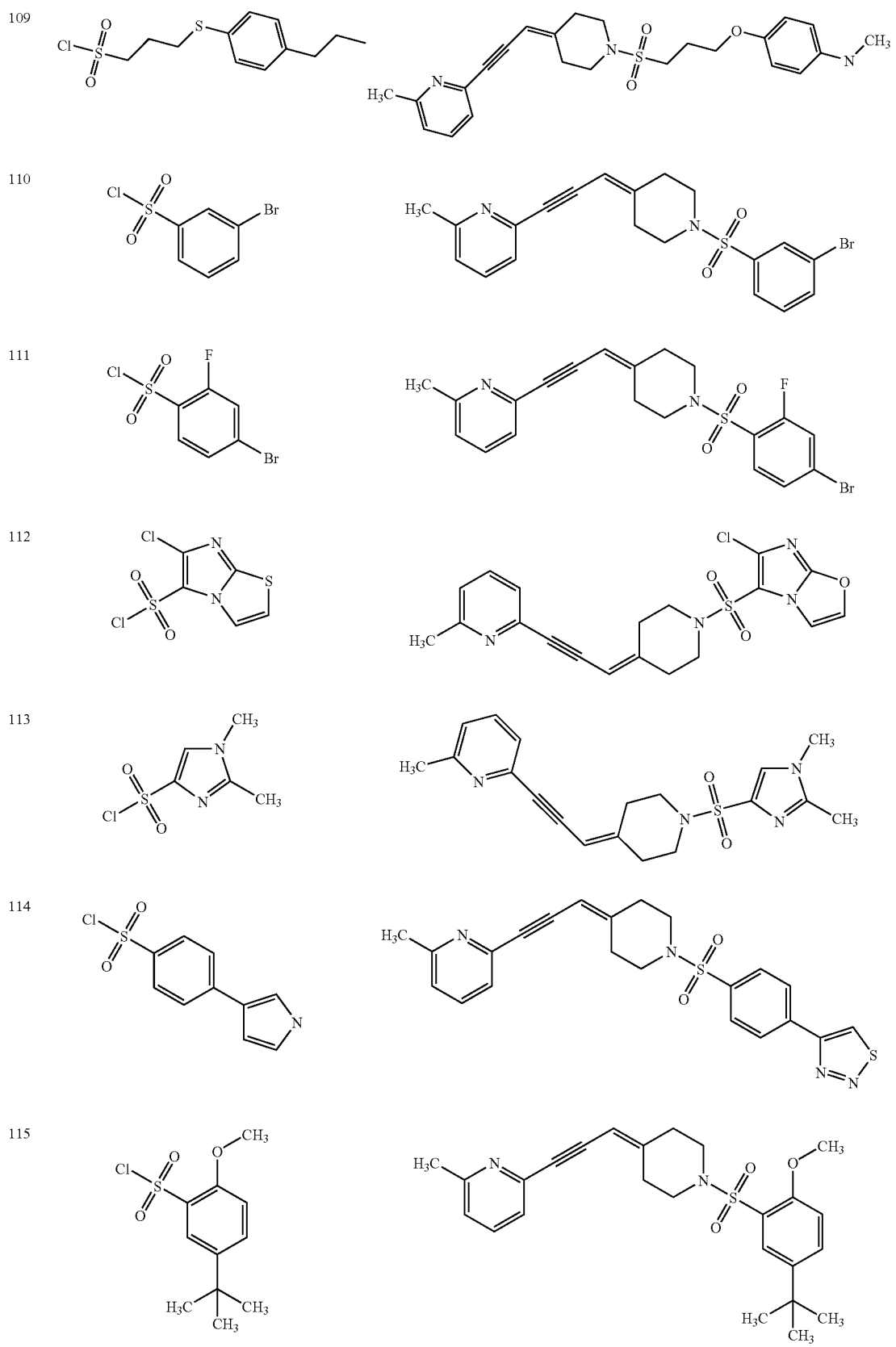

-continued

| Example | Chem. Name | LC-MS M/Z |
|---|---|---|
| 93 | 2-Methyl-6-{3-[1-(2-nitrobenzenesulfonyl)piperidin-4-ylidene]prop-1-ynyl}pyridine | 398.10 |
| 94 | 2-[3-(1-Benzenesulfonylpiperidin-4-ylidene)prop-1-ynyl]-6-methylpyridine | 353.20 |
| 95 | 1-(4-Methyl-3-{4-[3-(6-methylpyridin-2-yl)prop-2-ynylidene]piperidine-1-sulfonyl}phenyl)pyrrolidin-2-one | 450.17 |
| 96 | 2-{3-[1-(4-Methoxybenzenesulfonyl)piperidin-4-ylidene]prop-1-ynyl}-6-methylpyridine | 383.15 |
| 97 | 2-{3-[1-(4-Bromo-2,5-difluorobenzenesulfonyl)piperidin-4-ylidene]prop-1-ynyl}-6-methylpyridine | 468.99 |
| 98 | 2-Methyl-6-[3-(1-phenylmethanesulfonylpiperidin-4-ylidene)prop-1-ynyl]pyridine | 353.20 |
| 99 | 2-[3-(1-Ethanesulfonylpiperidin-4-ylidene)prop-1-ynyl]-6-methylpyridine | 305.22 |
| 100 | 3-Chloro-4-{4-[3-(6-methyl-pyridin-2-yl)prop-2-ynylidene]piperidine-1-sulfonyl}benzonitrile | 412.04 |
| 101 | 2-{3-[1-(3-Fluorophenylmethanesulfonyl)piperidin-4-ylidene]prop-1-ynyl}-6-methylpyridine | 385.18 |
| 102 | 2-[3-(1-Cyclohexylmethanesulfonylpiperidin-4-ylidene)prop-1-ynyl]-6-methylpyridine | 373.28 |
| 103 | 2-Methyl-6-{3-[1-(4-methyl-3-nitrobenzenesulfonyl)piperidin-4-ylidene]prop-1-ynyl}pyridine | 412.11 |
| 104 | 2-Methyl-6-{3-[1-(2,2,2-trifluoroethanesulfonyl)piperidin-4-ylidene]prop-1-ynyl}pyridine | 359.23 |
| 105 | 2-{3-[1-(4-isopropylbenzenesulfonyl)piperidin-4-ylidene]prop-1-ynyl}-6-methyl-pyridine | 395.19 |
| 106 | 4-{4-[3-(6-Methylpyridin-2-yl)prop-2-ynylidene]piperidine-1-sulfonyl}benzonitrile | 378.18 |
| 107 | 2-{3-[1-(5-Chloro-2-methoxy-4-methylbenzenesulfonyl)piperidin-4-ylidene]prop-1-ynyl}-6-methylpyridine | 431.07 |
| 108 | (1S,4R)-7,7-Dimethyl-1-{4-[3-(6-methylpyridin-2-yl)prop-2-ynylidene]piperidine-1-sulfonylmethyl}bicyclo[2.2.1]heptan-2-one | 427.15 |
| 109 | 2-(3-{1-[3-(4-Methoxyphenoxy)propane-1-sulfonyl]piperidin-4-ylidene}prop-1-ynyl)-6-methylpyridine | 441.14 |
| 110 | 2-{3-[1-(3-Bromobenzenesulfonyl)piperidin-4-ylidene]prop-1-ynyl}-6-methylpyridine | 433.03 |
| 111 | 2-{3-[1-(4-Bromo-2-fluorobenzenesulfonyl)piperidin-4-ylidene]prop-1-ynyl}-6-methylpyridine | 451.99 |
| 112 | 6-Chloro-5-{4-[3-(6-methylpyridin-2-yl)prop-2-ynylidene]piperidine-1-sulfonyl}imidazo[2,1-b]thiazole | 433.03 |
| 113 | 2-{3-[1-(1,2-Dimethyl-1H-imidazole-4-sulfonyl)piperidin-4-ylidene]prop-1-ynyl}-6-methylpyridine | 371.19 |
| 114 | 2-Methyl-6-{3-[1-(4-[1,2,3]thiadiazol-4-yl-benzenesulfonyl)piperidin-4-ylidene]prop-1-ynyl}pyridine | 437.09 |
| 115 | 2-{3-[1-(5-tert-Butyl-2-methoxybenzenesulfonyl)piperidin-4-ylidene]prop-1-ynyl}-6-methylpyridine | 439.12 |

EXAMPLE 116

2-Methyl-6-{3-[1-(2-nitrobenzoyl)piperidin-4-ylidene]prop-1-ynyl}pyridine

To a solution 2-nitrobenzoic acid (42.6 mg, 0.25 mmol) in $CH_2Cl_2$ (2 mL) and DMF (0.5 mL) stirred at 0-5° C., was added 1-hydroxybenzotriazole (50 mg, 0.322 mmol) and, after 30', 1-ethyl-3-(3-dimethylaminopropyl)carbodiimide (62 mg, 0.323 mmol). Afterwards, the Compound of Example 3 (53 mg, 0.25 mmol) was added. The reaction mixture was stirred at r.t. for 2 h and kept overnight at the same temperature. After dilution with water and 1 N NaOH, the organic layer was separated and washed with water, dried over $Na_2SO_4$ and evaporated to dryness in vacuo. Purification by flash chromatography ($CHCl_3$-1.4 N $MeOH/NH_3$ 100:0.1) yielded the title compound (82 mg).

EXAMPLE 117-162

Table VII

These compounds were synthesized following the procedure described in Example 116 substituting reagent B (see table VII below; commercially available) for 2-nitrobenzoic acid. Purification was carried out by automated flash liquid chromatography (Horizon™-Biotage) eluting with Petroleum Ether-EtOAc gradient from 100:0 to 20:80 or $CH_2Cl_2$-EtOAc from 100:0 to 20:80.

| Example | Reagent B | Structure |
|---|---|---|
| 117 | | 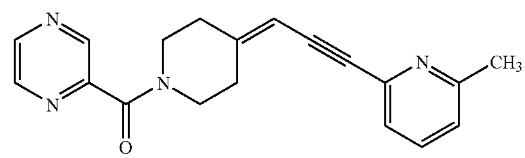 [SMILES: Cc1cccc(C#CC=C2CCN(C(=O)c3cnccn3)CC2)n1] |
| 118 | | 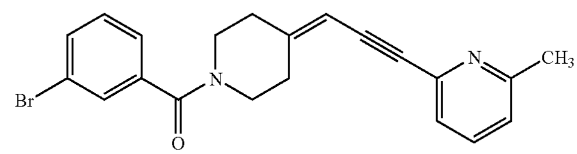 [SMILES: Cc1cccc(C#CC=C2CCN(C(=O)c3cccc(Br)c3)CC2)n1] |
| 119 | | 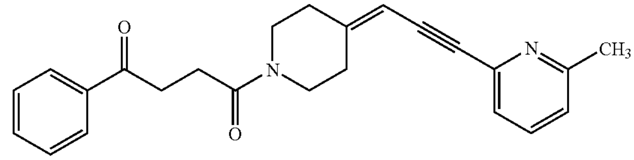 [SMILES: Cc1cccc(C#CC=C2CCN(C(=O)CCC(=O)c3ccccc3)CC2)n1] |
| 120 | | 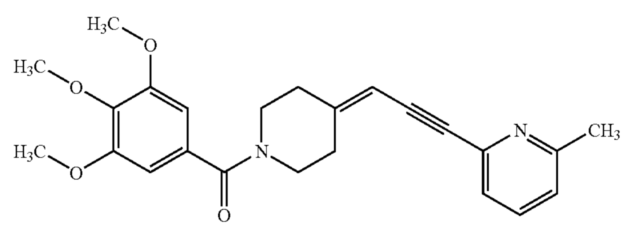 |
| 121 | | 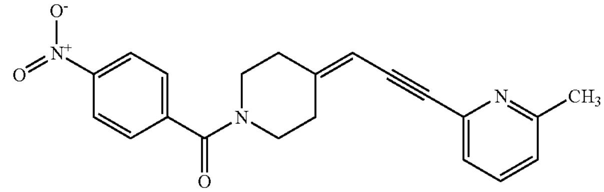 [SMILES: Cc1cccc(C#CC=C2CCN(C(=O)c3ccc([N+](=O)[O-])cc3)CC2)n1] |
| 122 | | 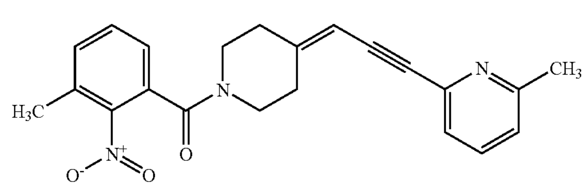 |

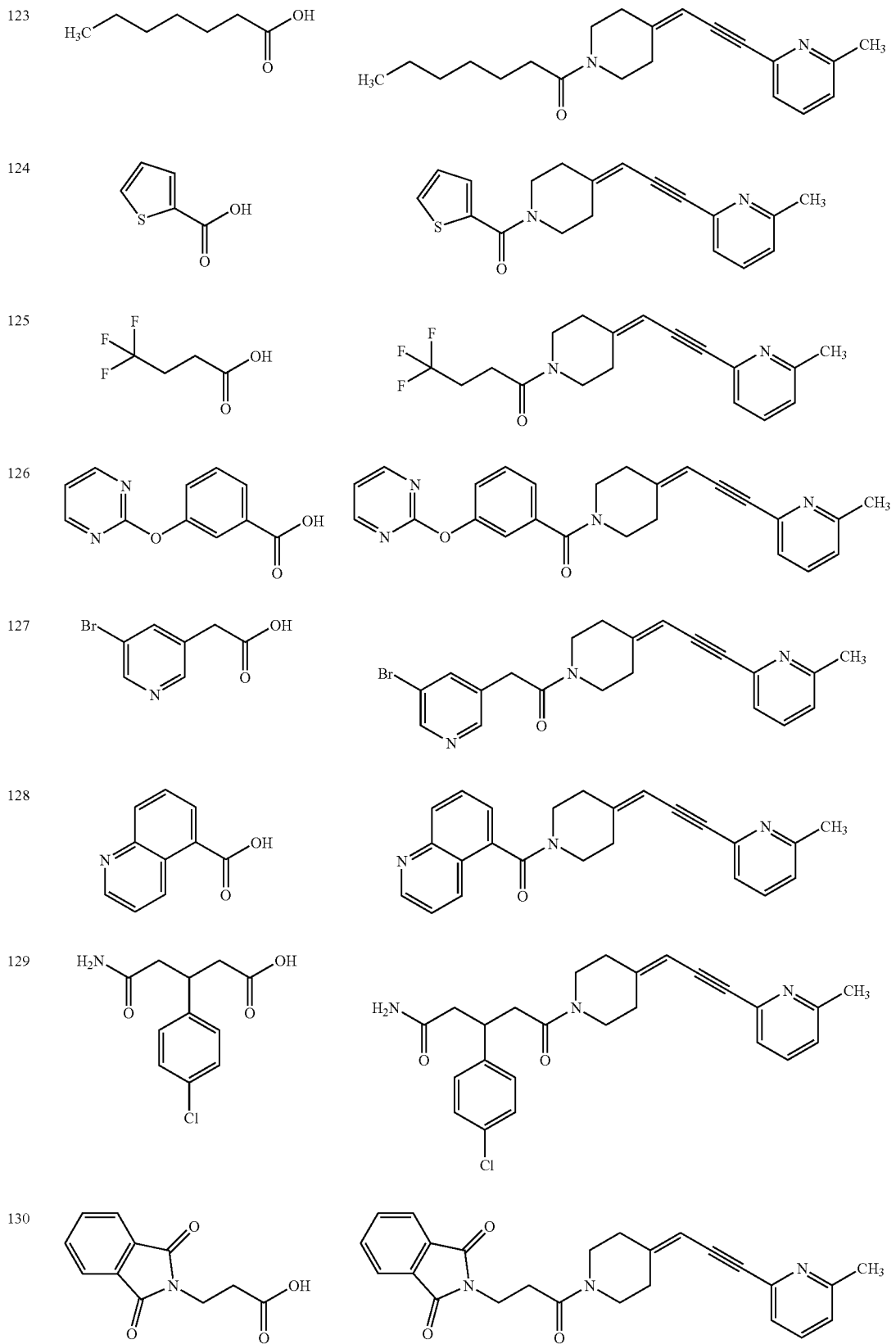

| 131 | 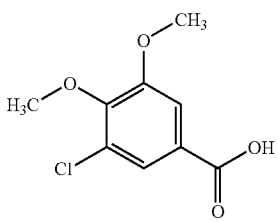 | 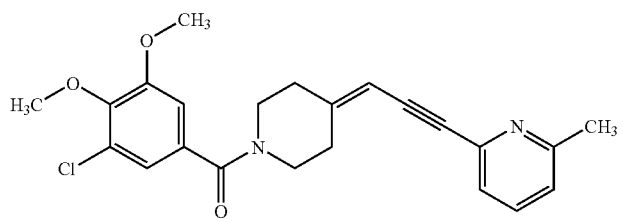 |
|---|---|---|
| 132 | 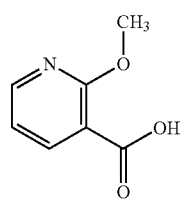 | 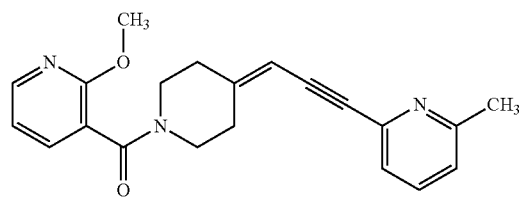 [SMILES: COc1ncccc1C(=O)N1CCC(=CC#Cc2cccc(C)n2)CC1] |
| 133 | 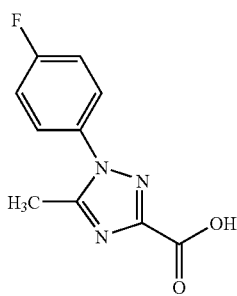 [SMILES: Cc1nc(C(=O)O)nn1-c1ccc(F)cc1] | 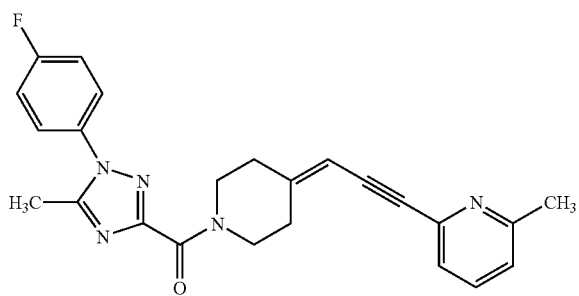 [SMILES: Cc1cccc(C#CC=C2CCN(C(=O)c3nc(C)n(-c4ccc(F)cc4)n3)CC2)n1] |
| 134 | 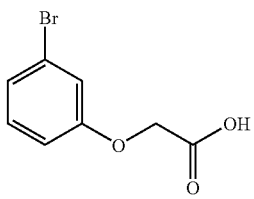 [SMILES: O=C(O)COc1cccc(Br)c1] | 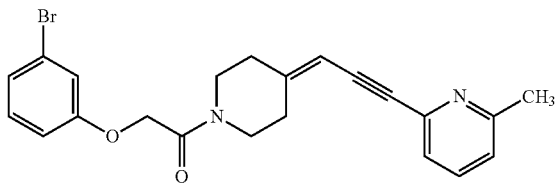 [SMILES: Cc1cccc(C#CC=C2CCN(C(=O)COc3cccc(Br)c3)CC2)n1] |
| 135 | 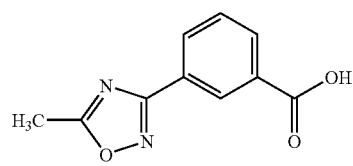 | 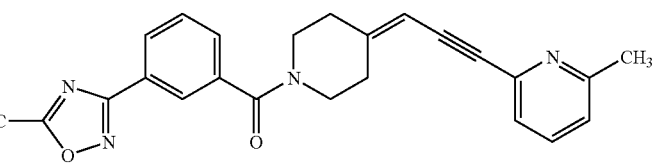 |
| 136 | 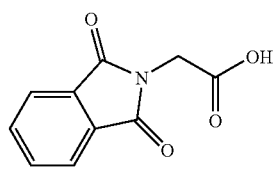 [SMILES: O=C(O)CN1C(=O)c2ccccc2C1=O] | 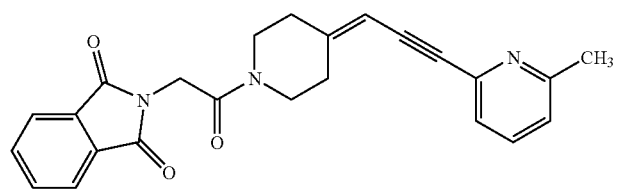 [SMILES: Cc1cccc(C#CC=C2CCN(C(=O)CN3C(=O)c4ccccc4C3=O)CC2)n1] |
| 137 | 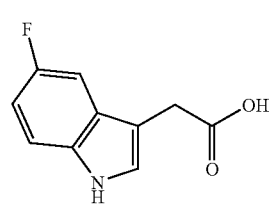 [SMILES: O=C(O)Cc1c[nH]c2ccc(F)cc12] | 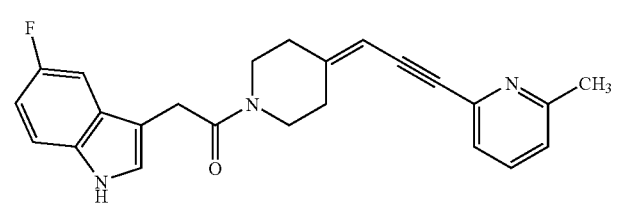 [SMILES: Cc1cccc(C#CC=C2CCN(C(=O)Cc3c[nH]c4ccc(F)cc34)CC2)n1] |

| 101 | 102 |
|---|---|
| 138 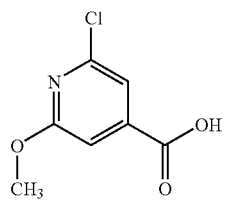 | 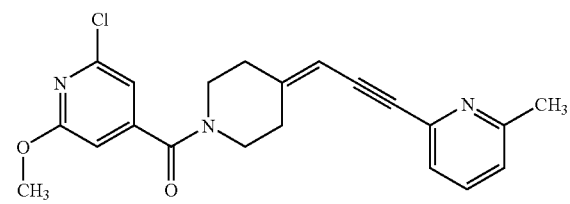 [SMILES: COc1cc(C(=O)N2CCC(=CC#Cc3cccc(C)n3)CC2)cc(Cl)n1] |
| 139 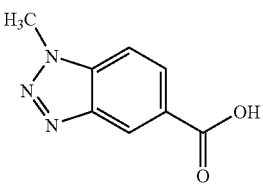 | 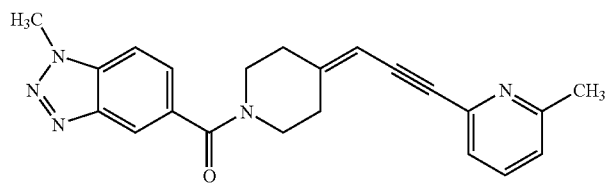 [SMILES: Cc1cccc(C#CC=C2CCN(C(=O)c3ccc4c(c3)nnn4C)CC2)n1] |
| 140 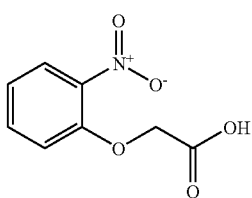 [SMILES: O=C(O)COc1ccccc1[N+](=O)[O-]] | 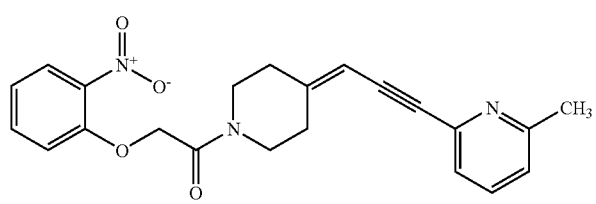 [SMILES: Cc1cccc(C#CC=C2CCN(C(=O)COc3ccccc3[N+](=O)[O-])CC2)n1] |
| 141 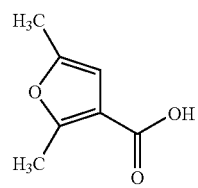 | 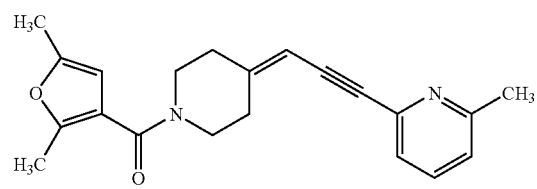 [SMILES: Cc1cccc(C#CC=C2CCN(C(=O)c3cc(C)oc3C)CC2)n1] |
| 142 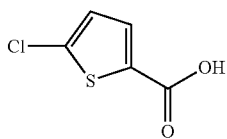 | 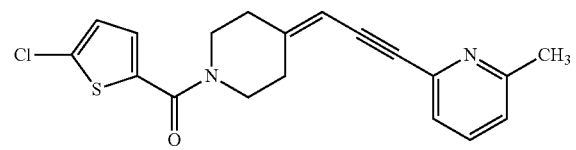 [SMILES: Cc1cccc(C#CC=C2CCN(C(=O)c3ccc(Cl)s3)CC2)n1] |
| 143 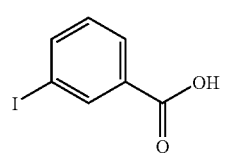 | 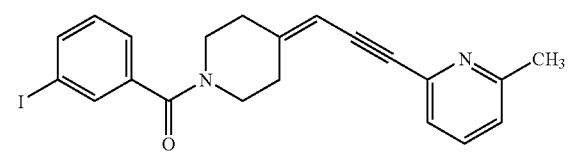 [SMILES: Cc1cccc(C#CC=C2CCN(C(=O)c3cccc(I)c3)CC2)n1] |
| 144 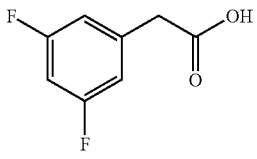 | 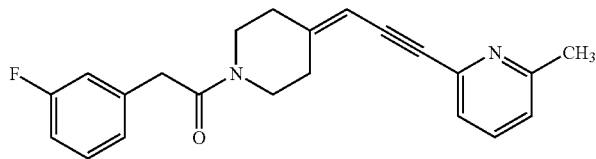 |
| 145 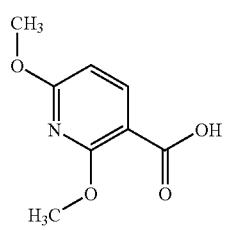 | 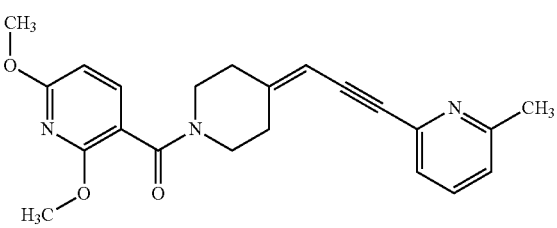 [SMILES: COc1ccc(C(=O)N2CCC(=CC#Cc3cccc(C)n3)CC2)c(OC)n1] |

| | 103 | 104 |
|---|---|---|
| 146 | 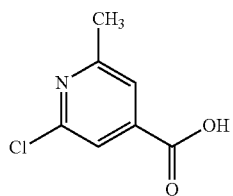 | 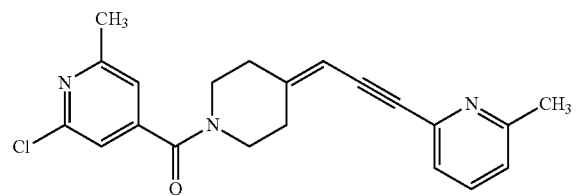 [SMILES: Cc1cc(C(=O)N2CCC(=CC#Cc3cccc(C)n3)CC2)cc(Cl)n1] |
| 147 | 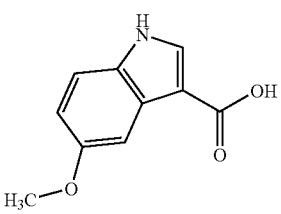 | 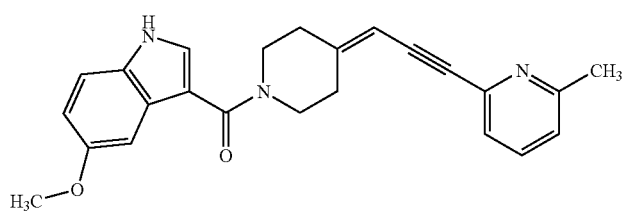 |
| 148 | 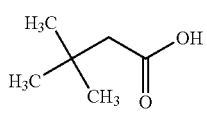 | 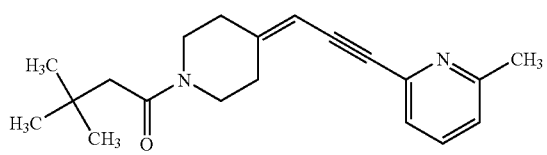 [SMILES: Cc1cccc(C#CC=C2CCN(C(=O)CC(C)(C)C)CC2)n1] |
| 149 | 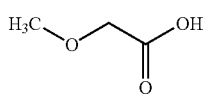 | 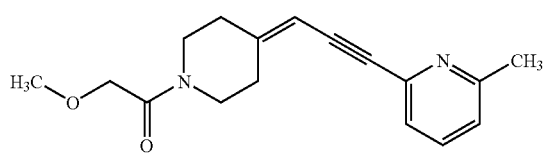 |
| 150 | 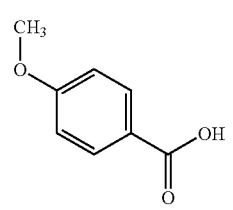 | 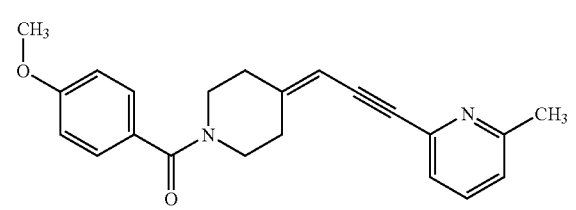 [SMILES: COc1ccc(C(=O)N2CCC(=CC#Cc3cccc(C)n3)CC2)cc1] |
| 151 | 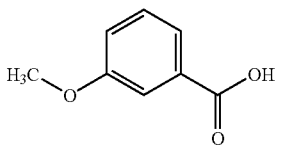 | 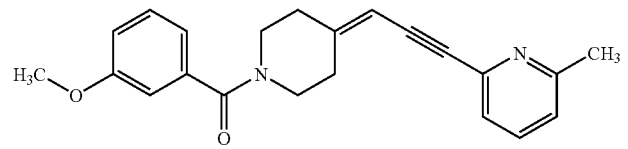 |
| 152 | 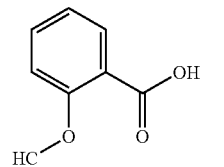 | 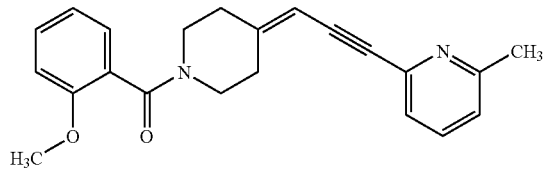 [SMILES: COc1ccccc1C(=O)N1CCC(=CC#Cc2cccc(C)n2)CC1] |
| 153 | 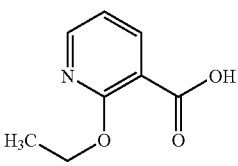 | 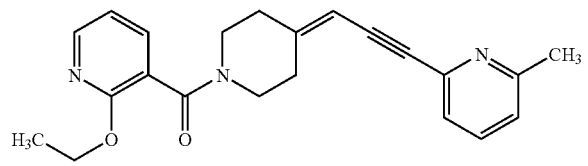 [SMILES: CCOc1ncccc1C(=O)N1CCC(=CC#Cc2cccc(C)n2)CC1] |

| 154 | 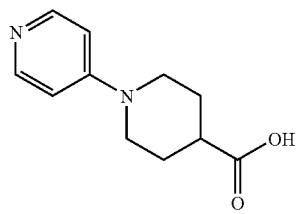 [SMILES: O=C(O)C1CCN(c2ccncc2)CC1] | 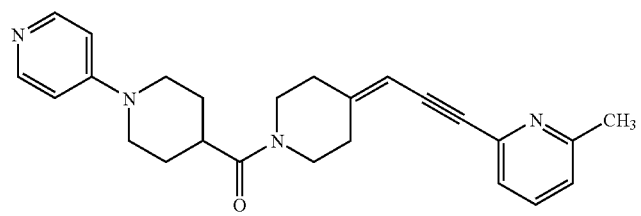 [SMILES: Cc1cccc(C#CC=C2CCN(C(=O)C3CCN(c4ccncc4)CC3)CC2)n1] |
|---|---|---|
| 155 | 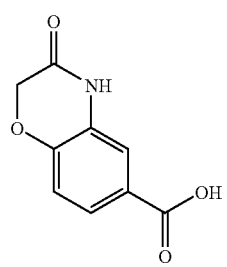 [SMILES: O=C1COc2ccc(C(=O)O)cc2N1] | 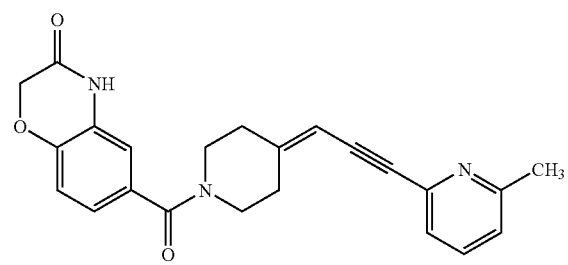 [SMILES: Cc1cccc(C#CC=C2CCN(C(=O)c3ccc4c(c3)NC(=O)CO4)CC2)n1] |
| 156 | 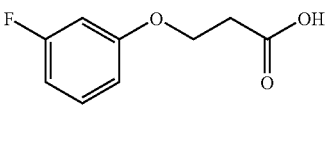 [SMILES: O=C(O)CCOc1cccc(F)c1] | 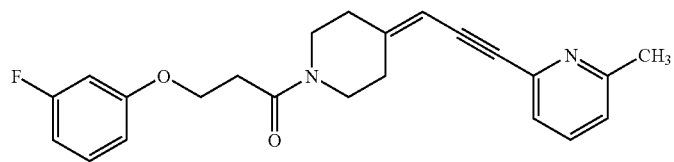 [SMILES: Cc1cccc(C#CC=C2CCN(C(=O)CCOc3cccc(F)c3)CC2)n1] |
| 157 | 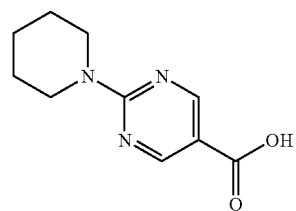 [SMILES: O=C(O)c1cnc(N2CCCCC2)nc1] | 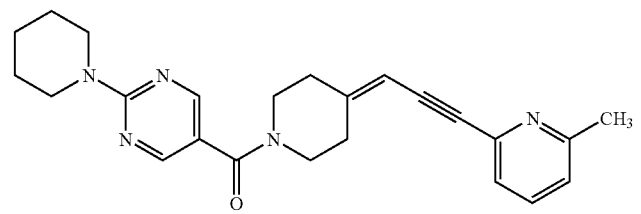 [SMILES: Cc1cccc(C#CC=C2CCN(C(=O)c3cnc(N4CCCCC4)nc3)CC2)n1] |
| 158 | 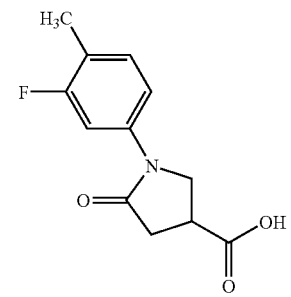 [SMILES: Cc1ccc(N2CC(C(=O)O)CC2=O)cc1F] | 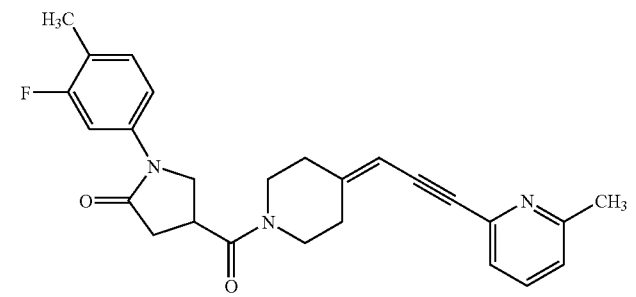 [SMILES: Cc1cccc(C#CC=C2CCN(C(=O)C3CC(=O)N(c4ccc(C)c(F)c4)C3)CC2)n1] |
| 159 | 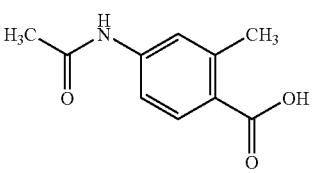 | 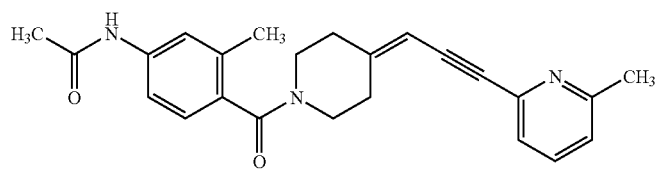 [SMILES: CC(=O)Nc1ccc(C(=O)N2CCC(=CC#Cc3cccc(C)n3)CC2)c(C)c1] |
| 160 | 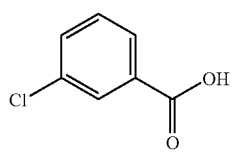 | 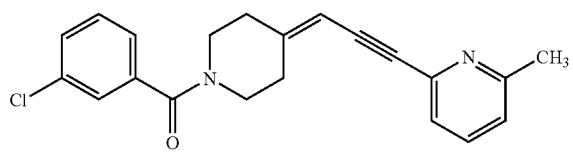 [SMILES: Cc1cccc(C#CC=C2CCN(C(=O)c3cccc(Cl)c3)CC2)n1] |

-continued

| | | |
|---|---|---|
| 161 | 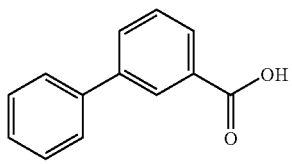 [SMILES: O=C(O)c1cccc(-c2ccccc2)c1] | 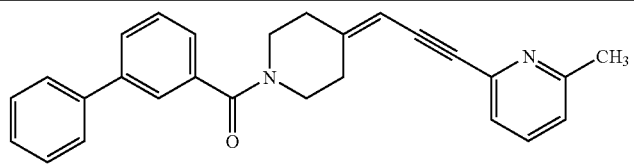 |
| 162 | 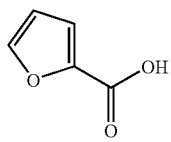 | 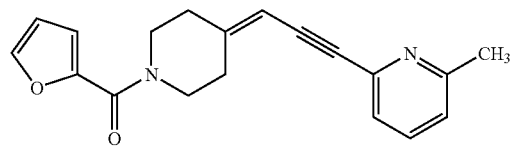 [SMILES: Cc1cccc(C#CC=C2CCN(C(=O)c3ccco3)CC2)n1] |

| Example | Chem. Name | LC-MS M/Z |
|---|---|---|
| 117 | 2-({4-[3-(6-Methylpyridin-2-yl)prop-2-ynylidene]piperidin-1-yl}carbonyl)pyrazine | 319.15 |
| 118 | 2-{3-[1-(3-Bromobenzoyl)piperidin-4-ylidene]prop-1-ynyl}-6-methylpyridine | 395.04 |
| 119 | 4-Oxo-4-[4-[3-(6-methylpyridin-2-yl)prop-2-ynylidene)piperidin-1-yl]-1-phenylbutan-1-one | 373.22 |
| 120 | 2-{3-[1-(3,4,5-Trimethoxybenzoyl)piperidin-4-ylidene]prop-1-ynyl}-6-methylpyridine | 407.15 |
| 121 | 2-Methyl-6-{3-[1-(4-nitrobenzoyl)piperidin-4-ylidene]prop-1-ynyl}pyridine | 362.24 |
| 122 | 2-Methyl-6-{3-[1-(3-methyl-2-nitrobenzoyl)piperidin-4-ylidene]prop-1-ynyl}pyridine | 376.23 |
| 123 | 2-[3-(1-Heptanoylpiperidin-4-ylidene)prop-1-ynyl]-6-methylpyridine | 325.38 |
| 124 | 2-Methyl-6-{3-[1-(thien-2-ylcarbonyl)piperidin-4-ylidene]prop-1-ynyl}pyridine | 323.14 |
| 125 | 2-Methyl-6-{3-[1-(4,4,4-trifluorobutanoyl)piperidin-4-ylidene]prop-1-ynyl}pyridine | 337.27 |
| 126 | 2-{3-[4-[3-(6-Methylpyridin-2-yl)prop-2-ynylidene]piperidin-1-yl]carbonyl]phenoxy}pyrimidine | 411.13 |
| 127 | 2-(3-{1-[(5-Bromopyridin-3-yl)acetyl]piperidin-4-ylidene}prop-1-ynyl 6-methylpyridine | 412.04 |
| 128 | 5-({4-[3-(6-Methylpyridin-2-yl)prop-2-ynylidene]piperidin-1-yl}carbonyl)quinoline | 368.18 |
| 129 | 3-(4-Chlorophenyl)-5-{4-[3-(6-methylpyridin-2-yl)prop-2-ynylidene]piperidin-1-yl}-5-oxopentanamide | 436.04 |
| 130 | 2-(3-{4-[3-(6-Methylpyridin-2-yl)prop-2-ynylidene]piperidin-1-yl}-3-oxopropyl)isoindole-1,3-dione | 414.41 |
| 131 | 2-{3-[1-(3-Chloro-4,5-dimethoxybenzoyl)piperidin-4-ylidene]prop-1-ynyl}-6-methylpyridine | 411.2 |
| 132 | 2-Methoxy-3-({4-[3-(6-methylpyridin-2-yl)prop-2-ynylidene]piperidin-1-yl}carbonyl)pyridine | 348.18 |
| 133 | 2-(3-{1-[(5-Methyl-1-(4-fluorophenyl)-1H 1,2,4-triazol-3-yl]carbonyl]piperidin-4-ylidene}prop-1-ynyl)-6-methylpyridine | 416.24 |
| 134 | 2-(3-{1-[(3-Bromophenoxy)acetyl]piperidin-4-ylidene}prop-1-ynyl)-6-methylpyridine | 424.98 |
| 135 | 2-Methyl-6-(3-{1-[3-(5-methyl-1,2,4-oxadiazol-3-yl)benzoyl]piperidin-4-ylidene}prop-1-ynyl)pyridine | 399.17 |
| 136 | 2-(2-{4-[3-(6-Methylpyridin-2-yl)prop-2-ynylidene]piperidin-1-yl}-2-oxoethyl)isoindole-1,3-dione | 400.08 |

-continued

| | | | |
|---|---|---|---|
| 137 | 5-Fluoro-2-(2-{4-[3-(6-methylpyridin-2-yl)prop-2-ynylidene]piperidin-1-yl}-2-oxoethyl)-1H-indole | 388.05 |
| 138 | 2-Chloro-6-methoxy-4-({4-[3-(6-methylpyridin-2-yl)prop-2-ynylidene]piperidin-1-yl}carbonyl)pyridine | 382.24 |
| 139 | 1-Methyl-5-({4-[3-(6-methylpyridin-2-yl)prop-2-ynylidene]piperidin-1-yl}carbonyl)-1H-1,2,3-benzotriazole | 372.17 |
| 140 | 2-Methyl-6-(3-{1-[(2-nitrophenoxy)acetyl]piperidin-4-ylidene}prop-1-ynyl)pyridine | 392.25 |
| 141 | 2-{3-[1-(2,5-Dimethyl-3-furoyl)piperidin-4-ylidene]prop-1-ynyl}-6-methylpyridine | 335.17 |
| 142 | 2-(3-{1-[(5-Chlorothien-2-yl)carbonyl]piperidin-4-ylidene}prop-1-ynyl)-6-methylpyridine | 357.06 |
| 143 | 2-{3-[1-(3-Iodobenzoyl)piperidin-4-ylidene]prop-1-ynyl}-6-methylpyridine | 443.12 |
| 144 | 2-(3-{1-[(3,5-Difluorophenyl)acetyl]piperidin-4-ylidene}prop-1-ynyl)-6-methylpyridine | 367.23 |
| 145 | 2,6-Dimethoxy-3-({4-[3-(6-methylpyridin-2-yl)prop-2-ynylidene]piperidin-1-yl}carbonyl)pyridine | 378.07 |
| 146 | 2-Chloro-6-methyl-4-({4-[3-(6-methylpyridin-2-yl)prop-2-ynylidene]piperidin-1-yl}carbonyl)pyridine | 366.35 |
| 147 | 5-Methoxy-3-({4-[3-(6-methylpyridin-2-yl)prop-2-ynylidene]piperidin-1-yl}carbonyl)-1H-indole | 386.2 |
| 148 | 2-{3-[1-(3,3-Dimethylbutanoyl)piperidin-4-ylidene]prop-1-ynyl}-6-methylpyridine | 311.2 |
| 149 | 2-{3-[1-(Methoxyacetyl)piperidin-4-ylidene]prop-1-ynyl}-6-methylpyridine | 285.2 |
| 150 | 2-{3-[1-(4-Methoxybenzoyl)piperidin-4-ylidene]prop-1-ynyl}-6-methylpyridine | 347.1 |
| 151 | 2-{3-[1-(3-Methoxybenzoyl)piperidin-4-ylidene]prop-1-ynyl}-6-methylpyridine | 347.18 |
| 152 | 2-{3-[1-(2-Methoxybenzoyl)piperidin-4-ylidene]prop-1-ylyl}-6-methylpyridine | 347 |
| 153 | 2-Ethoxy-3-({4-[3-(6-methylpyridin-2-yl)prop-2-ynylidene]piperidin-1-yl}carbonyl)pyridine | 362 |
| 154 | 2-Methyl-6-{3-[1-(1-(4-pyridyl)piperidin-4-ylcarbonyl)pipridin-4-ylidene]prop-1-ynyl}pyridine | 401 |
| 155 | 6-({4-[3-(6-Methylpyridin-2-yl)prop-2-ynylidene]piperidin-1-yl}carbonyl)-2H-1,4-benzoxazin-3(4H)-one | 388 |
| 156 | 2-{3-[1-[3-(3-Fluorophenoxy)propanoyl]piperidin-4-ylidene]prop-1-ynyl}-6-methylpyridine | 379.45 |
| 157 | 2-(1-Piperidinyl)-5-({4-[3-(6-methylpyridin-2-yl)prop-2-ynylidene]piperidin-1-yl}carbonyl)pyrimidine | 402.09 |
| 158 | 1-(3-Fluoro-4-methylphenyl)-4-({4-[3-(6-methylpyridin-2-yl)prop-2-ynylidene]piperidin-1-yl}carbonyl)pyrrolidin-2-one | 432.2 |
| 159 | 3-Methyl-4-{[4-(6-methyl-3-pyridin-2-ylprop-2-ynylidene)piperidin-1-yl]carbonyl}phenylacetamide | 388.17 |
| 160 | 2-{3-[1-(3-Chlorobenzoyl)piperidin-4-ylidene]prop-1-ynyl}-6-methylpyridine | 351.22 |
| 161 | 2-[3-[1-(1,1'-biphenyl-3-ylcarbonyl)piperidin-4-ylidene]prop-1-ynyl]-6-methylpyridine | 393.15 |
| 162 | 2-{3-[1-(2-Furoyl)piperidin-4-ylidene]prop-1-ynyl}-6-methylpyridine | 307.33 |

EXAMPLE 163

2-Methyl-6-{3-[1-(Phenylacetyl)piperidin-4-ylidene]prop-1-ynyl}pyridine

To a solution of phenylacetic acid (61.5 mg, 0.452 mmol) in 10 mL di $CH_2Cl_2$ was added PS-carbodiimide 1.25 mmol/g (480 mg, 0.6 mmol), while gently stirring at r.t. After 20 min., the Compound of Example 3 (64 mg, 0.301 mmol) was added. A very slow stirring was maintained overnight. Filtration, followed by washing the resin with $CH_2Cl_2$ and evaporation afforded a crude which was purified by flash chromatography ($CHCl_3$-1.4 N $MeOH/NH_3$ 100:0.2) yielding the title product (80 mg).

EXAMPLE 164-189

Table VIII

These compounds were synthesized following the procedure described in Example 163 substituting reagent B (see table VIII below; commercially available) for phenylacetic acid. Purification was carried out by automated flash liquid chromatography (Horizon™-Biotage) eluting with Petroleum Ether-EtOAc gradient from 100:0 to 20:80 or $CH_2Cl_2$-EtOAc from 100:0 to 20:80.

| Example | Reagent B | Structure |
|---|---|---|
| 164 | 4-phenylbutanoic acid | 1-(4-phenylbutanoyl)piperidin-4-ylidene derivative |
| 165 | 3-fluorobenzoic acid | 3-fluorobenzoyl derivative |
| 166 | 3-methylbenzoic acid | 3-methylbenzoyl derivative |
| 167 | 3-cyanobenzoic acid | 3-cyanobenzoyl derivative |
| 168 | 3-(trifluoromethoxy)benzoic acid | 3-(trifluoromethoxy)benzoyl derivative |
| 169 | 3-(trifluoromethyl)benzoic acid | 3-(trifluoromethyl)benzoyl derivative |
| 170 | 5-bromofuran-2-carboxylic acid | 5-bromofuran-2-carbonyl derivative |

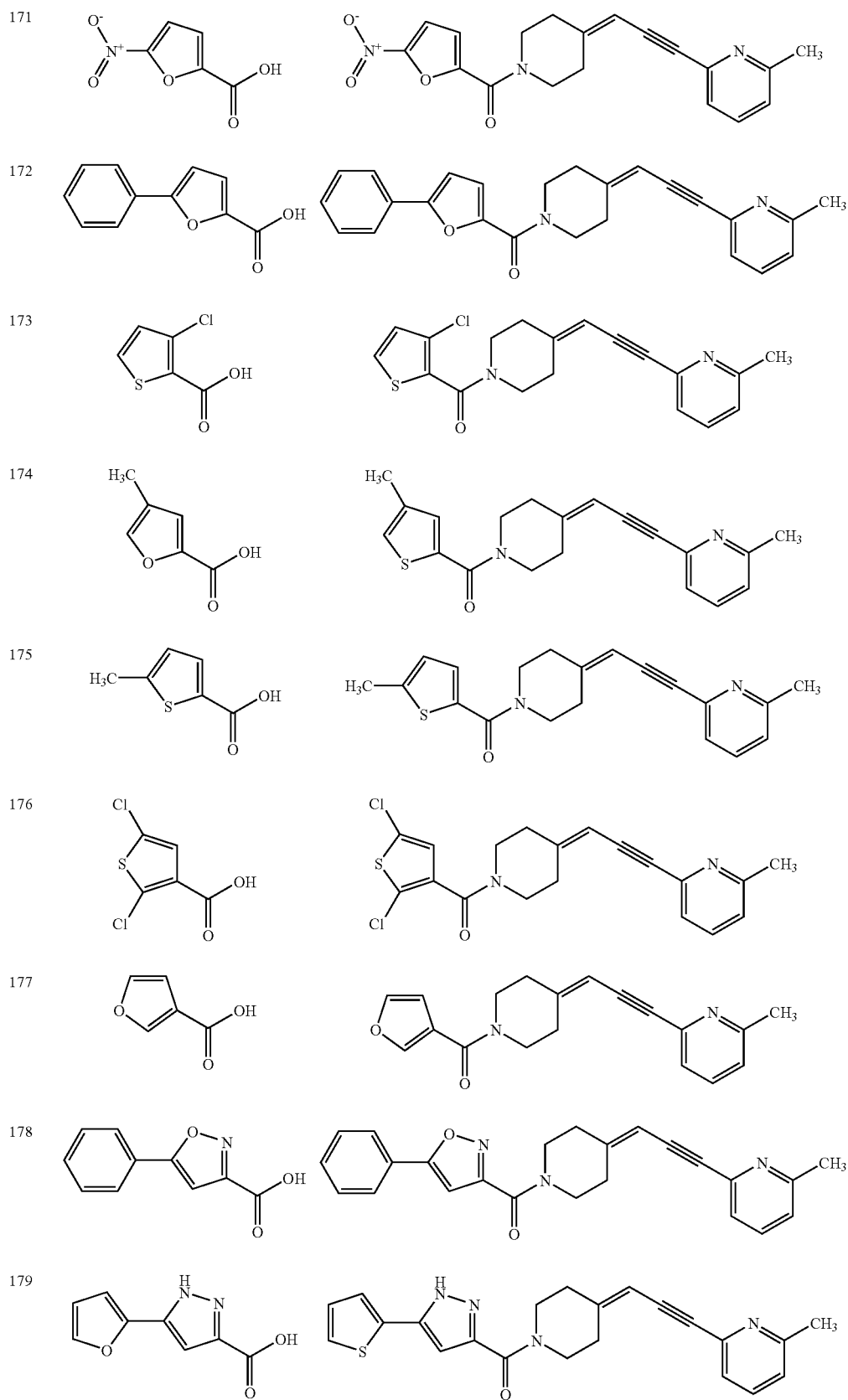

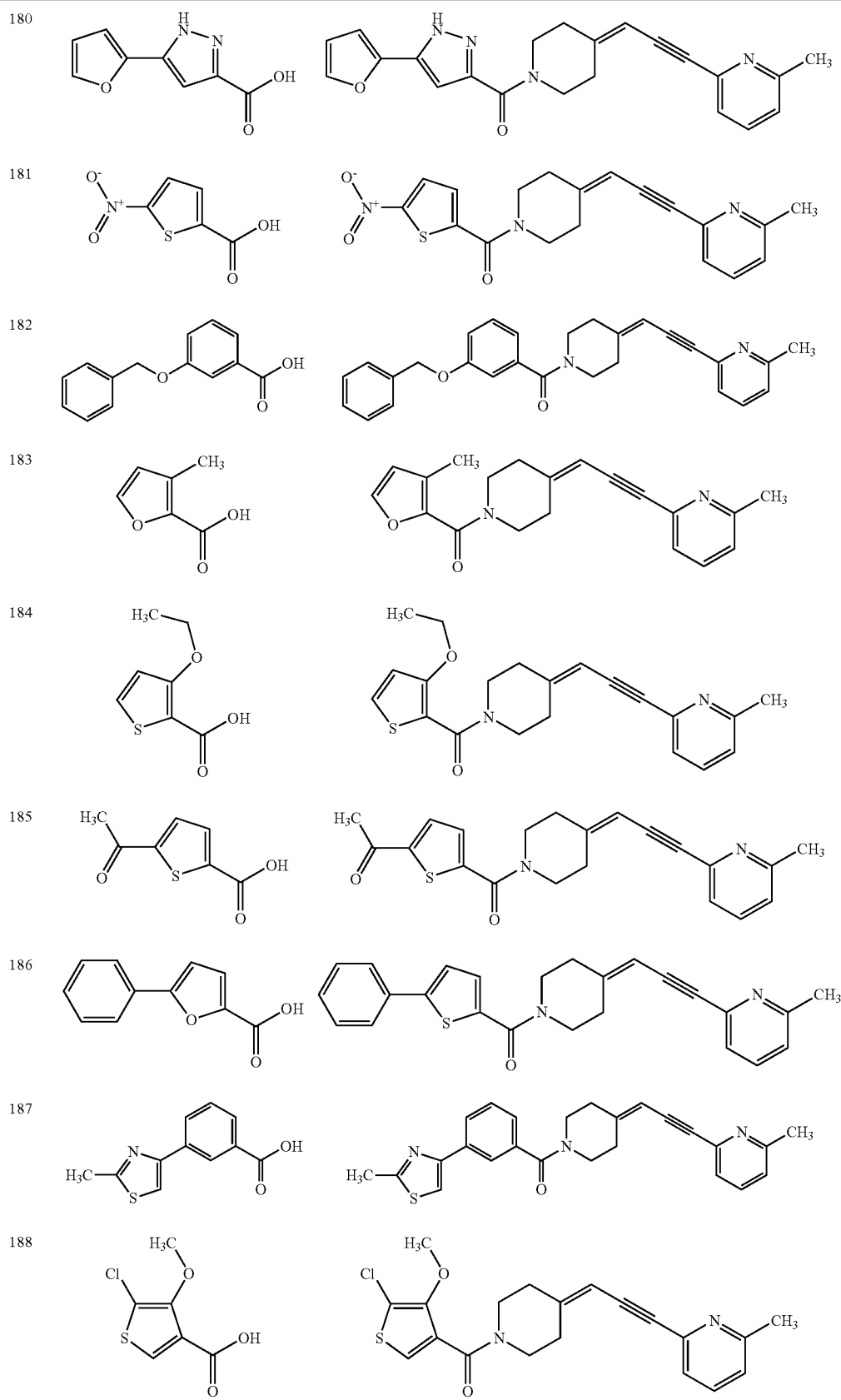

189 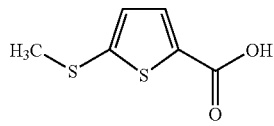 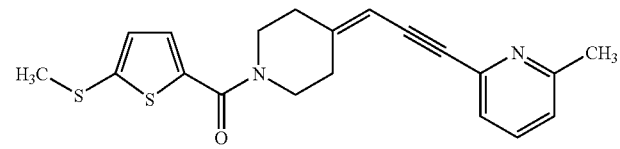

| Example | Chem. Name | LC-MS M/Z |
|---|---|---|
| 164 | 2-Methyl-6-{3-[1-(4-phenylbutanoyl)piperidin-4-ylidene]prop-1-ynyl}pyridine | 359.27 |
| 165 | 2-{3-[1-(3-Fluorobenzoyl)piperidin-4-ylidene]prop-1-ynyl}-6-methylpyridine | 335.34 |
| 166 | 2-{3-[1-(3-Methylbenzoyl)piperidin-4-ylidene]prop-1-ynyl}-6-methylpyridine | 331.42 |
| 167 | 3-({4-[3-(6-Methylpyridin-2-yl)prop-2-ynylidene]piperidin-1-yl}carbonyl)benzonitrile | 342.28 |
| 168 | 2-Methyl-6-{3-[1-(3-trifluoromethoxybenzoyl)piperidin-4-ylidene]prop-1-ynyl}pyridine | 401.41 |
| 169 | 2-Methyl-6-{3-[1-(3-trifluoromethylbenzoyl)piperidin-4-ylidene]prop-1-ynyl}pyridine | 385.05 |
| 170 | 2-{3-[1-(5-Bromo-2-furoyl)piperidin-4-ylidene]prop-1-ynyl}-6-methylpyridine | 386.14 |
| 171 | 2-Methyl-6-{3-[1-(5-nitro-2-furoyl)piperidin-4-ylidene]prop-1-ynyl}pyridine | 352.19 |
| 172 | 2-Methyl-6-{3-[1-(5-phenyl-2-furoyl)piperidin-4-ylidene]prop-1-ynyl}pyridine | 383.24 |
| 173 | 2-(3-{1-[(3-Chlorothien-2-yl)carbonyl]piperidin-4-ylidene}prop-1-ynyl)-6-methylpyridine | 357.09 |
| 174 | 2-Methyl-6-(3-{1-[(4-methylthien-2-yl)carbonyl]piperidin-4-ylidene}prop-1-ynyl)pyridine | 337.16 |
| 175 | 2-Methyl-6-(3-{1-[(5-methylthien-2-yl)carbonyl]piperidin-4-ylidene}prop-1-ynyl)pyridine | 337.14 |
| 176 | 2-(3-{1-[(2,5-Dichlorothien-3-yl)carbonyl]piperidin-4-ylidene}prop-1-ynyl)-6-methylpyridine | 392.31 |
| 177 | 2-{3-[1-(3-Furoyl)piperidin-4-ylidene]prop-1-ynyl}-6-methylpyridine | 307.24 |
| 178 | 2-Methyl-6-(3-{1-[(5-phenylisoxazol-3-yl)carbonyl]piperidin-4-ylidene}prop-1-ynyl)pyridine | 384.71 |
| 179 | 2-Methyl-6-(3-{1-[(5-thien-2-yl-1H-pyrazol-3-yl)carbonyl]piperidin-4-ylidene}prop-1-ynyl)pyridine | 389.06 |
| 180 | 2-[3-(1-{[5-(2-Furyl)-1H-pyrazol-3-yl]carbonyl}piperidin-4-ylidene)prop-1-ynyl]-6-methylpyridine | 373.32 |
| 181 | 2-Methyl-6-(3-{1-[(5-nitrothien-2-yl)carbonyl]piperidin-4-ylidene}prop-1-ynyl)pyridine | 368.25 |
| 182 | 2-{3-[1-[3-(Benzyloxy)benzoyl]piperidin-4-ylidene]prop-1-ynyl}pyridine | 422.04 |
| 183 | 2-Methyl-6-{3-[1-(3-methyl-2-furoyl)piperidin-4-ylidene]prop-1-ynyl}pyridine | 321.06 |
| 184 | 2-(3-{1-[(3-Ethoxythien-2-yl)carbonyl]piperidin-4-ylidene}prop-1-ynyl}-6-methylpyridine | 367.18 |
| 185 | 1-[5-({4-[3-(6-methylpyridin-2-yl)prop-2-ynylidene]piperidin-1-yl}carbonyl)thien-2-yl]ethanone | 365.22 |
| 186 | 2-Methyl-6-(3-{1-[(5-phenylthien-2-yl)carbonyl]piperidin-4-ylidene}prop-1-ynyl)pyridine | 39931 |
| 187 | 2-[3-[1-(2-Methyl-1,3-thiazol-4-yl)benzoylpiperidin-4-ylidene]prop-1-ynyl]-6-methylpyridine | 414.21 |

| | | |
|---|---|---|
| 188 | 2-(3-{1-[(5-Chloro-4-methoxythien-3-yl)carbonyl]piperidin-4-ylidene}prop-1 ynyl)-6-methylpyridine | 387.4 |
| 189 | 2-Methyl-6-[3-(1-{[5-(methylthio)thien-2-yl]carbonyl}piperidin-4-ylidene)prop 1-ynyl]pyridine | 369.25 |

EXAMPLE 190

2-(3-{1-[(3-Chloro-4-methylthien-2-yl)carbonyl]piperidin-4-ylidene}prop-1-ynyl)-6-methylpyridine To a solution of the Compound of Example 3 (64 mg, 0.301 mmol) and TEA (70 µL) in $CH_2Cl_2$ (8 mL) stirred at r.t. was added 3-chloro-4-methylthienyl chloride (66.6 mg, 0.331 mmol) in 2 mL of $CH_2Cl_2$. The reaction mixture was stirred for 6 h at r.t. After dilution with water and 1 N NaOH, the organic layer was separated and washed with water, dried over $Na_2SO_4$ and evaporated to dryness in vacuo. Purification by flash chromatography ($CHCl_3$) yielded the title compound (112 mg).
MS: $[M+H]^+$=371.86
By the same method the following compounds were obtained using the proper commercial acid chlorides:

EXAMPLE 191

2-Methyl-6-(3-{1-[3-(1,3-thiazol-2-yl)benzoyl]piperidin-4-ylidene}prop-1-ynyl)pyridine

MS: $[M+H]^+$=400.70

EXAMPLE 192

2-(3-{[4-[3-(6-Methylpyridin-2-yl)prop-2-ynylidene]piperidin-1-yl]carbonyl}phenyl)pyrimidine

MS: $[M+H]^+$=395.51

EXAMPLE 193

5-[1-(3-Nitropyridin-2-yl)piperidin-4-ylidene]pent-3-yn-2-one

To a solution of Compound 1c (52 mg; 0.213 mmol), acetyl chloride (46 mL, 0.647 mmol), bis(triphenyl)palladium(II) dichloride (4.49 mg, 0.0064 mmol) and copper (I) iodide (1.62 mg, 0.085 mmol) in anhydrous THF (5 mL), was added triethylamine (85 µL, 0.61 mmol) and the reaction mixture was stirred, in a closed vessel, at 60° C. for 5 h, cooled to r.t. poured into water and extracted with EtOAc. The combined extracts were washed with NaOH 0.1N, water, dried over $Na_2SO_4$ and evaporated to dryness in vacuo. Purification by flash chromatography (EtOAc—Petroleum Ether 25:75), afforded 17.5 mg of the title product.
MS: $[M+H]^+$=286.10

EXAMPLE 194-198

Table IX

These compounds were synthesized following the procedure described in Example 193 substituting reagent B (see table IX below; commercially available) for acetyl chloride. Purification was carried out by automated flash liquid chromatography (Horizon™-Biotage) eluting with Petroleum Ether-EtOAc gradient from 100:0 to 20:80 or $CH_2Cl_2$-EtOAc from 100:0 to 20:80.

| Example | Reagent B | Structure | Chem. Name |
|---|---|---|---|
| 194 | 4-fluorobenzoyl chloride | 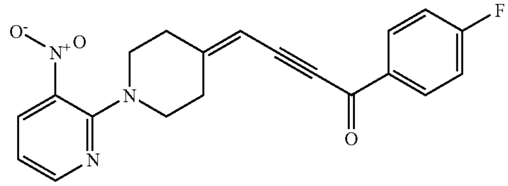 | 1-(4-Fluorophenyl)-4-[1-(3-nitropyridin 2-yl)piperidin-4-ylidene]but-2-yn-1-one |
| 195 | pivaloyl chloride | 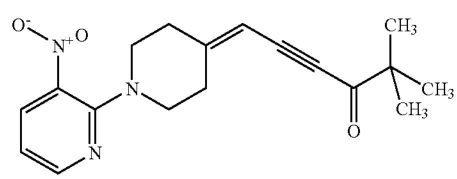 | 2,2-Dimethyl-6-[1-(3-nitropyridin-2-yl)piperidin-4-ylidene]hex-4-yn-3-one |
| 196 | thiophene-2-carbonyl chloride | 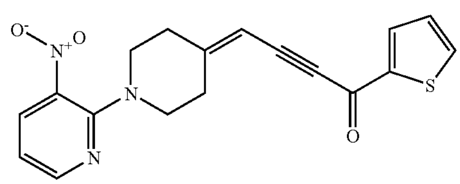 | 4-[1-(3-Nitropyridin-2-yl)piperidin-4-ylidene]-1-thiophen-2-ylbut-2-yn-1-one |

| Example | Reagent B | Structure | Chem. Name |
|---|---|---|---|
| 197 | 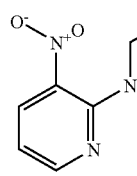 | 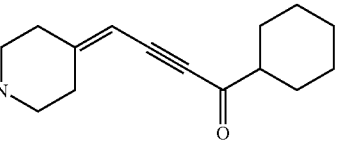 | 1-Cyclohexyl-4-[1-(3-nitropyridin-2-yl)piperidin-4-ylidene]but-2-yn-1-one |
| 198 | 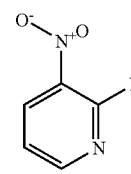 | 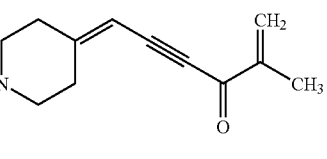 | 2-Methyl-6-[1-(3-nitropyridin-2-yl)piperidin-4-ylidene]hex-1-en-4-yn-3-one |

EXAMPLE 199

2-{4-[3-(3,5-Difluoro-4-methoxyphenyl)prop-2-ynylidene]piperidin-1-yl}-3-nitropyridine A mixture of Compound 1c (50 mg, 0.206 mmol), 4-bromo-2,6-difluoroanisole (45.9 mL, 0.206 mmol), bis(triphenylphosphine)palladium(II)dichloride (7.23 mg, 0.012 mmol), CuI (3.92 mg, 0.206 mmol) in anhydrous and degassed triethylamine (3 mL) was heated at 80° C. under a nitrogen atmosphere for 2 h in a sealed vessel. The reaction mixture was cooled, filtered on Celite, poured into water and extracted with EtOAc. The combined organic layers were washed with brine, dried on $Na_2SO_4$ and evaporated to dryness in vacuo to afford a residue, which was purified by flash chromatography (EtOAc—Petroleum Ether 10:90) affording the title product (22 mg).
MS: $[M+H]^+=386.52$

EXAMPLE 200-215

Table X

These compounds were synthesized following the procedure described in Example 199 substituting reagent B (see table X below; commercially available) for 4-bromo-2,6-difluoroanisole.

Purification was carried out by automated flash liquid chromatography (Horizon™-Biotage) eluting with Petroleum Ether-EtOAc gradient from 100:0 to 20:80.

| Example | Reagent B | Structure |
|---|---|---|
| 200 | 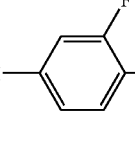 | 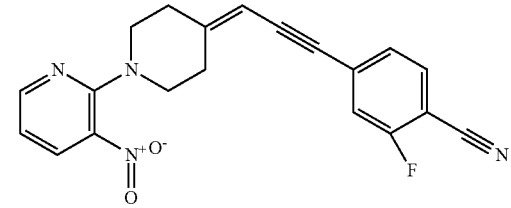 |
| 201 | 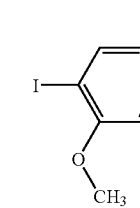 | 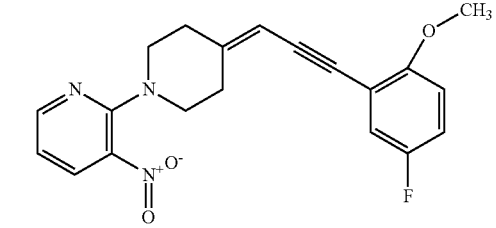 |
| 202 | 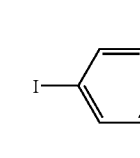 | 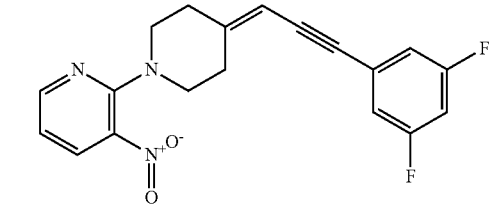 |

-continued
| 203 | 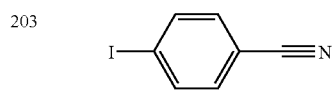 | 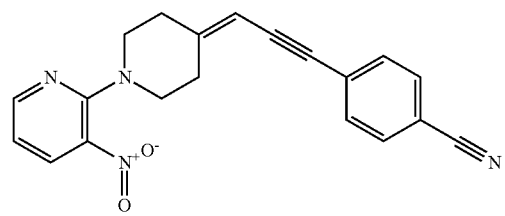 |
| 204 | 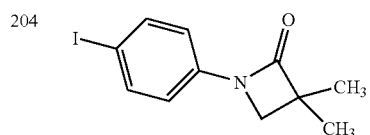 | 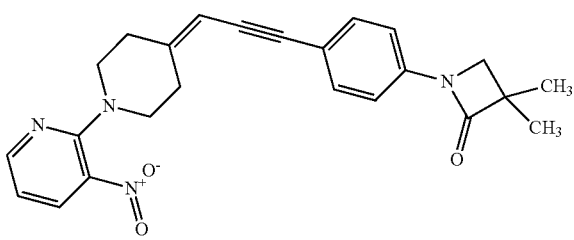 |
| 205 | 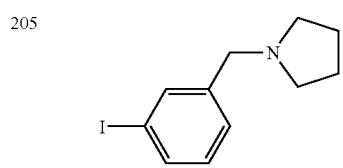 | 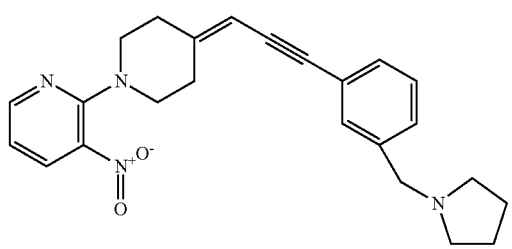 |
| 206 | 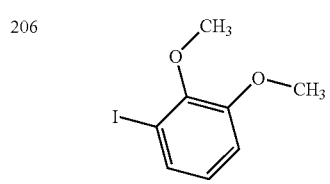 | 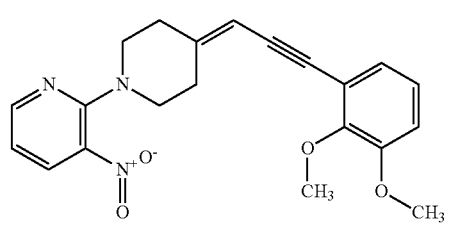 |
| 207 | 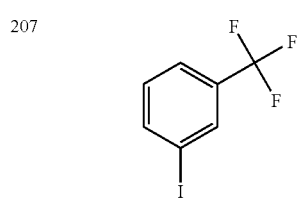 | 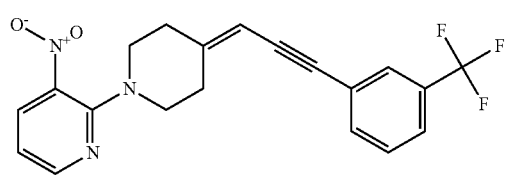 |
| 208 | 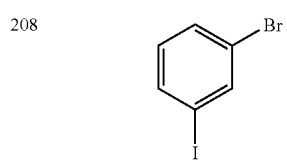 | 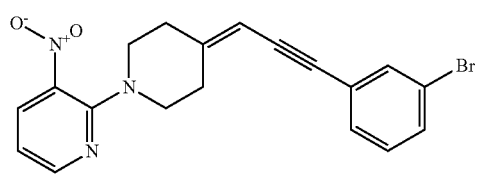 |
| 209 | 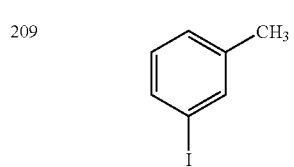 | 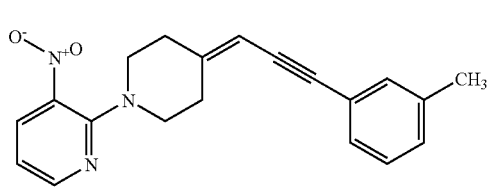 |

| | | |
|---|---|---|
| 210 | 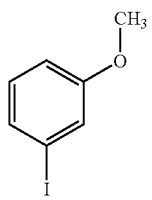 | 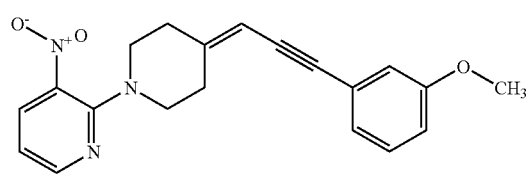 |
| 211 | 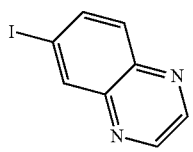 [SMILES: Ic1ccc2nccnc2c1] | 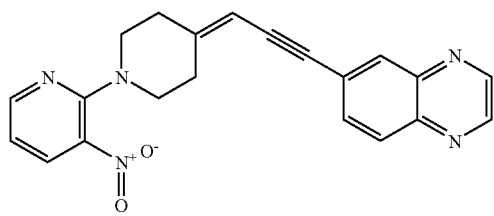 |
| 212 | 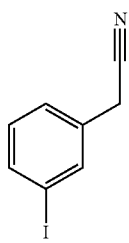 | 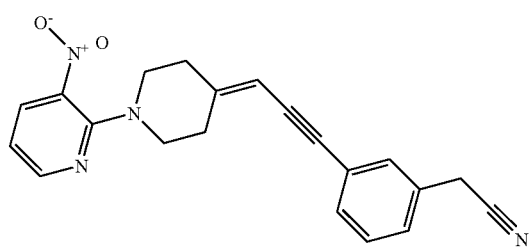 |
| 213 | 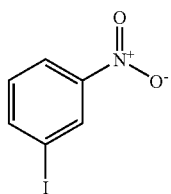 | 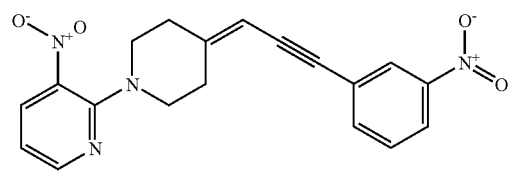 |
| 214 | 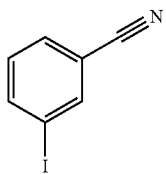 | 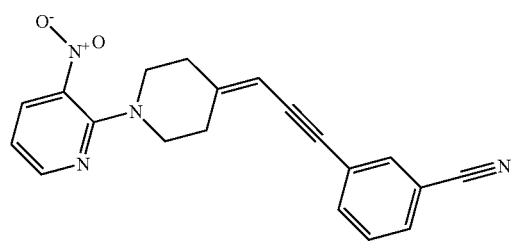 |
| 215 | 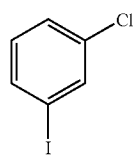 | 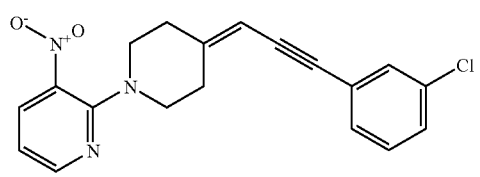 |

| Example | Chem. Name | LC-MS M/Z |
|---|---|---|
| 200 | 2-Fluoro-4-{3-[1-(3-nitropyridin-2-yl)piperidin-4-ylidene]prop-1-yn-1-yl}benzonitrile | 363.3 |
| 201 | 2-{4-[3-(5-Fluoro-2-methoxyphenyl)prop-2-ynylidene]piperidin-1-yl}-3-nitropyridine | 368.4 |
| 202 | 2-{4-[3-(3,5-Difluorophenyl)prop-2-yn-1-ylidene]piperidin-1-yl}-3-nitropyridine | 356.3 |
| 203 | 4-{3-[1-(3-Nitropyridin-2-yl)piperidin-4-ylidene]prop-1-yn-1-yl}benzonitrile | 345.4 |
| 204 | 3,3-Dimethyl-1-{4-[1-(3-nitropyridin-2-yl)piperidin-4-ylidene]prop-1-ynylphenyl}azetidin-2-one | 417.5 |
| 205 | 3-Nitro-2-{4-[3-(3-pyrrolidin-1-ylmethylphenyl)prop-2-yn-1-ylidene]piperidin-1-yl}pyridine | 403.5 |
| 206 | 2-{4-[3-(2,3-Dimethoxyphenyl)prop-2-yn-1-ylidene]piperidin-1-yl}-3-nitropyridine | 380.4 |
| 207 | 3-Nitro-2-(4-{3-[3-(trifluoromethyl)phenyl]prop-2-yn-1-ylidene}piperidin-1-yl)pyridine | 388.3 |
| 208 | 2-{4-[3-(3-Bromophenyl)prop-2-yn-1-ylidene]piperidin-1-yl}-3-nitropyridine | 399.3 |
| 209 | 2-{4-[3-(3-Methylphenyl)prop-2-yn-1-ylidene]piperidin-1-yl}-3-nitropyridine | 334.4 |
| 210 | 2-{4-[3-(3-Methoxyphenyl)prop-2-yn-1-ylidene]piperidin-1-yl}-3-nitropyridine | 350.4 |
| 211 | 6-{3-[1-(3-Nitropyridin-2-yl)piperidin-4-ylidene]prop-1-yn-1-yl}quinoxazoline | 372.4 |
| 212 | (3-{3-[1-(3-Nitropyridin-2-yl)piperidin-4-ylidene]prop-1-yn-1-yl}phenyl)acetonitrile | 359.4 |
| 213 | 3-Nitro-2-{4-[3-(3-nitrophenyl)prop-2-yn-1-ylidene]piperidin-1-yl}pyridine | 365.4 |
| 214 | 3-{3-[1-(3-Nitropyridin-2-yl)piperidin-4-ylidene]prop-1-yn-1-yl}benzonitrile | 345.4 |
| 215 | 2-{4-[3-(3-Chlorophenyl)prop-2-yn-1-ylidene]piperidin-1-yl}-3-nitropyridine | 354.8 |

EXAMPLE 216 tert-Butyl 4-(3-phenylprop-2-yn-1-yl)piperidine-1-carboxylate

The title compound was obtained as described for the Compound of Example 1, but using in the last step Compound 30a instead of Compound 1c and iodobenzene instead of 2-bromo-6-methylpyridine. The crude was purified by automated flash liquid chromatography (Horizon™-Biotage) eluting with Petroleum Ether-EtOAc 6:4 affording the title product as a brownish oil.

MS: [M+H]$^+$=300.32

EXAMPLE 217 tert-Butyl 4-hept-2-ynylidenepiperidine-1-carboxylate

A mixture of palladium tetrakis(triphenylphosphine) (21 mg, 0.018 mmol), butylamine (2.5 mL) and Compound 49a (200 mg, 0.724 mmol) were stirred at room temperature for 45 minutes. Copper iodide (10.3 mg, 0.05 mmol) was then added, followed by hex-1-yne (41.6 µL, 0.362 mmol). The solution was heated for 3-5 hours at 70° C. till change in colour to depth blue. The reaction was quenched with ammonium chloride, extracted with diethyl ether, washed with brine, dried over magnesium sulphate, filtered, concentrated to dryness and purified by preparative HPLC-MS e affording the title product (78 mg).

MS: [M+H]$^+$=278.4

EXAMPLE 218-226

These compounds were synthesized following the procedure described below (method A or method B, Table XI) using commercially available starting materials. Purification was carried out by automated flash liquid chromatography (Horizon™-Biotage) eluting with Petroleum Ether-EtOAc gradient from 100:0 to 20:80 or by classical flash chromatography (Petroleum Ether-EtOAc mixtures).

Method A

A mixture of Compound 1c (36 mg; 0.148 mmol), Reagent B (0.296 mmol), bis(triphenylposphine)palladium(II)dichloride (3.60 mg, 0.0051 mmol) and tetrabutylammonium fluoride (155 mg, 0.593 mmol) was heated in a sealed vessel at 80° C. and the melted mixture was stirred at 80° C. for 1.5 hours, cooled to r.t. and rinsed with EtOAc. The EtOAc solution was washed with water, dried over Na$_2$SO$_4$ and evaporated to dryness in vacuo. Purification by flash chromatography (EtOAc-ETP 15:85), afforded the title products.

Method B

A solution of Compound 1c (23 mg; 0.946 mmol), Reagent B (0.253 mmol), tetrakis(triphenylphosphine)palladium(0) (8 mg, 0.0069 mmol) and copper(I) iodide (2 mg, 0.0105 mmol) in triethylamine (4 mL), in a sealed vessel, was stirred at 90° C. for 2 h, cooled to r.t., poured into water and extracted with EtOAc. The EtOAc solution was washed with water, dried over Na$_2$SO$_4$ and evaporated to dryness in vacuo. Purification by flash chromatography (EtOAc-ETP 2:8), afforded the title products.

| Example | Reagent B | Structure |
|---|---|---|
| 218 | 5-bromo-2-(trifluoromethyl)pyridine | 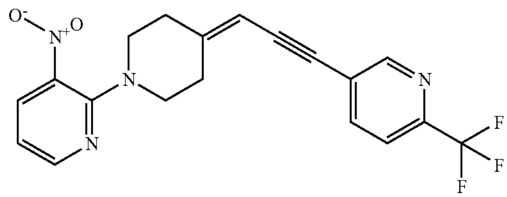 |
| 219 | 2-fluoro-3-iodo-6-methylpyridine | 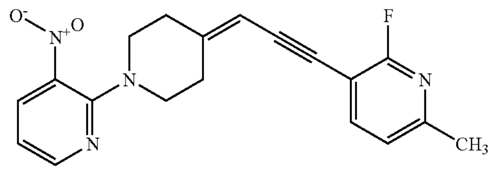 |
| 220 | 3-bromo-2-chloro-4-iodopyridine | 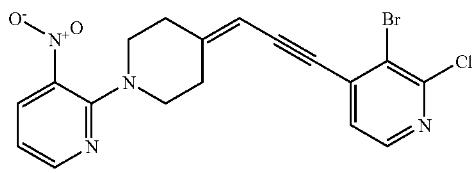 |
| 221 | 3-bromo-2-fluoro-4-iodopyridine | 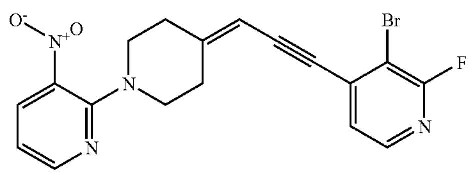 |
| 222 | 2-bromo-3-fluoro-4-methylpyridine | 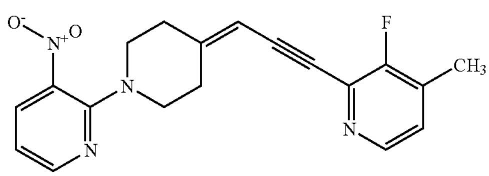 |
| 223 | 3-bromo-5-fluoropyridine | 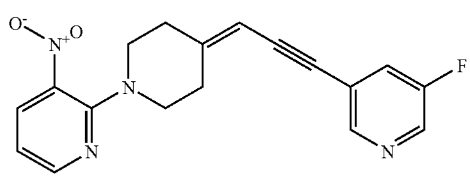 |
| 224 | 6-bromo-2-fluoropyridine | 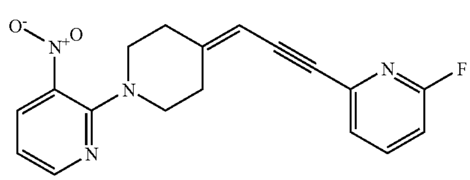 |
| 225 | 2-isopropoxy-5-fluoropyridine | 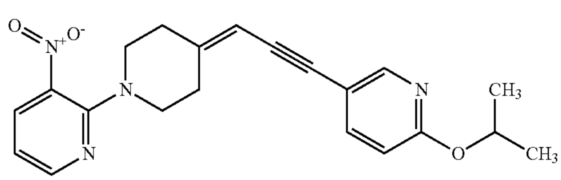 |

| | | LC-MS | |
| Example | Chem. Name | M/Z | Method |
|---|---|---|---|
| | 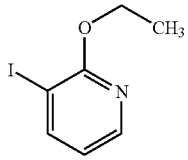 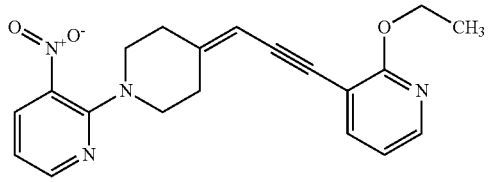 | | |
| 218 | 3-Nitro-2-(4-{3-[6-(trifluoromethyl)pyridin-3-yl]prop-2-ynylidene}piperidin-1-yl)pyridine | 389.10 | A |
| 219 | 2-Fluoro-6-methyl-3-{3-[1-(3-nitropyridin-2-yl)piperidin-4-ylidene]prop-1-yn-1-yl}pyridine | 353.14 | B |
| 220 | 3-Bromo-2-chloro-4-{3-[1-(3-nitropyridin-2-yl)piperidin-4-ylidene]prop-1-yn-1-yl}pyridine | 434.99 | B |
| 221 | 3-Bromo-2-fluoro-4-{3-[1-(3-nitropyridin-2-yl)piperidin-4-ylidene]prop-1-yn-1-yl}pyridine | 418.97 | B |
| 222 | 3-Fluoro-4-methyl-2-{3-[1-(3-nitropyridin-2-yl)piperidin-4-ylidene]prop-1-yn-1-yl}pyridine | 353.14 | A |
| 223 | 2-{4-[3-(5-Fluoropyridin-3-yl)prop-2-yn-1-ylidene]piperidin-1-yl}-3-nitropyridine | 339.16 | A |
| 224 | 2-{4-[3-(6-Fluoropyridin-2-yl)prop-2-yn-1-ylidene]piperidin-1-yl}-3-nitropyridine | 339.16 | A |
| 225 | 2-{4-[3-(6-Isopropoxypyridin-3-yl)prop-2-ynylidene]piperidin-1-yl}-3-nitropyridine | 379.23 | B |
| 226 | 2-Ethoxy-3-{3-[1-(3-nitropyridin-2-yl)piperidin-4-ylidene]prop-1-yn-1-yl}pyridine | 365.11 | B |

EXAMPLE 227

2-{4-[3-(6-Methylpyridin-2-yl)prop-2-yn-1-ylidene]piperidin-1-yl}-5-nitropyridine The title compound was prepared following the procedure described for the compound of Example 59, but substituting NMP with N,N-dimethylacetamide and substituting 2-fluoropyridine with 2-bromo-5-nitropyridine. Purification was carried out by automated flash liquid chromatography (Horizon™-Biotage) eluting with CHCl$_3$-1.4 N MeOH NH$_3$ 100:0.5.

$^1$H-NMR (CDCl$_3$, δ): 2.42-2.54 (m, 2H), 2.67 (s, 3H); 2.75-2.90 (m, 2H), 3.83-3.95 (m, 4H), 5.70 (s, 1H), 6.60-6.70 (m, 1H), 7.12-7.20 (m, 1H); 7.28-7.38 (m, 1H); 7.60-7.70 (m, 1H); 8.20-8.30 (m, 1H); 9.08 (d, J=4 Hz, 1H).

MS: [M+H]$^+$=335.17

EXAMPLE 228

2-{4-[3-(3,5-Difluorophenyl)prop-2-yn-1-ylidene]piperidin-1-yl}-6-methoxy-3-nitropyridine tert-Butyl 4-[3-(3,5-difluorophenyl)prop-2-ynylidene]piperidine-1-carboxylate (Compound 228a)

A mixture of the Compound 49a (0.110 g, 0.40 mmol), palladium tetrakis(triphenylphosphine) (0.023 g, 0.02 mmol), copper(I) iodide (0.0078 g, 0.04 mmol) and 1-ethynyl-3,5-difluorobenzene (49 μL, 0.4 mmol) and TEA (2.5 mL) was heated for 3 h at 80° C. Afterwards, the reaction mixture was cooled, poured into water and extracted with EtOAc. The combined organic layers were washed with brine, dried on Na$_2$SO$_4$ and evaporated to dryness in vacuo to afford a residue (0.062 g.), used in the next step without further purification.

$^1$H-NMR (CDCl$_3$, δ): 1.50 (s, 9H), 2.27-2.37 (m, 2H), 2.52-2.60 (m, 2H), 3.45-3.55 (m, 4H), 5.56 (s, 1H), 6.74-6.82 (m, 1H), 6.91-6.98 (m, 2H).

MS: [M+H]$^+$=334.15

4-[3-(3,5-Difluorophenyl)prop-2-ynylidene]piperidine (Compound 228b)

To a solution of Compound 228a (0.090 g, 0.27 mmol) in CHCl$_3$ (1 mL) was added trifluoroacetic acid (0.42 mL, 5.4 mmol) and the reaction mixture was then stirred at 70° C. for 15 min. until the complete conversion of the reagent was observed by LC-MS. After cooling to r.t., water was added and the solution was alkalinized by addition of 2 N NaOH. The solution was extracted with CH$_2$Cl$_2$, the organic layer washed with brine and dried over Na$_2$SO$_4$ affording the title compound (0.051 g).

$^1$H-NMR (CDCl$_3$, δ): 1.85 (s, 1H, broad), 2.27-2.38 (m, 2H), 2.52-2.62 (m, 2H), 2.90-3.00 (m, 4H), 5.49 (s, 1H), 6.72-6.81 (m, 1H), 6.90-6.98 (m, 2H).

MS: [M+H]$^+$=234.26

2-{4-[3-(3,5-Difluorophenyl)prop-2-yn-1-ylidene]piperidin-1-yl}-6-methoxy-3-nitropyridine A solution of Compound 228b (0.046 mg, 0.197 mmol), 2-chloro-6-methoxy-3-nitropyridine (34.6 mg, 0.18 mmol), potassium carbonate (50.3 mg, 0.36 mmol) in N,N-dimethylacetamide was heated in a microwave oven at 165° C. for 3 min. Afterwards, the reaction mixture was cooled, poured into water and extracted with EtOAc. The combined organic layers were washed with brine, dried on $Na_2SO_4$ and evaporated to dryness in vacuo to afford a residue, which was purified by flash chromatography (EtOAc—Petroleum Ether 5:95) affording the title product (0.058 g).
MS: $[M+H]^+=386.16$

EXAMPLE 229

5-Bromo-2-{4-[3-(6-methylpyridin-2-yl)prop-2-yn-1-ylidene]piperidin-1-yl}pyrimidine The title compound was prepared following the procedure described for the compound of Example 59, but substituting NMP with N,N-dimethylacetamide and substituting 2-fluoropyridine with 5-bromo-2-iodopyrimidine and reacting the mixture at r.t. Purification was carried out by automated flash liquid chromatography (Horizon™-Biotage) eluting with $CHCl_3$-1.4 N MeOH $NH_3$ 100:0.5. White solid. Yield: 64.1%.
$^1$H-NMR (CDCl$_3$, δ): 2.35-2.45 (m, 2H), 2.59 (s, 3H); 2.63-2.75 (m, 2H), 3.83-3.95 (m, 4H), 5.65 (s, 1H), 7.04-7.14 (m, 1H), 7.22-7.30 (m, 1H); 7.50-7.60 (m, 1H); 8.32 (s, 2H).
MS: $[M+H]^+=370.10$

EXAMPLE 230

3-Methyl-2-{4-[3-(6-methylpyridin-2-yl)prop-2-yn-1-ylidene]piperidin-1-yl}-5-nitropyridine The title compound was prepared following the procedure described for the compound of Example 59, but substituting N,N-dimethylacetamide for NMP and substituting 2-bromo-3-methyl-5-nitropyridine for 2-fluoropyridine. Purification was carried out by automated flash liquid chromatography (Horizon™-Biotage) eluting with $CHCl_3$-1.4 N MeOH $NH_3$ 100:0.25. Yellow solid. Yield: 97.3%.
$^1$H-NMR (CDCl$_3$, δ): 2.39 (s, 3H), 2.46-2.56 (m, 2H), 2.59 (s, 3H); 2.74-2.85 (m, 2H), 3.51-3.61 (m, 4H), 5.66 (s, 1H), 7.10 (d, J=8.0 Hz, 1H), 7.27 (d, J=8.0 Hz, 1H); 7.56 (t, J=8.0 Hz, 1H); 8.15 (s, 1H), 8.98 (s, 1H).
MS: $[M+H]^+=349.23$

EXAMPLE 231

5-Methyl-6-{4-[3-(6-methylpyridin-2-yl)prop-2-yn-1-ylidene]piperidin-1-yl}pyridine-3-carbonitrile The title compound was prepared following the procedure described for the compound of Example 59, but substituting N,N-dimethylacetamide for NMP and substituting 5-cyano-2-fluoro-3-methylpyridine for 2-fluoropyridine. Purification was carried out by automated flash liquid chromatography (Horizon™-Biotage) eluting with EtOAc—Petroleum Ether 2:8. Yellowish solid. Yield: 81.3%.
$^1$H-NMR (CDCl$_3$, δ): 2.33 (s, 3H), 2.45-2.56 (m, 2H), 2.66 (s, 3H); 2.77-2.88 (m, 2H), 3.40-3.51 (m, 4H), 5.65 (s, 1H), 7.15 (d, J=8.0 Hz, 1H), 7.32 (d, J=8.0 Hz, 1H); 7.57 (s, 1H); 7.58-7.75 (m, 1H), 8.40 (s, 1H).
MS: $[M+H]^+=329.22$

EXAMPLE 232

5-{4-[3-(6-Methylpyridin-2-yl)prop-2-yn-1-ylidene]piperidin-1-yl}pyridine-2-carbonitrile A mixture of the compound of Example 3 (0.102 g, 0.48 mmol), 5-bromo-2-cyanopyridine (0.073 g, 0.40 mmol), cesium carbonate (0.658 g, 2 mmol), 1,3-bis(2,6-diisopropylphenyl)imidazolium chloride (8.8 mg, 0.05 mmol), palladium(II)acetate (0.0046 mg, 0.05 mmol), in anhydrous and degassed THF (3 mL) was heated in a microwave oven at 110° C. for 15 min in a sealed vessel. The reaction mixture was cooled, poured into water and extracted with EtOAc. The combined organic layers were washed with brine, dried on $Na_2SO_4$ and evaporated to dryness in vacuo to afford a residue, which was purified by flash chromatography (EtOAc—Petroleum Ether 1:1) affording the title product (0.013 g).
$^1$H-NMR (CDCl$_3$, δ): 2.45-2.54 (m, 2H), 2.61 (s, 3H), 2.72-2.90 (m, 2H), 3.48-3.60 (m, 4H), 5.68 (s, 1H), 7.05-7.20 (m, 2H), 7.22-7.35 (m, 1H); 7.50-7.70 (m, 2H); 8.35 (s, 1H).
MS: $[M+H]^+=315.17$

EXAMPLE 233

2-Methyl-6-{3-[1-(4-methylpyridin-3-yl)piperidin-4-ylidene]prop-1-yn-1-yl}pyridine A mixture of the compound of Example 3 (0.102 g, 0.48 mmol), 3-bromo-4-methylpyridine (0.046 g, 0.40 mmol), cesium carbonate (0.658 g, 2 mmol), 2-(dicyclohexylphosphino)biphenyl (8.8 mg, 0.024 mmol), palladium(II)acetate (0.0027 mg, 0.012 mmol), in anhydrous and degassed toluene (3 mL) was heated in a microwave oven at at 150° C. for 15 min in a sealed vessel. The reaction mixture was cooled, poured into water and extracted with EtOAc. The combined organic layers were washed with brine, dried on $Na_2SO_4$ and evaporated to dryness in vacuo to afford a residue, which was purified by flash chromatography (CHCl$_3$-1.4 N MeOH $NH_3$ 100:0.25) affording the title product (0.008 g).
$^1$H-NMR (CDCl$_3$, δ): 2.38 (s, 3H), 2.47-2.54 (m, 2H), 2.58 (s, 3H), 2.77-2.87 (m, 2H), 3.04-3.12 (m, 4H), 5.63 (s, 1H), 7.05-7.12 (m, 1H), 7.13-7.20 (m, 1H), 7.25-7.30 (m, 1H); 7.50-7.60 (m, 1H); 8.20-8.30 (m, 2H).
MS: $[M+H]^+=304.19$

EXAMPLE 234

4-{4-[3-(6-Methylpyridin-2-yl)prop-2-yn-1-ylidene]piperidin-1-yl}isoquinoline

A mixture of the compound of Example 3 (0.076 g, 0.36 mmol), 4-bromoisoquinoline (0.064 g, 0.30 mmol), cesium carbonate (0.494 g, 1.5 mmol), 2,2'-bis(diphenylphosphino)-1,1'binaphthalene (0.011 g, 0.024 mmol), palladium(II)acetate (0.0027 mg, 0.012 mmol) in anhydrous and degassed toluene (3 mL) was heated at reflux under a nitrogen atmosphere for 18 h. The reaction mixture was cooled, poured into water and extracted with EtOAc. The combined organic layers were washed with brine, dried on $Na_2SO_4$ and evaporated to dryness in vacuo to afford a residue, which was purified by flash chromatography (CHCl$_3$-1.4 N MeOH $NH_3$ 100:0.25) affording the title product (0.061 g).
$^1$H-NMR (CDCl$_3$, δ): 2.59 (s, 3H), 2.62-2.73 (m, 2H), 2.91-3.02 (m, 2H), 3.23-3.36 (m, 4H), 5.70 (s, 1H), 7.11 (d, J=8.0 Hz, 1H), 7.29 (d, J=8.0 Hz, 1H), 7.57 (t, J=8.0 Hz, 1H); 7.75 (t, J=8.0 Hz, 1H); 7.89 (t, J=8.0 Hz, 1H); 8.10 (d, J=8.0 Hz, 1H); 8.15 (s, 1H); 8.23 (d, J=8.0 Hz, 1H); 9.04 (S, 1H).
MS: $[M+H]^+=340.21$

EXAMPLE 235

5-Methyl-2-{4-[3-(6-methylpyridin-2-yl)prop-2-ynylidene]piperidin-1-yl}cyclopent-2-en-1-one A mixture of the Compound of Example 3 (500 mg, 2.36 mmol), 3-methyl-1,2-cyclopentanedione (350 mg, 3.11 mmol), acetic acid (0.18 mL, 3.11 mmol) in ethanol (10 mL) was refluxed for 8 h. The reaction mixture was evaporated, poured into water and extracted with EtOAc. The combined organic layers were washed with brine, dried on $Na_2SO_4$ and evaporated to dryness in vacuo to afford a residue, which was purified by automated flash liquid chromatography (Horizon™-Biotage) eluting with Petroleum Ether-EtOAc 85:15, affording the title product as a brown solid.

MS: $[M+H]^+=307.61$

EXAMPLE 236 tert-Butyl 4-{1-[(methoxycarbonyl)oxy]-3-(6-methylpyridin-2-yl)prop-2-yn-1-yl}piperidine-1-carboxylate To a solution of the Compound of Example 39 (50 mg, 0.15 mmol), triethylamine (65 µL, 0.45 mmol) and 4-dimethylaminopyridine (10 mg, 0.07 mmol) in 3 mL of $CH_2Cl_2$ cooled at 0-5° C., methyl chloroformate (23 µL, 0.30 mmol) was added dropwise. The reaction mixture was stirred at r.t. overnight. Afterwards, it was evaporated to dryness and purified by automated flash liquid chromatography (Horizon™-Biotage) eluting with Petroleum Ether-EtOAc 8:2 affording the title product (0.28 g) as a brown oil.

MS: $[M+H]^+=389.51$

EXAMPLE 237

3-(6-Methylpyridin-2-yl)-1-[1-(3-nitropyridin-2-yl) piperidin-4-yl]prop-2-yn-1-ol 3-(6-Methyl-pyridin-2-yl)-1-piperidin-4-yl-prop-2-yn-1-ol (Compound 237a)

The title compound was prepared following the procedure described for the compound of Example 3, using the Compound of Example 39 instead of the Compound of Example 2. After the usual work-up procedure, the crude was used in the next step without further purification.

MS: $[M+H]^+=231.23$ 3-(6-Methylpyridin-2-yl)-1-[1-(3-nitropyridin-2-yl) piperidin-4-yl]prop-2-yn-1-ol A well homogenised mixture of Compound 237a (200 mg, 0.86 mmol), 2-bromo-3-nitropyridine (194 mg, 0.95 mmol) and triethylamine (249 µL, 1.74 mmol) in N,N-dimethylacetamide (15 mL) was stirred at r.t. for 4 h. Afterwards, the reaction mixture was poured into water and extracted with EtOAc. The combined organic layers were washed with brine, dried on $Na_2SO_4$ and evaporated to dryness in vacuo to afford a residue, which was purified by flash chromatography eluting with Petroleum Ether-EtOAc 7:3, affording the title product (225 mg) as a yellow oil.

MS: $[M+H]^+=353.40$

EXAMPLE 238

2-Methyl-6-{3-[1-(3-nitrothien-2-yl)piperidin-4-ylidene]prop-1-ynyl}pyridine

The title compound was prepared following the procedure described for the compound of Example 237, using the Compound of Example 3 instead of Compound 237a and 2-chloro-3-nitrothiophene instead of 2-bromo-3-nitropyridine. The crude was purified by automated flash liquid chromatography (Horizon™-Biotage) eluting with Petroleum Ether-EtOAc 1:1 affording the title product as a yellow solid.

MS: $[M+H]^+=340.45$

EXAMPLE 239

2-Methyl-6-{3-[1-(5-nitrofuran-2-yl)piperidin-4-ylidene]prop-1-yn-1-yl}pyridine

A suspension of the Compound of Example 3 (100 mg, 0.47 mmol), 2-bromo-5-nitrofuran (98 mg, 0.51 mmol) and potassium carbonate (72 mg, 0.52 mmol) in DMF (2 mL) was stirred at r.t. for 4 h. Afterwards, the reaction mixture was poured into water and extracted with EtOAc. The combined organic layers were washed with brine, dried on $Na_2SO_4$ and evaporated to dryness in vacuo to afford a residue, which was purified by flash chromatography eluting with Petroleum Ether-EtOAc 6:4 affording the title product (94 mg) as a yellow solid.

MS: $[M+H]^+=324.33$

EXAMPLE 240

5-{4-[3-(6-Methylpyridin-2-yl)prop-2-ynylidene] piperidin-1-yl}-N-phenyl-2-furamide A well homogenised mixture of the Compound of Example 3 (100 mg, 0.47 mmol) and N-phenyl-5-bromofuran-2-carboxamide (125 mg, 0.47 mmol) was stirred at 120° C. for 8 h. The reaction mixture was poured into water and extracted with EtOAc. The combined organic layers were washed with brine, dried on $Na_2SO_4$ and evaporated to dryness in vacuo to afford a residue, which was purified by flash chromatography eluting with Petroleum Ether-EtOAc 7:3, affording the title product (36 mg) as a brown solid.

MS: $[M+H]^+=398.51$

EXAMPLE 241

2-Methyl-6-{3-[1-(2-methyl-4-nitro-1H-imidazol-5-yl)piperidin-4-ylidene]prop-1-yn-1-yl}pyridine A well homogenised mixture of the Compound of Example 3 (100 mg, 0.47 mmol), 5-bromo-2-methyl-4-nitro-1H-imidazole (97 mg, 0.47 mmol) and potassium bicarbonate was stirred at 120° C. for 8 h. The reaction mixture was poured into water and extracted with EtOAc The combined organic layers were washed with brine, dried on $Na_2SO_4$ and evaporated to dryness in vacuo to afford a residue, which was purified by automated flash liquid chromatography (Horizon™-Biotage), eluting with Petroleum Ether-EtOAc 7:3, affording the title product as a brown solid.

MS: $[M+H]^+=338.40$

EXAMPLE 242

2-{4-[1-Methoxy-3-(6-methylpyridin-2-yl)prop-2-yn-1-yl]piperidin-1-yl}-3-nitropyridine To a solution of the Compound of Example 237 (70 mg, 0.19 mmol) in THF anhydrous was added 60% sodium hydride in mineral oil (12 mg, 0.3 mmol) and the resulting suspension was stirred at r.t.; after 30 min. was dropped iodomethane (25 µL, 0.4 mmol) and the reaction mixture stirred overnight at r.t. Afterwards, it was quenched with a saturated aq. solution of ammonium chloride and extracted with EtOAc. The combined organic layers were washed with brine, dried on Na$_2$SO$_4$ and evaporated to dryness in vacuo to afford a residue, which was purified by automated flash liquid chromatography (Horizon™-Biotage) eluting with Petroleum Ether-EtOAc 65:35, affording the title product (48 mg) as a yellow oil.
MS: [M+H]$^+$=367.51

EXAMPLE 243

Methyl 3-(6-methylpyridin-2-yl)-1-[1-(2-nitropyridin-2-yl)piperidin-4-yl]prop-2-yn-1-yl carbonate The title compound was prepared following the procedure described for the compound of Example 236, but using the Compound of Example 237 instead of the Compound of Example 39. The crude was purified by automated flash liquid chromatography (Horizon™-Biotage) eluting with Petroleum Ether-EtOAc 8:2, affording the title product as a oil.
MS: [M+H]$^+$=395.44

EXAMPLE 244

3-Nitro-2-[4-(3-phenylprop-2-yn-1-yl)piperidin-1-yl]pyridine 4-(3-Phenyl-prop-2-ynyl)piperidine (Compound 244a)

The title compound was prepared following the procedure described for the compound of Example 3, using the Compound of Example 216 instead of the Compound of Example 2. After the usual work-up procedure, the crude was used for the next step without purification.
MS: [M+H]$^+$=200.31

3-Nitro-2-[4-(3-phenylprop-2-yn-1-yl)piperidin-1-yl]pyridine

The title compound was prepared following the procedure described for the compound of Example 237, using the Compound 244a instead of Compound 237a. The crude was purified by automated flash liquid chromatography (Horizon™-Biotage) eluting with Petroleum Ether/EtOAc 9-1, affording the title product as a yellow oil.
MS: [M+H]$^+$=322.45

EXAMPLE 245

6-Methyl-3-nitro-2-[4-(3-phenylprop-2-ynyl)piperidin-1-yl]nitropyridine

The title compound was obtained as described for the Compound of Example 244, but using 2-chloro-3-nitro-6-picoline instead of 2-bromo-3-nitropyridine. The crude was purified by automated flash liquid chromatography (Horizon™-Biotage) eluting with Petroleum Ether-EtOAc 6:4 affording the title product as a brownish oil.
MS: [M+H]$^+$=300.32

EXAMPLE 246

6-Methyl-2-{4-[3-(6-methylpyridin-2-yl)prop-2-yn-1-yl]piperidin-1-yl}-3-nitropyridine The title compound was prepared following the procedure described for the Compound of Example 31, using 2-chloro-3-nitro-6-picoline instead of 2-bromo-3-nitropyridine. The crude was purified by automated flash liquid chromatography (Horizon™-Biotage) eluting with Petroleum Ether/EtOAc 7:3, affording the title product as a yellow oil.
MS: [M+H]$^+$=351.51

EXAMPLE 247 tert-Butyl 4-[3-(3,5-difluorophenyl)prop-2-yn-1-yl]piperidine-1-carboxylate

The title compound was obtained as described for the Compound of Example 1, but using in the last step Compound 30a instead of Compound 1c and 3,5-difluoroiodobenzene instead of 2-bromo-6-methylpyridine. The crude was purified by automated flash liquid chromatography (Horizon™-Biotage) eluting with Petroleum Ether-EtOAc 85:15, affording the title product as a colorless oil.
MS: [M+H]$^+$=336.98

EXAMPLE 248

2-{4-[3-(3,5-Difluorophenyl)prop-2-yn-1-yl]piperidin-1-yl}-6-methyl-3-nitropyridine 4-[3-(3,5-Difluorophenyl)prop-2-ynyl]piperidine (Compound 248a)

The title compound was prepared following the procedure described for the Compound of Example 3, using the Compound of Example 247 instead of the Compound of Example 2. After the usual work-up procedure, the crude was used for the next step without further purification.
MS: [M+H]$^+$=236.32

2-{4-[3-(3,5-Difluorophenyl)prop-2-yn-yl]piperidin-1-yl}-6-methyl-3-nitropyridine The title compound was prepared following the procedure described for the Compound of Example 237, but using Compound 248a instead of Compound 237a and 2-chloro-3-nitro-6-picoline instead of 2-bromo-3-nitropyridine. The crude was purified by automated flash liquid chromatography (Horizon™-Biotage) eluting with Petroleum Ether-EtOAc 9:1, affording the title product as a yellow oil.
MS: [M+H]$^+$=372.45

EXAMPLE 249

2-{4-[3-(3,5-Difluorophenyl)prop-2-yn-1-yl]piperidin-1-yl}benzonitrile

The title compound was prepared following the procedure described for the compound of Example 42, but using Compound 248a instead of the Compound of Example 3 and 2-bromobenzonitrile instead of bromobenzene. The crude was purified by preparative RP LC-MS chromatography, using MS-C18 XTerra column 30×50 mm eluting with ammonium bicarbonate 20 mM pH 8 buffer-acetonitrile gradient, affording the title product as a brown oil.
MS: [M+H]$^+$=337.45

EXAMPLE 250 tert-Butyl 4-[1-fluoro-3-(6-methylpyridin-2-yl)prop-2-yn-1-yl]piperidine-1-carboxylate Into a solution of the Compound of Example 39 (300 mg, 0.91 mmol) in anhydrous CH$_2$Cl$_2$ (10 mL) cooled at −78° C.

was dropped diethylaminosulfur trifluoride (144 µL, 1.01 mmol). The reaction mixture was kept at the same temperature for 2 h, then warmed up to r.t., quenched with water and extracted with $CH_2Cl_2$. The combined organic layers were washed with brine, dried on $Na_2SO_4$ and evaporated to dryness in vacuo to afford a residue, which was purified by automated flash liquid chromatography (Horizon™-Biotage) eluting with Petroleum Ether-EtOAc 7:3, affording the title product (140 mg) as an oil.
MS: $[M+H]^+=333.44$

EXAMPLE 251

2-{4-[1-Fluoro-3-(6-methylpyridin-2-yl)prop-2-ynyl]piperidin-1-yl}-6-methyl-3-nitropyridine 2-(3-Fluoro-3-piperidin-4-yl-prop-1-ynyl)-6-methyl-pyridine (Compound 251a)

The title compound was prepared following the procedure described for the compound of Example 3, using Compound 250 instead of the Compound of Example 2. After the usual work-up procedure, the crude was used for the next step without further purification.
MS: $[M+H]^+=233.24$ 2-{4-[1-Fluoro-3-(6-methylpyridin-2-yl)prop-2-ynyl]piperidin-1-yl}-6-methyl-3-nitropyridine The title compound was prepared following the procedure described for the compound of Example 237, using Compound 251a instead of Compound 237a and 2-chloro-3-nitro-6-picoline instead of 2-bromo-3-nitropyridine. The crude was purified by automated flash liquid chromatography (Horizon™-Biotage) eluting with Petroleum Ether-EtOAc 9:1, affording the title product as a yellow oil.
MS: $[M+H]^+=369.44$

EXAMPLE 252 tert-Butyl (3E)-3-[3-(6-methylpyridin-2-yl)prop-2-ynylidene]pyrrolidine-1-carboxylate tert-Butyl (3E)-3-(3-trimethylsylylprop-2-ynylidene)pyrrolidine-1-carboxylate (Compound 252a)

The title compound was prepared following the procedure described for Compound 1b using N-boc-3-pyrrolidinone instead of 1-(3-nitropyridin-2-yl)piperidin-4-one. The crude was purified by automated flash liquid chromatography (Horizon™-Biotage) eluting with Petroleum Ether-EtOAc 85:15, affording the title product as a colorless oil.
MS: $[M+H]^+=280.52$ tert-Butyl (3E)-3-prop-2-ynylidenepyrrolidine-1-carboxylate (Compound 252b)

The title compound was prepared following the procedure described for Compound 1c using Compound 252a instead of Compound 1b. The crude was purified by automated flash liquid chromatography (Horizon™-Biotage) eluting with Petroleum Ether-EtOAc 95:5, affording the title product as a colorless oil.
MS: $[M+H]^+=208.74$ tert-Butyl (3E)-3-[3-(6-methylpyridin-2-yl)prop-2-ynylidene]pyrrolidine-1-carboxylate The title compound was obtained as described for the Compound of Example 1, but using in the last step Compound 252b instead of Compound 1c. The crude was purified by automated flash liquid chromatography (Horizon™-Biotage) eluting with Petroleum Ether-EtOAc 7:3, affording the title product as a brownish oil.
MS: $[M+H]^+=299.40$

EXAMPLE 253 AND 254

2-[4-(1-Methyl-3-phenylprop-2-ynylidene)piperidin-1-yl]-3-nitropyridine and

2-[4-(1-Methylene-3-phenylprop-2-ynyl)piperidin-1-yl]-3-nitropyridine tert-Butyl 4-(1-hydroxy-1-methyl-3-phenylprop-2-ynyl)piperidine-1-carboxylate (Compound 253a)

Into a solution of 4-acetylpiperidine-1-carboxylic acid tert-butyl ester (0.67 g, 2.95 mmol), prepared as described in WO2004041777, in THF (20 mL) cooled at −10° C. was dropped a 1M solution of phenylethynylmagnesium bromide in THF (4.5 mL, 4.5 mmol). The reaction mixture was stirred at room temperature overnight. Afterwards, it was quenched with a saturated aq. solution of ammonium chloride and extracted with EtOAc. The combined organic layers were washed with brine, dried on $Na_2SO_4$ and evaporated to dryness in vacuo to afford a residue, which was purified by automated flash liquid chromatography (Horizon™-Biotage) eluting with Petroleum Ether-EtOAc 7:3, affording the title product as a pale yellow oil.
MS: $[M+H]^+=330.54$ tert-Butyl 4-(1-methyl-3-phenylprop-2-ynylidene)piperidine-1-carboxylate (Compound 253 b) and tert-Butyl 4-(1-methylene-3-phenylprop-2-ynyl)piperidine-1-carboxylate (Compound 253 c)

A well homogenised mixture of Compound 253a (0.3 g, 0.911 mmol) and Burgess' reagent (Methyl N-(triethylammoniumsulphonyl)carbamate) (0.35 g, 1.49 mmol) was heated at 60° C. for 2 h. Afterwards, the reaction mixture was cooled, poured into water and extracted with EtOAc. The combined organic layers were washed with brine, dried on $Na_2SO_4$ and evaporated to dryness in vacuo to afford a residue, which was purified by automated flash liquid chromatography (Horizon™-Biotage) eluting with Petroleum Ether-EtOAc 95:5, affording the title products as an oily mixture.
MS: $[M+H]^+=312.54$ 4-(1-Methyl-3-phenylprop-2-ynylidene)piperidine (Compound 253 d) and 4-(1-Methylene-3-phenylprop-2-ynyl)piperidine (Compound 253 e)

The title compounds were prepared following the procedure described for the compound of Example 3, but using the mixture of Compounds 253b and 253c instead of the Compound of Example 2. After the usual work-up procedure, the crude was used for the next step without further purification.
MS: $[M+H]^+=212.32$ 2-[4-(1-Methyl-3-phenylprop-2-ynylidene)piperidin-1-yl]-3-nitropyridine and 2-[4-(1-Methylene-3-phenylprop-2-ynyl)piperidin-1-yl]-3-nitropyridine The title compounds were prepared following the procedure described for the compound of Example 237, but using the mixture of Compounds 253d and 253e instead of Compound 237a and 2-chloro-3-nitropyridine instead of 2-bromo-3-nitropyridine. The crude was purified by preparative RP LC-MS chromatography, using MS-C18 XTerra column 30×50 mm eluting with ammonium bicarbonate 20 mM pH 8 buffer-acetonitrile gradient affording the two title products.
MS: $[M+H]^+=333.35$

EXAMPLE 253

$^1$H-NMR (CDC$_3$δ): 1.97 (s, 3H), 2.57-2.60 (m, 2H), 2.83-2.86 (m, 2H), 3.50-3.56 (m, 4H), 6.73-6.76 (m, 1H), 7.28-7.35 (m, 3H), 7.44-7.46 (m, 2H), 8.13-8.17 (m, 1H), 8.36-8.37 (m, 1H)

EXAMPLE 254

$^1$H-NMR (CDCl$_3$δ): 1.80-1.98 (m, 4H), 2.37-48 (m, 1H), 3.08-3.15 (m, 2H), 3.93-3.97 (m, 2H), 5.39 (s, 1H), 5.49 (s, 1H), 6.73-6.75 (m, 1H), 7.28-7.33 (m, 3H), 7.44-7.46 (m, 2H), 8.13-8.17 (m, 1H), 8.36-8.37 (m, 1H)

EXAMPLE 255

3-Nitro-2-{4-[(2E)-3-phenylprop-2-enylidene]piperidin-1-yl}pyridine tert-Butyl 4-[(2E)-3-phenylprop-2-enylidene]piperidine-1-carboxylate (Compound 255a)

Lithium bis(trimethylsilyl)amide (1M sol. in THF, 2.63 mL, 2.63 mmol) was added at −60° C. under nitrogen atmosphere to a solution of diethyl cinnamylphosphonate (0.629 mL, 2.64 mmol). After 15 min. under stirring at the same temperature, N-Boc-4-piperidone (500 mg, 2.51 mmol) dissolved in THF (5 ml) was added. Stirring and cooling was maintained for 30 min and, after 2 h, the reaction mixture was quenched with water and with EtOAc. The combined extracts were washed, dried over Na$_2$SO$_4$ and evaporated to dryness affording the title product (752 mg), that was used in the next step without further purification.
MS: $[M+H]^+=300.25$ 4-[(2E)-3-Phenylprop-2-enylidene]piperidine (Compound 255b)

To a solution of Compound 255a (752 mg, 2.51 mmol) in CHCl$_3$ (15 mL) was added trifluoroacetic acid (0.967 mL, 12.6 mmol) and the reaction mixture was stirred at 25° C. for 24 h, until the complete conversion of the reagent was observed by LC-MS. Water was added followed by aq. NaOH (2 N) to give alkaline pH. Separation of the organic layer and extraction of the aqueous layer with CH$_2$Cl$_2$, washing with brine and drying over Na$_2$SO$_4$ the combined organic layers, afforded the title compound. The crude was purified by flash chromatography (CHCl$_3$-1.6 M methanolic ammonia 100:5) affording the title product (359 mg).
MS: $[M+H]^+=200.22$ 3-Nitro-2-{4-[(2E)-3-phenylprop-2-enylidene]piperidin-1-yl}pyridine A well homogenised mixture of Compound 255b (175 mg, 0.878 mmol), 2-chloro-3-nitropyridine (153 mg, 0.966 mmol) and triethylamine (0.139 mL, 0.97 mmol) was stirred at 25° C. for 24 h. The reaction crude was purified by flash chromatography (EtOAc—Petroleum Ether 8:2) affording the title product (270 mg).
MS: $[M+H]^+=322.20$
$^1$H-NMR (CDCl3δ): 2.45-2.50 (m, 2H), 2.65-2.70 (m, 2H), 3.50-3.60 (m, 4H), 6.14 (d, 1H), 6.56 (d, 1H), 6.70-6.80 (m, 1H), 6.95-7.15 (m, 1H) 7.20-7.45 (m, 5H), 8.16 (d, 1H), 8.37 (d, 1H).

EXAMPLE 256

1-(3-Nitropyridin-2-yl)-4-(3-phenylprop-2-ynyl)piperidin-4-ol tert-Butyl 1-oxa-6-azaspiro[2.5]octane-6-carboxylate (Compound 256a)

Trimethylsulfoxonium iodide (580 mg, 2.64 mmol) was added to a suspension of NaH (106 mg, 2.64 mmol) at 0° C. under nitrogen atmosphere. After 15 min. under stirring at the same temperature, N-Boc-4-piperidone (500 mg, 2.51 mmol) dissolved in DMF (5 mL) was added. Stirring was continued and, after 2 h at r.t., the reaction mixture was quenched with water and EtOAc. The combined extracts were washed, dried over Na$_2$SO$_4$ and evaporated to dryness. The crude residue was purified by flash chromatography (EtOAc—Petroleum Ether 9:1) affording the title product (380 mg).
MS: $[M+H]^+=214.19$ tert-Butyl 4-hydroxy-4-(3-phenylprop-2-ynyl)piperidine-1-carboxylate (Compound 256b)

Boron trifluoride diethyl etherate (0.131 mL, 1.03 mmol) followed by lithium phenylacetylide (1M in THF, 1.03 mL, 1.03 mmol) was dropped into a solution of Compound 256a (200 mg, 0.938 mmol) in THF (5 mL) stirred at −75° C. under nitrogen atmosphere. Stirring and cooling were kept on for 2 h and after overnight stirring at r.t., the reaction mixture was quenched with water and EtOAc. The combined extracts were washed, dried over Na$_2$SO$_4$ and evaporated to dryness. The residue was purified by flash chromatography (EtOAc—Petroleum Ether 85:15) affording the title product (272 mg).
MS: $[M+H]+=316.26$ 4-(3-Phenylprop-2-ynyl)piperidin-4-ol (Compound 256c)

To a solution of Compound 256b (179 mg, 0.57 mmol) in CHCl$_3$ (3 mL) was added trifluoroacetic acid (0.219 mL, 2.84 mmol) and the reaction mixture was then stirred at 25° C. for 24 h until the complete conversion of the reagent was observed by LC-MS. Afterwards, to the reaction mixture was added water, followed by aq. 2 N NaOH to give alkaline pH. Separation of the organic layer and extraction of the aqueous layer with CH$_2$Cl$_2$, washing the combined organic layers with brine and drying over Na$_2$SO$_4$ afforded the title compound (122 mg).
MS: $[M+H]+=216.15$ 1-(3-Nitropyridin-2-yl)-4-(3-phenylprop-2-ynyl)piperidin-4-ol A well homogenised mixture of the Compound 256c (115 mg, 0.53 mmol), 2-chloro-3-nitropyridine (93.1 mg, 0.587 mmol) and triethyl amine (0.092 mL, 0.641 mmol) was stirred at 25° C. for 24 h. The reaction crude was purified by flash chromatography (EtOAc—Petroleum Ether 8:2) affording the title product (178 mg).

MS: [M+H]+=338.15
$^1$H-NMR (CDCl$_3$δ): 1.80-2.0 (m, 4H), 2.68 (s, 2H), 3.40-3.55 (m, 2H), 3.60-3.75 (m, 2H), 6.70-6.80 (m, 1H), 7.25-7.50 (m, 5H) 8.10-8.15 (m, 1H), 8.30-8.40 (m, 1H).

EXAMPLE 257

2-{4-[3-(6-Methylpyridin-2-yl)prop-2-ynylidene]piperidin-1-yl}-3-nitroimidazo[1,2-a]pyridine A well homogenised mixture of the Compound of Example 3 (150 mg, 0.71 mmol), 2-chloro-3-nitroimidazo[1,2-a]pyridine (154 mg, 0.778 mmol) and triethylamine (0.152 mL, 1.06 mmol) was stirred at 25° C. for 24 h. The reaction crude was purified by flash chromatography (EtOAc—Petroleum Ether 1:1) affording the title product (146 mg).

MS: [M+H]$^+$=374.22
$^1$H-NMR (CDCl$_3$δ): 2.50-2.70 (m, 5H), 2.85-2.90 (m, 2H), 2.78-2.87 (m, 1H), 3.75-3.85 (m, 4H), 5.68 (s, 1H), 7.25-7.30 (m, 1H), 7.45-7.65 (m, 3H), 9.50 (d, 2H).

EXAMPLE 258

1-[1'-(3-Nitropyridin-2-yl)piperidin-4-yl]-3-phenylprop-2-yn-1-one

Ethyl 1-(3-nitropyridin-2-yl)piperidine-4-carboxylate (Compound 258a)

A mixture of 2-chloro-3-nitropyridine (1 g, 6.31 mmol), ethyl 4-pyridinecarboxylate (1.19 g, 7.57 mmol) and potassium carbonate (1.31 g, 9.47 mmol) in n-butanol (25 mL) was stirred at reflux for 2 hours, cooled to r.t., poured into water and extracted with diethyl ether. The combined organic layers were washed with brine, dried on Na$_2$SO$_4$ and evaporated to dryness in vacuo to afford a residue, which was purified by flash chromatography (EtOAc—Petroleum Ether 2:8) affording the title product (1.38 g).

MS: [M+H]$^+$=280.09

1-(3-Nitropyridin-2-yl)piperidine-4-carboxylic acid (Compound 258b)

To a solution of KOH (0.46 g, 8.16 mmol) in methanol (30 mL) and water (30 mL) was added Compound 258a (1.14 g, 4.08 mmol). The solution was stirred at r.t. for 1.5 hours, poured into water, acidified with 2M HCl and extracted with EtOAc. The combined organic layers were washed with brine, dried on Na$_2$SO$_4$ and evaporated to dryness in vacuo to afford the title product (1.38 g).

$^1$H-NMR (CDCl$_3$δ): 1.82-2.00 (m, 2H), 2.02-2.12 (m, 2H), 2.61-2.73 (m, 1H), 3.10-3.22 (m, 2H), 3.75-3.90 (m, 2H), 6.75-6.82 (m, 1H), 8.15 (dd, 1H, J=4 Hz, J=8 Hz), 8.38 (dd, 1H, J=1.5 Hz, J=4 Hz),
MS: [M+H]$^+$=252.12

1-[1-(3-Nitropyridin-2-yl)piperidin-4-yl]-3-phenylprop-2-yn-1-one

To a solution of Compound 258b in anhydrous toluene (10 mL), thionyl chloride (0.29 mL, 3.98 mmol was added and the resulting mixture was stirred at reflux for 1 hour, cooled to r.t and evaporated to dryness in vacuo. The residue was dissolved in anhydrous toluene (5 mL); to this solution was added phenylacetylene (0.09 mL, 0.80 mmol), palladium(II) acetate (18 mg, 0.08 mmol), triethylamine (0.34 mL, 2.4 mmol). The mixture was stirred in a microwave oven at 110° C. for 1 hour, cooled to r.t., poured into water and extracted with EtOAc. The combined organic layers were washed with brine, dried on Na$_2$SO$_4$ and evaporated to dryness in vacuo to afford a residue, which was purified by flash chromatography (EtOAc—Petroleum Ether 25:75) affording the title product (77 mg).

MS: [M+H]$^+$=336.18
$^1$H-NMR (CDCl$_3$δ): 1.90-2.04 (m, 2H), 2.15-2.22 (m, 2H), 2.78-2.87 (m, 1H), 3.18-3.28 (m, 2H), 3.88-3.95 (m, 2H), 6.75-6.82 (m, 1H), 7.40-7.46 (m, 2H), 7.48-7.52 (m, 1H), 7.60-7.65 (m, 2H), 8.15 (dd, 1H, J=4 Hz, J=8 Hz), 8.38 (dd, 1H, J=1.5 Hz, J=4 Hz),

EXAMPLE 259

3-Nitro-2-(4-{3-[3-(trifluoromethoxy)phenyl]prop-2-ynylidene}piperidin-1-yl)pyridine A mixture of Compound 1c (60 mg, 0.25 mmol), 3-(trifluoromethoxy)iodobenzene (41.6 µL, 0.26 mmol), bis(triphenylphosphine)palladium(II)dichloride (8.65 mg, 0.01 mmol), CuI (4.69 mg, 0.1 mmol) in anhydrous and degassed triethylamine (3 mL) was heated at 80° C. under a nitrogen atmosphere for 2 h in a sealed vessel. The reaction mixture was cooled, filtered on Celite, poured into water and extracted with EtOAc. The combined organic layers were washed with brine, dried on Na$_2$SO$_4$ and evaporated to dryness in vacuo to afford a residue, which was purified by flash chromatography (EtOAc—Petroleum Ether 5:95) affording the title product (57 mg).

MS: [M+H]$^+$=404.35
$^1$H-NMR (CDCl$_3$δ): 2.50-2.53 (m, 2H), 2.75-2.78 (m, 2H), 3.53-3.58 (m, 4H), 5.64 (s, 1H), 6.78-6.81 (m, 1H), 7.17-7.19 (m, 1H), 7.28-7.30 (m, 1H) 7.34-7.37 (m, 2H), 8.17-8.19 (m, 1H), 8.37-8.38 (m, 1H).

EXAMPLE 260

1-(3'-Nitro-3,6-dihydro-2H-1,2'-bipyridin-4-yl)-3-phenylprop-2-yn-1-one

3'-Nitro-3,6-dihydro-2H-1,2'-bipyridine-4-carboxylic acid (Compound 260a)

A well homogenised mixture of isoguvacine hydrochloride (497 mg, 3.04 mmol), 2-chloro-3-nitro-pyridine (482 mg, 3.04 mmol) and potassium carbonate (882 mg, 6.38 mmol), was stirred at 60° C. for 1.5 h. The reaction mixture was cooled, poured into a solution of water and formic acid (pH=3) and extracted with dichloromethane. The combined organic layers were washed with brine, dried on Na$_2$SO$_4$ and evaporated to dryness in vacuo to afford a residue, which was purified by flash chromatography (EtOAc—Petroleum Ether-Acetic Acid 20:80:0.05) affording the title product (332 mg).

MS: [M+H]$^+$=250.2

N-methoxy-N-methyl-3'-nitro-3,6-dihydro-2H-1,2'-bipyridine-4-carboxamide (Compound 26b)

To a solution of Compound 260a (100 mg, 0.40 mmol) in methanol (10 mL) stirred at r.t., was added DMT-MM (4-(4,6-Dimethoxy-1,3,5-triazin-2-yl)-4-methylmorpholinium chloride, 142 mg, 0.52 mmol), N-methylmorpholine (88.4 µL, 0.81 mmol) and N,O-dimethylhydroxylamine hydrochloride (60 mg, 0.615 mmol). The reaction mixture was stirred at r.t. for 3 h. The solvent was evaporated to dryness in vacuo. The residue was diluted with aq. 1N NaOH and dichloromethane. The combined organic layers were washed with brine, dried on $Na_2SO_4$ and evaporated to dryness in vacuo to afford a residue, which was purified by flash chromatography (EtOAc—Petroleum Ether 60:40) affording the title product (90 mg).

MS: $[M+H]^+=293.3$

1-(3'-Nitro-3,6-dihydro-2H-1,2'-bipyridin-4-yl)-3-phenylprop-2-yn-1-one

Into a solution of phenylacetylene (69.3 µL, 0.631 mmol) in anhydrous THF (15 mL) stirred at −78° C. under $N_2$ stream, was dropped a solution of butyllithium (2.5 M in THF, 253 µL, 0.63 mmol) and the mixture was stirred at −78° C. for 20 min. To the resulting solution was added dropwise a solution of Compound 260b (84 mg, 0.29 mmol) in anhydrous THF (5 mL). The reaction mixture was stirred at −50° for 1.5 h., then it was allowed to warm up to −10° C. Afterwards, it was quenched with ammonium chloride and extracted with EtOAc. The combined organic layers were washed with brine, dried on $Na_2SO_4$ and evaporated to dryness in vacuo to afford a residue, which was purified by flash chromatography (EtOAc—Petroleum Ether 20:80) affording the title product (69 mg).

MS: $[M+H]^+=334.3$
$^1$H-NMR (CDCl$_3$,δ): 2.68 (m, 2H), 3.72-3.75 (m, 2H), 4.16-4.17 (m, 2H), 6.81-6.84 (m, 1H), 7.35-7.40 (m, 1H), 7.40-7.47 (m, 2H), 7.47-7.51 (m, 1H), 7.61-7.63 (m, 2H), 8.20-8.22 (m, 1H), 8.39-8.40 (m, 1H).

EXAMPLE 261

1-{3-[1-(3-Nitropyridin-2-yl)piperidin-4-ylidene]prop-1-ynyl}pyrrolidin-2-one

2-[4-(3-Bromoprop-2-ynylidene)piperidin-1-yl]-3-nitropyridine (Compound 261a)

A mixture of Compound 1c (200 mg, 0.82 mmol), CBr$_4$ (0.54 mg, 1.65 mmol), potassium hydroxide (0.138 mg, 2.46 mmol), 18-C-6 crown ether (21.8 mg, 0.823 mmol) and 10 mL of benzene was stirred at 65° C. for 11 h.

The reaction mixture was cooled to r.t., diluted with EtOAc, washed with water, dried over $Na_2SO_4$ and evaporated to dryness in vacuo. The crude residue was purified by automated flash liquid chromatography (Horizon™-Biotage) eluting with PE-EtOAc gradient from 98:2 to 80:20, affording the title products (111 mg) as a mixture with the starting material (77:23 Compound 261a:Compound 1c) and used as it was in the further reaction step.

1-{3-[1-(3-Nitropyridin-2-yl)piperidin-4-ylidene]prop-1-ynyl}pyrrolidin-2-one A mixture of Compound 261a (111 mg, 0.345 mmol), cupric sulphate (11 mg, 0.69 mmol), 1,10-phenantroline (24.9 mg, 0.138 mmol), $K_2CO_3$ (95.4 mg, 0.69 mmol), 2-pyrrolidone (39.7 µl, 0.518 mmol) and 5 mL of toluene was stirred at 80° C. for 12 h. The reaction mixture was cooled to r.t., diluted with EtOAc, washed with water, dried over $Na_2SO_4$ and evaporated to dryness in vacuo. The crude residue was purified by automated flash liquid chromatography (Horizon™-Biotage) eluting with PE-EtOAc gradient from 98:2 to 0:10, giving the title product (2 mg)

$^1$H-NMR (CDCl$_3$, δ): 2.10-2.20 (m, 2H), 2.41-2.53 (m, 4H), 2.65-2.70 (m, 2H), 3.40-3.52 (m, 4H), 3.72-3.76 (m, 2H), 5.60 (s, 1H), 6.75-6.78 (m, 1H,), 8.14-8.17 (m, 1H), 8.35 (s, 1H)

MS: $[M+H]^+=327.15$

EXAMPLE 262

2-Methyl-6-(3-{1-[5-(trifluoromethyl)pyridin-3-yl]piperidin-4-ylidene}prop-1-ynyl)pyridine A vial was filled with a mixture of the compound of Example 3 (84.9 mg, 0.4 mmol), 3-bromo-5-(trifluoromethyl)pyridine (93 mg, 0.4 mmol), DIPEA (140 µL, 0.8 mmol), 1 mL of anhydrous N-methylpyrrolidone and sealed. The vial was heated in a microwave oven at 160° C. (200 W) for 2 h. The reaction mixture was then cooled to r.t., diluted with EtOAc, washed with water, dried over $Na_2SO_4$ and evaporated to dryness in vacuo. The crude black oily residue was purified by preparative RP LC-MS chromatography, using MS-C18 XTerra column 30×50 mm eluting with ammonium bicarbonate 20 mM pH 8 buffer-acetonitrile gradient affording 1.8 mg of the title compound.

$^1$H-NMR (CDCl$_3$, δ): 2.42-2.53 (m, 2H), 2.59 (s, 3H), 2.79-2.82 (m, 2H), 3.43-3.47 (m, 4H), 5.67 (s, 1H), 7.10 (d, 1H, J=8.0), 7.27 (d, 1H, J=8.0 Hz), 7.35 (s, 1H), 7.56 (t, 1H, J=8.0 Hz), 8.33 (s, 1H), 8.50 (s, 1H).

MS: $[M+H]^+=358.4$

EXAMPLE 263

2-{4-[3-(6-Methylpyridin-2-yl)prop-2-ynylidene]piperidin-1-yl}-5-phenylnicotinonitrile Following the procedure reported above for the compound of Example 262 but replacing 5-(trifluoromethyl)pyridine with 2-chloro-5-phenylnicotinonitrile the title product was synthesized. After the reaction work-up, the residue was purified by automated flash liquid chromatography (Horizon™-Biotage) eluting with PE-EtOAc gradient from 9:1 to 4:6, affording the title product (10%).

$^1$H-NMR (CDCl$_3$, δ): 2.52-2.57 (m, 2H), 2.62 (s, 3H), 2.75-2.80 (m, 2H), 3.85-3.95 (m, 4H), 5.68 (s, 1H), 7.08-7.15 (m, 1H), 7.25-7.70 (m, 7H), 8.00 (s, 1H), 8.61 (s, 1H).

MS: $[M+H]^+=391.35$

EXAMPLE 264

2-Methyl-6-(3-{1-[2-propoxypyridin-3-yl]piperidin-4-ylidene}prop-1-ynyl)pyridine Into a flamed flask flushed with nitrogen a mixture of CuI (19.4 mg. 0.1 mmol)), $K_3PO_4$ (425 mg, 2 mmol), ethylene glycol (112 µL), 3-iodo-2-propoxypyridine (263 mg, 1 mmol) in 1 mL of n-Butanol were added 255 mg of the compound of Example 3 dissolved in 1 mL of n-Butanol. The suspension was heated at 100° C. for 5 h. The reaction mixture was then cooled to r.t., diluted with EtOAc, washed with aq., NaHCO$_3$ and water, dried over $Na_2SO_4$ and evaporated to dryness in vacuo. After the work-up the residue was purified by automated flash liquid chromatography (Horizon™-Biotage) eluting with PE-EtOAc 8:2. affording the title product (32 mg, 10%).

¹H-NMR (CDCl₃, δ): 1.10 (t, J=8.0 Hz, 3H); 1.85-1.92 (m, 2H); 2.53-2.56 (m, 2H); 2.58 (s, 3H); 2.83-2.85 (m, 2H); 3.14-3.19 (m, 4H); 4.35 (t, J=8.0 Hz, 2H); 5.60 (s, 1H); 6.82-6.85 (m, 1H); 7.08-7.10 (m, 2H); 7.26-7.28 (m, 1H); 7.55 (t, J=8.0 Hz, 1H); 7.80 (d, J=8.0 Hz, 1H).

MS: [M+H]⁺=348.43

EXAMPLE 265

7-{4-[3-(6-Methylpyridin-2-yl)prop-2-ynylidene]piperidin-1-yl}pyrido[2,3-b]pyrazine Following the procedure reported for the compound Example 234 and using 7-bromopyrido[2,3-b]pyrazine instead of 4-bromoisoquinoline the title compound was prepared. Purification was done by automated flash liquid chromatography (Horizon™-Biotage) eluting with CHCl₃-1.4 N NH₃ sol. in MeOH 100:0.25. Yield: 16%.

¹H-NMR (CDCl₃, δ): 2.50-2.70 (m, 5H); 2.85-2.88 (m, 2H); 3.60-3.64 (m, 4H); 5.70 (s, 1H); 7.11 (d, J=8.0 Hz, 1H); 7.28 (d, J=8.0 Hz, 1H); 7.54-7.58 (m, 2H); 8.80 (m, 2H); 9.95 (d, J=4.0 Hz, 1H).

MS: [M+H]⁺=342.41

EXAMPLE 266

2-{4-[3-(6-Methylpyridin-2-yl)prop-2-ynylidene]piperidin-1-yl}thiophene-3-carbonitrile Following the procedure reported for the compound of Example 234 and using 2-bromo-3-cyanothiophene instead of 4-bromoisoquinoline the title compound was prepared. Purification was done by RP LC-MS chromatography, using MS-C18 XTerra column 30×50 mm eluting with ammonium bicarbonate 20 mM pH 8 buffer-acetonitrile gradient affording the compound of the title. Yield: 22%.

¹H-NMR (CDCl₃, δ): 2.53-2.58 (m, 5H); 2.83-2.85 (m, 2H); 3.58-3.60 (m, 4H); 5.66 (s, 1H); 6.51 (d, J=8.0 Hz, 1H); 6.90 (d, J=8.0 Hz, 1H); 7.10 (d, J=8.0 Hz, 1H); 7.27 (d, J=8.0 Hz, 1H); 7.56 (t, J=8.0 Hz, 1H).

MS: [M+H]⁺=320.36

EXAMPLE 267

2-Ethoxy-5-{4-[3-(6-methylpyridin-2-yl)prop-2-ynylidene]piperidin-1-yl}pyridine Following the procedure reported for the compound of Example 234 and using 5-bromo-2-ethoxypyridine instead of 4-bromoisoquinoline and tol-BINAP (2,2'-bis(di-p-tolylphosphino)-1,1'-binaphthyl) instead of BINAP the title compound was prepared. After the work-up, the residue was purified by automated flash liquid chromatography (Horizon™-Biotage) eluting with PE-EtOAc 8:2. affording the title product as a yellow oil. Yield: 10%.

¹H-NMR (CDCl₃, δ): 1.40 (t, J=8.0 Hz, 3H); 2.45-2.56 (m, 2H); 2.59 (s, 3H); 2.75-2.87 (m, 2H); 3.10-3.30 (m, 4H); 4.32 (q, J=8.0 Hz, 2H); 5.61 (s, 1H); 6.69 (d, J=8.0 Hz, 1H); 7.10 (d, J=8.0 Hz, 1H); 7.27 (d, J=8.0 Hz, 1H); 7.30-7.40 (m, 1H); 7.56 (t, J=8.0 Hz, 1H); 7.83 (s, 1H).

MS: [M+H]⁺=334.19

EXAMPLE 268

2-{4-[3-(2,6-Difluorophenyl)prop-2-ynylidene]piperidin-1-yl}-3-nitropyridine The title compound was prepared as described for the compound of Example 237 but starting from Compound 248a instead of compound 237a and using diisopropylethylamine (DIPEA) instead of triethylamine and 2-chloro-3-nitropyridine instead of 2-bromo-3-nitropyridine. After the work-up, the residue was purified by automated flash liquid chromatography (Horizon™-Biotage) eluting with PE-EtOAc gradient from 9:1 to 7:3 affording the title product. Yellow oil. Yield: 55%.

¹H-NMR (CDCl₃, δ): 2.5-2.6 (m, 2H), 2.8 (m, 2H), 3.5-3.6 (m, 4H), 5.7 (m, 1H), 6.75-6.85 (m, 1H), 6.9-7.0 (m, 2H), 7.2-7.3 (m, 1H), 8.15-8.20 (m, 1H), 8.35-8.40 (m, 1H)

MS: [M+H]⁺=356.34

EXAMPLE 269-272

These compounds (see table XII) were prepared following the procedure described in Example 199 but substituting reagent B for 4-bromo-2,6-difluoroanisole.

Purification was carried out by automated flash liquid chromatography (Horizon™-Biotage) eluting with Petroleum Ether-EtOAc gradient from 100:0 to 20:80.

TABLE XII

| Example | Reagent B (Note) | Chem. Name | LC-MS M/Z | ¹H-NMR (CDCl₃, δ) |
|---------|------------------|------------|-----------|---------------------|
| 269 | 1-(3-iodobenzyl)-1H-pyrazole | 1-(3-Nitro-2-pyridyl)-4-{3-[3-(1H-pyrazol-1-ylmethyl)phenyl]prop-2-ynylidene}piperidine | 400.45 | 2.45-2.55 (m, 2H), 2.7-2.8 (m, 2H), 3.45-3.55 (m, 4H), 5.3 (m, 2H), 5.6 (m, 1H), 6.25-6.35 (m, 1H), 6.75-6.85 (m, 1H), 7.15-7.25 (m, 1H), 7.3 (m, 2H), 7.4 (m, 2H), 7.6 (m, 1H), 8.15-8.20 (m, 1H), 8.35-8.40 (m, 1H) |
| 270 | N-(3-iodopyridin-2-yl)pivalamide THF as co-solvent; r.t. | 2,2-Dimethyl-3-{3-[1-(3-nitropyridin-2-yl)piperidin-4-ylidene]prop-1-ynyl}pyridin-2-ylpropanamide | 420.48 | 1.4 (s, 9H), 2.45-2.55 (m, 2H), 2.7-2.8 (m, 2H), 3.5-3.6 (m, 4H), 5.7 (m, 1H), 6.8 (m, 1H), 7.25 (m, 1H), 7.9-8.0 (m, 1H), 8.2 (m, 1H), 8.4 (m, 1H), 8.5 (m, 1H), 9.2 (s, 1H) |
| 271 | 1-(3-iodobenzyl)-4-methyl-piperazine | 1-Methyl-4-[3-[3-(1-(3-nitro-2-pyridyl)piperidin-4-ylideneprop-1-ynyl)benzyl]piperazine | 432.54 | |

TABLE XII-continued

| Example | Reagent B (Note) | Chem. Name | LC-MS M/Z | $^1$H-NMR (CDCl$_3$, δ) |
|---------|------------------|------------|-----------|------------------------|
| 272 | 1-(3-iodophenyl)ethanone | 1-(3-{3-[1-(3-Nitropyridin-2-yl)piperidin-4-ylidene]prop-1-ynyl}phenyl)ethanone | 362.40 | 2.45-2.55 (m, 2H), 2.6 (s, 3H), 2.7-2.8 (m, 2H), 3.45-3.55 (m, 4H), 5.65 (m, 1H), 6.8 (m, 1H), 7.4-7.5 (m, 1H), 7.6-7.7 (d, 1H), 7.9 (d, 1H), 8.0 (s, 1H), 8.2 (d, 1H), 8.4 (m, 1H) |

EXAMPLE 273

2-{4-[3-(4-Fluoropyridin-2-yl)prop-2-ynylidene]piperidin-1-yl}-6-methyl-3-nitropyridine tert-Butyl 4-[3-(4-fluoropyridin-2-yl)prop-2-ynylidene]piperidine-1-carboxylate (Compound 273a)

The title compound was prepared following the procedure described for the Compound of Example 199, but using Compound 2b instead of Compound 1c and 2-chloro-4-fluoropyridine instead of 4-bromo-2,6-difluoroanisole. After the usual work-up procedure, purification was carried out by automated flash liquid chromatography (Horizon™-Biotage) eluting with PE-EtOAc gradient from 95:5 to 60:40. Yield: 38.5%.

MS: [M+H]$^+$=317.2

4-Fluoro-2-(3-piperidin-4-ylideneprop-1-ynyl)pyridine (Compound 273b)

Compound 273a was converted into the title compound by using the procedure described for Compound 228b. Compound 273b was used in the next step without further purification. Yield: 76%

MS: [M+H]$^+$=217.2

2-{4-[3-(4-Fluoropyridin-2-yl)prop-2-ynylidene]piperidin-1-yl}-6-methyl-3-nitropyridine The title product was prepared following the method described above for the Compound of Example 237 replacing 2-bromo-3-nitropyridine with 2-chloro-6-methyl-3-nitropyridine and using N-methylpyrrolidone instead of N,N-dimethylacetamide. Purification by automated flash liquid chromatography (Horizon™-Biotage) eluting with a PE-EtOAc gradient from 95:5 to 60:40 afforded the title compound as a yellow solid. Yield: 36%.

$^1$H-NMR (CDCl$_3$, δ): 2.49 (s, 3H), 2.50-2.57 (m, 2H), 2.75-2.85 (m, 2H), 3.45-3.60 (m, 4H), 5.65 (s, 1H), 6.63 (d, J=8 Hz, 1H), 6.95-7.05 (m, 1H), 7.17 (d, J=8 Hz, 1H), 8.10 (d, J=8 Hz, 1H), 8.52-8.60 (m, 1H).
MS: [M+H]$^+$=353.2

EXAMPLE 274

2-{4-[3-(3,5-Difluorophenyl)prop-2-ynylidene]piperidin-1-yl}-6-methyl-3-nitropyridine 4-(3-Trimethylsilylprop-2-ynylidene)piperidine (Compound 274a)

The title compound was synthesized following the procedure described for the compound of Example 3 starting from Compound 2a instead of the Compound of Example 2.

An alternative procedure that can be utilized to carry out the reaction includes stirring at r.t (instead at 70° C.) for 4 h and overnight resting.

The reaction mixture was washed with water and aq. K$_2$CO$_3$, dried on anhydrous Na$_2$SO$_4$ and evaporated to dryness in vacuo and used in the next step without further purification.

MS: [M+H]$^+$=194.24

6-Methyl-2-[4(1-trimethysilylbut-2-ynylidenepiperidin-1-yl)-3-nitropyridine (Compound 274b)

Method A: The title compound was synthesized following the procedure described for the Compound of Example 273, but replacing Compound 273a and 2-bromo-3-nitropyridine respectively with Compound 274a and 2-chloro-6-methyl-3-nitropyridine. The crude residue obtained from a standard work-up procedure was used in the next step without further purification.

Method B: The title compound was prepared starting from 1-(6-methyl-3-nitro-2-pyridyl)-4-piperidone instead of 1-(3-nitro-2-pyridyl)-4-piperidone and following the procedure described for Compound 1b. The crude residue was used as an intermediate without further purification.

MS: [M+H]$^+$=330.27

6-Methyl-3-Nitro-2-(4-prop-2-ynylidenepiperidin-1-yl)pyridine (Compound 274c)

The title compound was synthesized following the procedure described for Compound 1c, but using Compound 274b instead of Compound 1b. Purification by automated flash liquid chromatography (Horizon™-Biotage) eluting with a PE-Acetone gradient from 97:3 to 9:1 afforded the title compound. Yield: 29%.

MS: [M+H]$^+$=258.08

2-{4-[3-(3,5-Difluorophenyl)prop-2-ynylidene]piperidin-1-yl}-6-methyl-3-nitropyridine To a suspension of Compound 274c (70 mg, 0.27 mmol), sodium acetate trihydrate (74.2 mg, 0.55 mmol) and 1-bromo-3,5-difluorobenzene (33.5 μl, 0.27 mmol) in 2.05 mL of DMF flushed with nitrogen was added tetrakis(triphenylphosphine)palladium(0) (15.8 mg, 0.014 mmol) and the reaction mixture was put into a microwave oven (Biotage) at 120° C. for 10 min. Dilution with EtOAc, washing with H$_2$O and drying over Na$_2$SO$_4$ followed by evaporation and purification of the residue by automated flash liquid chromatography (Horizon™-Biotage) (PE-CH$_2$Cl$_2$ 6:4) afforded 74 mg (73.7%) of the title compound.

$^1$H-NMR (CDCl$_3$, δ): 2.49-2.53 (s and m, 5H), 2.72-2.78 (m, 2H), 3.51-3.59 (m, 4H), 5.61 (s, 1H), 6.64 (d, 1H, J=8 Hz), 6.75-6.82 (m, 1H), 6.94-6.98 (m, 2H), 8.11 (d, 1H, J=8 Hz)
MS: [M+H]$^+$=370.27

EXAMPLE 275

2-{4-[3-(3-Fluorophenyl)prop-2-ynylidene]piperidin-1-yl}-6-methyl-3-nitropyridine From 1-bromo-3-fluorobenzene. Purification by automated flash chromatography (Horizon™-Biotage) PE-EtOAc gradient from 97.5:2.5 to 9:1. Orange solid. Yield: 82%

$^1$H-NMR (CDCl$_3$, δ): 2.48-2.51 (m, 5H), 2.74-2.77 (m, 2H), 3.51-3.58 (m, 4H), 5.62 (s, 1H), 6.62 (d, 1H, J=8 Hz), 6.98-7.07 (m, 1H), 7.14 (d, 1H, J=8 Hz), 7.22 (m, 1H), 7.27-7.33 (m, 1H), 8.11 (d, 1H, J=8 Hz)
MS: [M+H]$^+$=352.49

EXAMPLE 276

6-Methyl-3-nitro-2-[4-(3-pyridin-2-ylprop-2-ynylidene)piperidin-1-yl]pyridine

From 2-bromopyridine. Purification by automated flash chromatography (Horizon™-Biotage) PE-EtOAc gradient from 9:1 to 7:3. Yellow solid. Yield: 42%

$^1$H-NMR (CDCl$_3$, δ): 2.48-2.53 (s and m, 5H), 2.78-2.83 (m, 2H), 3.49-3.59 (m, 4H), 5.65 (s, 1H), 6.62 (d, 1H, J=8 Hz), 7.21-7.26 (m, 1H), 7.43-7.47 (dd, 1H), 7.66-7.71 (m, 1H), 8.10 (d, 1H, J=8 Hz), 8.59-8.63 (dd, 1H)
MS: [M+H]$^+$=335.34

EXAMPLE 277

2-{4-[3-(6-Fluoropyridin-2-yl)prop-2-ynylidene]piperidin-1-yl}-6-methyl-3-nitropyridine From 2-bromo-6-fluoropyridine. Purification by automated flash chromatography (Horizon™-Biotage) PE-EtOAc gradient from 95:5 to 9:1. Yellow oil. Yield: 68%

$^1$H-NMR (CDCl$_3$, δ): 2.49-2.54 (s and m, 5H), 2.77-2.82 (m, 2H), 3.51-3.59 (m, 4H), 5.64 (s, 1H), 6.64 (d, 1H, J=8 Hz), 6.86-6.91 (dd, 1H), 7.27-7.34 (dd, 1H), 7.73-7.80 (m, 1H), 8.12 (d, 1H, J=8 Hz
MS: [M+H]$^+$=353.33

EXAMPLE 278

2-{4-[3-(2-Fluoropyridin-5-yl)prop-2-ynylidene]piperidin-1-yl}-6-methyl-3-nitropyridine From 5-bromo-2-fluoropyridine. Purification by automated flash chromatography (Horizon™-Biotage) PE-EtOAc gradient from 95:5 to 8:2. Yellow solid. Yield: 54%

$^1$H-NMR (CDCl$_3$, δ): 2.49-2.53 (s and m, 5H), 2.73-2.78 (m, 2H), 3.51-3.59 (m, 4H), 5.62 (s, 1H), 6.64 (d, 1H, J=8 Hz), 6.90-6.95 (dd, 1H), 7.79-7.85 (dd, 1H), 8.11 (d, 1H, J=8 Hz), 8.31 (s, 1H)
MS: [M+H]$^+$=353.33

EXAMPLE 279

2-{4-[3-(2-Fluoropyridin-4-yl)prop-2-ynylidene]piperidin-1-yl}-6-methyl-3-nitropyridine From 4-iodo-2-fluoropyridine. Purification by automated flash chromatography (Horizon™-Biotage) PE-EtOAc gradient from 9:1 to 8:2. Yellow solid. Yield: 60%

$^1$H-NMR (CDCl$_3$, δ): 2.51-2.55 (s and m, 5H), 2.74-2.79 (m, 2H), 3.52-3.60 (m, 4H), 5.64 (s, 1H), 6.65 (d, 1H, J=8 Hz), 6.94 (s, 1H), 7.16-7.19 (dd, 1H), 8.12 (d, 1H, J=8 Hz), 8.185 (d, 1H, J=4 Hz)
MS: [M+H]$^+$=353.33

EXAMPLE 280

2-{4-[3-(3-Fluoropyridin-5-yl)prop-2-ynylidene]piperidin-1-yl}-6-methyl-3-nitropyridine From 3-bromo-5-fluoroyridine. Purification by automated flash chromatography (Horizon™-Biotage) PE-EtOAc gradient from 93:7 to 7:3. Yellow solid. Yield: 56%

$^1$H-NMR (CDCl$_3$, δ): 2.49-2.54 (s and m, 5H), 2.73-2.78 (m, 2H), 3.51-3.60 (m, 4H), 5.64 (s, 1H), 6.64 (d, 1H, J=8 Hz), 6.45-6.49 (m, 1H), 8.11 (d, 1H, J=8 Hz), 8.41 (s, 1H), 8.50 (s, 1H)
MS: [M+H]$^+$=353.33

EXAMPLE 281

5-{3-[1-(6-Methyl-3-nitropyridin-2-yl)piperidin-4-ylidene]prop-1-ynyl}nicotinonitrile From 5-bromonicotinonitrile. Purification by automated flash chromatography (Horizon™-Biotage) PE-EtOAc gradient from 9:1 to 7:3. Yellow solid. Yield: 73%

$^1$H-NMR (CDCl$_3$, δ): 2.51-2.55 (s and m, 5H), 2.74-2.79 (m, 2H), 3.52-3.61 (m, 4H), 5.65 (s, 1H), 6.65 (d, 1H, J=8 Hz), 7.97 (s, 1H), 8.12 (d, 1H, J=8 Hz), 8.77 (s, 1H), 8.84 (s, 1H)
MS: [M+H]$^+$=360.33

EXAMPLE 282

2-{4-[3-(2,5-Difluorophenyl)prop-2-ynylidene]piperidin-1-yl}-6-methyl-3-nitropyridine From 2,5-difluoroiodobenzene. Purification by automated flash chromatography (Horizon™-Biotage) PE-EtOAc 97.5:2.5. Yellow solid. Yield: 63%

$^1$H-NMR (CDCl$_3$, δ): 2.49-2.53 (s and m, 5H), 2.75-2.80 (m, 2H), 3.51-3.59 (m, 4H), 5.65 (s, 1H), 6.63 (d, 1H, J=8 Hz), 6.96-7.08 (m, 2H), 7.09-7.15 (m, 1H), 8.11 (d, 1H, J=8 Hz)
MS: [M+H]$^+$=370.34

EXAMPLE 283

2-{4-[3-(3,5-Difluorophenyl)prop-2-ynylidene]piperidin-1-yl}-6-methylnicotinonitrile The title compound was synthesized following the procedure reported for the compound of Example 59 replacing the compound of Example 3, 2-fluoropyridine and TEA respectively with Compound 228b, 2-chloro-6-methylnicotinonitrile and potassium carbonate. Purification by automated flash chromatography (Horizon™-Biotage) eluting with PE-EtOAc 95:5. Yellow solid. Yield: 61%

$^1$H-NMR (CDCl$_3$, δ): 2.40-2.55 (m, 5H); 2.70-2.80 (m, 2H); 3.75-3.88 (m, 4H); 5.60 (s, 1H); 6.63 (d, J=8.0 Hz, 1H); 6.70-6.88 (m, 1H); 6.90-7.00 (m, 2H); 7.68 (d, J=8.0 Hz, 1H).
MS: [M+H]$^+$=350.11

EXAMPLE 284

2-{4-[3-(3-Fluorophenyl)prop-2-ynylidene]piperidin-1-yl}-6-methylnicotinonitrile

6-methyl-2-(4-prop-2-(3-trimethylsilyl)ynylidenepiperidin-1-yl)nicotinonitrile (Compound 284a)

The title compound was prepared by refluxing a solution of DIPEA and Compound 274a in MeCN for 20 h with 2-chloro-6-methylnicotinonitrile. After the usual work-up, the crude residue was purified by automated flash chromatography (Horizon™-Biotage) eluting with PE-EtOAc 98:2. Yield: 51%.

The purified product contained a quote of the corresponding desilylated alkyne, but was used as an intermediate without further purification.

2-{4-[3-(3-Fluorophenyl)prop-2-ynylidene]piperidin-1-yl}-6-methylnicotinonitrile The title compound was prepared in the same way as the Compound of Example 274 but replacing 1-bromo-3,5-difluorobenzene with 1-fluoro-3-iodobenzene and Compound 274c with Compound 284a. The residue coming from the work-up procedure was purified by preparative RP LC-MS chromatography, using MS-C18 XTerra column 30×50 mm eluting with ammonium bicarbonate 20 mM pH 8 buffer-acetonitrile gradient affording the title compound as a colourless oil. Yield: 20.4%

$^1$H-NMR (CDCl$_3$, δ): 2.45-2.55 (m, 5H); 2.72-2.82 (m, 2H); 3.78-3.90 (m, 4H); 5.62 (s, 1H); 6.63 (d, J=8.0 Hz, 1H); 6.98-7.06 (m, 1H); 7.12-7.18 (m, 1H); 7.21-7.26 (m, 1H); 7.26-7.34 (m, 1H); 7.68 (d, J=8.0 Hz, 1H).

MS: [M+H]$^+$=332.40

The following compounds were prepared in the same way as the Compound of Example 284 but substituting respectively the shown haloderivatives for 1-fluoro-3-iodobenzene haloderivatives:

EXAMPLE 285

6-Methyl-2-[4-[3-(4-pyridyl)prop-2-ynylidene]piperidin-1-yl]nicotinonitrile

From 4-iodopyridine. Purification by automated flash chromatography (Horizon™-Biotage) PE-EtOAc 7:3. Beige solid. Yield: 84.7%.

$^1$H-NMR (CDCl$_3$, δ): 2.47 (s, 3H); 2.51-2.55 (m, 2H); 2.72-2.83 (m, 2H); 3.78-3.90 (m, 4H); 5.65 (s, 1H); 6.64 (d, J=8.0 Hz, 1H); 7.36 (d, J=8.0 Hz, 2H); 7.68 (d, J=8.0 Hz, 1H); 8.59 (d, J=8.0 Hz, 2H).

MS: [M+H]$^+$=315.25

EXAMPLE 286

6-Methyl-2-[4-[3-(2-fluoro-6-pyridyl)prop-2-ynylidene]piperidin-1-yl]nicotinonitrile From 2-bromo-6-fluoropyridine. Purification by automated flash chromatography (Horizon™-Biotage) PE-EtOAc 9:1. Pale yellow oil. Yield: 81.7%

$^1$H-NMR (CDCl$_3$, δ): 2.47 (s, 3H); 2.48-2.55 (m, 2H); 2.75-2.85 (m, 2H); 3.77-3.90 (m, 4H); 5.63 (s, 1H); 6.63 (d, J=8.0 Hz, 1H); 6.85-6.93 (m, 1H); 7.30-7.35 (m, 1H); 7.67 (d, J=8.0 Hz, 1H); 7.70-7.80 (m, 1H).

MS: [M+H]$^+$=333.38

EXAMPLE 287

6-Methyl-2-[4-[3-(5-cyano-3-pyridyl)prop-2-ynylidene]piperidin-1-yl]nicotinonitrile From 5-bromonicotinonitrile. Purification by automated flash chromatography (Horizon™-Biotage) PE-EtOAc 9:1. White solid. Yield: 65.1%

$^1$H-NMR (CDCl$_3$, δ): 2.50 (s, 3H); 2.50-2.60 (m, 2H); 2.72-2.83 (m, 2H); 3.79-3.92 (m, 4H); 5.64 (s, 1H); 6.66 (d, J=8.0 Hz, 1H); 7.70 (d, J=8.0 Hz, 1H); 7.98 (s, 1H); 8.78 (s, 1H); 8.84 (s, 1H).

MS: [M+H]$^+$=340.38

EXAMPLE 288

6-Methyl-2-[4-[3-(2-fluoro-4-pyridyl)prop-2-ynylidene]piperidin-1-yl]nicotinonitrile From 2-fluoro-4-iodopyridine. Purification by automated flash chromatography (Horizon™-Biotage) PE-EtOAc 95:5. White solid. Yield: 62.2%

$^1$H-NMR (CDCl$_3$, δ): 2.50 (s, 3H); 2.50-2.60 (m, 2H); 2.73-2.83 (m, 2H); 3.79-3.92 (m, 4H); 5.64 (s, 1H); 6.66 (d, J=8.0 Hz, 1H); 6.95 (s, 1H); 7.19 (d, J=4.0 Hz, 1H); 7.71 (d, J=8.0 Hz, 1H); 8.19 (d, J=4.0 Hz, 1H).

MS: [M+H]$^+$=332.45

EXAMPLE 289

6-Methyl-2-[4-[3-(2-pyridyl)prop-2-ynylidene]piperidin-1-yl]nicotinonitrile

From 2-iodopyridine. Purification by automated flash chromatography (Horizon™-Biotage) PE-EtOAc 72:28. Orange oil. Yield: 76.2%

$^1$H-NMR (CDCl$_3$, δ): 2.46 (s, 3H); 2.47-2.57 (m, 2H); 2.77-2.88 (m, 2H); 3.77-3.92 (m, 4H); 5.65 (s, 1H); 6.62 (d, J=8.0 Hz, 1H); 7.22-7.30 (m, 1H); 7.42-7.53 (m, 1H); 7.61-7.77 (m, 1H); 8.60-7.65 (m, 1H).

MS: [M+H]$^+$=315.46

EXAMPLE 290

6-Methyl-2-[4-[3-(2,5-difluorophenyl-pyridyl)prop-2-ynylidene]piperidin-1-yl]nicotinonitrile From 2,5-difluoroiodobenzene. Purification by automated flash chromatography (Horizon™-Biotage) PE-Et$_2$O 85:15. Orange solid. Yield: 96.2%

$^1$H-NMR (CDCl$_3$, δ): 2.50 (s, 3H); 2.51-2.57 (m, 2H); 2.74-2.85 (m, 2H); 3.79-3.92 (m, 4H); 5.65 (s, 1H); 6.64 (d, J=8.0 Hz, 1H); 6.95-7.08 (m, 2H); 7.09-7.16 (m, 1H); 7.70 (d, J=8.0 Hz, 1H).

MS: [M+H]$^+$=350.46

EXAMPLE 291

6-Methyl-2-[4-[3-(5-cyano-2-pyridyl)prop-2-ynylidene]piperidin-1-yl]nicotinonitrile From 2-chloro-5-cyanopyridine. Purification by automated flash chromatography (Horizon™-Biotage) PE-Et$_2$O 6:4. Yellow solid. Yield: 45.2%

¹H-NMR (CDCl₃, δ): 2.52 (s, 3H); 2.53-2.60 (m, 2H); 2.78-2.89 (m, 2H); 3.81-3.93 (m, 4H); 5.68 (s, 1H); 6.66 (d, J=8.0 Hz, 1H); 7.52 (d, J=8.0 Hz, 1H); 7.72 (d, J=8.0 Hz, 1H); 7.92 (d, J=8.0 Hz, 1H); 8.85 (s, 1H).
MS: [M+H]⁺=340.38

EXAMPLE 292

6-Methyl-2-[4-(1-methyl-3-(5-fluoro-2-pyridyl)prop-2-ynylidene)piperidin-1-yl]nicotinonitrile From 5-bromo-2-fluoropyridine. Purification by automated flash chromatography (Horizon™-Biotage) PE-EtOAc 95:5. Brownish oil. Yield: 54.8%
¹H-NMR (CDCl₃, δ): 2.50 (s, 3H); 2.50-2.57 (m, 2H); 2.72-2.82 (m, 2H); 3.79-3.92 (m, 4H); 5.62 (s, 1H); 6.65 (d, J=8.0 Hz, 1H); 6.88-6.98 (m, 1H); 7.70 (d, J=8.0 Hz, 1H); 7.77-7.89 (m, 1H); 8.31 (s, 1H).
MS: [M+H]⁺=333.31

EXAMPLE 293

6-Methyl-2-[4-(1-methyl-3-(5-fluoro-3-pyridyl)prop-2-ynylidene)piperidin yl]nicotinonitrile From 3-bromo-5-fluoropyridine. Purification by automated flash chromatography (Horizon™-Biotage) PE-EtOAc 85:15. Yellowish solid. Yield: 42.8%
¹H-NMR (CDCl₃, δ): 2.48 (s, 3H); 2.49-2.58 (m, 2H); 2.72-2.83 (m, 2H); 3.79-3.92 (m, 4H); 5.63 (s, 1H); 6.64 (d, J=8.0 Hz, 1H); 7.42-7.50 (m, 1H); 7.69 (d, J=8.0 Hz, 1H); 8.41 (s broad, 1H); 8.50 (s broad, 1H).
MS: [M+H]⁺=333.38

EXAMPLE 294

2-{4-[3-(3-Fluorophenyl)prop-2-ynylidene]piperidin-1-yl}-4-methoxynicotinonitrile 4-Methoxy-2-(4-(3-(trimethylsilyl)prop-2-ynylidene)piperidin-1-yl)nicotinonitrile (Compound 294a)

The title compound was synthesized following the procedure described for the Compound of Example 262 replacing 3-bromo-5-(trifluoromethyl)pyridine with 2-chloro-4-methoxynicotinonitrile, the compound of Example 3 with compound 274a and stirring at 135° C. Purification by automated flash chromatography (Horizon™-Biotage) PE-EtOAc 100:30 afforded an ivory solid. Yield: 35%.
MS: [M+H]⁺=326.31

2-{4-[3-(3-Fluorophenyl)prop-2-ynylidene]piperidin-1-yl}-4-methoxynicotinonitrile The title compound was prepared in the same way as the Compound of Example 274 but replacing Compound 274c with Compound 294a and 1-bromo-3,5-difluorobenzene with 3-iodofluorobenzene and adding 1 molar equivalent of tetrabutylammonium fluoride monohydrate to the starting reaction mixture. Purification by automated flash chromatography (Horizon™-Biotage) PE-EtOAc 100:30, then by CHCl₃ followed by a final purification by preparative RP LC-MS chromatography, using MS-C18 XTerra column 30×50 mm eluting with ammonium bicarbonate 20 mM pH 8 buffer-acetonitrile gradient afforded a colourless oil. Yield: 20.4%. LCPREP. Colourless oil. Yield: 20.4%

¹H-NMR (CDCl₃, δ): 2.51-2.54 (m, 2H), 2.77-2.79 (m, 2H), 3.81-3.87 (m, 4H), 3.99 (s, 3H), 5.62 (s, 1H), 6.39 (d, 1H, J=8 Hz), 7.00-7.05 (m, 1H), 7.13-7.16 (m, 1H), 7.22-7.24 (m, 1H), 7.27-7.32 8M, 1H), 8.23 (d, 1H, J=4 Hz)
MS: [M+H]⁺=348.43

The following compounds were prepared in the same way as the Compound of Example 294 but substituting 1-fluoro-3-iodobenzene respectively with the indicated halo derivatives:

EXAMPLE 295

2-{4-[3-(3,5-difluorophenyl)prop-2-ynylidene]piperidin-1-yl}-4-methoxynicotinonitrile From 3,5-difluorobromobenzene. Purification by automated flash chromatography (Horizon™-Biotage) CHCl₃-MeOH/NH₃ 100:0.1. Ochre yellow solid. Yield: 65%
¹H-NMR (CDCl₃, δ): 2.50-2.53 (m, 2H), 2.74-2.77 (m, 2H), 3.79-3.85 (m, 4H), 3.98 (s, 3H), 5.60 (s, 1H), 6.37 (d, 1H, J=4 Hz), 6.76-6.81 (m, 1H), 6.95-6.97 (m, 2H), 8.22 (d, 1H, J=8 Hz)
MS: [M+H]⁺=366.35

EXAMPLE 296

2-{4-[3-(2,5-difluorophenyl)prop-2-ynylidene]piperidin-1-yl}-4-methoxynicotinonitrile From 2,5-difluoroiodobenzene. Purification by automated flash chromatography (Horizon™-Biotage) CHCl₃-MeOH/NH₃ 100:0.07. Ivory solid. Yield: 84%
¹H-NMR (CDCl₃, δ): 2.51-2.53 (m, 2H), 2.77-2.80 (m, 2H), 3.80-3.85 (m, 4H), 3.98 (s, 3H), 5.64 (s, 1H), 6.37 (d, 1H, J=4 Hz), 6.97-7.07 (m, 2H), 7.10-7.15 (m, 1H), 8.22 (d, 1H, J=8 Hz)
MS: [M+H]⁺=366.35

EXAMPLE 297

4-Methoxy-2-[4-(3-pyridin-2-ylprop-2-ynylidene)piperidin-1-yl]nicotinonitrile

From 2-bromopyridine. Purification by automated flash chromatography (Horizon™-Biotage) CHCl₃-MeOH/NH₃ 100:0.05. Pale yellow oil. Yield: 25%
¹H-NMR (CDCl₃, δ): 2.51-2.54 (m, 2H), 2.81-2.84 (m, 2H), 3.79-3.84 (m, 4H), 3.97 (s, 3H), 5.66 (s, 1H), 6.37 (d, 1H, J=4 Hz), 7.24-7.27 (m, 1H), 7.46-7.48 (m, 1H), 7.69-7.73 (m, 1H), 8.22 (d, 1H, J=4 Hz), 8.61-8.62 (m, 1H)
MS: [M+H]⁺=331.35

EXAMPLE 298

2-{4-[3-(6-fluoro-2-pyridyl)prop-2-ynylidene]piperidin-1-yl}-4-methoxynicotinonitrile From 2-bromo-6-fluoropyridine. Purification by automated flash chromatography (Horizon™-Biotage) CHCl₃-MeOH/NH₃ 100:0.05. Vitreous yellow solid. Yield: 47%
¹H-NMR (CDCl₃, δ): 2.51-2.53 (m, 2H), 2.78-2.81 (m, 2H), 3.79-3.84 (m, 4H), 3.98 (s, 3H), 5.63 (s, 1H), 6.37 (d, 1H, J=4 Hz), 6.87-6.89 (m, 1H), 7.28-7.33 (m, 1H), 7.72-7.78 (m, 1H), 8.22 (d, 1H, J=4 Hz)
MS: [M+H]⁺=349.41

EXAMPLE 299

2-{4-[3-(6-fluoro-3-pyridyl)prop-2-ynylidene]piperidin-1-yl}-4-methoxynicotinonitrile From 5-bromo-2-fluoropyridine. Purification by automated flash chromatography (Horizon™-Biotage) CHCl$_3$-MeOH/NH$_3$ 100:0.05. Ivory solid. Yield: 40%

$^1$H-NMR (CDCl$_3$, δ): 2.51-2.53 (m, 2H), 2.75-2.78 (m, 2H), 3.80-3.85 (m, 4H), 3.98 (s, 3H), 5.62 (s, 1H), 6.38 (d, 1H, J=4 Hz), 6.91-6.94 (m, 1H), 7.80-7.85 (m, 1H), 8.22 (d, 1H, J=4 Hz), 8.31 (s, 1H)

MS: [M+H]$^+$=349.41

EXAMPLE 300

2-{4-[3-(2-fluoro-4-pyridyl)prop-2-ynylidene]piperidin-1-yl}-4-methoxynicotinonitrile From 2-fluoro-4-iodopyridine. Purification by automated flash chromatography (Horizon™-Biotage) PE-EtOAc 10:3. Hazel-brown solid. Yield: 97%

$^1$H-NMR (CDCl$_3$, δ): 2.52-2.55 (m, 2H), 2.75-2.78 (m, 2H), 3.80-3.85 (m, 4H), 3.98 (s, 3H), 5.63 (s, 1H), 6.38 (d, 1H, J=4 Hz), 6.95 (s, 1H), 7.17-7.19 (m, 1H), 8.18 (d, 1H, J=4 Hz), 8.22 (d, 1H, J=4 Hz)

MS: [M+H]$^+$=349.41

EXAMPLE 301

2-{4-[3-(5-fluoro-3-pyridyl)prop-2-ynylidene]piperidin-1-yl}-4-methoxynicotinonitrile From 3-bromo-5-fluoroyridine. Purification by automated flash chromatography (Horizon™-Biotage) PE-EtOAc 10:3. Ivory solid. Yield: 76%

$^1$H-NMR (CDCl$_3$, δ): 2.51-2.54 (m, 2H), 2.75-2.78 (m, 2H), 3.80-3.85 (m, 4H), 3.98 (s, 3H), 5.63 (s, 1H), 6.38 (d, 1H, J=8 Hz), 7.43-7.46 (m, 1H), 8.22 (d, 1H, J=4 Hz), 8.41 (s, 1H), 8.50 (s, 1H)

MS: [M+H]$^+$=349.41

EXAMPLE 302

2-{4-[3-(5-cyanopyridin-3-yl)prop-2-ynylidene]piperidin-1-yl}-4-methoxynicotinonitrile From 3-bromo-5-cyanoyridine. Purification by automated flash chromatography (Horizon™-Biotage) PE-EtOAc 10:3. Vitreous rosy solid. Yield: 71%

$^1$H-NMR (CDCl$_3$, δ): 2.52-2.55 (m, 2H), 2.76-2.78 (m, 2H), 3.81-3.85 (m, 4H), 3.99 (s, 3H), 5.64 (s, 1H), 6.39 (d, 1H, J=4 Hz), 7.98 (s, 1H), 8.22 (d, 1H, J=4 Hz), 8.77 (s, 1H), 8.84 (s, 1H)

MS: [M+H]$^+$=356.41

EXAMPLE 303

2-{4-[3-(5-cyanopyridin-2-yl)prop-2-ynylidene]piperidin-1-yl}-4-methoxynicotinonitrile From 2-chloro-5-cyanoyridine. Purification by automated flash chromatography (Horizon™-Biotage) PE-EtOAc 10:3. Vitreous yellow solid. Yield: 7%

$^1$H-NMR (CDCl$_3$, δ): 2.52-2.55 (m, 2H), 2.80-2.82 (m, 2H), 3.81-3.85 (m, 4H), 3.98 (s, 3H), 5.67 (s, 1H), 6.39 (d, 1H, J=4 Hz), 7.52 (d, 1H, J=4 Hz), 7.92 (d, 1H, J=4 Hz), 8.22 (d, 1H, J=4 Hz), 8.85 (s, 1H)

MS: [M+H]$^+$=356.48

EXAMPLE 304

6-Methyl-2-[4-(1-methyl-3-phenylprop-2-ynylidene)piperidin-1-yl]nicotinonitrile

The title compound was synthesized following the procedure described for the Compound of Example 262 replacing 3-bromo-5-(trifluoromethyl)pyridine with 2-chloro-6-methylnicotinonitrile and the compound of Example 3 with Compound 253d. Purification by automated flash chromatography (Horizon™-Biotage) PE-EtOAc 9:1 afforded a colorless oil. Yield: 35%.

$^1$H-NMR (CDCl$_3$, δ): 1.98 (s, 3H), 2.48 (s, 3H), 2.57-2.60 (m, 2H), 2.84-2.87 (m, 2H), 3.83-3.88 (m, 4H), 4.18 (s, 3H), 6.59-6.61 (m, 1H), 7.34-7.36 (m, 3H), 7.45-7.47 (m, 2H), 7.68-7.70 (m, 1H).

MS: [M+H]$^+$=328.51

The following compounds were prepared in the same way as the Compound of Example 274 but substituting 1-bromo-3,5-difluorobenzene respectively with the shown halo derivatives:

EXAMPLE 305

6-Methyl-2-[4-[3-(6-bromo-2-pyridyl)prop-2-ynylidene]piperidin-1-yl]nicotinonitrile

Method A

The title compound was prepared in the same way as the Compound of Example 274 but substituting 1-bromo-3,5-difluorobenzene with 2,6-dibromopyridine. Purification by automated flash chromatography (Horizon™-Biotage) PE-EtOAc gradient from 1:0 to 8:2. Yellow solid. Yield: 30%

MS: [M+H]$^+$: 413.2

$^1$H-NMR (CDCl$_3$, δ): 2.45-2.60 (m, 5H), 2.72-2.85 (m, 2H), 3.45-3.60 (m, 4H), 5.65 (s, 1H), 6.63 (d, J=8 Hz, 1H) 7.25-7.58 (m, 3H), 8.11 (d, J=8 Hz, 1H).

Method B

Tert-butyl 4-[3-(6-bromopyridin-2-yl)prop-2-ynylidene]piperidine-1-carboxylate (Compound 305a)

The title compound was prepared from Compound 2a (in place of Compound 274c) following the procedure described for the compound of Example 274, using 2,6-dibromopyridine instead of 1-bromo-3,5-difluorobenzene and adding 1 molar equivalent of tetrabutylammonium fluoride monohydrate to the starting reaction mixture. After the work-up, the residue was purified by automated flash liquid chromatography (Horizon™-Biotage) eluting with PE-EtOAc gradient from 10:0 to 8:2 affording the title product. White solid. Yield: 68%.

2-Bromo-6-(3-piperidin-4-ylideneprop-1-ynyl)pyridine (Compound 305b)

The title product was prepared following the method described for the Compound of Example 3 but using as starting material Compound 305a instead of the Compound of Example 2 and stirring at ambient temperature for 3 days. The reaction mixture was evaporated to dryness in vacuo, taking up the residue several times with chloroform to remove excess trifluoroacetic acid.

6-Methyl-2-[4-[3-(6-bromo-2-pyridyl)prop-2-ynylidene]piperidin-1-yl]nicotinonitrile The title compound was prepared as described for the compound of Example 237 but starting from Compound 305b instead of compound 237a and 2-chloro-6-methyl-3-nitropyridine instead of 2-bromo-3-nitropyridine. An additional equivalent of TEA was used. After the work-up, the residue was purified by automated flash liquid chromatography (Horizon™-Biotage) eluting with PE-EtOAc gradient from PE:EtAc 95:5 to 6:4 affording the title product. Yellow oil. Yield: 95%.

The title compound was prepared as described for the compound of Example 237 but starting from Compound 305b instead of compound 237a and 2-chloro-6-methyl-3-nitropyridine instead of 2-bromo-3-nitropyridine. An additional equivalent of TEA was used. After the work-up, the residue was purified by automated flash liquid chromatography (Horizon™-Biotage) eluting with PE-EtOAc gradient from PE:EtAc 95:5 to 6:4 affording the title product. Yellow oil. Yield: 95%.

EXAMPLE 306

2-{4-[3-(3-Ethoxyphenyl)prop-2-ynylidene]piperidin-1-yl}-6-methyl-3-nitropyridine The title Compound was prepared from Compound 274c following the procedure described for the compound of Example 274 but using 3-ethoxybromobenzene instead of 1-bromo-3,5-difluorobenzene and adding 1 molar equivalent of tetrabutylammonium fluoride monohydrate to the starting reaction mixture. After the work-up, the residue was purified by automated flash liquid chromatography (SP1™-Biotage) eluting with PE-EtOAc gradient from PE:EtAc 1:0 to 8:2 affording the title product. Yellow solid. Yield: 46%.
MS: [M+H]$^+$ 378.44
$^1$H-NMR (CDCl$_3$, δ): 1.4-1.5 (m, 3H), 2.5-2.6 (m, 5H), 2.8 (m, 2H), 3.5-3.6 (m, 4H), 4.0-4.1 (m, 2H), 5.6 (m, 1H), 6.6 (d, 1H), 6.85-6.9 (d, 1H), 6.95-7.0 (s, 1H), 7.1 (d, 1H), 7.2-7.3 (m, 1H), 8.10-8.15 (d, 1H)

EXAMPLE 307

1-(3-{3-[1-(6-methyl-3-nitropyridin-2-yl)piperidin-4-ylidene]prop-1-ynyl}phenyl)ethanone The title compound was prepared in the same way as the Compound of Example 199 but substituting Compound 274c for Compound 1c and 1-(3-iodophenyl)ethanone for 4-bromo-2,6-difluoranisole. After the work-up, the residue was purified by automated flash liquid chromatography (SP1™-Biotage) eluting with PE-EtOAc gradient from 9:1 to 8:2 affording the title product. Yellow oil. Yield: 84.3%.
MS: [M+H]$^+$ 376.43

EXAMPLE 308

3-{3-[1-(6-Methyl-3-nitropyridin-2-yl)piperidin-4-ylidene]prop-1-ynyl}phenylacetamide The title Compound was prepared from Compound 274c following the procedure described for the compound of Example 274 using 3-bromoacetanilide instead of 1-bromo-3,5-difluorobenzene and adding 1 molar equivalent of tetrabutylammonium fluoride monohydrate to the starting reaction mixture. After the work-up, the residue was purified by automated flash liquid chromatography (SP1™-Biotage) eluting with PE-EtOAc gradient from 7:3 to 4:6 affording the title product. Orange oil. Yield: 54%.
$^1$H-NMR (CDCl$_3$, δ): 2.2 (s, 3H), 2.5-2.6 (m, 2H), 2.8 (m, 2H), 3.5-3.6 (m, 4H), 5.6 (m, 1H), 6.6 (d, 1H), 7.05-7.15 (s, 1H), 7.18-7.22 (d, 1H), 7.25-7.35 (m, 1H), 7.45-7.55 (d, 1H), 7.6 (s, 1H), 8.10-8.15 (d, 1H)
MS: [M+H]$^+$ 391.44

EXAMPLE 309

(1-{3-[1-(6-Methyl-3-nitropyridin-2-yl)piperidin-4-ylidene]prop-1-ynyl}phenyl)acetone The title Compound was prepared from Compound 274c following the procedure described for the compound of Example 274 using 3-bromophenylacetone instead of 1-bromo-3,5-difluorobenzene and adding 1 molar equivalent of tetrabutylammonium fluoride monohydrate to the starting reaction mixture. After the work-up, the residue was purified by automated flash liquid chromatography (SP1™-Biotage) eluting with PE-EtOAc gradient from 9:1 to 7:3 affording the title product. Orange oil. Yield: 41%.
$^1$H-NMR (CDCl$_3$, δ): 2.2 (s, 3H), 2.5-2.6 (s, 5H), 2.8 (m, 2H), 3.5-3.6 (m, 4H), 3.7 (s, 2H), 5.6 (m, 1H), 6.6 (d, 1H), 7.1-7.2 (m, 1H), 7.25 (m, 1H), 7.35 (m, 1H), 7.5 (d, 1H), 8.10-8.15 (d, 1H)
MS: [M+H]$^+$ 390.45

EXAMPLE 310-311

6-methyl-2-{(3Z)-3-[3-(6-methylpyridin-2-yl)prop-2-ynylidene]piperidin-1-yl}-3-nitropyridine 6-methyl-2-{(3E)-3-[3-(6-methylpyridin-2-yl)prop-2-ynylidene]piperidin-1-yl}-3-nitropyridine tert-Butyl (3Z)-3-(3-trimethylsylylprop-2-ynylidene)piperidine-1-carboxylate (Compound 310a)

tert-Butyl (3E)-3-(3-trimethylsylylprop-2-ynylidene)piperidine-1-carboxylate (Compound 311a)

The title compounds were synthesized following the procedure described for Compound 1b but using tert-butyl 3-oxopiperidine-1-carboxylate instead of 1-(3-nitropyridin-2-yl)piperidin-4-one. After the work-up, the residue was purified by automated flash liquid chromatography (SP1™-Biotage) eluting with PE-EtOAc gradient from PE-EtOAc 95:5 to 8:2 affording the title product. The less polar collected fractions corresponded to Compound 310a (9.5%). The last eluted collected fractions were attributed to Compound 311a (10.3%).
Compound 310a MS: [M+H]$^+$ 294.24
Compound 311a MS: [M+H]$^+$ 294.26 tert-Butyl (3Z)-3-[3-(6-methylpyridin-2-yl)prop-2-ynylidene]piperidine-1-carboxylate (Compound 310b)

tert-Butyl (3E)-3-[3-(6-methylpyridin-2-yl)prop-2-ynylidene]piperidine-1-carboxylate (Compound 311b)

Starting respectively from compounds 310a and 311a the title compounds were prepared following the procedure reported for the compound of example 274 but replacing 1-bromo-3,5-difluorobenzene with 2-bromo-6-methylpyridine. After the work-up, the residue was purified by automated flash liquid chromatography (SP1™-Biotage) eluting with PE-EtOAc gradient from PE-EtOAc 85:15 to 5:5 affording the title products. Compound 310b: 61%. Compound 311b: 47%

Compound 310b MS: [M+H]$^+$ 313.35
Compound 311b MS: [M+H]$^+$ 313.33

2-Methyl-6-[(3Z)-3-piperidin-3-ylideneprop-1-ynyl]pyridine (Compound 310c)

2-Methyl-6-[(3E)-3-piperidin-3-ylideneprop-1-ynyl]pyridine (Compound 311c)

The title compounds were obtained following the procedure described for the compound of Example 3 and replacing respectively the Compound of Example 2 with Compound 310b or 311b and used without further purification in the next step.

Compound 310c MS: [M+H]$^+$ 213.33
Compound 311c MS: [M+H]$^+$ 213.41

6-methyl-2-{(3Z)-3-[3-(6-methylpyridin-2-yl)prop-2-ynylidene]piperidin-1-yl}-3-nitropyridine 6-methyl-2-{(3E)-3-[3-(6-methylpyridin-2-yl)prop-2-ynylidene]piperidin-1-yl}-3-nitropyridine The title compound was prepared as described for the compound of Example 237 but starting from Compound 310c or 311c instead of compound 237a and using 2-chloro-6-methyl-3-nitropyridine instead of 2-bromo-3-nitropyridine. After the work-up, the residue was purified by automated flash liquid chromatography (SP1™-Biotage) eluting with PE-EtOAc gradient from PE-EtOAc 7:3 to 6:4 affording the title products. Example 310:18%. Example 310: 11%

Compound 310a $^1$H-NMR (CDCl$_3$, δ): 1.87 (s, 2H), 2.46-2.53 (m, 5H), 2.60 (s, 3H), 3.61 (s, 2H), 4.35 (s, 2H), 5.62 (s, 1H), 6.57-6.59 (d, 1H,), 7.11-7.13 (m, 1H), 7.35-7.37 (s, 1H), 7.61 (bs, 1H), 8.06-8.08 (d, 1H)

MS: [M+H]$^+$ 349.41

Compound 311a $^1$H-NMR (CDCl$_3$, δ): 1.86-1.92 (m, 2H), 2.46 (s, 3H), 2.62 (s, 3H) 2.75-2.78 (m, 2H), 3.46-3.49 (m, 2H), 4.30 (s, 2H), 5.69 (s, 1H), 6.59-6.61 (d, 1H), 7.11-7.13 (m, 2H), 7.56-7.69 (s, 1H), 8.08-8.10 (d, 1H)

MS: [M+H]$^+$ 349.34

EXAMPLE 312

2-[1-(6-Methyl-3-nitropyridin-2-yl)piperidin-4-yl]-4-(6-methylpyridin-2-yl)but-3-yn-2-ol tert-Butyl 4-(1-hydroxy-1-methylprop-2-ynyl)piperidine-1-carboxylate (Compound 312a)

Using ethynylmagnesium bromide instead of phenylethynylmagnesium bromide the title compound was prepared following the procedure reported for Compound 253a. After the work-up, the residue was purified by automated flash liquid chromatography (Horizon™-Biotage) eluting with PE-EtOAc 7:3. White solid. Yield: 73%.

MS: [M+H]$^+$=254.63

2-Piperidin-4-ylbut-3-yn-2-ol (Compound 312b)

The title compounds were obtained following the procedure described for the compound of Example 3 and replacing the Compound of Example 2 with Compound 312a refluxing for 6 h. The crude was used without further purification in the next step.

MS: [M+H]$^+$=154.35

2-[1-(6-Methyl-3-nitropyridin-2-yl)piperidin-4-yl]but-3-yn-2-ol (Compound 312c)

The title compound was prepared as described for the compound of Example 237 but starting from Compound 312b instead of Compound 237a and 2-chloro-6-methyl-3-nitropyridine instead of 2-bromo-3-nitropyridine. After the work-up, the residue was purified by automated flash liquid chromatography (Horizon™-Biotage) eluting with PE-EtOAc from PE:EtOAc 9:1 affording the title products as yellow oil. Yield: 93%.

$^1$H-NMR (CDCl$_3$, δ):
MS: [M+H]$^+$=290.35

2-[1-(6-Methyl-3-nitropyridin-2-yl)piperidin-4-yl]-4-(6-methylpyridin-2-yl)but-3-yn-2-ol According to the Method B detailed for Examples 218-226 starting from Compound 312c and using 2-bromo-6-methylpyridine the title compound was prepared. After the work-up, the residue was purified by automated flash liquid chromatography (Horizon™-Biotage) eluting with PE-EtOAc 1:1 affording the title product as a yellow oil. Yield: 41%.

$^1$H-NMR (CDCl$_3$, δ): 1.71 (s, 3H), 1.85-1.94 (m, 3H), 2.46 (s, 3H), 2.67, (s, 3H), 3.00-306 (m, 2H), 3.91-4.02 (m, 2H), 6.54-6.56 (m, 1H), 7.20-7.22 (m, 1H), 7.32-7.34 (m, 2H), 7.67-7.71 (m, 1H), 8.05-8.07 (m, 1H).

MS: [M+H]$^+$=381.46

EXAMPLE 313

6-Methyl-2-[4-(1-methyl-3-phenylprop-2-ynylidene)piperidin-1-yl]-3-nitropyridine The title compound was prepared as described for the compound of Example 237 but starting from Compound 253d instead of Compound 237a and 2-chloro-6-methyl-3-nitropyridine instead of 2-bromo-3-nitropyridine. After the work-up, the residue was purified by automated flash liquid chromatography (Horizon™-Biotage) eluting with PE-EtOAc 9:1 affording the title products as yellow oil. Yield: 87%.

$^1$H-NMR (CDCl$_3$, δ): 1.97 (s, 3H), 2.51 (s, 3H), 2.56-2.59 (m, 2H), 2.83-2.86 (m, 2H), 3.52-3.56 (m, 4H), 6.59-6.61 (m, 1H), 7.31-7.35 (m, 3H), 7.44-7.46 (m, 2H), 8.09-8.11 (m, 1H).

MS: [M+H]$^+$=348.52

EXAMPLE 314

1-(1-Methyl-4-nitro-1H-imidazol-5-yl)-4-(1-methyl-3-phenylprop-2-ynylidene)piperidine The title compound was prepared as described for the compound of Example 237 but starting from Compound 253d instead of compound 237a and using 5-chloro-1-methyl-4-nitroimidazole instead of 2-bromo-3-nitropyridine. After the work-up, the residue was purified by automated flash liquid chromatography (Horizon™-Biotage) eluting with CH$_2$Cl$_2$-MeOH 98:2; affording the title product as a pale yellow oil. Yield: 36.6

¹H-NMR (CDCl₃, δ): 2.00 (s, 3H), 2.55-2.57 (m, 2H), 2.83-2.84 (m, 2H), 3.20-3.26 (m, 4H), 3.63 (s, 3H), 6.59-6.61 (m, 1H), 7.28-7.36 (m, 4H), 7.45-7.47 (m, 2H).
MS: [M+H]⁺=337.41

EXAMPLE 315

4-[3-(3,5-Difluorophenyl)prop-2-ynylidene]-1-(1-methyl-4-nitro-1H-imidazol-5-yl)piperidine 1-(1-Methyl-4-nitro-1H-imidazol-5-yl)-4-(3-trimethylsylylprop-2-ynylidene)piperidine (Compound 315a)

A mixture of Compound 274a (600 mg, 3.01 mmol), 5-chloro-1-methyl-4-nitroimidazole (752 mg, 4.68 mmol) and DIPEA (1.1 mL, 6.2 mmol) in 20 mL of DMF was stirred at 135° C. for 5 h. After the usual work-up procedure, the residue was purified by automated flash liquid chromatography (Horizon™-Biotage) eluting with EtOAc-MeOH gradient from 98:2 to 90:10; affording 250 mg of the title compound as mixture with the corresponding desilylated product.
MS: [M+H]⁺ 319.38

4-[3-(3,5-Difluorophenyl)prop-2-ynylidene]-1-(1-methyl-4-nitro-1H-imidazol-5-yl)piperidine The title compound was prepared according to the method described for the compound of Example 274 but using Compound 315a instead of Compound 274c. After the usual work-up procedure, the residue was purified by automated flash liquid chromatography (Horizon™-Biotage) eluting with EtOAc-MeOH gradient from 1:0 to 92:8; affording the title compound. Yield: 53%.
¹H-NMR (CDCl₃, δ): 2.51-2.54 (m, 2H); 2.75-2.77 (m, 2H); 3.24-3.29 (m, 4H); 3.63 (s, 3H); 5.63 (s, 1H); 6.67-6.81 (m, 1H); 6.95-6.97 (m, 2H); 7.28 (s, 1H)
MS: [M+H]⁺ 359.35

EXAMPLE 316

2-Methyl-6-{3-[1-(1-methyl-4-nitro-1H-imidazol-5-yl)piperidin-4-ylidene]prop-1-ynyl}pyridine The title compound was prepared according to the method described for the compound of Example 274 using Compound 315a instead of Compound 274c and 2-bromo-6-methylpyridine instead of 1-bromo-3,5-difluorobenzene. After the usual work-up procedure, the residue was purified by automated flash liquid chromatography (Horizon™-Biotage) eluting with EtOAc-MeOH gradient from 1:0 to 92:8; affording the title compound. Yield: 50%.
¹H-NMR (CDCl₃, δ): 2.51-2.54 (m, 2H); 2.62 (s, 3H) 2.84 (bs, 2H); 3.24-3.29 (m, 4H); 3.63 (s, 3H); 5.68 (s, 1H); 7.12-7.14 (m, 1H); 7.28 (s, 1H); 7.32 (s, 1H); 7.60 (bs, 1H)
MS: [M+H]⁺ 338.42

EXAMPLE 317

2-Methyl-6-{3-[1-(4-nitro-1H-imidazol-5-yl)piperidin-4-ylidene]prop-1-ynyl}pyridine To a solution of 1,4-dinitroimidazole (207 mg, 1.31 mmol) and sodium hydrogencarbonate (242 mg, 2.88 mmol) in 4 mL of water and 0.16 mL of acetone was added drop wise a solution of the compound of Example 3 (278 mg, 1.31 mmol) in acetone. The reaction mixture was refluxed for 2 h, poured into water and extracted with EtOAc. The crude residue was purified by automated flash liquid chromatography (Horizon™-Biotage) eluting with EtOAc-MeOH gradient from 1:0 to 92:8; affording the title compound not enough pure. So, it was purified again by preparative RP LC-MS chromatography, using MS-C18 XTerra column 30×50 mm eluting with ammonium bicarbonate 20 mM pH 8 buffer-acetonitrile gradient affording 4 mg of the title compound.
¹H-NMR (CDCl₃, δ): 2.52 (bs, 2H); 2.60 (s, 3H); 2.75 (bs, 2H); 3.73 (bs, 4H); 5.63 (s, 1H); 7.12-7.14 (d, 1H); 7.43-7.47 (s; 1H); 7.55 (s, 1H); 7.58-7.62 (s, 1H); 7.0-7.50 (bs, 1H)
MS: [M+H]⁺ 324.42

EXAMPLE 318

2-{4-[3-(2,5-Difluorophenyl)prop-2-ynylidene]piperidin-1-yl}thiophene-3-carbonitrile 2-[4-[(3-Trimethylsylyl)prop-2-ynylidene]piperidin-1-yl]thiophene-3-carbonitrile (Compound 318a)

The title compound was prepared following the procedure reported for the compound of Example 42 replacing 2-bromobenzene with 2-bromothiophene-3-carbonitrile, palladium(II)acetate with tris(dibenzylideneacetone)dipalladium (0), and the compound of Example 3 with Compound 274a. After the work-up, the residue was purified by automated flash liquid chromatography (SP1™-Biotage) eluting with PE-Diethyl Ether 95:5 affording the title product. Yellowish oil. Yield: 89%.
¹H-NMR (CDCl₃, δ): 0.23 (s, 9H); 2.43-2.51 (m, 2H); 2.69-2.78 (m, 2H); 3.49-3.62 (m, 4H); 5.45 (s, 1H); 6.47-6.53 (m, 1H); 6.86-6.92 (m, 1H).
MS: [M+H]⁺=301.37

2-{4-[3-(2,5-Difluorophenyl)prop-2-ynylidene]piperidin-1-yl}thiophene-3-carbonitrile The title Compound was prepared from Compound 318a following the procedure described for the compound of Example 274 using 2,5-difluoroiodobenzene instead of 1-bromo-3,5-difluorobenzene and adding 1 molar equivalent of tetrabutylammonium fluoride monohydrate to the starting reaction mixture. After the work-up, the residue was purified by automated flash liquid chromatography (SP1™-Biotage) eluting with PE-EtOAc 98:2 affording the title product. Yellow solid. Yield: 66%.
¹H-NMR (CDCl₃, δ): 2.51-2.62 (m, 2H); 2.77-2.88 (m, 2H); 3.55-3.78 (m, 4H); 5.67 (s, 1H); 6.47-6.57 (m, 1H); 6.92-6.95 (m, 1H); 6.96-7.18 (m, 3H).
MS: [M+H]⁺=341.43

EXAMPLE 319

6-Methyl-[4-{3-[3-(3-methyl-1,2,4-oxadiazol-5-yl)phenyl]prop-2-ynylidene}piperidin-1-yl]-3-nitropyridine The title Compound was prepared from Compound 274c following the procedure described for the compound of Example 274 using 5-(3-bromophenyl)-3-methyl-1,2,4-oxadiazole instead of 1-bromo-3,5-difluorobenzene and adding 1 molar equivalent of tetrabutylammonium fluoride monohydrate to the starting reaction mixture. After the work-up, the residue was purified by automated flash liquid chromatography (SP1™-Biotage) eluting with PE-EtOAc gradient from 9:1 to 7:3 affording the title product. Yellow oil. Yield: 61%.

¹H-NMR (CDCl₃, δ): 2.45-2.55 (m, 8H); 2.75-2.85 (m, 2H); 3.45-3.55 (m, 2H); 3.55-3.65 (m, 2H); 5.63 (s, 1H); 6.6 (d, 1H); 7.45-7.55 (m; 1H); 7.65 (d, 1H); 8.00-8.05 (d, 1H); 8.10 (d, 1H); 8.2 (s, 1H)

MS: [M+H]⁺=416.45

EXAMPLE 320

3-{4-[3-(6-Methylpyridin-2-yl)prop-2-ynylidene]piperidin-1-yl}pyrazine-2-carbonitrile The title compound was prepared as reported for the compound of Example 237 but starting from the compound of Example 3 instead of Compound 237a and using 2-chloro-3-cyanopyrazine instead of 2-bromo-3-nitropyridine After the work-up, the residue was purified by automated flash liquid chromatography (SP1™-Biotage) eluting with PE-EtOAc gradient from 7:3 affording the title product. Yellowish solid. Yield: 81%.

¹H-NMR (CDCl₃, δ): 2.52-2.55 (m, 2H); 2.60 (s, 3H); 2.81-2.84 (m, 2H); 3.87-3.93 (m, 4H); 5.69 (s, 1H); 7.11 (d, 1H, J=8 Hz); 7.27-7.29 (bs, 1H); 7.56-7.59 (m, 1H); 8.04 (s, 1H); 8.28 (s, 1H).

MS: [M+H]⁺=316.51

EXAMPLE 321

Affinity of Selected Antagonists for mGlu5 Receptor Subtype

Radioligand Binding Assay at metabotropic glutamate receptor 5 in rat brain.
Methods
a) Membrane preparation: male Sprague Dawley rats (200-300 g, Charles River, Italy) were killed by cervical dislocation and the forebrain (cortex, striatum and hippocampus) was homogenized (2×20 sec) in 50 vols of cold 50 mM Tris buffer pH 7.4, using a Politron homogenizer (Kinematica). Homogenates were centrifuged at 48000×g for 15 min, resuspended in 50 vols of the same buffer, incubated at 37° C. for 15 min and centrifuged and resuspended two more times. The final pellets were frozen and stored at −80° C. until use.
b) Binding assay: pellets from rat forebrain were resuspended in 100 vols of 20 mM HEPES, 2 mM MgCl₂, 2 mM CaCl₂, pH 7.4. The membranes were incubated in a final volume of 1 ml for 60 min at 25° C. with 4 nM [³H]MPEP in the absence or presence of competing drugs. Non-specific binding was determined in the presence of 10 µM MPEP (Spooren W. et al., Trends Pharmacol Sci. 22, 331-337, 2001). The incubation was stopped by the addition of cold Tris buffer pH 7.4 and rapid filtration through 0.5% polyethyleneimine pretreated Filtermat 1204-401 (Wallac) filters. The filters were then washed with cold buffer and the radioactivity retained on the filters was counted by liquid scintillation spectrometry.
c) Data Analysis: the inhibition of specific binding of the radioligands by the tested compounds was analyzed to estimate the inhibitory concentration 50% (IC₅₀) value by using the non-linear curve-fitting software Prism 4.0 (Graphpad, San Diego, Calif.). The IC₅₀ value was converted to an affinity constant (Ki) by the equation of Cheng & Prusoff (Cheng, Y. C. & Prusoff, W. H. Biochem. Pharmacol. 22, 3099-3108, 1973).
Results
The affinity (Ki) of the compounds of the instant invention for mGlu5 receptor is between 0.1 and 1000 nM. For instance, Compound of Example 1 has a Ki of 0.37 nM.

EXAMPLE 322

Affinity of Selected Antagonists for mGlu1 Receptor Subtype

Radioligand Binding Assay at metabotropic glutamate receptor 1 in rat brain.
Methods
a) Membrane preparation: male Sprague Dawley rats (200-300 g, Charles River, Italy) were killed by cervical dislocation and the cerebella were homogenized (2×20 sec) in 50 vols of cold 50 mM Tris buffer pH 7.4, using a Politron homogenizer (Kinematica). Homogenates were centrifuged at 48000×g for 15 min, resuspended in 50 vols of the same buffer, incubated at 37° C. for 15 min and centrifuged and resuspended two more times. The final pellets were frozen and stored at −80° C. until use.
b) Binding assay: pellets from rat cerebellum were resuspended in 50 mM Tris, 1.2 mM MgCl₂, 2 mM CaCl₂, pH 7.4; membranes were incubated in a final volume of 1 ml for 30 min at 0° C. with 1.5 nM [³H] R214127 in absence or presence of competing drugs. Non-specific binding was determined in the presence of 1 µM R214127 (Lavreysen H et al Mol. Pharmacol. 63:1082-1093, 2003). The incubation was stopped by the addition of cold Tris buffer pH 7.4 and rapid filtration through 0.5% polyethyleneimine pretreated Filtermat 1204-401 (Wallac) filters. The filters were then washed with cold buffer and the radioactivity retained on the filters was counted by liquid scintillation spectrometry.
c) Data Analysis: the inhibition of specific binding of the radioligands by the tested compounds was analyzed to estimate the inhibitory concentration 50% (IC₅₀) value by using the non-linear curve-fitting software Prism 4.0 (Graphpad, San Diego, Calif.). The IC₅₀ value was converted to an affinity constant (Ki) by the equation of Cheng & Prusoff (Cheng, Y. C. & Prusoff, W. H. Biochem. Pharmacol. 22, 3099-3108, 1973).
Results
The affinity of the compounds of the instant invention for mGlu1 receptor is at least 10 times lower than their affinity for mGlu5 receptor.

EXAMPLE 323

Affinity of Selected Antagonists for Group II (mGlu2+mGlu3) Receptor Subtypes

Radioligand Binding Assay at Group II metabotropic glutamate receptors in rat brain.
Methods
a) Membrane preparation: male Sprague Dawley rats (200-300 g, Charles River, Italy) were killed by cervical dislocation and the forebrain (cortex, striatum and hippocampus) was homogenized (2×20 sec) in 50 vols of cold 50 mM Tris buffer pH 7.4, using a Politron homogenizer (Kinematica). Homogenates were centrifuged at 48000×g for 15 min, resuspended in 50 vols of the same buffer, incubated at 37° C. for 15 min and centrifuged and resuspended two more times. The final pellets were frozen and stored at −80° C. until use.
b) Binding assay: pellets of rat forebrain were washed three times with ice-cold assay buffer (10 mM potassium phosphate+100 nM potassium bromide, ph 7.6). Final pellets were resuspended in 200 vols of the assay buffer and membranes incubated in a final volume of 1 ml for 30 min at 0° C. with 1 mM [³H]LY341495 in the absence or presence of competing drugs. Non-specific binding was determined in the presence of 1 mM 1-glutamate (Wright R. A. et al. J. Pharmacol. Exp. Ther. 298:453-460, 2001; Mutel V et al. J. Neurochem. 75, 2590-2601, 2000). The incubation was stopped by the addition of cold Tris buffer pH 7.4 and rapid filtration through 0.5% polyethyleneimine pretreated Filtermat 1204-401

(Wallac) filters. The filters were then washed with cold buffer and the radioactivity retained on the filters was counted by liquid scintillation spectrometry.

c) Data Analysis: the inhibition of specific binding of the radioligands by the tested compounds was analyzed to estimate the inhibitory concentration 50% ($IC_{50}$) value by using the non-linear curve-fitting software Prism 4.0 (Graphpad, San Diego, Calif.). The $IC_{50}$ value was converted to an affinity constant (Ki) by the equation of Cheng & Prusoff (Cheng, Y. C. & Prusoff, W. H. Biochem. Pharmacol. 22, 3099-3108, 1973).

Results

The compounds of the instant invention did not affect [$^3$H]LY341495 binding to Group II (mGlu2+mGlu3) metabotropic glutamate receptors up to 1000 nM.

EXAMPLE 324

Determination of Functional Activity at mGlu5 receptor as Accumulation of Inositol Phosphate To determine the mode of action (agonist, antagonist or inverse agonist) of the test compounds at mGlu5 receptor, the concentration dependence of the stimulation of inositol phosphate production in response to the agonist (glutamate or quisqualic acid) was compared in the absence and presence of different concentrations of the test compounds themselves, measured in cells expressing mGlu5 receptor.

The cells were preincubated with the glutamate-degrading enzyme (1 U/ml glutamate pyruvate transaminase) and 2 mM pyruvate to avoid the possible action of glutamate released from the cells. The stimulation was then conducted in a medium containing 10 mM LiCl, and different concentrations of the agonist (glutamate or quisqualic acid) or compounds to be tested for agonistic activity.

When antagonist activity was studied, test compounds were added to cell cultures 20 min prior to the addition of the agonist and further incubated in the presence of the agonist.

The incubation was stopped adding ice cold perchloric acid then samples were neutralized, centrifuged and the supernatant utilized for the determination of inositol phosphate (IP) accumulation using The Biotrak D-myo-Inositol 1,4,5-trisphosphate assay system from Amersham Biosciences. D-myo-Inositol 1,4,5-trisphosphate ($IP_3$) may be measured in the range 0.19-25 pmol (0.08-10.5 ng) per tube. In the assay, unlabelled $IP_3$ competes with a fixed amount of [$^3$H]-labelled $IP_3$ for a limited number of bovine adrenal $IP_3$ binding proteins. The bound $IP_3$ is then separated from the free $IP_3$ by centrifugation, which brings the binding protein to the bottom of the tube. The free $IP_3$ in the supernatant can then be discarded by simple decantation, leaving the bound fraction adhering to the tube. Measurement of the radioactivity in the tube enables the amount of unlabelled $IP_3$ in the sample to be determined by interpolation from a standard curve.

$EC_{50}/IC_{50}$ were determined by nonlinear regression analysis using the software Prism 4.0 (Graphpad, San Diego, Calif.).

Results

The compounds of the instant invention showed antagonistic activity.

EXAMPLE 325

Effect on Cystometry in Conscious Rats

Methods:

Male Sprague-Dawley rats [Crl: CD® (SD) IGS BR] of 300-400 g b.w. supplied by Charles River Italia were used. The animals were housed with free access to food and water and maintained on a forced 12-hour-light/12-hour-dark cycle at 22-24° C. of temperature, except during the experiment. To quantify urodynamic parameters in conscious rats, cystometrographic studies were performed according to the procedure previously reported (Guarneri et al., Pharmacol. Res. 24: 175, 1991).

Briefly, the rats were anaesthetised by intraperitoneal administration of 3 ml/kg of Equithensin solution (pentobarbital 30 mg/kg and chloral hydrate 125 mg/kg) and placed in a supine position. An approximately 10 mm long midline incision was made in the shaved and cleaned abdominal wall. The urinary bladder was gently freed from adhering tissues, emptied and then cannulated via an incision in the bladder body, using a polyethylene cannula (0.58 mm internal diameter, 0.96 mm external diameter) which was permanently sutured with silk thread. The cannula was exteriorised through a subcutaneous tunnel in the retroscapular area, where it was connected to a plastic adapter in order to avoid the risk of removal by the animal. For drug testing, the rats were utilised one day after implantation.

On the day of the experiment, the rats were placed in modified Bollman cages, i.e., restraining cages that were large enough to permit the rats to adopt a normal crouched posture, but narrow enough to prevent turning around. After a stabilisation period of about 20 minutes, the free tip of the bladder cannula was connected through a T-shaped tube to a pressure transducer (Statham P23XL) and to a peristaltic pump (Gilson Minipuls 2) for continuous infusion of a warm (37° C.) saline solution into the urinary bladder, at a constant rate of 0.1 ml/minute. The intraluminal-pressure signal during infusion of saline into the bladder (cystometrogram) was continuously recorded on a polygraph (Rectigraph-8K San-ei with BM614/2 amplifier from Biomedica Mangoni) or stored on PC by data acquisition system (PowerLab, Chart 4 software, AD Instruments). From the cystometrogram, bladder volume capacity (BVC) was evaluated. BVC (in ml) is defined as the volume of saline infused into the bladder necessary to induce detrusor contraction followed by micturition. Basal BVC value was evaluated as the mean of the values observed in the cystometrograms recorded in an initial period of 30-60 minutes. At this point in the assay, the infusion was interrupted and the test compounds were administered orally by a stomach tube. The bladder infusion restarted and changes in BVC were evaluated from the mean values obtained in the cystometrograms observed during 1, 2, and 3 hours after treatment. The compounds were administered in a volume of 2 ml/kg. Groups of control animals received the same amount of vehicle corresponding to a solution 0.5% methocel in water.

Under the given test conditions, measurement of BVC is equivalent to measurement of interval time between micturitions.

Statistical Analysis

Each experimental group was composed of 4-11 animals. All data were expressed as mean±standard error. The percent change of BVC versus the basal value, as well as Δ value (difference in ml) of BVC (BVC at time "x" minus basal value), were also evaluated for each rat/time. In the figures, data are reported as % change versus the basal value.

Statistical analysis on BVC values, as well as on Δ values, was performed by S.A.S./STAT software, version 6.12. The difference between vehicle and active treatment effect was evaluated on Δ values of BVC, whereas the difference between the values at different times versus the basal values was evaluated on original BVC data.

Results

The time course of the effects of the orally administered doses of Example 1 is shown in FIG. 1. The compound administered at 1 and 3 mg/kg p.o. proved effective in increasing the bladder volume capacity (FIG. 1).

Figure 2:
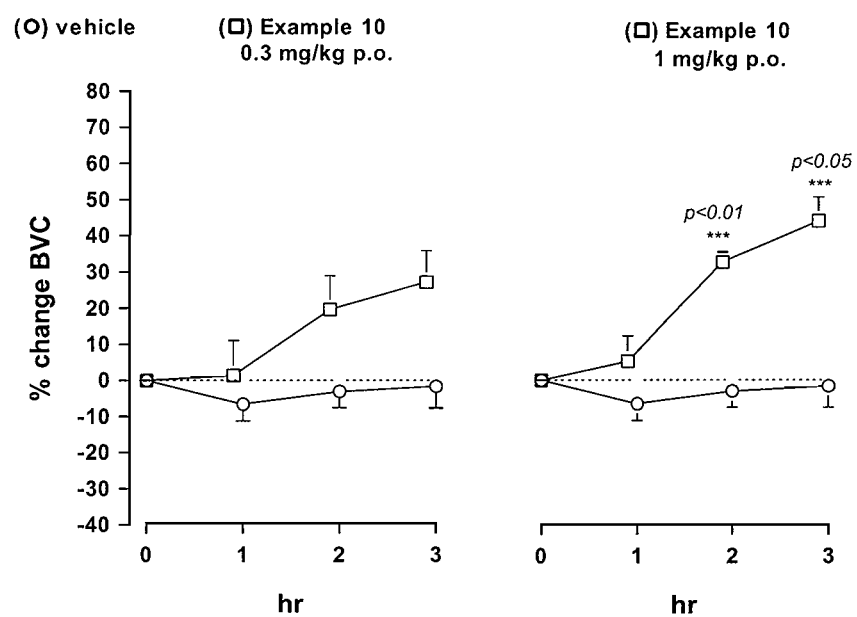
FIG. 2: time course of the effect on rat bladder volume capacity of Example 10, administered at 0.3 and 1 mg/kg, orally, vs vehicle treated controls.

The time course of the effects of the orally administered doses of Example 10 is shown in FIG. 2. The administration of 0.3 mg/kg slightly increased the bladder volume capacity (not statistical significant); the dose of 1 mg/kg proved effective in increasing bladder volume capacity (effect statistically significant after 2 and 3 hours from treatment).

The same results were obtained with Example 5 and 6.

Figure 3:
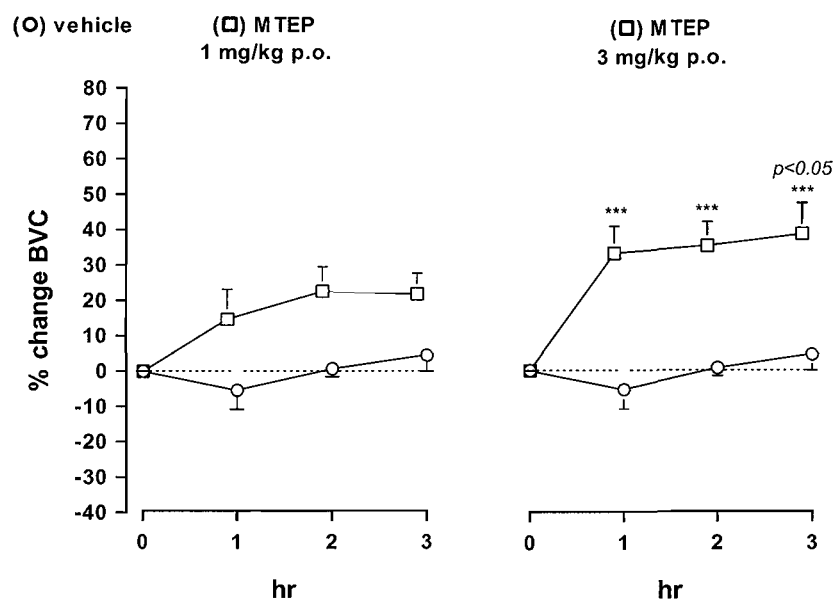
FIG. 3: time course of the effect on rat bladder volume capacity of the reference molecule, MTEP, administered at 1 and 3 mg/kg, orally, vs vehicle treated controls.

The time course of the effect of the reference compound MTEP, orally administered at 1 and 3 mg/kg, is shown in FIG. 3. The dose of 1 mg/kg showed only a slight increase of bladder volume capacity, whereas the dose of 3 mg/kg induced a sustained increase of this parameter, that resulted statistically significant from the vehicle group after 3 hours from treatment.

The activity of compounds of the invention and reference standard expressed as MED (i.e. Minimal Effective Dose that induces statistically significant increase of bladder volume capacity) is given in Table 1.

TABLE 1

| Examples | "In vivo" cystometryMED (mg/kg os) |
|---|---|
| Example 1 | 3 |
| Example 5 | 0.1 |
| Example 6 | 1 |
| Example 9 | 1 |
| Example 10 | 1 |
| Example 35 | 3 |
| Example 43 | 3 |
| Example 55 | 0.3 |
| Example 56 | 1 |
| Example 67 | 1 |
| Example 202 | 3 |
| Example 208 | 0.3 |
| MTEP | 3 |

EXAMPLE 326

Plasma Extravasation in the Dura Mater of Rats Induced by Electrical Stimulation of the Trigeminal Ganglion Electrical stimulation of the trigeminal ganglion induces inflammation in the dura mater which causes plasma extravasation. This animal model is widely accepted for testing drugs useful in migraine.

Male Wistar rats weighing 175-190 g are anaesthetised with 50 mg/kg i.p. of pentobarbital and the jugular vein is cannulated for injection of drugs. The animals are placed in a stereotaxic frame. Symmetrical boreholes are drilled 3.0 mm laterally and 3.2 mm posteriorly from bregma and the electrodes are lowered 9.5 mm from dura mater. The test compound or control-vehicle solution are administered intravenously 10 min prior to electrical stimulation of the right trigeminal ganglion (5 min; 2.0 mA, 5 Hz, 5 ms duration and Evans blue (30 mg/kg i.v.), is given 5 min prior to electrical stimulation as a marker of plasma protein extravasation. 15 minutes after the end of the stimulation period the animals are perfused with 50 ml saline via the left cardiac ventricle to remove intravascular Evans blue. The dura mater is removed, blotted dry and weighed. Tissue Evans blue is extracted in 0.3 ml formamide at 50° C. for 24 h. Dye concentrations are measured with a spectrophotometer at 620 nm wavelength, interpolated on a standard curve and expressed as ng Evans blue content per mg tissue weight.

Extravasation is expressed as the quotient calculated by dividing the Evan's blue content of the stimulated side by the Evan's blue content of the unstimulated side.

EXAMPLE 327

GERD Model in Dogs

Beagle dogs are equipped with a chronic esophagostomy to allow passage of a manometric catheter and a pH probe along the esophagus and the stomach.

Following recording of the basal pressure of the Lower Esophageal Sphincter and the stomach, compounds under evaluation and vehicle for control are administered by intravenous route.

Transient Lower Esophageal Sphincter Relaxations (TLESRs) and acid reflux are induced by infusion of an acidified meal followed by stomach distension using a peristaltic pump infusing air at 40 ml/min, in accordance to Stakeberg J. and Lehmann A., (Neurogastroenterol. Mot. (1999) 11: 125-132). Active compounds reduce dose-dependently the frequency of TLESRs and TLESRs associated with acid reflux. The activity is determined as % inhibition of both parameters as compared to vehicle control.

We claim:

1. A compound of the Formula A

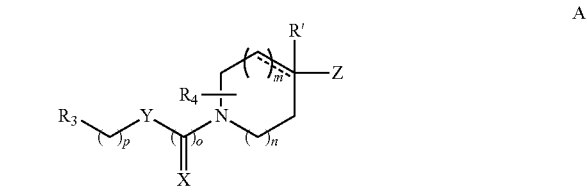

A wherein:

R' is absent or is selected from the group consisting of hydrogen and hydroxyl;

Z is chosen from the group consisting of

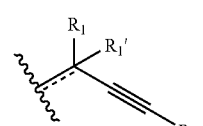

i

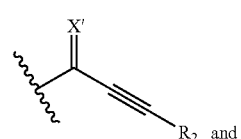

ii and

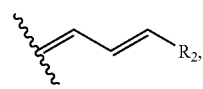

iii wherein

X' is chosen from the group consisting of O and $CH_2$;

$R_1$ is chosen from the group consisting of hydrogen, $C_1$-$C_6$ alkyl, hydroxyl, halogen, —OC(O)O $C_1$-$C_6$ alkyl, $C_1$-$C_6$ alkoxy, phenyl, di $C_1$-$C_6$ alkyl amino, and $C_5$ heterocyclic group containing 1 heteroatoms chosen from the group consisting of N;

$R_1$' is absent or is hydrogen or hydroxy; and $R_2$ is optionally substituted pyridyl;
$R_3$ is chosen from the group consisting of hydrogen, optionally substituted $C_1$-$C_6$ alkyl optionally interrupted by 1 heteroatom selected from the group consisting of —$NR_8$—, —O—, and —$SO_2$—, wherein $R_8$ is chosen from the group consisting of $C_1$-$C_6$ alkyl; optionally substituted mono or bicyclic $C_1$-$C_9$ heteroaromatic group containing 1 to 3 heteroatoms chosen from the group consisting of N, $NR_9$, S, and O wherein $R_9$ is chosen from the group consisting of H, $C_1$-$C_6$ alkyl; optionally substituted monocyclic $C_4$-$C_5$ heterocyclic group containing 1 to 2 heteroatoms chosen from the group consisting of N and O; optionally substituted mono $C_6$ aromatic; and optionally substituted $C_3$-$C_6$ cycloalkyl;
$R_4$ is chosen independently for each position capable of substitution from the group consisting of hydrogen and $C_1$-$C_6$ alkyl;
X is chosen from the group consisting of O and S;
Y is absent or chosen from the group consisting of —$SO_2$—, —NH—, —N($C_1$-$C_6$ alkyl)- and —O—;
m is 0, 1 or 2
n is 0, 1 or 2
o is 0 or 1
p is 0, 1, 2, 3, 4 or 5;
---- is an optional double bond with the proviso that there cannot be two or more optional double bonds present;

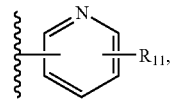

represents the point of attachment to the nitrogen containing ring and;
wherein the optional substitutents are selected from the group consisting of $C_1$-$C_6$ alkyl, $C_2$-$C_6$ alkenyl, $C_2$-$C_6$ alkynyl, and $C_3$-$C_9$ mono and bicycloalkyl which can be optionally interrupted by 1-3 heteroatoms chosen from the group consisting of NR*, S, $SO_2$, and O wherein R* is chosen from the group consisting of H, —C(O)$C_1$-$C_6$ alkyl, benzyl, phenyl and $C_1$-$C_6$ alkyl, and can be further substituted with 1-8 substituents chosen from the group consisting of oxo, halogen, cyano, nitro, hydroxy, phenyl and —$NH_2$ with the proviso that oxo groups are not adjacent to one another; and
wherein the optional substitutents are selected from the group consisting of oxo, nitro, halogen, cyano, hydroxy, —$SO_2$($C_1$-$C_6$ alkyl), —O($C_1$-$C_6$ alkyl), —NRR wherein R** is independently chosen for each occurrence from the group consisting of H, —C(O)$C_1$-$C_6$ alkyl, benzyl, phenyl and $C_1$-$C_6$ alkyl; and
wherein the optional substitutents are selected from the group consisting of —O—($C_1$-$C_8$ heteroaromatic), —O—($C_2$-$C_8$ heterocyclic), —C(O)—($C_1$-$C_8$ heteroaromatic), —C(O)—($C_1$-$C_8$ heterocyclic)-($CH_2$)$_q$—($C_1$-$C_8$ heteroaromatic), —($CH_2$)$_q$—($C_2$-$C_8$ heterocyclic), —NR*—($C_1$-$C_8$ heteroaromatic), —NR*—($C_2$-$C_8$ heterocyclic); —O-(phenyl), —C(O)-(phenyl), —C(O)NR*-($C_1$-$C_8$ heteroaromatic), —C(O)NR*-($C_2$-$C_8$ heterocyclic), —C(O)NR*-(phenyl), —($CH_2$)$_q$-(phenyl), —NR*-(phenyl), —NR*C(O)-(phenyl), —NR*C(O)—($C_1$-$C_8$ heteroaromatic), —NR*C(O)—($C_2$-$C_8$ heterocyclic); —OC(O)-(phenyl), —OC(O)—($C_1$-$C_8$ heteroaromatic), and —OC(O)—($C_2$-$C_8$ heterocyclic) wherein said heteroaromatic and heterocyclic rings contain from 1 to 3 heteroatoms chosen from the group consisting of —N—, —N($C_1$-$C_6$ alkyl), O, S, and $SO_2$; and said phenyl, heterocyclic and heteroaromatic rings can be further substituted with 1 to 3 groups selected from halogen, hydroxy, cyano, nitro, and $C_1$-$C_6$ alkyl; R* is chosen independently for each occurrence from the group consisting of H and $C_1$-$C_6$ alkyl; and q is 0-6; and
enantiomers, diastereomers and N-oxides thereof; and pharmaceutically acceptable salts thereof; with the proviso that two heteroatoms may not be covalently bound to one another unless present in a heteroaromatic ring, a sulfonamide linkage or as an N-oxide; with the proviso that when Z is one of formulas ii or iii, $R_2$ is optionally substituted phenyl and m and n are both 1.

2. The compound according to claim 1 wherein Z is formulas ii or iii, $R_3$ is optionally substituted mono- or bicyclic $C_1$-$C_2$ heteroaromatic group containing 1 to 3 heteroatoms chosen from the group consisting of N, $NR_9$, S, and O wherein $R_9$ is chosen from the group consisting of H, $C_1$-$C_6$ alkyl; m and n are 1; X' is O or $CH_2$, Y is absent and p and o are 0.

3. The compound according to claim 1 wherein $R_3$ is

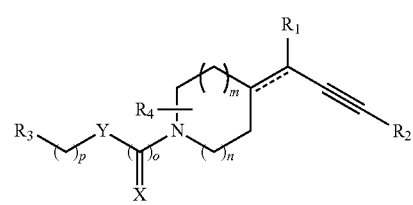

wherein
$R_{11}$ is independently chosen for each position capable of substitution from the group consisting of H, halogen, $CF_3$, trifluoromethoxy, —C(O)—($C_{1-6}$ alkyl), —NH($C_{1-6}$ alkyl), —N(di $C_{1-6}$ alkyl), nitro, cyano, hydroxy, $C_{1-6}$ alkyl, and $C_{1-6}$ alkoxy.

4. The compound of claim 1, wherein the compound is represented by the Formula I

I wherein:
$R_1$ is chosen from the group consisting of hydrogen, $C_1$-$C_6$ alkyl, $C_3$-$C_{14}$ cycloalkyl hydroxyl, cyano, halogen, —C(O)O $C_1$-$C_6$ alkyl, —C(O)$C_1$-$C_6$ alkyl, —OC(O)O $C_1$-$C_6$ alkyl, —OC(O)$C_1$-$C_6$ alkyl, $C_1$-$C_6$ alkylthio, $C_1$-$C_6$ alkoxy, phenyl, di $C_1$-$C_6$ alkyl amino, and optionally substituted $C_2$-$C_9$ heterocyclic group containing 1 to 3 heteroatoms chosen from the group consisting of N, $NR_5$, S, $SO_2$ and O wherein $R_5$ is chosen from the group consisting of H, —C(O)$C_1$-$C_6$ alkyl, benzyl, phenyl and $C_1$-$C_6$ alkyl;
$R_2$ is optionally substituted pyridyl;
$R_3$ is chosen from the group consisting of hydrogen, optionally substituted $C_1$-$C_6$ alkyl optionally interrupted by 1 heteroatom selected from the group consisting of —$NR_8$—, —O—, and —$SO_2$—, wherein $R_8$ is chosen from the group consisting of $C_1$-$C_6$ alkyl; optionally substituted mono bi or tricyclic $C_1$-$C_{14}$ heteroaromatic group containing 1 to 3 heteroatoms chosen from the group consisting of N, NR$_9$, S, and O wherein R$_9$ is chosen from the group consisting of H, and C$_1$-C$_6$ alkyl; optionally substituted monocyclic, bi, or tricyclic C$_4$-C$_5$ heterocyclic group containing 1 to 2 heteroatoms chosen from the group consisting of N and O; optionally substituted monocyclic, C$_6$ aromatic; and optionally substituted C$_3$-C$_6$ cycloalkyl;

R$_4$ is chosen independently for each position capable of substitution from the group consisting of hydrogen and C$_1$-C$_6$ alkyl;

X is chosen from the group consisting of O and S;

Y is absent or chosen from the group consisting of —SO$_2$—, —NH—, —N(C$_1$-C$_6$ alkyl)- and —O—;

m is 0, 1 or 2 n is 0, 1 or 2 o is 0 or 1 p is 0, 1, 2, 3, 4 or 5

---- is an optional double bond and;

enantiomers, diastereomers and N-oxides thereof; and pharmaceutically acceptable salts thereof; with the proviso that two heteroatoms may not be covalently bound to one another unless present in a heteroaromatic ring or as a sulfonamide linkage.

5. A compound according to claim 4 selected from the group consisting of Formula II and III;

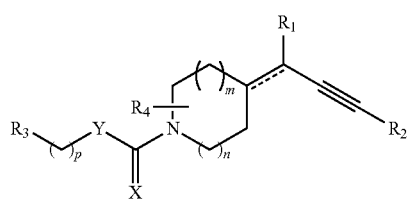

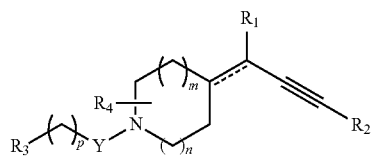

and enantiomers, diastereomers and N-oxides thereof; and pharmaceutically acceptable salts thereof.

6. The compound according to claim 1 wherein R$_1$ is hydrogen or fluorine.

7. The compound according to claim 1 wherein R$_4$ is hydrogen.

8. The compound according to claim 1 wherein m is 1 and n is 0 or 1.

9. The compound according to claim 1 wherein X is O and Y is NH or —N(C$_1$-C$_6$ alkyl)-.

10. The compound according to claim 1 wherein X is S and Y is NH or —N(C$_1$-C$_6$ alkyl).

11. The compound according to claim 1 wherein X is O and Y is O.

12. The compound according to claim 1 wherein X is O and Y is absent.

13. The compound according to claim 1 wherein o is 0 and Y is SO$_2$.

14. The compound according to claim 4 wherein R$_2$ is chosen from the group consisting of

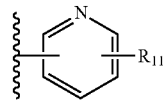

wherein R$_{11}$ is independently chosen for each position capable of substitution from the group consisting of H, halogen, CF$_3$, trifluoromethoxy, —C(O)—(C$_{1-6}$ alkyl), —NH(C$_{1-6}$ alkyl), —N(di C$_{1-6}$ alkyl), nitro, cyano, hydroxy, C$_{1-6}$ alkyl, and C$_{1-6}$ alkoxy.

15. The compound according to claim 14 wherein R$_2$ is

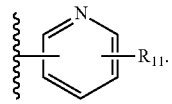

16. The compound according to claim 15 wherein R$_2$ is

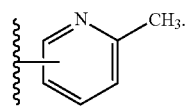

17. The compound according to claim 16 wherein R$_2$ is

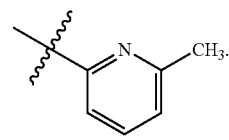 [SMILES: *c1cccc(C)n1]

18. The compound according to claim 4 wherein R$_2$ is chosen from the group consisting of

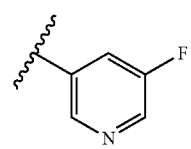

19. The compound according to claim 1 wherein R$_3$ is chosen from the group consisting of is

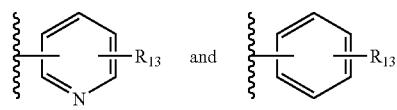

wherein R$_{13}$ is independently selected for each position capable of substitution from the group consisting of H, halogen, CF$_3$, trifluoromethoxy, —C(O)—(C$_{1-6}$ alkyl), —NH(C$_{1-6}$ alkyl), —N(di C$_{1-6}$ alkyl), nitro, cyano, hydroxy, C$_{1-6}$ alkyl, and C$_{1-6}$ alkoxy.

20. The compound according to claim 1 wherein R$_3$ is chosen from the group consisting of H, CF$_3$, trifluoromethoxy, C$_{1-6}$ alkyl, and C$_{1-6}$ alkoxy:

175

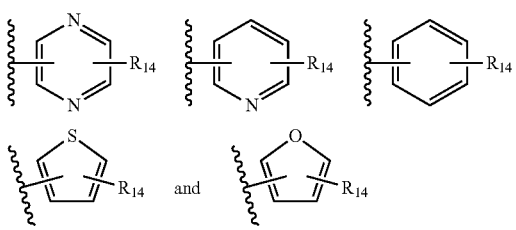

wherein $R_{14}$ is independently selected for each position capable of substitution from the group consisting of H, halogen, $CF_3$, trifluoromethoxy, —C(O)—($C_{1-6}$ alkyl), —NH($C_{1-6}$ alkyl), —N(di $C_{1-6}$ alkyl), nitro, cyano, hydroxy, $C_{1-6}$ alkyl, and $C_{1-6}$ alkoxy.

21. The compound according to claim 20 wherein $R_3$ is

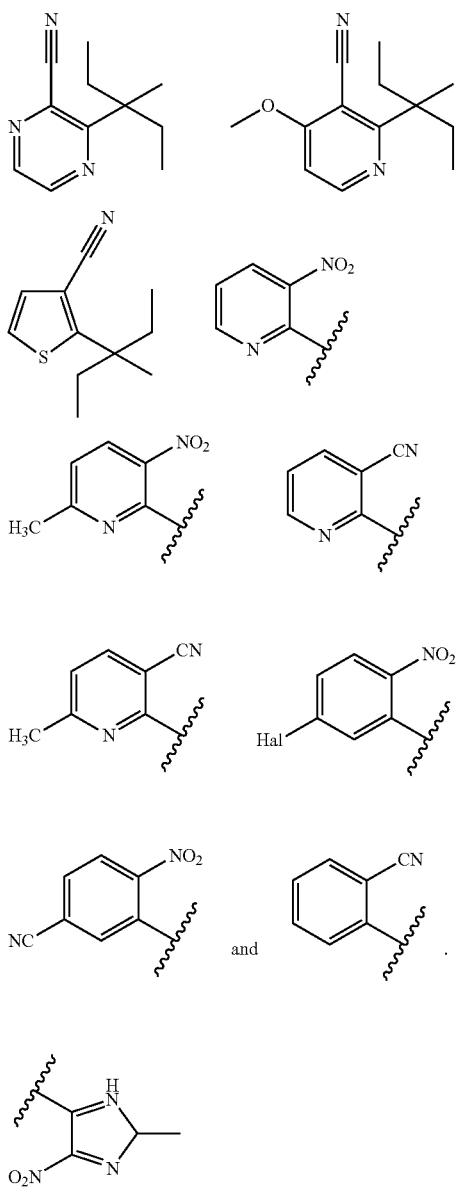

176

22. The compound according to claim 4 chosen from the group consisting of Formula IV and V

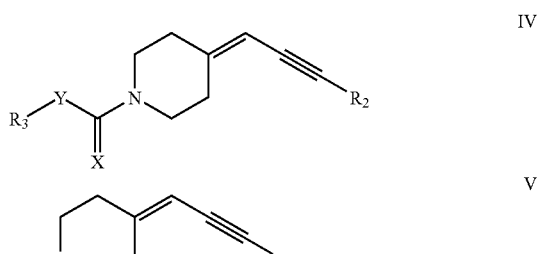

enantiomers, diastereomers and N-oxides thereof; and pharmaceutically acceptable salts thereof.

23. The compound of claim 1 chosen from the group consisting of
- 2-{4-[3-(6-Methylpyridin-2-yl)prop-2-ynylidene]piperidin-1-yl}-3-nitropyridine
- tert-Butyl 4-[3-(6-methylpyridin-2-yl)prop-2-ynylidene]piperidine-1-carboxylate
- 2-Methyl-6-(3-piperidin-4-ylideneprop-1-ynyl)pyridine
- 2-Methyl-6-{3-[1-(2-nitrophenyl)piperidin-4-ylidene]prop-1-ynyl}pyridine
- 6-Methyl-2-{4-[3-(6-methylpyridin-2-yl)prop-2-ynylidene]piperidin-1-yl}-3nitropyridine
- 6-Methoxy-2-{4-[3-(6-methylpyridin-2-yl)prop-2-ynylidene]piperidin-1-yl}-3-nitropyridine
- 2-Methyl-6-{3-[1-(5-methyl-2-nitrophenyl)piperidin-4-ylidene]prop-1-ynyl}pyridine
- 2-{3-[1-(5-Methoxy-2-nitrophenyl)piperidin-4-ylidene]prop-1-ynyl}-6-methylpyridine
- 3-Nitro-2-[4-(3-pyridin-2-ylprop-2-ynylidene)piperidin-1-yl]pyridine
- 3-Nitro-2-[4-(3-pyridin-3-ylprop-2-ynylidene)piperidin-1-yl]pyridine
- 4-[3-(6-Methylpyridin-2-yl)prop-2-ynylidene]-N-phenylpiperidine-1-carboxamide
- 4-({4-[3-(6-Methylpyridin-2-yl)prop-2-ynylidene]piperidin-1-yl}carbonyl)morpholine
- 2-[3-(1-Benzoylpiperidin-4-ylidene)prop-1-ynyl]-6-methylpyridine
- N-Butyl-4-[3-(6-methylpyridin-2-yl)prop-2-ynylidene]piperidine-1-carbothioamide
- N-Ethyl-4-[3-(6-methylpyridin-2-yl)prop-2-ynylidene]piperidine-1-carbothioamide
- N-(tert-Butyl)-4-[3-(6-methylpyridin-2-yl)prop-2-ynylidene]piperidine-1-carboxamide
- 4-[3-(6-Methylpyridin-2-yl)prop-2-ynylidene]-N-(3-nitrophenyl)piperidine-1-carboxamide
- 2-Methyl-6-{3-[1-(3-nitrobenzoyl)piperidin-4-ylidene]prop-1-ynyl}pyridine
- Ethyl 4-[3-(6-methylpyridin-2-yl)prop-2-ynylidene]piperidine-1-carboxylate
- N-Cyclohexyl-4-[3-(6-methylpyridin-2-yl)prop-2-ynylidene]piperidine-1-carbothioamide
- 4-[3-(6-Methylpyridin-2-yl)prop-2-ynylidene]-N-phenylpiperidine-1-carbothioamide
- 4-[3-(6-Methylpyridin-2-yl)prop-2-ynylidene]-N-(1-phenylethyl)piperidine-1-carboxamide
- 2-[3-(1-Butyrylpiperidin-4-ylidene)prop-1-ynyl]-6-methylpyridine N-Butyl-4-[3-(6-methylpyridin-2-yl)prop-2-ynylidene]piperidine-1-carboxamide
N-Ethyl-4-[3-(6-methylpyridin-2-yl)prop-2-ynylidene]piperidine-1-carboxamide
2-[3-(1-Benzylpiperidin-4-ylidene)prop-1-ynyl]-6-methylpyridine
2-[3-(1-Butylpiperidin-4-ylidene)prop-1-ynyl]-6-methylpyridine
tert-Butyl 4-[3-(6-methylpyridin-2-yl)-1-phenylprop-2-ynylidene]piperidine-1-carboxylate
tert-Butyl 4-[3-(6-methylpyridin-2-yl)prop-2-ynyl]piperidine-1-carboxylate
2-{4-[3-(6-Methylpyridin-2-yl)prop-2-ynyl]piperidin-1-yl}-3-nitropyridine
3-Nitro-2-[4-(3-pyridin-4-ylprop-2-ynylidene)piperidin-1-yl]pyridine
4-{5-[3-[1-(3-Nitropyridin-2-yl)piperidin-4-ylidene]prop-1-ynyl]pyridin-2-yl}morpholine
2-{4-[3-(6-Fluoropyridin-3-yl)prop-2-ynylidene]piperidin-1-yl}-3-nitropyridine
1-(6-{3-[1-(3-Nitropyridin-2-yl)piperidin-4-ylidene]prop-1-ynyl}pyridin-2-yl)ethanone
2-{4-[3-(6-Isopropoxypyridin-3-yl)prop-2-ynylidene]piperidin-1-yl}-3-nitropyridine
2-{4-[3-(3-Methoxypyridin-2-yl)prop-2-ynylidene]piperidin-1-yl}-3-nitropyridine
tert-Butyl 4-[1-hydroxy-3-(6-methylpyridin-2-yl)prop-2-ynyl]piperidine-1-carboxylate
tert-Butyl 4-[1-(dimethylamino)-3-(6-methylpyridin-2-yl)prop-2-ynyl]piperidine-1-carboxylate
tert-Butyl 4-[3-(6-methylpyridyn-2-yl)-1-piperidin-1-yl-prop-2-ynyl)piperidine-1-carboxylate
2-Methyl-6-[3-(1-phenylpiperidin-4-ylidene)prop-1-ynyl]pyridine
2-{4-[3-(6-Methylpyridin-2-yl)prop-2-ynylidene]piperidin-1-yl}benzonitrile
2-{3-[1-(4-Methoxy-2-nitrophenyl)piperidin-4-ylidene]prop-1-ynyl}-6-methylpyridine
tert-Butyl 4-[3-(5-cyanopyridin-3-yl)prop-2-ynylidene]piperidine-1-carboxylate
tert-Butyl 4-[3-(6-cyanopyridin-3-yl)prop-2-ynylidene]piperidine-1-carboxylate
5-{3-[1-(3-Nitropyridin-2-yl)piperidin-4-ylidene]prop-1-ynyl}nicotinonitrile
5-{3-[1-(3-Nitropyridin-2-yl)piperidin-4-ylidene]prop-1-ynyl}pyridine-2-carbonitrile
2,6-Difluoro-4-{4-[3-(6-methylpyridin-2-yl)prop-2-ynylidene]piperidin-1-yl}benzonitrile
4-Methoxy-3-{4-[3-(6-methylpyridin-2-yl)prop-2-ynylidene]piperidin-1-yl}benzonitrile
4-Bromo-2-fluoro-6-{4-[3-(6-methylpyridin-2-yl)prop-2-ynylidene]piperidin-1-yl}benzonitrile
2-{3-[1-(4-Fluoro-2-nitrophenyl)piperidin-4-ylidene]prop-1-ynyl}-6-methylpyridine
4-{4-[3-(6-Methylpyridin-2-yl)prop-2-ynylidene]piperidin-1-yl}-3-nitrobenzonitrile
2-(2,5-Dimethyl-1H-pyrrol-1-yl)-5-[4-[3-(6-methylpyridin-2-yl)prop-2-yn-1-ylidene]piperidin-1-yl]pyrimidine
6-{4-[3-(6-Methylpyridin-2-yl)prop-2-yn-1-ylidene]piperidin-1-yl}quinoxaline
2-Methyl-6-[3-(1-pyridin-2-ylpiperidin-4-ylidene)prop-1-yn-1-yl]pyridine
6-{4-[3-(6-Methylpyridin-2-yl)prop-2-yn-1-ylidene]piperidin-1-yl}pyridine-2-carbonitrile
(4-{4-[3-(6-Methylpyridin-2-yl)prop-2-ynylidene]piperidin-1-yl}-3-nitrophenyl)methanol
2-{4-[3-(6-Methylpyridin-2-yl)prop-2-yn-1-ylidene]piperidin-1-yl}-3-(trifluoromethyl)pyridine
2-Methyl-6-(3-{1-[6-(trifluoromethyl)pyridin-2-yl]piperidin-4-ylidene}prop-1-yn-1-yl)pyridine
2-{4-[3-(6-Methylpyridin-2-yl)prop-2-yn-1-ylidene]piperidin-1-yl}-5-(trifluoromethyl)pyridine
2-{4-[3-(6-Methylpyridin-2-yl)prop-2-ynylidene]piperidin-1-yl}nicotinonitrile
2-Methoxyethyl 4-[3-(6-methylpyridin-2-yl)prop-2-ynylidene]piperidine-1-carboxylate
2-Cyanoethyl 4-[3-(6-methylpyridin-2-yl)prop-2-ynylidene]piperidine-1-carboxylate
Benzyl 4-[3-(6-methylpyridin-2-yl)prop-2-ynylidene]piperidine-1-carboxylate
2-Fluoro-4-nitrophenyl 4-[3-(6-methylpyridin-2-yl)prop-2-ynylidene]piperidine-1-carboxylate
Thiophen-2-ylmethyl 4-[3-(6-methylpyridin-2-yl)prop-2-ynylidene]piperidine-1-carboxylate
Pyridin-2-yl 4-[3-(6-methylpyridin-2-yl)prop-2-ynylidene]-piperidine-1-carboxylate
1-Methylpiperidin-4-yl 4-[3-(6-methylpyridin-2-yl)prop-2-ynylidene]piperidine-1-carboxylate
2-(1H-Indol-3-yl)ethyl 4-[3-(6-methylpyridin-2-yl)prop-2-ynylidene]piperidine-1-carboxylate
2,2,2-Trifluoro-1-trifluoromethylethyl 4-[3-(6-methylpyridin-2-yl)prop-2-ynylidene]piperidine-1-carboxylate
2,3,4-Trifluorophenyl 4-[3-(6-methylpyridin-2-yl)prop-2-ynylidene]piperidine-1-carboxylate
Cyclohexyl 4-[3-(6-methylpyridin-2-yl)prop-2-ynylidene]piperidine-1-carboxylate
Cyclobutylmethyl 4-[3-(6-methylpyridin-2-yl)-prop-2-ynylidene]piperidine-1-carboxylate
5-Bromopyridin-2-yl 4-[3-(6-methylpyridin-2-yl)prop-2-ynylidene]piperidine-1-carboxylate
3-Benzyloxypropyl 4-[3-(6-methylpyridin-2-yl)prop-2-ynylidene]piperidine-1-carboxylate
4,6-Dimethylpyrimidin-2-yl 4-[3-(6-methylpyridin-2-yl)prop-2-ynylidene]piperidine-1-carboxylate
N-Methyl-4-[3-(6-methylpyridin-2-yl)prop-2-ynylidene]-N-phenylpiperidine-1-carboxamide
N-Diethyl-4-[3-(6-methylpyridin-2-yl)prop-2-ynylidene]piperidine-1-carboxamide
N-Dimethyl-4-[3-(6-methylpyridin-2-yl)prop-2-ynylidene]piperidine-1-carboxamide
N-Methyl-4-[3-(6-methylpyridin-2-yl)prop-2-ynylidene]-N-(3-nitrophenyl)piperidine-1-carboxamide
N-Butyl-N-methyl-4-[3-(6-methylpyridin-2-yl)prop-2-ynylidene]piperidine-1-carboxamide
N-tert-Butyl-N-methyl-4-[3-(6-methylpyridin-2-yl)prop-2-ynylidene]piperidine-1-carboxamide
N-Ethyl-N-methyl-4-[3-(6-methylpyridin-2-yl)prop-2-ynylidene]piperidine-1-carboxamide
N-(1-Phenylethyl)-N-methyl-4-[3-(6-methylpyridin-2-yl)prop-2-ynylidene]piperidine-1-carboxamide
N-Ethyl-N-(1-methylethyl)-4-[3-(6-methylpyridin-2-yl)prop-2-ynylidene]piperidine-1-carboxamide
2-Methyl-6-{3-[1-(toluene-4-sulfonyl)piperidin-4-ylidene]prop-1-ynyl}pyridine
2-Methyl-6-{3-[1-(2-nitrobenzenesulfonyl)piperidin-4-ylidene]prop-1-ynyl}pyridine
2-[3-(1-Benzenesulfonylpiperidin-4-ylidene)prop-1-ynyl]-6-methylpyridine
1-(4-Methyl-3-{4-[3-(6-methylpyridin-2-yl)prop-2-ynylidene]piperidine-1-sulfonyl}phenyl)pyrrolidin-2-one
2-{3-[1-(4-Methoxybenzenesulfonyl)piperidin-4-ylidene]prop-1-ynyl}-6-methylpyridine 2-{3-[1-(4-Bromo-2,5-difluorobenzenesulfonyl)piperidin-4-ylidene]prop-1-ynyl}-6-methylpyridine
2-Methyl-6-[3-(1-phenylmethanesulfonylpiperidin-4-ylidene)prop-1-ynyl]pyridine
2-[3-(1-Ethanesulfonylpiperidin-4-ylidene)prop-1-ynyl]-6-methylpyridine
3-Chloro-4-{4-[3-(6-methylpyridin-2-yl)prop-2-ynylidene]piperidine-1-sulfonyl}benzonitrile
2-{3-[1-(3-Fluorophenylmethanesulfonyl)piperidin-4-ylidene]prop-1-ynyl}-6-methylpyridine
2-[3-(1-Cyclohexylmethanesulfonylpiperidin-4-ylidene)prop-1-ynyl]-6-methylpyridine
2-Methyl-6-{3-[1-(4-methyl-3-nitrobenzenesulfonyl)piperidin-4-ylidene]prop-1-ynyl}pyridine
2-Methyl-6-{3-[1-(2,2,2-trifluoroethanesulfonyl)piperidin-4-ylidene]prop-1-ynyl}pyridine
2-{3-[1-(4-Isopropylbenzenesulfonyl)piperidin-4-ylidene]prop-1-ynyl}-6-methyl-pyridine
4-{4-[3-(6-Methylpyridin-2-yl)prop-2-ynylidene]piperidine-1-sulfonyl}benzonitrile
2-{3-[1-(5-Chloro-2-methoxy-4-methylbenzenesulfonyl)piperidin-4-ylidene]prop-1-ynyl}-6-methylpyridine
(1S,4R)-7,7-Dimethyl-1-{4-[3-(6-methylpyridin-2-yl)prop-2-ynylidene]piperidine-1-sulfonylmethyl}bicyclo[2.2.1]heptan-2-one
2-(3-{1-[3-(4-Methoxyphenoxy)propane-1-sulfonyl]piperidin-4-ylidene}prop-1-ynyl)-6-methylpyridine
2-{3-[1-(3-Bromobenzenesulfonyl)piperidin-4-ylidene]prop-1-ynyl}-6-methylpyridine
2-{3-[1-(4-Bromo-2-fluorobenzenesulfonyl)piperidin-4-ylidene]prop-1-ynyl}-6-methylpyridine
6-Chloro-5-{4-[3-(6-methylpyridin-2-yl)prop-2-ynylidene]piperidine-1-sulfonyl}imidazo[2,1-b]thiazole
2-{3-[1-(1,2-Dimethyl-1H-imidazole-4-sulfonyl)piperidin-4-ylidene]prop-1-ynyl}-6-methylpyridine
2-Methyl-6-{3-[1-(4-[1,2,3]thiadiazol-4-ylbenzenesulfonyl)piperidin-4-ylidene]prop-1-ynyl}pyridine
2-{3-[1-(5-tert-Butyl-2-methoxybenzenesulfonyl)piperidin-4-ylidene]prop-1-ynyl}-6-methylpyridine
2-Methyl-6-{3-[1-(2-nitrobenzoyl)piperidin-4-ylidene]prop-1-ynyl}pyridine
2-({4-[3-(6-Methylpyridin-2-yl)prop-2-ynylidene]piperidin-1-yl}carbonyl)pyrazine
2-{3-[1-(3-Bromobenzoyl)piperidin-4-ylidene]prop-1-ynyl}-6-methylpyridine
4-Oxo-4-[4-[3-(6-methylpyridin-2-yl)prop-2-ynylidene)piperidin-1-yl]-1-phenylbutan-1-one
2-{3-[1-(3,4,5-Trimethoxybenzoyl)piperidin-4-ylidene]prop-1-ynyl}-6-methylpyridine
2-Methyl-6-{3-[1-(4-nitrobenzoyl)piperidin-4-ylidene]prop-1-ynyl}pyridine
2-Methyl-6-{3-[1-(3-methyl-2-nitrobenzoyl)piperidin-4-ylidene]prop-1-ynyl}pyridine
2-[3-(1-Heptanoylpiperidin-4-ylidene)prop-1-ynyl]-6-methylpyridine
2-Methyl-6-{3-[1-(thien-2-ylcarbonyl)piperidin-4-ylidene]prop-1-ynyl}pyridine
2-Methyl-6-{3-[1-(4,4,4-trifluorobutanoyl)piperidin-4-ylidene]prop-1-ynyl}pyridine
2-{3-[4-[3-(6-Methylpyridin-2-yl)prop-2-ynylidene]piperidin-1-yl]carbonyl]phenoxy}pyrimidine
2-(3-{1-[(5-Bromopyridin-3-yl)acetyl]piperidin-4-ylidene}prop-1-ynyl)-6-methylpyridine
5-({4-[3-(6-Methylpyridin-2-yl)prop-2-ynylidene]piperidin-1-yl}carbonyl)quinoline
3-(4-Chlorophenyl)-5-{4-[3-(6-methylpyridin-2-yl)prop-2-ynylidene]piperidin-1-yl}-5-oxopentanamide
2-(3-{4-[3-(6-Methylpyridin-2-yl)prop-2-ynylidene]piperidin-1-yl}-3-oxopropyl)isoindole-1,3-dione
2-{3-[1-(3-Chloro-4,5-dimethoxybenzoyl)piperidin-4-ylidene]prop-1-ynyl}-6-methylpyridine
2-Methoxy-3-({4-[3-(6-methylpyridin-2-yl)prop-2-ynylidene]piperidin-1-yl}carbonyl)pyridine
2-(3-{1-[(5-Methyl-1-(4-fluorophenyl)-1H-1,2,4-triazol-3-yl)carbonyl]piperidin-4-ylidene}prop-1-ynyl)-6-methylpyridine
2-(3-{1-[(3-Bromophenoxy)acetyl]piperidin-4-ylidene}prop-1-ynyl)-6-methylpyridine
2-Methyl-6-(3-{1-[3-(5-methyl-1,2,4-oxadiazol-3-yl)benzoyl]piperidin-4-ylidene}prop-1-ynyl)pyridine
2-(2-{4-[3-(6-Methylpyridin-2-yl)prop-2-ynylidene]piperidin-1-yl}-2-oxoethyl)isoindole-1,3-dione
5-Fluoro-2-(2-{4-[3-(6-methylpyridin-2-yl)prop-2-ynylidene]piperidin-1-yl}-2-oxoethyl)-1H-indole
2-Chloro-6-methoxy-4-({4-[3-(6-methylpyridin-2-yl)prop-2-ynylidene]piperidin-1-yl}carbonyl)pyridine
1-Methyl-5-({4-[3-(6-methylpyridin-2-yl)prop-2-ynylidene]piperidin-1-yl}carbonyl)-1H-1,2,3-benzotriazole
2-Methyl-6-(3-{1-[(2-nitrophenoxy)acetyl]piperidin-4-ylidene}prop-1-ynyl)pyridine
2-{3-[1-(2,5-Dimethyl-3-furoyl)piperidin-4-ylidene]prop-1-ynyl}-6-methylpyridine
2-(3-{1-[(5-Chlorothien-2-yl)carbonyl]piperidin-4-ylidene}prop-1-ynyl)-6-methylpyridine
2-{3-[1-(3-Iodobenzoyl)piperidin-4-ylidene]prop-1-ynyl}-6-methylpyridine
2-(3-{1-[(3,5-Difluorophenyl)acetyl]piperidin-4-ylidene}prop-1-ynyl)-6-methylpyridine
2,6-Dimethoxy-3-({4-[3-(6-methylpyridin-2-yl)prop-2-ynylidene]piperidin-1-yl}carbonyl)pyridine
2-Chloro-6-methyl-4-({4-[3-(6-methylpyridin-2-yl)prop-2-ynylidene]piperidin-1-yl}carbonyl)pyridine
5-Methoxy-3-({4-[3-(6-methylpyridin-2-yl)prop-2-ynylidene]piperidin-1-yl}carbonyl)-1H-indole
2-{3-[1-(3,3-Dimethylbutanoyl)piperidin-4-ylidene]prop-1-ynyl}-6-methylpyridine
2-{3-[1-(Methoxyacetyl)piperidin-4-ylidene]prop-1-ynyl}-6-methylpyridine
2-{3-[1-(4-Methoxybenzoyl)piperidin-4-ylidene]prop-1-ynyl}-6-methylpyridine
2-{3-[1-(3-Methoxybenzoyl)piperidin-4-ylidene]prop-1-ynyl}-6-methylpyridine
2-{3-[1-(2-Methoxybenzoyl)piperidin-4-ylidene]prop-1-ynyl}-6-methylpyridine
2-Ethoxy-3-({4-[3-(6-methylpyridin-2-yl)prop-2-ynylidene]piperidin-1-yl}carbonyl)pyridine
2-Methyl-6-{3-[1-(1-(4-pyridyl)piperidin-4-ylcarbonyl)piperidin-4-ylidene]prop-1-ynyl}pyridine
6-({4-[3-(6-Methylpyridin-2-yl)prop-2-ynylidene]piperidin-1-yl}carbonyl)-2H-1,4-benzoxazin-3(4H)-one
2-{3-[1-[3-(3-Fluorophenoxy)propanoyl]piperidin-4-ylidene]prop-1-ynyl}-6-methylpyridine
2-(1-Piperidinyl)-5-({4-[3-(6-methylpyridin-2-yl)prop-2-ynylidene]piperidin-1-yl}carbonyl)pyrimidine
1-(3-Fluoro-4-methylphenyl)-4-({4-[3-(6-methylpyridin-2-yl)prop-2-ynylidene]piperidin-1-yl}carbonyl)pyrrolidin-2-one
3-Methyl-4-{[4-(6-methyl-3-pyridin-2-ylprop-2-ynylidene)piperidin-1-yl]carbonyl}phenylacetamide
2-{3-[1-(3-Chlorobenzoyl)piperidin-4-ylidene]prop-1-ynyl}-6-methylpyridine 2-[3-[1-(1,1'-biphenyl-3-ylcarbonyl)piperidin-4-ylidene]prop-1-ynyl]-6-methylpyridine
2-{3-[1-(2-Furoyl)piperidin-4-ylidene]prop-1-ynyl}-6-methylpyridine
2-Methyl-6-{3-[1-(phenylacetyl)piperidin-4-ylidene]prop-1-ynyl}pyridine
2-Methyl-6-{3-[1-(4-phenylbutanoyl)piperidin-4-ylidene]prop-1-ynyl}pyridine
2-{3-[1-(3-Fluorobenzoyl)piperidin-4-ylidene]prop-1-ynyl}-6-methylpyridine
2-{3-[1-(3-Methylbenzoyl)piperidin-4-ylidene]prop-1-ynyl}-6-methylpyridine
3-({4-[3-(6-Methylpyridin-2-yl)prop-2-ynylidene]piperidin-1-yl}carbonyl)benzonitrile
2-Methyl-6-{3-[1-(3-trifluoromethoxybenzoyl)piperidin-4-ylidene]prop-1-ynyl}pyridine
2-Methyl-6-{3-[1-(3-trifluoromethylbenzoyl)piperidin-4-ylidene]prop-1-ynyl}pyridine
2-{3-[1-(5-Bromo-2-furoyl)piperidin-4-ylidene]prop-1-ynyl}-6-methylpyridine
2-Methyl-6-{3-[1-(5-nitro-2-furoyl)piperidin-4-ylidene]prop-1-ynyl}pyridine
2-Methyl-6-{3-[1-(5-phenyl-2-furoyl)piperidin-4-ylidene]prop-1-ynyl}pyridine
2-(3-{1-[(3-Chlorothien-2-yl)carbonyl]piperidin-4-ylidene}prop-1-ynyl)-6-methylpyridine
2-Methyl-6-(3-{1-[(4-methylthien-2-yl)carbonyl]piperidin-4-ylidene}prop-1-ynyl)pyridine
2-Methyl-6-(3-{1-[(5-methylthien-2-yl)carbonyl]piperidin-4-ylidene}prop-1-ynyl)pyridine
2-(3-{1-[(2,5-Dichlorothien-3-yl)carbonyl]piperidin-4-ylidene}prop-1-ynyl)-6-methylpyridine
2-{3-[1-(3-Furoyl)piperidin-4-ylidene]prop-1-ynyl}-6-methylpyridine
2-Methyl-6-(3-{1-[(5-phenylisoxazol-3-yl)carbonyl]piperidin-4-ylidene}prop-1-ynyl)pyridine
2-Methyl-6-(3-{1-[(5-thien-2-yl-1H-pyrazol-3-yl)carbonyl]piperidin-4-ylidene}prop-1-ynyl)pyridine
2-[3-(1-{[5-(2-Furyl)-1H-pyrazol-3-yl]carbonyl}piperidin-4-ylidene)prop-1-ynyl]-6-methylpyridine
2-Methyl-6-(3-{1-[(5-nitrothien-2-yl)carbonyl]piperidin-4-ylidene}prop-1-ynyl)pyridine
2-{3-[1-[3-(Benzyloxy)benzoyl]piperidin-4-ylidene]prop-1-ynyl}pyridine
2-Methyl-6-{3-[1-(3-methyl-2-furoyl)piperidin-4-ylidene]prop-1-ynyl}pyridine
2-(3-{1-[(3-Ethoxythien-2-yl)carbonyl]piperidin-4-ylidene}prop-1-ynyl)-6-methylpyridine
1-[5-({4-[3-(6-methylpyridin-2-yl)prop-2-ynylidene]piperidin-1-yl}carbonyl)thien-2-yl]ethanone
2-Methyl-6-(3-{1-[(5-phenylthien-2-yl)carbonyl]piperidin-4-ylidene}prop-1-ynyl)pyridine
2-[3-[1-(2-Methyl-1,3-thiazol-4-yl)benzoylpiperidin-4-ylidene]prop-1-ynyl]-6-methylpyridine
2-(3-{1-[(5-Chloro-4-methoxythien-3-yl)carbonyl]piperidin-4-ylidene}prop-1-ynyl)-6-methylpyridine
2-Methyl-6-[3-(1-{[5-(methylthio)thien-2-yl]carbonyl}piperidin-4-ylidene)prop-1-ynyl]pyridine
2-(3-{1-[(3-Chloro-4-methylthien-2-yl)carbonyl]piperidin-4-ylidene}prop-1-ynyl)-6-methylpyridine
2-Methyl-6-(3-{1-[3-(1,3-thiazol-2-yl)benzoyl]piperidin-4-ylidene}prop-1-ynyl)pyridine
2-(3-{[4-[3-(6-Methylpyridin-2-yl)prop-2-ynylidene]piperidin-1-yl]carbonyl}phenyl)pyrimidine
3-Nitro-2-(4-{3-[6-(trifluoromethyl)pyridin-3-yl]prop-2-ynylidene}piperidin-1-yl)pyridine
2-Fluoro-6-methyl-3-{3-[1-(3-nitropyridin-2-yl)piperidin-4-ylidene]prop-1-yn-1-yl}pyridine
3-Bromo-2-chloro-4-{3-[1-(3-nitropyridin-2-yl)piperidin-4-ylidene]prop-1-yn-1-yl}pyridine
3-Bromo-2-fluoro-4-{3-[1-(3-nitropyridin-2-yl)piperidin-4-ylidene]prop-1-yn-1-yl}pyridine
3-Fluoro-4-methyl-2-{3-[1-(3-nitropyridin-2-yl)piperidin-4-ylidene]prop-1-yn-1-yl}pyridine
2-{4-[3-(5-Fluoropyridin-3-yl)prop-2-yn-1-ylidene]piperidin-1-yl}-3-nitropyridine
2-{4-[3-(6-Fluoropyridin-2-yl)prop-2-yn-1-ylidene]piperidin-1-yl}-3-nitropyridine
2-{4-[3-(6-Isopropoxypyridin-3-yl)prop-2-ynylidene]piperidin-1-yl}-3-nitropyridine
2-Ethoxy-3-{3-[1-(3-nitropyridin-2-yl)piperidin-4-ylidene]prop-1-yn-1-yl}pyridine
2-{4-[3-(6-Methylpyridin-2-yl)prop-2-yn-1-ylidene]piperidin-1-yl}-5-nitropyridine
5-Bromo-2-{4-[3-(6-methylpyridin-2-yl)prop-2-yn-1-ylidene]piperidin-1-yl}pyrimidine
3-Methyl-2-{4-[3-(6-methylpyridin-2-yl)prop-2-yn-1-ylidene]piperidin-1-yl}-5-nitropyridine
5-Methyl-6-{4-[3-(6-methylpyridin-2-yl)prop-2-yn-1-ylidene]piperidin-1-yl}pyridine-3-carbonitrile
5-{4-[3-(6-Methylpyridin-2-yl)prop-2-yn-1-ylidene]piperidin-1-yl}pyridine-2-carbonitrile
2-Methyl-6-{3-[1-(4-methylpyridin-3-yl)piperidin-4-ylidene]prop-1-yn-1-yl}pyridine
4-{4-[3-(6-Methylpyridin-2-yl)prop-2-yn-1-ylidene]piperidin-1-yl} isoquinoline
5-Methyl-2-{4-[3-(6-methylpyridin-2-yl)prop-2-ynylidene]piperidin-1-yl}cyclopent-2-en-1-one
tert-Butyl 4-{1-[(methoxycarbonyl)oxy]-3-(6-methylpyridin-2-yl)prop-2-yn-1-yl}piperidine-1-carboxylate
3-(6-Methylpyridin-2-yl)-1-[1-(3-nitropyridin-2-yl)piperidin-4-yl]prop-2-yn-1-ol
2-Methyl-6-{3-[1-(3-nitrothien-2-yl)piperidin-4-ylidene]prop-1-ynyl}pyridine
2-Methyl-6-{3-[1-(5-nitrofuran-2-yl)piperidin-4-ylidene]prop-1-yn-1-yl}pyridine
5-{4-[3-(6-Methylpyridin-2-yl)prop-2-ynylidene]piperidin-1-yl}-N-phenyl-2-furamide
2-Methyl-6-{3-[1-(2-methyl-4-nitro-1H-imidazol-5-yl)piperidin-4-ylidene]prop-1-yn-1-yl}pyridine
2-{4-[1-Methoxy-3-(6-methylpyridin-2-yl)prop-2-yn-1-yl]piperidin-1-yl}-3-nitropyridine
Methyl 3-(6-methylpyridin-2-yl)-1-[1-(2-nitropyridin-2-yl)piperidin-4-yl]prop-2-yn-1-yl carbonate
6-Methyl-2-{4-[3-(6-methylpyridin-2-yl)prop-2-yn-1-yl]piperidin-1-yl}-3-nitropyridine
tert-Butyl 4-[1-fluoro-3-(6-methylpyridin-2-yl)prop-2-yn-1-yl]piperidine-1-carboxylate
2-{4-[1-Fluoro-3-(6-methylpyridin-2-yl)prop-2-ynyl]piperidin-1-yl}-6-methyl-3-nitropyridine
tert-Butyl (3E)-3-[3-(6-methylpyridin-2-yl)prop-2-ynylidene]pyrrolidine-1-carboxylate
2-{4-[3-(6-Methylpyridin-2-yl)prop-2-ynylidene]piperidin-1-yl}-3-nitroimidazo[1,2-a]pyridine
1-[1-(3-Nitropyridin-2-yl)piperidin-4-yl]-3-phenylprop-2-yn-1-one
1-3'-(Nitro-3,6-dihydro-2H-1,2'-bipyridin-4-yl)-3-phenylprop-2-yn-1-one
2-Methyl-6-(3-{1-[5-(trifluoromethyl)pyridin-3-yl]piperidin-4-ylidene}-prop-1-ynyl)pyridine
2-{4-[3-(6-Methylpyridin-2-yl)prop-2-ynylidene]piperidin-1-yl}-5-phenylnicotinonitrile 2-Methyl-6-(3-{1-[2-propoxypyridin-3-yl]piperidin-4-ylidene}prop-1-ynyl)pyridine
7-{4-[3-(6-Methylpyridin-2-yl)prop-2-ynylidene]piperidin-1-yl}pyrido[2,3-b]pyrazine
2-{4-[3-(6-Methylpyridin-2-yl)prop-2-ynylidene]piperidin-1-yl}thiophene-3-carbonitrile
2-Ethoxy-5-{4-[3-(6-methylpyridin-2-yl)prop-2-ynylidene]piperidin-1-yl}pyridine
2-{4-[3-(4-Fluoropyridin-2-yl)prop-2-ynylidene]piperidin-1-yl}-6-methyl-3-nitropyridine
6-Methyl-3-nitro-2-[4-(3-pyridin-2-ylprop-2-ynylidene)piperidin-1-yl]pyridine
2-{4-[3-(6-Fluoropyridin-2-yl)prop-2-ynylidene]piperidin-1-yl}-6-methyl-3-nitropyridine
2-{4-[3-(2-Fluoropyridin-5-yl)prop-2-ynylidene]piperidin-1-yl}-6-methyl-3-nitropyridine
2-{4-[3-(2-Fluoropyridin-4-yl)prop-2-ynylidene]piperidin-1-yl}-6-methyl-3-nitropyridine
2-{4-[3-(3-Fluoropyridin-5-yl)prop-2-ynylidene]piperidin-1-yl}-6-methyl-3-nitropyridine
5-{3-[1-(6-Methyl-3-nitropyridin-2-yl)piperidin-4-ylidene]prop-1-ynyl}nicotinonitrile
6-Methyl-2-[4-[3-(4-pyridyl)prop-2-ynylidene]piperidin-1-yl]nicotinonitrile
6-Methyl-2-[4-[3-(2-fluoro-6-pyridyl)prop-2-ynylidene]piperidin-1-yl]nicotinonitrile
6-Methyl-2-[4-[3-(5-cyano-3-pyridyl)prop-2-ynylidene]piperidin-1-yl]nicotinonitrile
6-Methyl-2-[4-[3-(2-fluoro-4-pyridyl)prop-2-ynylidene]piperidin-1-yl]nicotinonitrile
6-Methyl-2-[4-[3-(2-pyridyl)prop-2-ynylidene]piperidin-1-yl]nicotinonitrile
6-ethyl-2-[4-[3-(5-cyano-2-pyridyl)prop-2-ynylidene]piperidin-1-yl]nicotinonitrile
6-Methyl-2-[4-(1-methyl-3-(5-fluoro-2-pyridyl)prop-2-ynylidene)piperidin-1-yl]nicotinonitrile
6-Methyl-2-[4-(1-methyl-3-(5-fluoro-3-pyridyl)prop-2-ynylidene)piperidin-1-yl]nicotinonitrile
4-Methoxy-2-[4-(3-pyridin-2-ylprop-2-ynylidene)piperidin-1-yl]nicotinonitrile
2-{4-[3-(6-fluoro-2-pyridyl)prop-2-ynylidene]piperidin-1-yl}-4-methoxynicotinonitrile
2-{4-[3-(6-fluoro-3-pyridyl)prop-2-ynylidene]piperidin-1-yl}-4-methoxynicotinonitrile
2-{4-[3-(2-fluoro-4-pyridyl)prop-2-ynylidene]piperidin-1-yl}-4-methoxynicotinonitrile
2-{4-[3-(5-fluoro-3-pyridyl)prop-2-ynylidene]piperidin-1-yl}-4-methoxynicotinonitrile
2-{4-[3-(5-cyanopyridin-3-yl)prop-2-ynylidene]piperidin-1-yl}-4-ethoxynicotinonitrile
2-{4-[3-(5-cyanopyridin-2-yl)prop-2-ynylidene]piperidin-1-yl}-4-ethoxynicotinonitrile
6-Methyl-2-[4-[3-(6-bromo-2-pyridyl)prop-2-ynylidene]piperidin-1-yl]nicotinonitrile
6-methyl-2-{(3Z)-3-[3-(6-methylpyridin-2-yl)prop-2-ynylidene]piperidin-1-yl}-3-nitropyridine
6-methyl-2-{(3E)-3-[3-(6-methylpyridin-2-yl)prop-2-ynylidene]piperidin-1-yl}-3-nitropyridine
2-[1-(6-Methyl-3-nitropyridin-2-yl)piperidin-4-yl]-4-(6-methylpyridin-2-yl)but-3-yn-2-ol
2-Methyl-6-{3-[1-(1-methyl-4-nitro-1H-imidazol-5-yl)piperidin-4-ylidene]prop-1-ynyl}pyridine;
2-Methyl-6-{3-[1-(4-nitro-1H-imidazol-5-yl)piperidin-4-ylidene]prop-1-ynyl}pyridine;
3-{-4-[3-(6-Methylpyridin-2-yl)prop-2-ynylidene]piperidin-1-yl}pyrazine-2-carbonitrile;
or a pharmaceutically acceptable salt thereof.

24. A pharmaceutical composition comprising a pharmaceutically acceptable excipient or diluent and a therapeutically effective amount of a compound according to claim 1 or a pharmaceutically acceptable salt thereof.

25. A method of treating neuromuscular dysfunctions of the lower urinary tract comprising administering to a mammal in need of such treatment an effective amount of a compound of Formula A

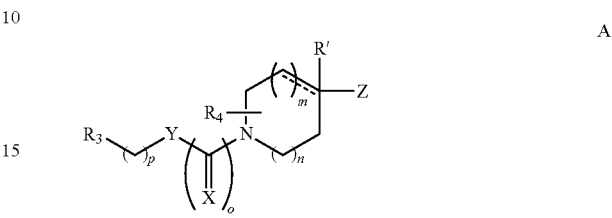

wherein:
R' is absent or is selected from the group consisting of hydrogen and hydroxyl;
Z is chosen from the group consisting of

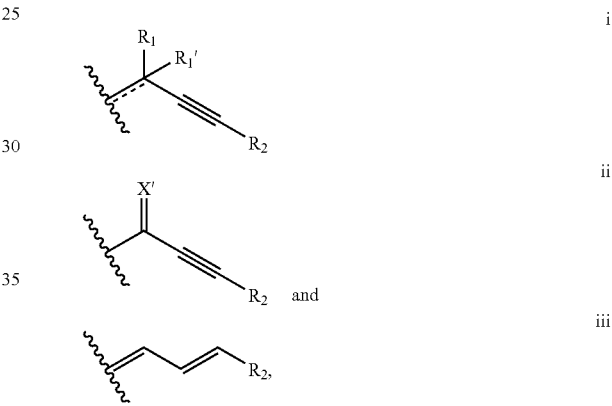

wherein
X' is chosen from the group consisting of O and $CH_2$;
$R_1$ is chosen from the group consisting of hydrogen, $C_1$-$C_6$ alkyl, hydroxyl, halogen, OC(O)O $C_1$-$C_6$ alkyl, $C_1$-$C_6$ alkoxy, phenyl, di $C_1$-$C_6$ alkyl amino, and $C_5$ heterocyclic group containing 1 heteroatoms chosen from the group consisting of N;
$R_1'$ is absent or is hydrogen or hydroxy; and
$R_2$ is optionally substituted pyridyl;
$R_3$ is chosen from the group consisting of hydrogen, optionally substituted $C_1$-$C_6$ alkyl optionally interrupted by 1 heteroatom selected from the group consisting of —$NR_8$—, —O—, and —$SO_2$—, wherein $R_8$ is chosen from the group consisting of $C_1$-$C_6$ alkyl; optionally substituted mono or bicyclic $C_1$-$C_9$ heteroaromatic group containing 1 to 3 heteroatoms chosen from the group consisting of N, $NR_9$, S, and O wherein $R_9$ is chosen from the group consisting of H, $C_1$-$C_6$ alkyl; optionally substituted monocyclic $C_4$-$C_5$ heterocyclic group containing 1 to 2 heteroatoms chosen from the group consisting of N and O; optionally substituted monocyclic $C_6$ aromatic; and optionally substituted $C_3$-$C_6$ cycloalkyl;
$R_4$ is chosen independently for each position capable of substitution from the group consisting of hydrogen and $C_1$-$C_6$ alkyl;

X is chosen from the group consisting of O and S;

Y is absent or chosen from the group consisting of —$SO_2$—, —NH—, —N($C_1$-$C_6$ alkyl)- and —O—;

m is 0, 1 or 2 n is 0, 1 or 2 o is 0 or 1 p is 0, 1, 2, 3, 4 or 5;

---- is an optional double bond with the proviso that there cannot be two or more optional double bonds present;

{ represents the point of attachment to the nitrogen containing ring and;

wherein the optional substituents are selected from the group consisting of $C_1$-$C_6$ alkyl, $C_2$-$C_6$ alkenyl, $C_2$-$C_6$ alkynyl, and $C_3$-$C_9$ mono and bicycloalkyl which can be optionally interrupted by 1-3 heteroatoms chosen from the group consisting of NR*, S, $SO_2$, and O wherein R* is chosen from the group consisting of H, —C(O)$C_1$-$C_6$ alkyl, benzyl, phenyl and $C_1$-$C_6$ alkyl, and can be further substituted with 1-8 substituents chosen from the group consisting of oxo, halogen, cyano, nitro, hydroxy, phenyl and —$NH_2$ with the proviso that oxo groups are not adjacent to one another; and wherein the optional substituents are selected from the group consisting of oxo, nitro, halogen, cyano, hydroxy, —$SO_2$($C_1$-$C_6$ alkyl), —O($C_1$-$C_6$ alkyl), —NRR wherein R is independently chosen for each occurrence from the group consisting of H, —C(O)$C_1$-$C_6$ alkyl, benzyl, phenyl and $C_1$-$C_6$ alkyl; and wherein the optional substituents are selected from the group consisting of —O—($C_1$-$C_8$ heteroaromatic), —O—($C_2$-$C_8$ heterocyclic), —C(O)—($C_1$-$C_8$ heteroaromatic), —C(O)—($C_2$-$C_8$ heterocyclic)-($CH_2$)$_q$—($C_1$-$C_8$ heteroaromatic), —($CH_2$)$_q$($C_2$-$C_8$ heterocyclic), —NR*-($C_1$-$C_8$ heteroaromatic), —NR*-($C_2$-$C_8$ heterocyclic); —O-(phenyl), —C(O)-(phenyl), —C(O)NR*-($C_1$-$C_8$ heteroaromatic), —C(O)NR*-($C_2$-$C_8$ heterocyclic), —C(O)NR*-(phenyl), —($CH_2$)$_q$-(phenyl), —NR*-(phenyl), —NR*C(O)-(phenyl), —NR*C(O)—($C_1$-$C_8$ heteroaromatic), —NR*C(O)—($C_2$-$C_8$ heterocyclic); —OC(O)-(phenyl), —OC(O)—($C_1$-$C_8$ heteroaromatic), and —OC(O)—($C_2$-$C_8$ heterocyclic) wherein said heteroaromatic and heterocyclic rings contain from 1 to 3 heteroatoms chosen from the group consisting of —N—, —N($C_1$-$C_6$ alkyl), O, S, and $SO_2$; and said phenyl, heterocyclic and heteroaromatic rings can be further substituted with 1 to 3 groups selected from halogen, hydroxy, cyano, nitro, and $C_1$-$C_6$ alkyl; R*** is chosen independently for each occurrence from the group consisting of H and $C_1$-$C_6$ alkyl; and q is 0-6; and enantiomers, diastereomers and N-oxides thereof; and pharmaceutically acceptable salts thereof; with the proviso that two heteroatoms may not be covalently bound to one another unless present in a heteroaromatic ring, a sulfonamide linkage or as an N-oxide.

26. The method according to claim 25 wherein said neuromuscular dysfunction is selected from the group consisting of urinary urgency, overactive bladder, increased urinary frequency, decreased urinary compliance (decreased bladder storage capacity), cystitis, interstitial cystitis, incontinence, urine leakage, enuresis, dysuria, urinary hesitancy and difficulty in emptying the bladder.

27. The method according to claim 25 wherein said compound is administered in combination with an antimuscarinic drug.

28. The method according to claim 27 wherein said antimuscarinic drug is selected from the group consisting of oxybuynin, tolterodine, darifenacin, solifenacin, trospium, imidafenacin, fesoterodine and temiverine.

29. The method according to claim 25 wherein said compound is administered with an α1-adrenergic antagonist.

30. The method according to claim 29 wherein said α1-adrenergic antagonist is selected from the group consisting of prazosin, doxazosin, terazosin, alfuzosin, silodosin and tamsulosin.

31. The method according to claim 25 wherein said compound is administered in combination with a serotonin or a noradrenaline reuptake inhibitor or a combination thereof.

32. The method according to claim 31 wherein said the serotonin or noradrenaline reuptake inhibitor is selected form the group consisting of duloxetine, milnacipran, amoxapine, venlafaxine, des-venlafaxine, sibutramine, tesofensine and des-methylsibutramine.

33. The method according to claim 25 wherein said compound is administered in combination with a selective or non-selective COX inhibitor.

34. The method according to claim 33 wherein said selective or non-selective COX inhibitor is selected from the group consisting of ibuprofen, naproxen, benoxaprofen, flurbiprofen, fenoprfen, ketoprofen, indoprofen, pirprofen, carprofen, tioxaprofe, suprofen, tiaprofenic acid, fluprofen, indomethacin, sulindac, tolmetin, zomepirac, diclofenac, fenclofenac, ibufenac, acetyl salicylic acid, piroxicam, tenoxicam, nabumetone, ketorolac, azapropazone, mefenamic acid, tolfenamic acid, diflunisal, acemetacin, fentiazac, clidanac, meclofenamic acid, flufenamic acid, niflumic acid, flufenisal, sudoxicam, etodolac, salicylic acid, benorylate, isoxicam, 2-fluoro-α-methyl[1,1'-biphenyl]-4-acetic acid 4-(nitrooxy) butyl ester, meloxicam, parecoxib and nimesulide.

35. The method according to claim 25 wherein said mammal is a human.

36. A method for antagonizing an mGlu5 receptor in a mammal having neuromuscular dysfunction of the lower urinary tract comprising administering an effective amount of a compound of Formula A

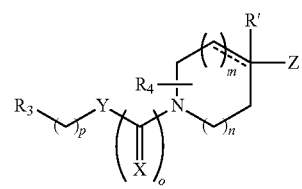

wherein:
R' is absent or is selected from the group consisting of hydrogen and hydroxyl;
Z is chosen from the group consisting of

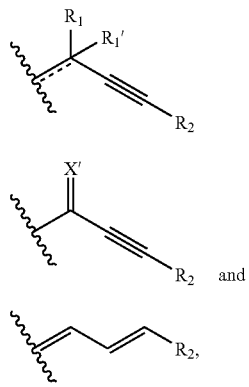

wherein
X' is chosen from the group consisting of O and $CH_2$;
$R_1$ is chosen from the group consisting of hydrogen, $C_1$-$C_6$ alkyl, hydroxyl, halogen, —OC(O)O $C_1$-$C_6$ alkyl, $C_1$-$C_6$ alkoxy, phenyl, di $C_1$-$C_6$ alkyl amino, and $C_5$ heterocyclic group containing 1 heteroatom chosen from the group consisting of N;
$R_1'$ is absent or is hydrogen or hydroxy; and
$R_2$ is optionally substituted pyridyl;
$R_3$ is chosen from the group consisting of hydrogen, optionally substituted $C_1$-$C_6$ alkyl optionally interrupted by 1 heteroatoms selected from the group consisting of —$NR_8$—, —O—, and —$SO_2$—, wherein $R_8$ is chosen from the group consisting of $C_1$-$C_6$ alkyl; optionally substituted mono or bicyclic $C_1$-$C_9$ heteroaromatic group containing 1 to 3 heteroatoms chosen from the group consisting of N, $NR_9$, S, and O wherein $R_9$ is chosen from the group consisting of H and $C_1$-$C_6$ alkyl; optionally substituted monocyclic $C_4$-$C_5$ heterocyclic group containing 1 to 2 heteroatoms chosen from the group consisting of N and O; optionally substituted monocyclic $C_6$ aromatic; and optionally substituted $C_3$-$C_6$ cycloalkyl;
$R_4$ is chosen independently for each position capable of substitution from the group consisting of hydrogen and $C_1$-$C_6$ alkyl;
X is chosen from the group consisting of O and S;
Y is absent or chosen from the group consisting of —$SO_2$—, —NH—, —N($C_1$-$C_6$ alkyl)- and —O—;
m is 0, 1 or 2
n is 0, 1 or 2
o is 0 or 1
p is 0, 1, 2, 3, 4 or 5;
---- is an optional double bond with the proviso that there cannot be two or more optional double bonds present;

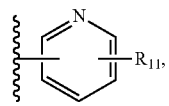

represents the point of attachment to the nitrogen containing ring and;
wherein the optional substituents are selected from the group consisting of $C_1$-$C_6$ alkyl, $C_2$-$C_6$ alkenyl, $C_2$-$C_6$ alkynyl, and $C_3$-$C_9$ mono and bicycloalkyl which can be optionally interrupted by 1-3 heteroatoms chosen from the group consisting of NR*, S, $SO_2$, and O wherein R* is chosen from the group consisting of H, —C(O)$C_1$-$C_6$ alkyl, benzyl, phenyl and $C_1$-$C_6$ alkyl, and can be further substituted with 1-8 substituents chosen from the group consisting of oxo, halogen, cyano, nitro, hydroxy, phenyl and —$NH_2$ with the proviso that oxo groups are not adjacent to one another; and wherein the optional substituents are selected from the group consisting of oxo, nitro, halogen, cyano, hydroxy, —$SO_2$($C_1$-$C_6$ alkyl), —O($C_1$-$C_6$ alkyl), —NRR wherein R is independently chosen for each occurrence from the group consisting of H, —C(O)$C_1$-$C_6$ alkyl, benzyl, phenyl and $C_1$-$C_6$ alkyl; and wherein the optional substituents are selected from the group consisting of —O—($C_1$-$C_8$ heteroaromatic), —O—($C_2$-$C_8$ heterocyclic), —C(O)—($C_1$-$C_8$ heteroaromatic), —C(O)—($C_2$-$C_8$ heterocyclic)-($CH_2$)$_q$—($C_1$-$C_8$ heteroaromatic), —($CH_2$)$_q$—($C_2$-$C_8$ heterocyclic), —NR*-($C_1$-$C_8$ heteroaromatic), —NR*-($C_2$-$C_8$ heterocyclic); —O-(phenyl), —C(O)-(phenyl), —C(O)NR*-($C_1$-$C_8$ heteroaromatic), —C(O) NR*-($C_2$-$C_8$ heterocyclic), —C(O)NR*-(phenyl), —($CH_2$)$_q$-(phenyl), —NR*-(phenyl), —NR*C(O)-(phenyl), —NR*C(O)—($C_1$-$C_8$ heteroaromatic), —NR*C(O)—($C_2$-$C_8$ heterocyclic); —OC(O)-(phenyl), —OC(O)—($C_1$-$C_8$ heteroaromatic), and —OC(O)—($C_2$-$C_8$ heterocyclic) wherein said heteroaromatic and heterocyclic rings contain from 1 to 3 heteroatoms chosen from the group consisting of —N—, —N($C_1$-$C_6$ alkyl), O, S, and $SO_2$; and said phenyl, heterocyclic and heteroaromatic rings can be further substituted with 1 to 3 groups selected from halogen, hydroxy, cyano, nitro, and $C_1$-$C_6$ alkyl; R*** is chosen independently for each occurrence from the group consisting of H and $C_1$-$C_6$ alkyl; and q is 0-6; and enantiomers, diastereomers and N-oxides thereof; and pharmaceutically acceptable salts thereof; with the proviso that two heteroatoms may not be covalently bound to one another unless present in a heteroaromatic ring, a sulfonamide linkage or as an N-oxide.

37. The method according to claim 36 wherein Z is formulas ii or iii, $R_3$ is optionally substituted mono- or bicyclic $C_1$-$C_9$ heteroaromatic group containing 1 to 3 heteroatoms chosen from the group consisting of N, $NR_9$, S, and O wherein $R_9$ is chosen from the group consisting of H, $C_1$-$C_6$ alkyl; m and n are 1; X' is O or $CH_2$, Y is absent and p and o are 0.

38. The method according to claim 36 wherein $R_3$ is wherein
$R_{11}$ is independently chosen for each position capable of substitution from the group consisting of H, halogen, $CF_3$, trifluoromethoxy, —C(O)—($C_{1-6}$ alkyl), —NH ($C_{1-6}$ alkyl), —N(di $C_{1-6}$ alkyl), nitro, cyano, hydroxy, $C_{1-6}$ alkyl, and $C_{1-6}$ alkoxy.-

39. The method according to claim 36, wherein the compound is represented by the Formula I

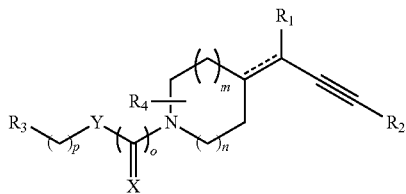

wherein:
- $R_1$ is chosen from the group consisting of hydrogen, $C_1$-$C_6$ alkyl, $C_3$-$C_{14}$ cycloalkyl hydroxyl, cyano, halogen, —C(O)O $C_1$-$C_6$ alkyl, —C(O)$C_1$-$C_6$ alkyl, —OC(O)O $C_1$-$C_6$ alkyl, —OC(O)$C_1$-$C_6$ alkyl, $C_1$-$C_6$ alkylthio, $C_1$-$C_6$ alkoxy, phenyl, di $C_1$-$C_6$ alkyl amino, and optionally substituted $C_2$-$C_9$ heterocyclic group containing 1 to 3 heteroatoms chosen from the group consisting of N, $NR_5$, S, $SO_2$ and O wherein $R_5$ is chosen from the group consisting of H, —C(O)$C_1$-$C_6$ alkyl, benzyl, phenyl and $C_1$-$C_6$ alkyl;
- $R_2$ is optionally substituted pyridyl;
- $R_3$ is chosen from the group consisting of hydrogen, optionally substituted $C_1$-$C_6$ alkyl optionally interrupted by 1 heteroatoms selected from the group consisting of —$NR_8$—, —O—, and —$SO_2$, wherein $R_8$ is chosen from the group consisting of $C_1$-$C_6$ alkyl; optionally substituted mono bi or tricyclic $C_1$-$C_{14}$ heteroaromatic group containing 1 to 3 heteroatoms chosen from the group consisting of N, $NR_9$, S, and O wherein $R_9$ is chosen from the group consisting of H and $C_1$-$C_6$ alkyl; optionally substituted monocyclic, bi, or tricyclic $C_4$-$C_5$ heterocyclic group containing 1 to 2 heteroatoms chosen from the group consisting of N and O; optionally substituted monocyclic aromatic; and optionally substituted $C_3$-$C_6$ cycloalkyl;
- $R_4$ is chosen independently for each position capable of substitution from the group consisting of hydrogen and $C_1$-$C_6$ alkyl;
- X is chosen from the group consisting of O and S;
- Y is absent or chosen from the group consisting of —$SO_2$—, —NH—, —N($C_1$-$C_6$ alkyl)- and —O—;
- m is 0, 1 or 2
- n is 0, 1 or 2
- o is 0 or 1
- p is 0, 1, 2, 3, 4 or 5
- ---- is an optional double bond and;

enantiomers, diastereomers and N-oxides thereof; and pharmaceutically acceptable salts thereof; with the proviso that two heteroatoms may not be covalently bound to one another unless present in a heteroaromatic ring or as a sulfonamide linkage.

40. A method according to claim 39, wherein the compound is selected from the group consisting of Formula II and III;

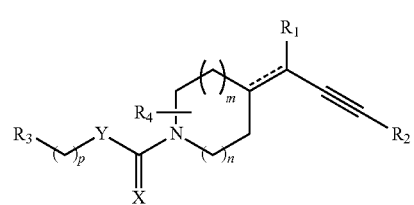

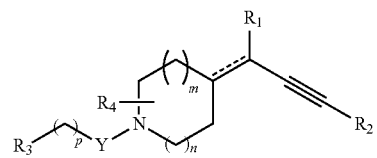

and enantiomers, diastereomers and N-oxides thereof; and pharmaceutically acceptable salts thereof.

* * * * *